United States Patent
Ward et al.

(10) Patent No.: US 10,876,103 B2
(45) Date of Patent: Dec. 29, 2020

(54) PROTEIN PRODUCTION IN FILAMENTOUS FUNGAL CELLS IN THE ABSENCE OF INDUCING SUBSTRATES

(71) Applicants: DANISCO US INC., Palo Alto, CA (US); VTT TECHNICAL RESEARCH CENTRE OF FINLAND LTD., Espoo (FI)

(72) Inventors: Michael Ward, Palo Alto, CA (US); Yun Luo, Glen Mills, CA (US); Felipe Oseas Bendezu, Chadds Ford, PA (US); Mari Valkonen, Nahkela (FI); Markku Saloheimo, Helsinki (FI); Nina Aro, Porvoo (FI); Tiina Pakula, Espoo (FI)

(73) Assignees: DANISCO US INC, Palo Alto, CA (US); VTT TECHNICAL RESEARCH CENTRE OF FINLAND LTD, Espoo (FI)

( * ) Notice: Subject to any disclaimer, the term of this patent is extended or adjusted under 35 U.S.C. 154(b) by 0 days.

(21) Appl. No.: 16/336,500

(22) PCT Filed: Oct. 3, 2017

(86) PCT No.: PCT/US2017/054983
§ 371 (c)(1),
(2) Date: Mar. 26, 2019

(87) PCT Pub. No.: WO2018/067599
PCT Pub. Date: Apr. 12, 2018

(65) Prior Publication Data
US 2019/0309276 A1 Oct. 10, 2019

Related U.S. Application Data

(60) Provisional application No. 62/403,787, filed on Oct. 4, 2016.

(51) Int. Cl.
| | | |
|---|---|---|
| C12N 1/14 | (2006.01) | |
| C07K 14/37 | (2006.01) | |
| C12N 15/80 | (2006.01) | |
| C12P 21/02 | (2006.01) | |
| C12N 9/42 | (2006.01) | |

(52) U.S. Cl.
CPC ............ *C12N 9/2437* (2013.01); *C07K 14/37* (2013.01); *C12N 1/14* (2013.01); *C12N 15/80* (2013.01); *C12P 21/02* (2013.01); *C12Y 302/01004* (2013.01)

(58) Field of Classification Search
None
See application file for complete search history.

(56) References Cited

FOREIGN PATENT DOCUMENTS

| WO | 2011/151512 A2 | 12/2011 |
| WO | WO 2011/151512 | * 12/2011 |
| WO | 2017/177289 A2 | 10/2017 |

OTHER PUBLICATIONS

Peterson et al , Microbiology,vol. 158, No. 1, pp. 58-68 (Year: 2012).*
Witkowski et al (Biochemistry 38:11643-11650, 1999) (Year: 1999).*
Seffernick et al., (Bacteriol. 183(8): 2405-2410, 2001 (Year: 2001).*
Whisstock et al., (Quarterly Reviews of Biophysics 2003, vol. 36 (3): 307-340) (Year: 2003).*
Devos et al., (Proteins: Structure, Function and Genetics, 2000, vol. 41: 98-107) (Year: 2000).*
Peterson et al., "Trichoderma reesei RUT-C30—Thirty years of strain improvement", Microbiology, 2012, pp. 58-68, vol. 158, No. 1.
Hakkinen et al., "Screening of candidate regulators for cellulase and hemicellulase production in Trichoderma reesei and identification of a factor essential for cellulase production", Biotechnol Biofuels, 2014, 7, 14.
International Search Report—PCT/US2017/054983—dated Dec. 5, 2017.
Written Opinion—PCT/US2017/054983—dated Dec. 5, 2017.

* cited by examiner

*Primary Examiner* — Padmavathi Baskar

(57) ABSTRACT

Certain embodiments of the disclosure are directed to variant filamentous fungal cells, compositions thereof and methods thereof for increased production of one or more proteins of interest. More particularly, in certain embodiments, the disclosure is directed to variant filamentous fungal (host) cells derived from parental filamentous fungal cells, wherein the variant host cells comprise a genetic modification which enables the expression/production of a protein of interest (POI) in the absence of inducing substrate. In certain embodiments, a variant fungal host cell of the disclosure comprises a genetic modification which increases the expression of a variant activator of cellulase expression 3 (ace3) gene encoding an Ace3 protein referred to herein as Ace3-L.

10 Claims, 29 Drawing Sheets

Specification includes a Sequence Listing.

```
              1          10          20          30          40          50          60
              |          |           |           |           |           |           |
Ace3-S        ------------------------------------------------------------
Ace3-SC       ------------------------------------------------------------
Ace3-L        ------------------------------------------------------MGSAAPAQGSVAAAA
Ace3-LN       ------------------------------------------------------MGSAAPAQGSVAAAA
Ace3-LC       ------------------------------------------------------MGSAAPAQGSVAAAA
Ace3-EL       MATAAAAAGGAAVAAGADTGEAAGSSSTGPPGLPGTRTGSVAMGSAAPAQGSVAAAA

Ace3-S        ---------------MLRYSPVLHLDTLSLPPLTNALP----------------------
Ace3-SC       ---------------MLRYSPVLHLDTLSLPPLTNALP----------------------
Ace3-L        GGPPAAGAGAGAGAVHALTTSPESASASASQPGSPTASTTPPQNSLVSAATSFHHHPRGRLVSR
Ace3-LN       GGPPAAGAGAGAGAVHALTTSPESASASASQPGSPTASTTPPQNSLVSAATSFHHHPRGRLVSR
Ace3-LC       GGPPAAGAGAGAGAVHALTTSPESASASASQPGSPTASTTPPQNSLVSAATSFHHHPRGRLVSR
Ace3-EL       GGPPAAGAGAGAGAVHALTTSPESASASASQPGSPTASTTPPQNSLVSAATSFHHHPRGRLVSR

Ace3-S        ------RPKCEYLSAVDSCTHCRDAHVQCTFDLPLARRGPKARKKSDQPGQPPPDPSS
Ace3-SC       ------RPKCEYLSAVDSCTHCRDAHVQCTFDLPLARRGPKARKKSDQPGQPPPDPSS
Ace3-L        ACDRCRRRKAKCEYLSAVDSCTHCRDAHVQCTFDLPLARRGPKARKKSDQPGQPPPDPSS
Ace3-LN       ACDRCRRRKAKCEYLSAVDSCTHCRDAHVQCTFDLPLARRGPKARKKSDQPGQPPPDPSS
Ace3-LC       ACDRCRRRKAKCEYLSAVDSCTHCRDAHVQCTFDLPLARRGPKARKKSDQPGQPPPDPSS
Ace3-EL       ACDRCRRRKAKCEYLSAVDSCTHCRDAHVQCTFDLPLARRGPKARKKSDQPGQPPPDPSS

Ace3-S        LSTAARPGQMPPPLTFSGPAVAALQPFASSSLSPDAAWEPVEPLSIDNGLPRQPLGDLPG
Ace3-SC       LSTAARPGQMPPPLTFSGPAVAALQPFASSSLSPDAAWEPVEPLSIDNGLPRQPLGDLPG
Ace3-L        LSTAARPGQMPPPLTFSGPAVAALQPFASSSLSPDAAWEPVEPLSIDNGLPRQPLGDLPG
Ace3-LN       LSTAARPGQMPPPLTFSGPAVAALQPFASSSLSPDAAWEPVEPLSIDNGLPRQPLGDLPG
Ace3-LC       LSTAARPGQMPPPLTFSGPAVAALQPFASSSLSPDAAWEPVEPLSIDNGLPRQPLGDLPG
Ace3-EL       LSTAARPGQMPPPLTFSGPAVAALQPFASSSLSPDAAWEPVEPLSIDNGLPRQPLGDLPG
```

FIG. 1B

| | |
|---|---|
| Ace3-S | LSTIQNISTRQRWIHLANAMTLRNTTLERVSKRCIDLFFDYLYPLTPLVYEPALRDVLAY |
| Ace3-SC | LSTIQNISTRQRWIHLANAMTLRNTTLERVSKRCIDLFFDYLYPLTPLVYEPALRDVLAY |
| Ace3-L | LSTIQNISTRQRWIHLANAMTLRNTTLERVSKRCIDLFFDYLYPLTPLVYEPALRDVLAY |
| Ace3-LN | LSTIQNISTRQRWIHLANAMTLRNTTLERVSKRCIDLFFDYLYPLTPLVYEPALRDVLAY |
| Ace3-LC | LSTIQNISTRQRWIHLANAMTLRNTTLERVSKRCIDLFFDYLYPLTPLVYEPALRDVLAY |
| Ace3-EL | LSTIQNISTRQRWIHLANAMTLRNTTLERVSKRCIDLFFDYLYPLTPLVYEPALRDVLAY |
| | |
| Ace3-S | IFSQPLPGVNQPSPLSQLTPDPTTGTTPLNAAESWAGFGQPSGSRTVGSRLAPWADSTFT |
| Ace3-SC | IFSQPLPGVNQPSPLSQLTPDPTTGTTPLNAAESWAGFGQPSGSRTVGSRLAPWADSTFT |
| Ace3-L | IFSQPLPGVNQPSPLSQLTPDPTTGTTPLNAAESWAGFGQPSGSRTVGSRLAPWADSTFT |
| Ace3-LN | IFSQPLPGVNQPSPLSQLTPDPTTGTTPLNAAESWAGFGQPSGSRTVGSRLAPWADSTFT |
| Ace3-LC | IFSQPLPGVNQPSPLSQLTPDPTTGTTPLNAAESWAGFGQPSGSRTVGSRLAPWADSTFT |
| Ace3-EL | IFSQPLPGVNQPSPLSQLTPDPTTGTTPLNAAESWAGFGQPSGSRTVGSRLAPWADSTFT |
| | |
| Ace3-S | LVTAVCAEAAFMLPKDIFPEGESVSEILLEASRDCLHQHLEADLENPTANSIAIRYFHSN |
| Ace3-SC | LVTAVCAEAAFMLPKDIFPEGESVSEILLEASRDCLHQHLEADLENPTANSIAIRYFHSN |
| Ace3-L | LVTAVCAEAAFMLPKDIFPEGESVSEILLEASRDCLHQHLEADLENPTANSIAIRYFHSN |
| Ace3-LN | LVTAVCAEAAFMLPKDIFPEGESVSEILLEASRDCLHQHLEADLENPTANSIAIRYFHSN |
| Ace3-LC | LVTAVCAEAAFMLPKDIFPEGESVSEILLEASRDCLHQHLEADLENPTANSIAIRYFHSN |
| Ace3-EL | LVTAVCAEAAFMLPKDIFPEGESVSEILLEASRDCLHQHLEADLENPTANSIAIRYFHSN |
| | |
| Ace3-S | CLHAAGKPKYSWHIFGEAIRLAQVMQLHEEAALEGLVPIEAEFRRCFWILYLGDKSAAI |
| Ace3-SC | CLHAAGKPKYSWHIFGEAIRLAQVMQLHEEAALEGLVPIEAEFRRCFWILYLGDKSAAI |
| Ace3-L | CLHAAGKPKYSWHIFGEAIRLAQVMQLHEEAALEGLVPIEAEFRRCFWILYLGDKSAAI |
| Ace3-LN | CLHAAGKPKYSWHIFGEAIRLAQVMQLHEEAALEGLVPIEAEFRRCFWILYLGDKSAAI |
| Ace3-LC | CLHAAGKPKYSWHIFGEAIRLAQVMQLHEEAALEGLVPIEAEFRRCFWILYLGDKSAAI |
| Ace3-EL | CLHAAGKPKYSWHIFGEAIRLAQVMQLHEEAALEGLVPIEAEFRRCFWILYLGDKSAAI |

FIG. 1C

| | |
|---|---|
| Ace3-S | LNNRPITIHKYCFDAGITTLYPSGIEDEFLSTASEPPRKSFISGFNANVRLWQSAADLLL |
| Ace3-SC | LNNRPITIHKYCFDAGITTLYPSGIEDEFLSTASEPPRKSFISGFNANVRLWQSAADLLL |
| Ace3-L | LNNRPITIHKYCFDAGITTLYPSGIEDEFLSTASEPPRKSFISGFNANVRLWQSAADLLL |
| Ace3-LN | LNNRPITIHKYCFDAGITTLYPSGIEDEFLSTASEPPRKSFISGFNANVRLWQSAADLLL |
| Ace3-LC | LNNRPITIHKYCFDAGITTLYPSGIEDEFLSTASEPPRKSFISGFNANVRLWQSAADLLL |
| Ace3-EL | LNNRPITIHKYCFDAGITTLYPSGIEDEFLSTASEPPRKSFISGFNANVRLWQSAADLLL |
| | |
| Ace3-S | EIRVLQDQMQHFRGTMPPNHVLPSADRQHLDSLYVRFITCLDDLPPYLQSCTLAMAAMA |
| Ace3-SC | EIRVLQDQMQHFRGTMPPNHVLPSADRQHLDSLYVRFITCLDDLPPYLQSCTLAMAAMA |
| Ace3-L | EIRVLQDQMQHFRGTMPPNHVLPSADRQHLDSLYVRFITCLDDLPPYLQSCTLAMAAMA |
| Ace3-LN | EIRVLQDQMQHFRGTMPPNHVLPSADRQHLDSLYVRFITCLDDLPPYLQSCTLAMAAMA |
| Ace3-LC | EIRVLQDQMQHFRGTMPPNHVLPSADRQHLDSLYVRFITCLDDLPPYLQSCTLAMAAMA |
| Ace3-EL | EIRVLQDQMQHFRGTMPPNHVLPSADRQHLDSLYVRFITCLDDLPPYLQSCTLAMAAMA |
| | |
| Ace3-S | EGNGSAESKQYVIQCINLQVTFHCLRMVITQKFEDLSYFAPGVEQADLRKSEIVRDMLRV |
| Ace3-SC | EGNGSAESKQYVIQCINLQVTFHCLRMVITQKFEDLSYFAPGVEQADLRKSEIVRDMLRV |
| Ace3-L | EGNGSAESKQYVIQCINLQVTFHCLRMVITQKFEDLSYFAPGVEQADLRKSEIVRDMLRV |
| Ace3-LN | EGNGSAESKQYVIQCINLQVTFHCLRMVITQKFEDLSYFAPGVEQADLRKSEIVRDMLRV |
| Ace3-LC | EGNGSAESKQYVIQCINLQVTFHCLRMVITQKFEDLSYFAPGVEQADLRKSEIVRDMLRV |
| Ace3-EL | EGNGSAESKQYVIQCINLQVTFHCLRMVITQKFEDLSYFAPGVEQADLRKSEIVRDMLRV |
| | |
| Ace3-S | MNEAPFWGLQANGEPNVEKIRLIGASLLAIIHRNQDSPLATRARSDFSVLLDILTRLDSK |
| Ace3-SC | MNEAPFWGLQANGEPNVEKIRLIGASLLAIIHRNQDSPLATRARSDFSVLLDILTRLDSK |
| Ace3-L | MNEAPFWGLQANGEPNVEKIRLIGASLLAIIHRNQDSPLATRARSDFSVLLDILTRLDSK |
| Ace3-LN | MNEAPFWGLQANGEPNVEKIRLIGASLLAIIHRNQDSPLATRARSDFSVLLDILTRLDSK |
| Ace3-LC | MNEAPFWGLQANGEPNVEKIRLIGASLLAIIHRNQDSPLATRARSDFSVLLDILTRLDSK |
| Ace3-EL | MNEAPFWGLQANGEPNVEKIRLIGASLLAIIHRNQDSPLATRARSDFSVLLDILTRLDSK |
| | |
| Ace3-S | ASDQLRNTSTTVVG (SID NO:3) |
| Ace3-SC | ASD----------- (SID NO:8) |
| Ace3-L | ASD----------- (SID NO:6) |
| Ace3-LN | ASD----------- (SID NO:14) |
| Ace3-LC | ASDQLRNTSTTVVG (SID NO:10) |
| Ace3-EL | ASD----------- (SID NO:12) |

FIG. 1D

Ace3 SC Form (SEQ ID NO: 7)

```
ATGCTGCGCTACTCCCCCGTCTTACACCTGGATACTCTCCCTTCCTTGGCACCACCGACCAATGCTCTTCCCGCCGCCCAAAGTGCGAGTACCTCAGCGCTGTCGACGCACTGCCG
CGATGCCACGTGCAGTGCAGATGCCACTTTCGACCTGGCCTGCCGCGGACCTGACCATGAGGAAGAACGAGGAGCGACCAGCCGCGGCGACCAGCCCGGTGTCGAGCTCGCTCCACCGCGG
CTCGACCCGGCCCAGAGCGCCCGGCCCGCCCGGCAGATGCCCGCCCGCCCGGCTTCTCCGGCGACCTCTGCCCGGCGTAGCCCTCCGACTACATCTCGACGCGGCCAACGCCTGCGCAA
AGCATTGACAACGGCCTGCCCGGCGACCTCTGGGCGACCTCTTCTTGAAGCGATGTATCGACATCCGCCGCTGTCAGCTCCACAGCGAGCGCGCGCCGAGCAGCTGTACCGAGACCCTGGTATCGACGCCGGCCTGTCGACGCTGCCACAACGACATCTTCTCC
AGCCCTTGCCTGGGGTCAACCAACCATCGCCGCTTCAGCCTGTCACCGCCGCCTCCGACCCTCGGTCACCGCCGTCTGAGAGGCAGCCATTCATGCTACCCAAGGACATTTCCCCGAAGGAGAATC
CGTCTGCGGAAGAAGGTGCTCGTGTAGAAGCCCCTGCTCGAAGCTTGCTCGAGACCCTTGCTCGTATAGACCTGATCCGTCTGACCCTCCGACCGCCACATCGCATTGGGCGACACCTTGGAGCCCGCCCATCCAAGTACTGCTTCGACGCCGGCATCACCACGCTATACCC
GTCGGGTATCGCTGCTGAAGAGCAGTTCCTGAGACATGATGCAGCACATCTGAACGCCCCGGGAACAGAAGATCTCCGAACCATGTGCGGCTCGAGCGTCCGCGCCTGATTCTCATGTCCGCTTCATCACCTGC
TCGGACGATCTCGCCCCGGCATGTAATTACGGCCACATCTGCTAAATCGCCGTTGCTGAGCAGGCTGATCTCGAGAAGTCGGAGATTGTGCGAGACATGCTGAGGGTGA
GTTTCACTGTCCTCGCCGGCATGGTAATTACGGCAGGCCAAGACGAGCACTTGGCCTCTGACGAAGCTCAATGTCGTCTGTGCAATTCTGCCTAATTCGCCTTATCGGAGCTAGTTGCTGGCCATCA
TGAACGAGGCGCCCTTTTTGGGGCCTGCAGGCCAATGGCAGCCTCGGCACTTGCTGTCTGCTAATCTGTCCCTGATTATGTCGTCGCTCCGGATGCTGCTGCAGGTTGTCTGCGAGGCTCGGATATCTTCCCGGCGTGGGGCGAGAGCCTCGGCACTTGGTCGGCCTTATCGGAGCTAGTTTGCTGGCCATCA
TCCATCGCAACCAGGATTCACCCTTGGCTACGCGAGCCAGGAGGCGACTTTTCCGTGCTTTTGGATATTCTCACGCGGCTGGACTCGAAGCGTCGGACTAA
```

Ace3 Protein SC Form (SEQ ID NO: 8)

```
MLRYSPVLHLDTLSLPPLITNALPRPKCEYLSAVDSCTHCRDAHVQCTFDLPLARRGPKARKKSDQPGQPPEPDPSSLSTAARPGQMPPPLITFSGPAVAALQPFASSSLSPDAAWEPV
EPLSIDNGLPRQPLGDLPGLSTIQNISTRQRWIHLANAMTLRNTTLERVSKRCIDLFFDYLNPLITPLVYEPALRDVLAYIFSQPLPGVNQPSPLSQLIFDPTTGTTPLNAAESWAG
FGQPSGSRTVGSRLAPWADSTFTIVTAVCAEAAFMLPKDIFPEGESVSEILLEASRDCLHQHLEADLENPTANSIAIRYFHSNCLHAAGKPKYSWHIFGEAIRLAQVMQLHEEAAL
EGIVPIEAEFRRRCFWILYLGDKSAAILNNRPITIHKYCFDAGITTLYPSGIEDEFLSTASEPPRKSFISGFNANVRLMQSAADLILEIRVLQDQMMQHFRGTMPPNHVLPSADRQ
HLDSLYVRFTTCLDDLPPYLQSCTLAMAAMAEKGNGSAESKQYVIQCINLQVTFHCLRMVITQKFEDLSYFAPGVEQADLRKSEIVRDMLRVMNEAPFWGLQANGEPNVEKIRLIGA
SLLAIIHRNQDSPLATRARSDFSVLLDILITRLDSKASD
```

FIG. 13

Ace3 S Form (SEQ ID NO: 1)

```
ATGCTGCGCTACTCCCCCGTCTTACACCTGGATACTCTCCTTGCCACCTGACCAATGCTCTTCCCGCCCCAAAGTGCCGAGTACCTCAGCGCTGTGCGATAGCTGCACGCACTGCCGCGA
TGCCCACGTGCAGTGCACTTTGCACCTGCCCGCTGACCTTGCCCGGCGCGACGCGGCCCAAAGCGAGGAAGAGAGCGACCAGCCCGCTGATCGAGCTCGCTCAGCCCTGATCGAGCCCGGCGGCTCGAC
CCGGCCAGATGCCGCCGCCGCTCCCGGCTGACCTTGCCCGCCGAGCCGCCCGCAGTAGCCGCGGCCCCGACGCTGTCGTCGCCACTAGCCGCCCGACGCCGGCCGTCGTGCGGAGCCCGTTCAGCATTGAC
AACGGCCTGCCCCGGCAGCCGCTGGGCGACCTCTTCTTCGACTATCTGTATCTGCCTACCCCTGGTGTACGAGCCGGGCCTCCGAGCTGCTGCGATACATCTTCTCCAGCCTGCCTGGCG
GCGGTCTCGAAGCATCGCCGCTGTCACAGTTCACGCAGGCTCACGCAGGCCCCAGTCGTGACCCTCCAACGCTGCTGCCAGCCAGCGGCTCGGAACCGCTGGCGAGC
TCAACAAGCCATCGCGCCTGGGCCTGACTCCCTGGGGCTGCACCTGCGCGACTCACCCTTCACCCTGGTCACGCCCTGTGCGCAGAGCGCCATCATCGATTGCCTGCGCGAGGAGACATTTCCCGAAGGAGAATCCGTCTCTGAGATCTTGCTCGA
AGGCTGGCTCCCTGGGGCTGCTGCACCAGCACCCTCGAGGCCGACCCACCATTCCGACGCCCCTCCAACGAGGCACGAGGAAGCCAAGTACT
CGTGGCACATATTTGGGCTCGACAAGTCAGCGCTGCTACTCAACATCGGCTATTCCGGCCTCGACGCCGGCTGACCCTGACGCCGCGCCATCAACGCAGTATACCCGTCGGGTATCGAGGACGAGTTCCTGAGCAC
TACTTGGGCGACAAGTCAGCCGCTGCTACTCAACAATCGGCTATTCCGGCCTCGACGCCGGCTGACCCTGACGCCGCGCCATCAACGCAGTATACCCGTCGGGTATCGAGGACGAGTTCCTGAGCAC
GGCTCCGAGCCGCCCCCGAAGAGCTTCAATGTGCGGCTTCATATCCGGCTTCAACGCAGCTTCAATCCAGCTTCTCTATGTCCCGCTTCATCACCTCGTCGGTGCTCCCGCCGTACCCAGTCGTGCACT
TTCGAGGGACCATGCCCCCCGAACCATGCCTCCCTGCCCGCCAACCATGTCCCCGAACCGGGTCCCTGCCGGAGTCTGCCAAGCAGTCCAAGGCCACCGGTCTACTCTGCGCATGATGAACCTGACGTTCACTGTCTCGCCGCATGGTAATTACGCAGAAATTCGA
CTGCCGATGGCAGCAGGCGAAGGCAACGGGTCTGCCAAGCAGTCCAAGGCCACCGGTCTACTCTGCGCATGATGAACCTGACGTTCACTGTCTCGCCGCATGGTAATTACGCAGAAATTCGA
AGACCTCTCTTATTTGCTCCTGCGTTCCTTGTCTCCTCTCTTTCTGCACACCCCTTTTCTTCGACGACCCCCTGCTGGATATGTGCGAGACATGCTGAGGTGATGAACGAGGCGCCCTTTGGGCCTGCGCCTGCGCCTGTTGTGCTAAT
CAAACGTGAGTCGTTCCTTGTCTGATGCTGCAGGTTGAAAGATTCGCCTTATCGGAGCTAGTTTGCCTGGCCATCATCCATGCAACCAGGATTCACCCTTGGCTACGCGAGCCAGGAGCGACT
CTGTCCTGATTATGTTGTCTGGATGCTGCAGGTTGAAAGATTCGCCTTATCGGAGCTAGTTTGCCTGGCCATCATCCATGCAACCAGGATTCACCCTTGGCTACGCGAGCCAGGAGCGACT
TTTCCGTGCTTTGGATATTCTCACGCGCGTCGGTCTGGATGCTGCAGGTTGAAAGATTCGCCTTATCGGAGCTAGTTTGCCTGGCCATCATCCATGCAACCAGGATTCACCCTTGGCTACGCGAGCCAGGAGCGACT
TTTCCGTGCTTTGGATATTCTCACGCGCGTCGGACCAACTGAGGAATACGTCCACTACCGTTGTTGGCTAA
```

Ace3 Protein S Form (SEQ ID NO: 3)

```
MLRYSPVLHLDTLSLPPLTNALEPRKCEYLSAVDSCTHCRDAHVQCTFDLPLARRGPKARKKSDQPGQPPPDPSSLSTAARPGQMPPPLITFSGPAVAALQPFASSLSPDAAWEPVEPL
SIDNGLPRQPLGDLPGLSTIQNISTRQRWIHLANAMTLRNTTLERVSKRCIDLFFDYLYPLTPLVYEPALRDVLAYIPSQPLPGVNQFSPLSQLTPDFTTGTTPLNAAESWAGFGQPSG
SRTVGSRLAPWADSTFTLVTAVCAEAAFMLPKDIFPEGESVSEILLEASRDCLHQHLEADLENPTANSIAIRYFHSNCLHAAGKPKYSWHIFGEAIRLAQVMQLHEEAALEGLVPIEAE
FRRRCFWILYLGDKSAAILNNRPITIHKYCFDAGITHLYPSGIEDEFLSTASEPPRKSFISGFNANVRLWQSAADLLLEIRVLQDQMMQHFRGTMEPNHVLPSADRQHLDSLLYVRFITC
LDDLPPYLQSCTLAMAAMAEGNGSAESKQYVIQCINLQVTFHCLRMVITQKFEDLSYFAPGVEQADLRKSEIVRDMLRVMNEAPFWGLQANGEPNVEKIRLIGASLLAIIHRNQDSPLA
TRARSDFSVLLDILTRLDSKASDLRNTSTTVVG
```

FIG. 14

Ace3 L Form (SEQ ID NO: 4)

```
ATGGGCTCAGCAGCTCCGGCCCAGGGCTCTGTAGCTGCAGCTGCAGGGCCTCCAGCTGCTGGCGCTGGGGCTGGCGCTGTCCTGCCCGAGTCTGCTGCTCGGCCTCGC
AGCCCGGCTCGCCAACCGCCTCAACCACCGGCCTCAGCCCGCCCAGAGAACTCACTCGTGTCGCGCCGAACCTCCACCACCTCCAGAGGCCGTCTGGTGAGCAGAGCGTGCTGACCGCTGCCCTCGACTGCGGGCCG
CAAGGCCAAGGTCAGTCTTCATATGTCCTTACTGACCCCTTTGCTGTTGCTAGAGTCTTCCGGTCTCCCGTTCCCGTGTCTCATACTGCGTGCTCCCCCGTCCCTG
GTCCCTGCTCTTCATATGTCCTTACTGCCGTTGTGTTGAGAGTTGTGTGTATTGAATGACCACCACTGCACTGCTGCCAAAGTGCAGTGAGCCACTCCACCCACCTGCGCCACGGGCCCACCCGGCCCAGATGCCCCGGCGGCACT
ACAATGGCCAAGCGGTTGTGTGTGTTGAGAGTTGTGTGTATTGCACTGCTCCGCGAGTAGCTCCAGCCCGCGATAGCTGCCACCGGGCTGACCGGGCTGACCCGCCCAGATGCCCGGCCGCGGCACT
CGTCTTACACCTGGATACTCTCCTTGCCACCACTGACCAATGCTGACTCTCCCGCGCCCAAAGTGCGAGTACCTCAGCGCTTGTGATAGCTCGCACGCCCCCACCGGGCTGACCCGGGCTGACCCGCCAGATGCCCGGGCGCTGACT
TGCACCTTTCTCCGGCCCGCGGCCCAGTAGCCGCGCTTCGCGTTGCGCCGCCCCGTGTGCGCCCGTGTGCGCGCAGACCTGCGGGCTGCAAGATTGACAGCGCTCAGCATTGACAACGCCGCTGCCCCCGGCCAGCCGCT
GGGCGACCTGCCCGGCCTCTCCACCATCCAGAACATCTGACGGCGCCAACGCCATGGCCAACGCCATGACGACCTGGCAACACGACGCTAGAGCGGTCTCGAAGCGATTATCGAC
CTCTTCGACTACCTCTACCCCTCACCCCTGTGTGTACGAGCCGGGCTTGGGCGTCGGGCGTCGTCCAACGCTGCCAGCATACATCTCCTGGGTCCGGCGTCAACCATCGCCGGCTGTCACAGC
TCACCCAGACCCGACCACGGCCACCCGTCTGCGCAGGACAGCATTCATGCTACCCAAGGACATTTCCCAACGTGTCTGCTCTGAGGAGAATCCGTCTTGCTCGAACCCCGTCGGCCGGCGGCCTGGGGCTGCCCCAGCCTC
CACCCTGTCGACCTGCGACCTCACGGCCGAATCCGACGGCCAACTCGATTGCCATCCCGAGGGGCCTCCACTTCCACACCAAGGCCAATTTGGATCCTCGGTACCGCTCTGCTGGGCACTCGTTGGCACATATTTGCGAGGCGCAGCACCTG
GAGGCCAGCGCTGCACGGCCAACTCGATTGCCATCCCGAGGGGCCTCGGTGCCCTCGTCCCCATCCGAGGGCAGAGTTCCCGGCTCTTTTGGATCCTCGGTTACCTCGCGGGACAAGTCAGCGCTATACCTCAACAA
TCGCCCCATCACCATCCACAAGTACTGCTTCGACGGCCGGCTCTGGGATCTGCCTGAGATAGTCAGTCGGCAAGCCTGGGGTCCGAGCTGCGTCCAGAGTTCCTGAGAGACCCGTGGGTATCGGAAGATCAGATACAGATAGATCCAGCTGAGACCTCTTATTTGCTCTGGAGCTGATCTC
TTCAAGCAAATGTGCCGGCTCTGGAGTCCGCCGACCTTCTCCAGACATCCCGGCCCGTCATCGACCATCAGGCAGAATTGCAGAGCGGCCCAATGGCCGGCCAATGGCGAGAGTCCCGCCAGATGGCCCATGGCCTCTAATCGCGTCCTGAGTCCGCAGGTTGAAGATTGCC
CGACAGGCAGCAGTACGTGATACAGTGCCCAGATGCTGACCTGAGGTGATGCTGAGGTGATGCTGATCGCCAGGGGCTAATAACCAGCAGCCAATGCGGAGCCCCAATGGCCGCCAATGGCCGCCAATGGCCTCTAATCGCGTCCTGAGTCCGCAGGTTGAAGATTGCC
AGAAAGTCGGAGATTGTGCCAGACATGCTGAGGGTTGATGAACGAGGTGATGAACGAGGCGGCCCCTTGGGCCTGCGGCACTTGTTGCTAATCGTCCTGATTATGTTGTCTGGATGCTCAGGTTGAAGATTGCC
TTTCTTCGACGACCCCTCTCTTGTTCTTTATATCCTGCGAATGACCAGGGTAACCAGGGTATACATCGCGGGTCCAGGTCGGCACTTGGCGAGCCCAGATGACCTTTTCGTGTCTTTGCCGTATTCTCACCGCGGCTGGACCTGGAAGGCGTCGGA
CTAA
```

Ace3 Protein L Form (SEQ ID NO: 6)

```
MGSSAAPAQGSVAAAGGPAAGAGAVHALTTSESASASQPGSFTASTTPPQNSLVSAATSFHHHPRGRLVSRACDRCRRRKAKCEYLSAVDSCTHCRDAHVQCTFDLPLARRGPRARKKS
DQPGQPFPDPSSLSTAARPGQMPPPLTFSGPAVAALQPFASSLSFDAAWEPVEFLSIDNGLPRQPLGDLPGLSTIQNISTRQRWIHLANAMTLRNTTLERVSKRCIDLFFDYLYPLTPLVYE
PALRDVLAYIFSQPLFGVNQPSPLSQLTPDPTTGTTPLNAAESWAGFGQPSGSRTVGSRLAPWADSTTLVTAVCAEAAPMLFKDIFPEGESVSEILLEASRDCLHQHLEADLENPTANSIAI
RYFHSNCLHAAGKPKYSWHIFGEAIRLAQVMQLHEEAALEGLVPIEAEFRRCFWILYLGDKSAAILNNRPITIHKYCFDAGITTLYPSGIEDEFLSTASEPPRKSFISGFNANVRLWQSAAD
LLLEIRVIQDQMMQHFRGTMPPNHVLPSADRQHLDSLYVRPITCLDDLPPYLQSCTLAMAAMAEGMNGSAESKQYVIQCINLQVTPHCLRMVITQKFEDLSYFAPGVEQADLRKSEIVRDMLRV
MNEAPFWGLQAMGEPNVEKIRLIGASLLAIIHRNQDSPLATRARSDFSVLLDILTRLDSKASD
```

FIG. 15

Ace3 LC Form (SEQ ID NO: 9)

```
ATGGGCTCAGCAGCTCCGGCCCAGGGCTCTGTAGCTGCAGCTGCAGGCGGCCCTCCAGCTGCTGGCGCTGGCGCTGTCCAGCTGCCCTCACCACCTGCCACGCCCCTCACCACCTCGCCCTCGGCCTCGCAG
CCCGGCTCGCCAACCGCCCTCAACCACGCGCCTGGCCCTTTTCCGGCCCAGAACTCACTCGTTGCCGTTCCACCACCATCCCAGAGCCGGTTGGTGAGCAGAGCCCTGGGACGCTGGCGCGTGGGTCCTGGTCCT
GCCAAGTCAGTCTAGCCCTTTGCTCTGTGTGCATCTCGTTGTCATTGCCCTCCTCCCGTCCTGATGCTGCTCCTCCGTCTCCCGGTGACTGCGACTGCAGACAAGCATACATACATCAGCATACAATGGCA
GCTCTTCATATGTCCTTACTGCCCGTTCCTCTCCCCGTTCCCGTTCCTTGCACTCGTTCAATTGCACTGCTTGGTATTGTGTTGAGAGCTTCAGACACCGAGAGCCCCTCCTCCTCCGACGCTTCCCGGC
AGCGTTGTGTGTTGGGAAGTTGCTGTTCCCAACTCGTTCATACTCGTTGAGATTCTGCACTTGTTGGGAAAGTTGCTGTCACCCAGTTATCTCCCCCGTCCCCCGTCCTCCGACCTGCC
CTGGATACTCTCCTTGGCCACCACTGACCAAATGCTCCTTCCCCGGCCAAAGTGCCTCTTCCCCGGCCAAAGTGCCAGTCAGTCACAGTCCCCGATACCACTGCCACTGGCAGACCTGTGTGACCACCTGCC
CTGCCGACGTAGCCCGCCCTAGCCGTTCCCAGCGTTAGCGCCTCCGAGCCGCCCATAAGACCAGGATTCTAAGATGACCCCCATAACCGAAGAGCCCTGTCCACGCCTAATCCTGAATGCGCGCATTCTCAACGACTCATCCGCTGGGAGCCTAGTGCAGGCCTGGGACTCTGAGATATGAGGGCCAGGAGCCGATAGGAGCACGCAGTCCGAGCTGCAACGTGCACAAGTACTGC
CTCTCCACCAGAACATCTGACGAGCCGACTGCAGTGGAAGGAGAATCGTCTCTGAGACTGTGCAAGTCCTGCCATGCCAAGTCAAGGGCCTATACTCCAACAATCGGCCCAGGCCCTATCCAAGGCCCATACTCAACAATGTGCGGCTCTGCAGGTCC
TAAAACCCCCCATCCCTCACCCAGTGATTGCACGATCCATCATAAGCTGCCCTCCTGAGGGAGAGCCCAAGCATCCATTCCAATCCGGCAGAGCCAGAGAGCCGACAAGAGCAGAGAGCCAAGAGCAGAGCGACAAGAGCAGAGCCGACAGCAGAGCCGACAGTCTACAAAGTACGTCCCCGAGACCATGTGCGCAGATCCGTAAGATCCCATGAGCTCTACCCCCGCTATATCCTCTCTATATGCCTGGCCCTGAGAGTGAGATCCTGAGATGACTGCAGAGAGAGAGCAGTACCTG
GCGCTGATTTGCTGCTGGAAATCCGCTGCTGCAAGATCAGATGAGCATCTCGCCAAATCATCCAGGCTGCAGCTGCCAGTGAAGCAAGTCCAGTCCCACAAGATGTCTCAGAGCAACGGTCTGTGCATCGAGTCTCGCAGAGAGCAGAGCAGCCAAGCAAGAACGTGCTCATCACCTCGAGATCGATTCGATTCTCTCTATGTC
CGCTTCATCACCCTGGACGATCTCCCGCGATCCCCAGTCGTGCCACTGCACCCCTCTATTTGCTCTGCTGTCCTCTGTCCTGCCCTCGATCAAGCTCAGAGAAGCAAGCAATCGGAGGGGCTGAATCCCAGTCAAGATCTCGTCAAGGTCGCAAGAACCAGATCGAGACACATAGCAAGCTAGCTGCTGAGAGATTCGCAGACCCCCCCTCTCTCTCTTATATCCCTGC
CAGGTGACGTTTCACTGTCTGCGAGCATGGGCCTGCAGCCAAACGTGAGTCGTTCCTTGTCCTGCGTTTCCTTTGTCTGTCCTTTGTCCTGACGGTGAGATCGTTCAGAGATCCGGATGCACGAGGATGCTGAGGTGAGGATACCGACGACGAGCAGCTGCAACCTGCAGCTGCAGCAGCAGAGCGCAAAGTCGGAGACTGGAGATTGTGCGAGAACATGCTGAGGGTG
GATTCACCCTTGGCTACGCAGCGCCCAGGAGCGACTTTCCGTCGCTTTTCCGTCGTTTCCGTCTTTGGATATTCTCAGTATATCCACGCGGCCTGGAGTCCGAAGCGCTGCGAACGTCCACTACCGTTGTTGGCTAA
```

Ace3 Protein LC Form (SEQ ID NO: 10)

```
MGSAAPAQGSVAAAAGGPPAAGAGAGAVHALTTSPESASASQPGSPTASTTPPQNSLVSAATSFHHHPRGRLVSRACDRCRRRKAKCEYLSAVDSCTHCRDAHVQCTFDLPLARRGPKARKKSD
QPGQPPDPSSLSTAARPGQMPPPLFFSGPAVAALQPFASSSLSPDAAWEPVEPLSIDNGLPRQPLGDLPGLSTIQNISTRQRWIHLANAMTLRNTTLERVSKRCIDLFFDYLYPLTPLVYEPA
LRDVLAYIFSQPLPGVNQPFSPLSQLTFDPTTGTTFPLNAAESWAGFGQPSGSRTVGSRLAPWADSTFTLVTAVCAEAAFMLPKDIFPEGESVSEILLEASRDCLHQHLEADLENPTANSIATRYF
HSNCLRAAGKPKYSWHIFGEAIRLAQVMQLHEEAALEGLVPIEAEFRRRCFWILYLGDKSAAILNNRPIIHKYCFDAGITTLYPSGIEDEFLSTASEPPRKSFISGFNANVRLWQSAADLLLE
IRVLQDQMMQHFRGTMPPNNVLPSADRQHLDSLYVRFITCLDDLPPYLQSCTLAMAAMABGNGSAESKQYVIQCINLQVTIFHCLRMVITQKFEDLSYFAPGVEQADLRKSEIVRDMLRVMNEAP
FWGLQANGEPNVEKIRLIGASLLAIIHRNQDSPLATRARSDFSVLLDILTRLDSKASDQLRNTSTTVVG
```

FIG. 16

Ace3 EL Form (SEQ ID NO: 11)

ATGGCCACAGCGGCCCGGCCAGCAGCTGCGGCGGCGGCGGTTGCTGCGGGTGCAGACGCAGTGGCGTGCAGACCCGGCTGCCAGCCCGCTGGGTGGCA
CTGGAACGCAGTGCAGCGCCAATCAGTGCAGTGCGGCCTGCCCCAACTAACGCTGCCCGGCTGCACAGGCCCCCACCACTATACAGGCCCTCTCCAGGGC
TTCCAGGCACCCGAGCCTCCGTGCCGTCAGCTGGCTCGAGTCCCGGCCCGACTCTGCTAGCTGCAGGAACTCGCTGGAGCTGCGCTGTCCACGCCCTCAC
CACCTCGCCCGAGTCCGCTCGGCCGTCCCTCAGGCCAACCTCGTTGCCACCACCATCCAGAACCACCATCAGGAGGCCGTGGTG
AGCAGAGCGCCGACCGGCTGCCACGGCCAAGCCAAGGTCAGTCTAGGCCCAAGTCAGTCTTGCTGTGTGCATCTCTGTTGCAATGCTGCTGCTCCTCC
TACAAAGCATACAATACATACAGCCATACATGGGAGTTGGTGTTGAGAGTTGTGTATATGACCACTGACTCTCTCCTTGCCACCACTGCTCAGCCCCAACACCG
ACCCTCGCTCTTCAATGCTGGCTACTCCCCCGTCTTACACCTGGCTATAATGCCTCCCTTACACCTGCCCCCCAAGTCCAGAGTACCTCAGCGCTGTCGATAGCTCAGCGG
ACTCGCCGCGATGCCCACCGTGCAGTGCACTTTCGACCTGTCAGGCTCCCCCCTGGCGCGCCTGCCCTGAGGAAGAGCGGACCCCGTGCCCCGCCTGATCCCAACCGCGC
GGCTCGACCCGGCCAGATGCCCCGGCACCGCGCCGGCCCTTCCCGGCGACCTTCTCCACCATCCAGAACACTCCGGCCAGCGCCCAAAGCCATCTCTCCAAGCCCATCACCGAGACCCGCTCAGC
ATTGACAACGCGTCTCGAAGCGATGTATCGCGCTGTCACGACTCGACACCATGCCCTCCGAAGCTCTACCCCAAGGACATTTCCCGAAGGAGAATCCGTCTCTGAGATCTTGCTCGAAG
CGTCAACCAATCATGCCGTGCCGTGACTCGAACCACTCAAGATCAGCGCGGCGGCGAAGCGTCTCAGCTGCAGCCAAGTCCTGCGTGTCACAGCTGGGCGCAAGGCAGACCCGCAGGGCTCGG
AGGCTGGCTCCCTGGGACTGCCTCGACCAGCACCTCGAGGCCGACCTGAGCCAAAGTCAGTGGAGGAGCTCCAACTGGCCTGCGCGCTCCTCTACCGAGGAGATCCTTGCGCAGTCGGGGTCTCAAGTACTCGTG
GCACATATTTGGGACAAGAGCCGCTATACTCAACAATCGGCCCAAAATGTGCCGCTTCCCGGCCAGAGATCAGCGGCTGCCACAGGCTATACCCGGCCTGGGGTTCTGCGGCGACGAGTTCGCGGCCCCTGCTGCGCAGTCCCGAGCACGGCGTGCCCGACCCTCGGGCGGAATCCCCGAGGGAC
AGCCCCCCCGAACCATGTGCTGCCCCTCCGCCACAGCGACATCTCGCGATATCGCGAACAGCAGCTCAGCTCATCACCCTGCGGGGTGCTGAAGATGCAGCAGCGTTTCGAGGGAC
GCGATGGCAGAAGGCAACGGGTCTGCGCAGTCCAGGTCGTATATCCAAGTGTCGGCGCAAAGCATGGCTGCAGTGCGCGCATATGTCGCATGAAGACCTTTCTGCGCCGTGCTCTTTATT
TGTCCTGGCGGTTGAGCAGGTGATCCGAGACCCCTGCCACACCGCTCTTTCTCGCAGCCCTCCGCGCCAGTCAGTCTAACCACCAGGATCCCAGCACTTGCTTGAGAGCCCGGACTCAACGGACCCAAGCAACTGTTCCTGATTATGTTGT
CTGGATGCTGCAGGTTGAAAAGATTCGCCTTATCGGAGCTTTGCTTGCCTCTGCTGCAGGACCCGAGGAGCCAGGCGACTTTTCCGTGCTCTTTTGATATT
CTCACGGGCTGGACTCGAAGGCGTCGGACTAA

Ace3 Protein EL Form (SEQ ID NO: 12)

MATAAAAAKGAAVAAGALTGAAGSSSTGPPGLPGLPGTRTGSVAMGSAAPAQGSVAAAAGGFPAAGAGAGAVHALTTSFESASASQPGSPTASTTFPQNSLVSAATSFHHHPRGRLVSRACD
RCRRRKAKCEYLSAVDSCTHCRDAHVQCTFDLPLARRGPKARKKSDPGQPPFDPSSLSTAARPGQMPPPLTTSGPAVAALQPFASSSLSPDAAWEPVEPLSIDNGLPRQPLGDIPLGLSTIQN
ISTRQRWIHLANAMTLRNTTLERVSKRCIDLFFDYLLYPLTPLIVYEPALRDVLAXIFSQPLPGVNQPSPLSQLIPDFTTGTTPLNAAESWAGFGQPRSGSRTVGSRIAPWADSTFTIVTAVCAEA
AFMLPKDIFPEGEBSVSEILLEASRDCLHQHLEADLENPTANSIAIRYFHSNCLMAAGKPKYSWHIFGEAIRLAQVMQLHEEAALEGLVPIEAEFRRRCFWILYLGDKSAAILNNRPITIHKYC
FDAGITTLYESGIEDEFLSTASEPFRKSFISGFNANVRLMQSAADLLLEIRVLQDQMMQHFRGTMPPNHVLPSADRQHLDSLYVRFITCLDDLPPYLQSCTLAMAAMAEGNGSAESKQYVIQC
INLQVTFPHCLRMVITQKFEDLSYFAPGVEQADIRKSEIVRDMLRVMNEAPPWGLQANGEFNVEKIRLIGASLLAIIHRNQDSPLATRARSDFSVLLDILTRLDSKASD

FIG. 17

Ace3 LN Form (SEQ ID NO: 13)

ATGGGCTCAGCAGCTCCGGCCCAGGGCTCTGTAGCTGCAGCAGCAGGGCCCTCCAGCTGCTGGCGCTGCAGGCGGGCCTGGCGCTGTCCAGCCCCTCACCACCCTCGCCCGAGTCTGCCTCGGCCTCGCA
GCCCGGCTCGCCAACCGCCTCAACCACGCCGCCGAGAACTCACTCGTTCCACCACATCCGTTCCAACCTCGTTCCAGAGGCCGTCTGGTGAGCAGCAGCCGTCTGTGACCGCTGCCGCCGCCGGCGCA
AGGCCAAGTGCCAGTACCTCAGCGCTGTCGAGCCACGCACACCTGCCGCACTGCCACCTGCCCTGCCAGTGCGCCGACGCGGCCCTGCCGCTGCTCTCCGGAGCCTTCGACCTTCTGACGCTGTCGCT
CCCGGCCAGCCAGCCCGTGCCCAGCTCGAGCTCGGGACCCGTCGAGCCCATGACGACGCCATGACGCAGTAGCGCATTCTGAGCCAGAACATCTCGAGCCAGCCTGCCTGTCTGCT
GTCGCCGACCGCGGCCTGGCAACGCCATGACGTCGAGCCAACACGACGTCGAGGCCTCCGAAGCGATGTATCACAGCGCGGTGTTCAACCAACCATCGCCCTGCCTCTTCTTCTGACTACCTCACCCTCCACCCCTACCCCTCCACCCCCCCTCACCCCCCCTCA
GACGTGCTCCATACATCTTCTCCAGCGGCTCGGCGTCAACCAACATCGCCGCTTCCTGGCGTCAAGGCCTGCAACCATGCGGCCCATCCACGGCACCACCGGCACCACGGGACACCCGACCACCTGCCAGTCGTGGGCCGG
CTTTGGCCAGCCAGCGGCTCGCGAACCGTCGGCAGCAGGCTGGCTCCCTGGGCAGCGGCCTCTGCCGACCCTTCCAGCCCTGCTCCGAGACGCGCTGACTGGACCCGGTGACCTCCTGCCTCTTCCACTCGAGCGA
CCGAAGGAGAATCCGTCGGGGGAAGCCGTCTGCTCGAGATCTTGGCGAGGCCACGATATTGGCGAGGCCCACATCCGCGGAGCTGCCCTGCACGGAGCCTGCCGCCATCACGGCCTCGTCCCCATCGAGGGCAGA
TGCCTCCACGCCCTGGCGGCGTCTGCCTGCTTTGGATCTCGGCGAGCCACCAAGTCAGCGCCGCTATACTCAACAATCGGCCCATCCAGCTGCTTCGACGCCGGCATCACCACGCTATACCGTCGG
GTTCGGCCGTGCCGCTGCTTTGGATCCTGTACTTGGGCGACAAGCTGAGCCGCTATACTCAACAGCCAAGCTTTCAACGCAAGAGCTTCATACTCCGGCTTCAACGCAGCAGCATCGGCGCTGAGTCCGCGGAAATCGCGTGCTG
GTATCGAGGACCAGTTCCTGACGCACGGCACTCTGGCGAGCATGCCCGGACCCATGCCCCTCGAAGCATGTGCGGCATCGATTCTCATGTCCGCCGAGCCAGCATCGTATAACCTCTACTGTCCGCCTTGACGCATCTCCCGCC
CAAGATCAGATGATGCAGCATCGTGCACTCTGGCGATGGCAGCGATGGCAGCAGGAAGGCAGAAGGCAAACGGTCTGCCGAGTCCAAGCAGTCGATCAACCTGCGATACAGTCGATACAGTGCGAGACATGCTGAGGGTGATGAAGACAGCCCCCCCTCTCTCTTTTCTTCCACACCCTTTATATCCCTGCGACGA
GTACCTCCAGTCGTGCAGAAATTCGAAGACCTCTCTTATTTGCCTCGGCGTTGAGTCGCTGGCGTTGAGCAGGCTGTTGAGCAGGTCAGAAAGTCGGAGATTGTGCGAGACCCCCCCCTCTCTTTTCTTCCACACCCTTTATATCCCTGCGACGA
GCCAATGGCAGCCAAACGTGAGTCGTTGATTATGTTGTCTGGATGCTGCAGGTTGAAAAGATTCGCCTATCGGAGCTAGTTTGCTGGCCATCATCCATCCAGGATTCACCCTTGGCTACGCGACTCGGCCACT
AGCGACTTTCCGTGCTGTCTTTGATATTCTCACGCGGCTGGACTCGAAGGCGTCGACTAA

Ace3 Protein LN Form (SEQ ID NO: 14)

MGSAAPAQGSVAAAGGFPAAGAGAGAVHALTTSPESASASQPGSPTASTTPPQNSLVSAATSFHHHPRGRLVSRACDRCRRRAKCEYLSAVDSCTHCRDAHVQCITFDLPLARRGPKARKKSDQ
PGQPPDPSSLSTAARPGQMPPPLTFSGPAVAALQPFASSSLSPDAAWEPVEPLSIDNGLPRQPLGDLPGLSTIQNISTRQRWIHLANAMTLRNTTLERVSKRCIDLFFDYLYPLITPLIVYEPALR
DVLAYIFSQPLPGVNQPSPLSQLTFDPTTGTTPLNAAESWAGFGQPSGSRTVGSRLAPWADSTFTLVTAVCAEAAFMLPKDIFPEGESVSEILLEASRDCLHQHLEADLENPTANSIAIRYFHSN
CLHAAGKPKYSWHIFGEAIRLAQVMQLHEEAALEGLVPIEAEFRRRCFWILYLGDKSAAILNNRPITIHKYCFDAGITTLYPSGIEDEFLSTASEPPRKSFISGFNANVRLMQSAADLLEIRVL
QEDQMMQHFRGTMPPNHVLPSADRQHLDSLYVRFITCLDDLPFYLQSCTLAMAAMAEGNGSAESKQYVIQCINLQVTFHCLRMVITQKFEDLSYFAPGVEQADLRKSEIVREMLRVMNEAPFWGLQ
ANGEPNVEKIRLIGASLLAIIHRNQDSPLATRARSDFSVLLDILTRLDSKASD

FIG. 18

PROTEIN PRODUCTION IN FILAMENTOUS FUNGAL CELLS IN THE ABSENCE OF INDUCING SUBSTRATES

CROSS REFERENCE TO RELATED APPLICATIONS

This application claims benefit to U.S. Provisional Application No. 62/403,787, filed Oct. 4, 2016, which is hereby incorporated by reference in its entirety.

SEQUENCE LISTING

The sequence listing text file submitted herewith via EFS contains the file "NB41159WOPCT_SEQLISTING.txt" created on Oct. 2, 2017, which is 157 kilobytes in size. This sequence listing complies with 37 C.F.R. § 1.52(e) and is incorporated herein by reference in its entirety.

FIELD

The present disclosure is generally related to the fields of molecular biology, biochemistry, protein production and filamentous fungi. Certain embodiments of the disclosure are directed to variant filamentous fungal cells, compositions thereof and methods thereof for increased production of one or more proteins of interest. More particularly, in certain embodiments, the disclosure is directed to variant filamentous fungal (host) cells derived from parental filamentous fungal cells, wherein the variant host cells comprise a genetic modification which enables the expression/production of one or more proteins of interest (POI) in the absence of inducing substrate.

BACKGROUND

Cellulose, a component of lignocellulosic plant material, is the most abundant polysaccharide found in nature. Likewise, filamentous fungi are known in the art to be efficient degraders of plant biomass, and are in fact a major source of industrially relevant lignocellulosic degrading enzymes (referred to hereinafter collectively as "cellulase" enzymes). For example, filamentous fungi are known to produce extracellular cellulase enzymes (e.g., cellobiohydrolases, endoglucanases, β-glucosidases) that hydrolyze the β-(1,4)-linked glycosidic bonds of cellulose to produce glucose (i.e., thereby conferring the ability of these filamentous fungi to utilize cellulose for growth).

In particular, the filamentous fungus *Trichoderma reesei* (*T. reesei*; an anamorph of the fungus *Hypocrea jecorina*) is known to be an efficient producer of cellulase enzymes (see, e.g., PCT International Application Nos. WO1998/15619, WO2005/028636, WO2006/074005, WO1992/06221, WO1992/06209, WO1992/06183, WO2002/12465 and the like). As such, filamentous fungi such as *T. reesei* have been utilized for their ability to produce enzymes which are valuable in the production of such commodities as cellulosic derived ethanol, textiles and clothing, detergents, fibers, food and feed additives and other industrial uses.

The expression (and production) of these industrially relevant enzymes in *Trichoderma* are known to be dependent on the carbon source available for growth. More particularly, the production of cellulase enzymes by filamentous fungi is an energy-consuming process and as such, both inducing and repressing mechanisms have evolved in filamentous fungi to ensure the efficient production of these enzymes. For example, the various genes encoding enzymes needed for the degradation of plant cell wall material (i.e., cellulases/hemicellulases) are "activated" in the presence of an "inducing" substrate and "repressed" in the presence of easily metabolized carbon sources (e.g., D-glucose) that are preferred over plant biomass via a mechanism known as "carbon catabolite repression" (hereinafter, "CCR"). Thus, the cellulase genes are tightly repressed by glucose and are induced several thousand folds by cellulose and certain disaccharides (e.g., sophorose, lactose, gentiobiose). For example, the expression level of the major cellobiohydrolase 1 (cbh1) is "up-regulated" several thousand fold on media containing inducing carbon sources such as cellulose or sophorose, compared with glucose containing media (Ilmen et al., 1997). Furthermore, the addition of a "repressing" carbon source to "induced" *T. reesei* cultures was shown to override the (cellulose or sophorose) induction, thereby resulting in down-regulation of cellulase gene expression (el-Gogary et al., 1989; Ilmen et al., 1997). Thus, the expression of genes comprising the cellulase system (enzymes) are at least coordinated and regulated at the transcriptional level, wherein the gene members of this system act synergistically, and as noted above, are necessary for the efficient hydrolysis of cellulose to soluble oligosaccharides.

More specifically, a genome-wide analysis revealed that there are at least ten (10) cellulolytic and sixteen (16) xylanolytic enzyme encoding genes in *T. reesei* (Martinez et al., 2008). In particular, the most abundantly secreted enzymes are the two main cellobiohydrolases (EC. 3.2.1.91), cbh1 (cellobiohydrolase 1) and cbh2 (cellobiohydrolase 2), and the two major specific endo-β-1,4-xylanases (EC 3.3.1.8), xyn1 (endo-1,4-beta-xylanase 1) and xyn2 (endo-1,4-beta-xylanase 2), referred to herein as "major industrially relevant hemicellulases and cellulases" or "MIHCs". These MIHCs work together with additional enzymes to degrade cellulose and xylan, which results in the formation of soluble oligosaccharides and monosaccharides, such as cellobiose, D-glucose, xylobiose and D-xylose. In addition, sophorose is a product of the transglycosylation activity of some of these enzymes (Vaheri et al., 1979). More particularly, these soluble oligo- and monosaccharides (i.e., cellobiose, D-glucose, xylobiose, D-xylose and sophorose) have been reported in the literature to influence the expression of the MICHs in *T. reesei*. For example, the presence of D-glucose causes CCR, which results in the secretion of low quantities of MIHCs. Sophorose is believed to be the most potent inducer for the expression of cbh1 and cbh2. D-xylose modulates xyn1 and xyn2 expression in a concentration dependent manner.

In general, the commercial scale production of enzymes/polypeptides by filamentous fungi such as *Trichoderma* is typically by either solid or submerged culture, including batch, fed batch, and continuous flow processes. For example, one of the most problematic and expensive aspects of industrial cellulase production in *Trichoderma* is providing the appropriate inducer (i.e., inducing substrate) to the *Trichoderma* host cells. For example, as is the case for laboratory scale experiments, cellulase (enzyme) production on a commercial scale is "induced" by growing the fungal cells on solid cellulose (i.e., an inducing substrate) or by culturing the cells in the presence of a disaccharide inducer such as "lactose" (i.e., an inducing substrate).

Unfortunately, on an industrial scale, both methods of "induction" have drawbacks which result in high costs being associated with cellulase production. For example, as set forth above, cellulase synthesis is subject to both cellulose induction and glucose repression. Thus, a critical factor influencing the yield of cellulase enzymes under the control of an inducible promoter is the maintenance of a proper balance between cellulose substrate and glucose concentration (i.e., it is critical for obtaining reasonable commercial yields of the regulated gene product). Although cellulose is an effective and inexpensive inducer, controlling the glucose concentration when filamentous fungal cells are grown on solid cellulose can be problematic. At low concentrations of cellulose, glucose production may be too slow to meet the metabolic needs of active cell growth and function. On the other hand, cellulase synthesis can be halted by glucose repression when glucose generation is faster than its consumption. Thus, expensive process control schemes are required to provide slow substrate addition and monitoring of glucose concentration (Ju and Afolabi, 1999). Moreover, the slow continuous delivery of substrate can be difficult to achieve as a result of the solid nature of the cellulosic materials.

Some of the problems associated with the use of cellulose as an "inducing substrate" can be overcome through the use of soluble "inducing substrates" such as "lactose", "sophorose" or "gentiobiose". For example, when using lactose as an "inducing substrate", the lactose has to be provided at high concentrations so as to function as an inducer and a carbon source (e.g., see Seiboth, et. al., 2002). Sophorose is a more potent inducer than cellulose, but sophorose is expensive and difficult to manufacture. For example, a mixture of glucose, sophorose and other disaccharides (i.e., generated via enzymatic conversion of glucose) can be used for the efficient production of cellulases, which incurs a greater (production) cost than using glucose alone. Thus, while it is easier to handle and control than solid cellulose, the use of sophorose as an inducing substrate can nonetheless make the cost of producing cellulases prohibitively expensive.

Based on the foregoing, it is evident that there remains an ongoing and unmet need in the art for cost effective commercial scale production of enzymes/polypeptides by filamentous fungi without the need or requirement of providing costly inducing substrates (e.g., sophorose, lactose and the like) for such production. More particularly, there remains a need in the art for the commercial scale production of one or more endogenous lignocellulosic degrading enzymes by filamentous fungal host cells, wherein such filamentous fungal cells are capable of expressing one or more of these genes in the absence of an inducing substrate. In addition, there are further unmet needs in the art for cost effective production of one or more heterologous protein products expressed and produced in such filamentous fungal host cells, wherein the heterologous genes encoding such proteins are introduced into a fungal host cell, which is capable of expressing such heterologous genes in the absence of an inducing substrate.

BRIEF SUMMARY

Certain embodiments of the disclosure are related to the commercial scale production of enzymes/polypeptides by filamentous fungi without the need or requirement of providing costly inducing substrates (e.g., sophorose, lactose and the like) for such production. Thus, certain other embodiments are related to variant filamentous fungal cells, compositions thereof and methods thereof for increased production of one or more proteins of interest. For example, certain embodiments of the disclosure are directed to a variant filamentous fungal cell derived from a parental filamentous fungal cell, the variant cell comprising an introduced polynucleotide construct encoding an Ace3 protein comprising about 90% sequence identity to an Ace3 protein of SEQ ID NO: 6, wherein the variant cell produces an increased amount of a protein of interest (POI) in the absence of an inducing substrate relative to the parental cell, wherein the variant and parental cells are cultivated under similar conditions. In certain other embodiments, the variant cell produces an increased amount of a POI in the presence of an inducing substrate relative to the parental cell, wherein the variant and parental cells are cultivated under similar conditions.

In another embodiment of the variant cell, an encoded Ace3 protein comprising about 90% sequence identity to SEQ ID NO: 6, comprises "Lys-Ala-Ser-Asp" as the last four C-terminal amino acids. In another embodiment, an encoded Ace3 protein comprising about 90% sequence identity to SEQ ID NO: 6, comprises an N-terminal amino acid fragment of SEQ ID NO: 98 operably linked and preceding SEQ ID NO: 6. In certain other embodiments of the variant cell, the Ace-3 protein comprises about 90% sequence identity to SEQ ID NO: 12. In another embodiment, the introduced polynucleotide encoding an Ace3 protein comprises an open reading frame (ORF) sequence comprising about 90% identity to SEQ ID NO: 5.

In yet other embodiments of the variant cell, the POI is an endogenous POI or a heterologous POI. Thus, in certain embodiments, the variant cell comprises an introduced polynucleotide construct encoding a heterologous POI. In another embodiment, a polynucleotide construct encoding the heterologous POI is expressed under the control of a cellulose-inducible gene promoter. In certain other embodiments, an endogenous POI is a lignocellulose degrading enzyme. Thus, in other embodiments, a lignocellulose degrading enzyme is selected from the group consisting of cellulase enzymes, hemi-cellulase enzymes, or a combination thereof. In certain other embodiments, a lignocellulose degrading enzyme is selected from the group consisting of cbh1, cbh2, egl1, egl2, egl3, egl4, egl5, egl6, bgl1, bgl2, xyn1, xyn2, xyn3, bxl1, abf1, abf2, abf3, axe1, axe2, axe3, man1, agl1, agl2, agl3, glr1, swo1, cip1 and cip2. In yet other embodiments, a heterologous POI is selected from the group consisting of an α-amylase, an alkaline α-amylase, a β-amylase, a cellulase, a dextranase, an α-glucosidase, an α-galactosidase, a glucoamylase, a hemicellulase, a pentosanase, a xylanase, an invertase, a lactase, a naringanase, a pectinase, a pullulanase, an acid protease, an alkali protease, a bromelain, a neutral protease, a papain, a pepsin, a peptidase, a rennet, a rennin, a chymosin, a subtilisin, a thermolysin, an aspartic proteinase, a trypsin, a lipase, an esterase, a phospholipase, a phosphatase, a phytase, an amidase, an iminoacylase, a glutaminase, a lysozyme, a penicillin acylase; an isomerase, an oxidoreductases, a catalase, a chloroperoxidase, a glucose oxidase, a hydroxysteroid dehydrogenase, a peroxidase, a lyase, an aspartic β-decarboxylase, a fumarase, a histadase, a transferase, a ligase, an aminopeptidase, a carboxypeptidase, a chitinase, a cutinase, a deoxyribonuclease, an α-galactosidase, a β-galactosidase, a β-glucosidase, a laccase, a mannosidase, a mutanase, a polyphenol oxidase, a ribonuclease and a transglutaminase.

In another embodiment of the variant cell, the polynucleotide construct comprises a promoter sequence 5' and operably linked to the polynucleotide sequence encoding an Ace3 protein comprising about 90% sequence identity to SEQ ID NO: 6. In certain embodiments, the polynucleotide construct further comprises a native ace3 terminator sequence 3' and operably linked to the polynucleotide sequence encoding an Ace3 protein comprising about 90% sequence identity to SEQ ID NO: 6. In certain other embodiments, the polynucleotide construct is integrated into the fungal cell genome. In certain embodiments, the polynucleotide construct is integrated into a telomere site of the fungal cell genome. In certain other embodiments, the polynucleotide construct is integrated into a glucoamylase (gla1) gene locus of the fungal cell genome. In yet other embodiments, the polynucleotide construct comprises a nucleotide sequence comprising about 90% sequence identity to SEQ ID NO: 4, SEQ ID NO: 11 or SEQ ID NO: 13. In other embodiments, an encoded Ace3 protein comprises an amino acid sequence comprising 95% sequence identity to SEQ ID NO: 6, SEQ ID NO: 12 or SEQ ID NO: 14. Thus, in other embodiments, an encoded Ace3 protein comprises an amino acid sequence of SEQ ID NO: 6, SEQ ID NO: 12 or SEQ ID NO: 14.

In other embodiments, the variant cell comprises a genetic modification which expresses a polynucleotide encoding a wild-type xylanase regulator 1 (Xyr1) protein of SEQ ID NO: 48 or a variant xylanase regulator 1 (Xyr1) protein of SEQ ID NO: 46. In certain other embodiments, the variant cell comprises a genetic modification which reduces or prevents the expression of a gene encoding an endogenous carbon catabolite repressor 1 (Cre1) protein or an Ace1 protein. In yet another embodiment, the variant cell comprises a genetic modification which comprises expressing an Ace2 protein. In other embodiments, the filamentous fungal cell is a Pezizomycotina cell of the Ascomycota subphylum. In certain other embodiments, the filamentous fungal cell is a Trichoderma sp. cell.

In other embodiments, the disclosure is related a polynucleotide ORF encoding an Ace3 protein comprising about 90% sequence identity to SEQ ID NO: 6, SEQ ID NO: 12 or SEQ ID NO: 14.

In other embodiments, the disclosure is related a lignocellulose degrading enzyme produced by the variant cell of the disclosure. In other embodiments, the disclosure is related a heterologous POI produced by the variant cell of cell of the disclosure.

In other embodiments, the disclosure is related to a method for producing an endogenous protein of interest in a Trichoderma sp. fungal cell in the absence of an inducing substrate, the method comprising (i) introducing into the fungal cell a polynucleotide construct comprising in the 5' to 3' direction (a) a first nucleic acid sequence comprising a promoter and (b) a second nucleic acid sequence operably linked to the first nucleic acid sequence, wherein the second nucleic acid sequence encodes an Ace3 protein comprising about 90% sequence identity to SEQ ID NO: 6 and comprises "Lys-Ala-Ser-Asp" as the last four C-terminal amino acids, and (ii) fermenting the cells of step (i) under conditions suitable for fungal cell growth and protein production, wherein such suitable growth conditions do not include an inducing substrate. In certain embodiments of the method, the polynucleotide construct comprises a third nucleic acid sequence 3' and operably linked to the second nucleic acid, wherein the third nucleic acid sequence comprises a native ace3 terminator sequence. In another embodiment, the polynucleotide construct is integrated into the fungal cell genome. In certain embodiments, the polynucleotide construct is integrated into a telomere site of the fungal cell genome. In certain other embodiments, the polynucleotide construct is integrated into a glucoamylase (gla1) gene locus of the fungal cell genome. In other embodiments of the method, the polynucleotide construct comprises a nucleotide sequence comprising about 90% sequence identity to SEQ ID NO: 4, SEQ ID NO: 11 or SEQ ID NO: 13. In other embodiments, the encoded Ace3 protein comprises an amino acid sequence comprising 95% sequence identity to SEQ ID NO: 6, SEQ ID NO: 12 or SEQ ID NO: 14. In another embodiment, the encoded Ace3 protein comprises an amino acid sequence of SEQ ID NO: 6, SEQ ID NO: 12 or SEQ ID NO: 14.

In certain embodiments of the method, the step (i) promoter is selected from the group consisting of a rev3 promoter (SEQ ID NO: 15), a bxl promoter (SEQ ID NO: 16), a tkl1 promoter (SEQ ID NO: 17), a PID104295 promoter (SEQ ID NO: 18), a dld1 promoter (SEQ ID NO: 19), a xyn4 promoter (SEQ ID NO: 20), a PID72526 promoter (SEQ ID NO: 21), an axe1 promoter (SEQ ID NO: 22), a hxk1 promoter (SEQ ID NO: 23), a dic1 promoter (SEQ ID NO: 24), an opt promoter (SEQ ID NO: 25), a gut1 promoter (SEQ ID NO: 26) and a pki1 promoter (SEQ ID NO: 27).

In related embodiments of the method, the endogenous POI is a lignocellulose degrading enzyme. In certain embodiments, the lignocellulose degrading enzyme is selected from the group consisting of cellulase enzymes, hemi-cellulase enzymes, or a combination thereof. In certain embodiments, the cellulase enzymes are selected from the group consisting of cbh1, cbh2, egl1, egl2, egl3, egl4, egl5, egl6, bgl1, bgl2, swo1, cip1 and cip2. In another embodiment, the hemi-cellulase enzymes are selected from the group consisting of xyn1, xyn2, xyn3, xyn4, bxl1, abf1, abf2, abf3, axe1, axe2, axe3, man1, agl1, agl2, agl3 and girl.

In other embodiments of the method, step (i) further comprises an introduced polynucleotide construct encoding a heterologous POI. In certain embodiments, the polynucleotide construct encoding the heterologous POI is expressed under the control of a cellulose-inducible gene promoter. In certain embodiments, a cellulose-inducible gene promoter is selected from cbh1, cbh2, egl1, egl2, xyn2 or stp1.

In other embodiments, the method further comprising a genetic modification which expresses a polynucleotide encoding a wild-type xylanase regulator 1 (Xyr1) protein of SEQ ID NO: 48 or a variant xylanase regulator 1 (Xyr1) protein of SEQ ID NO: 46. In other embodiments, the method further comprising a genetic modification which reduces or prevents the expression of a gene encoding an endogenous carbon catabolite repressor 1 (Cre1) protein or an Ace1 protein. In yet another embodiment, the method further comprising a genetic modification which comprises expressing an Ace2 protein.

In other embodiments, the disclosure is related to a method for producing an endogenous protein of interest in a Trichoderma sp. fungal cell in the absence of an inducing substrate, the method comprising (i) introducing into the fungal cell a polynucleotide construct comprising in the 5' to 3' direction: (a) a first nucleic acid sequence comprising a promoter and (b) a second nucleic acid sequence operably linked to the first nucleic acid sequence, wherein the second nucleic acid sequence encodes an Ace3 protein comprises about 90% sequence identity to SEQ ID NO: 12, and (ii) fermenting the cells of step (i) under conditions suitable for fungal cell growth and protein production, wherein such suitable growth conditions do not include an inducing substrate. In other embodiments, the polynucleotide construct comprises a third nucleic acid sequence 3' and operably linked to the second nucleic acid, wherein the third nucleic acid sequence comprises a native ace3 terminator sequence. In other embodiments of the method, the polynucleotide construct is integrated into the fungal cell genome. In certain embodiments, the polynucleotide construct is integrated into a telomere site of the fungal cell genome. In certain other embodiments, the polynucleotide construct is integrated into a glucoamylase (gla1) gene locus of the fungal cell genome. The another embodiment of the method, the polynucleotide construct comprises a nucleotide sequence comprising about 90% sequence identity to SEQ ID NO: 4, SEQ ID NO: 11 or SEQ ID NO: 13. In certain embodiments, the encoded Ace3 protein comprises an amino acid sequence comprising 95% sequence identity to SEQ ID NO: 6, SEQ ID NO: 12 or SEQ ID NO: 14. In certain other embodiments, the encoded Ace3 protein comprises an amino acid sequence of SEQ ID NO: 6, SEQ ID NO: 12 or SEQ ID NO: 14.

Thus, in other embodiments of the method 8, the endogenous POI is a lignocellulose degrading enzyme. In particular embodiments, the lignocellulose degrading enzyme is selected from the group consisting of cellulase enzymes, hemi-cellulase enzymes, or a combination thereof. In another embodiment, the cellulase enzymes are selected from the group consisting of cbh1, cbh2, egl1, egl2, egl3, egl4, egl5, egl6, bgl1, bgl2, swo1, cip1 and cip2. In other embodiments, the hemi-cellulase enzymes are selected from the group consisting of xyn1, xyn2, xyn3, xyn4, bxl1, abf1, abf2, abf3, axe1, axe2, axe3, man1, agl1, agl2, agl3 and glr1.

In another embodiment of the method, step (i) further comprises an introduced polynucleotide construct encoding a heterologous POI. In certain embodiments, the polynucleotide construct encoding the heterologous POI is expressed under the control of a cellulose-inducible gene promoter. In certain other embodiments of the method, the step (i) promoter is selected from the group consisting of a rev3 promoter (SEQ ID NO: 15), a bxl promoter (SEQ ID NO: 16), a tkl1 promoter (SEQ ID NO: 17, a PID104295 promoter (SEQ ID NO: 18), a dld1 promoter (SEQ ID NO: 19), a xyn4 promoter (SEQ ID NO: 20), a PID72526 promoter (SEQ ID NO: 21), an axe1 promoter (SEQ ID NO: 22), a hxk1 promoter (SEQ ID NO: 23), a dic1 promoter (SEQ ID NO: 24), an opt promoter (SEQ ID NO: 25), a gut1 promoter (SEQ ID NO: 26) and a pki1 promoter (SEQ ID NO: 27). In another embodiment, the method further comprises a genetic modification which expresses a polynucleotide encoding a wild-type xylanase regulator 1 (Xyr1) protein of SEQ ID NO: 48 or a variant xylanase regulator 1 (Xyr1) protein of SEQ ID NO: 46. In certain other embodiments, the method further comprises a genetic modification which reduces or prevents the expression of a gene encoding an endogenous carbon catabolite repressor 1 (Cre1) protein or an Ace1 protein. In yet other embodiments, the method further comprises a genetic modification which comprises expressing an Ace2 protein.

In certain other embodiments, the disclosure is directed to a method for producing a heterologous protein of interest in a *Trichoderma* sp. fungal cell in the absence of an inducing substrate, the method comprising (i) introducing into the fungal cell a polynucleotide construct comprising in the 5' to 3' direction: (a) a first nucleic acid sequence comprising a constitutive promoter and (b) a second nucleic acid sequence operably linked to the first nucleic acid sequence, wherein the second nucleic acid sequence encodes an Ace3 protein comprising about 90% sequence identity to SEQ ID NO: 6 and comprises "Lys-Ala-Ser-Asp" as the last four C-terminal amino acids, and (ii) fermenting the cells of step (i) under conditions suitable for fungal cell growth and protein production, wherein such suitable growth conditions do not include an inducing substrate. Thus, in certain embodiments of the method, the fungal cell comprises an introduced polynucleotide construct encoding a heterologous POI, wherein the construct is introduced into in the fungal cell prior to step (i), during step (i) or after step (i). In another embodiment, the polynucleotide construct comprises a third nucleic acid sequence 3' and operably linked to the second nucleic acid, wherein the third nucleic acid sequence comprises a native ace3 terminator sequence. In other embodiments of the method, the polynucleotide construct is integrated into the fungal cell genome. In certain embodiments, the polynucleotide construct is integrated into a telomere site of the fungal cell genome. In other embodiments, the polynucleotide construct is integrated into a glucoamylase (gla1) gene locus of the fungal cell genome.

In certain other embodiments of the method, the polynucleotide construct comprises a nucleotide sequence comprising about 90% sequence identity to SEQ ID NO: 4, SEQ ID NO: 11 or SEQ ID NO: 13. In another embodiment, the encoded Ace3 protein comprises an amino acid sequence comprising 95% sequence identity to SEQ ID NO: 6, SEQ ID NO: 12 or SEQ ID NO: 14. In other embodiments, the encoded Ace3 protein comprises an amino acid sequence of SEQ ID NO: 6, SEQ ID NO: 12 or SEQ ID NO: 14. In other embodiments, the polynucleotide construct encoding the heterologous POI is expressed under the control of a cellulose-inducible gene promoter. In certain other embodiments, the heterologous POI is selected from the group consisting of an α-amylase, an alkaline α-amylase, a β-amylase, a cellulase, a dextranase, an α-glucosidase, an α-galactosidase, a glucoamylase, a hemicellulase, a pentosanase, a xylanase, an invertase, a lactase, a naringanase, a pectinase, a pullulanase, an acid protease, an alkali protease, a bromelain, a neutral protease, a papain, a pepsin, a peptidase, a rennet, a rennin, a chymosin, a subtilisin, a thermolysin, an aspartic proteinase, a trypsin, a lipase, an esterase, a phospholipase, a phosphatase, a phytase, an amidase, an iminoacylase, a glutaminase, a lysozyme, a penicillin acylase; an isomerase, an oxidoreductases, a catalase, a chloroperoxidase, a glucose oxidase, a hydroxysteroid dehydrogenase, a peroxidase, a lyase, an aspartic β-decarboxylase, a fumarase, a histadase, a transferase, a ligase, an aminopeptidase, a carboxypeptidase, a chitinase, a cutinase, a deoxyribonuclease, an α-galactosidase, a β-galactosidase, a β-glucosidase, a laccase, a mannosidase, a mutanase, a polyphenol oxidase, a ribonuclease and a transglutaminase.

In other embodiments of the method, the step (i) promoter is selected from the group consisting of a rev3 promoter (SEQ ID NO: 15), a bxl promoter (SEQ ID NO: 16), a tkl1 promoter (SEQ ID NO: 17, a PID104295 promoter (SEQ ID NO: 18), a dld1 promoter (SEQ ID NO: 19), a xyn4 promoter (SEQ ID NO: 20), a PID72526 promoter (SEQ ID NO: 21), an axe1 promoter (SEQ ID NO: 22), a hxk1 promoter (SEQ ID NO: 23), a dic1 promoter (SEQ ID NO: 24), an opt promoter (SEQ ID NO: 25), a gut1 promoter (SEQ ID NO: 26) and a pki1 promoter (SEQ ID NO: 27). In yet other embodiments, the method further comprises a genetic modification which expresses a polynucleotide encoding a wild-type xylanase regulator 1 (Xyr1) protein of SEQ ID NO: 48 or a variant xylanase regulator 1 (Xyr1) protein of SEQ ID NO: 46. In another embodiment, the method further comprises a genetic modification which reduces or prevents the expression of a gene encoding an endogenous carbon catabolite repressor 1 (Cre1) protein or an Ace1 protein. In yet other embodiments, the method further comprises a genetic modification which comprises expressing an Ace2 protein.

In another embodiment, the disclosure is directed to a method for producing a heterologous protein of interest in a *Trichoderma* sp. fungal cell in the absence of an inducing substrate, the method comprising (i) introducing into the fungal cell a polynucleotide construct comprising in the 5' to 3' direction: (a) a first nucleic acid sequence comprising a constitutive promoter and (b) a second nucleic acid sequence operably linked to the first nucleic acid sequence, wherein the second nucleic acid sequence encodes an Ace3 protein comprises about 90% sequence identity to SEQ ID NO: 12, and (ii) fermenting the cells of step (i) under conditions suitable for fungal cell growth and protein production, wherein such suitable growth conditions do not include an inducing substrate. In particular embodiments, the fungal cell comprises an introduced polynucleotide construct encoding a heterologous POI, wherein the construct is introduced into in the fungal cell prior to step (i), during step (i) or after step (i). In other embodiments, the polynucleotide construct comprises a third nucleic acid sequence 3' and operably linked to the second nucleic acid, wherein the third nucleic acid sequence comprises a native ace3 terminator sequence. In other embodiments of the method, the polynucleotide construct is integrated into the fungal cell genome. In certain embodiments, the polynucleotide construct is integrated into a telomere site of the fungal cell genome. In other embodiments, the polynucleotide construct is integrated into a glucoamylase (gla1) gene locus of the fungal cell genome. In yet other embodiments, the polynucleotide construct comprises a nucleotide sequence comprising about 90% sequence identity to SEQ ID NO: 4, SEQ ID NO: 11 or SEQ ID NO: 13. In certain embodiments, encoded Ace3 protein comprises an amino acid sequence comprising 95% sequence identity to SEQ ID NO: 6, SEQ ID NO: 12 or SEQ ID NO: 14. In another embodiment, the encoded Ace3 protein comprises an amino acid sequence of SEQ ID NO: 6, SEQ ID NO: 12 or SEQ ID NO: 14. In another embodiment of the method, the polynucleotide construct encoding the heterologous POI is expressed under the control of a cellulose-inducible gene promoter. In certain embodiments, the heterologous POI is selected from the group consisting of an α-amylase, an alkaline α-amylase, α-amylase, a cellulase, a dextranase, an α-glucosidase, an α-galactosidase, a glucoamylase, a hemicellulase, a pentosanase, a xylanase, an invertase, a lactase, a naringanase, a pectinase, a pullulanase, an acid protease, an alkali protease, a bromelain, a neutral protease, a papain, a pepsin, a peptidase, a rennet, a rennin, a chymosin, a subtilisin, a thermolysin, an aspartic proteinase, a trypsin, a lipase, an esterase, a phospholipase, a phosphatase, a phytase, an amidase, an iminoacylase, a glutaminase, a lysozyme, a penicillin acylase; an isomerase, an oxidoreductases, a catalase, a chloroperoxidase, a glucose oxidase, a hydroxysteroid dehydrogenase, a peroxidase, a lyase, an aspartic β-decarboxylase, a fumarase, a histadase, a transferase, a ligase, an aminopeptidase, a carboxypeptidase, a chitinase, a cutinase, a deoxyribonuclease, an α-galactosidase, a β-galactosidase, a β-glucosidase, a laccase, a mannosidase, a mutanase, a polyphenol oxidase, a ribonuclease and a transglutaminase.

In other embodiments of the method, the step (i) promoter is selected from the group consisting of a rev3 promoter (SEQ ID NO: 15), a bxl promoter (SEQ ID NO: 16), a tkl1 promoter (SEQ ID NO: 17, a PID104295 promoter (SEQ ID NO: 18), a dld1 promoter (SEQ ID NO: 19), a xyn4 promoter (SEQ ID NO: 20), a PID72526 promoter (SEQ ID NO: 21), an axe1 promoter (SEQ ID NO: 22), a hxk1 promoter (SEQ ID NO: 23), a dic1 promoter (SEQ ID NO: 24), an opt promoter (SEQ ID NO: 25), a gut1 promoter (SEQ ID NO: 26) and a pki1 promoter (SEQ ID NO: 27). In yet other embodiments, the method further comprises a genetic modification which expresses a polynucleotide encoding a wild-type xylanase regulator 1 (Xyr1) protein of SEQ ID NO: 48 or a variant xylanase regulator 1 (Xyr1) protein of SEQ ID NO: 46. In another embodiment, the method further comprises a genetic modification which reduces or prevents the expression of a gene encoding an endogenous carbon catabolite repressor 1 (Cre1) protein or an Ace1 protein. In yet other embodiments, the method further comprises a genetic modification which comprises expressing an Ace2 protein.

In certain other embodiments, the disclosure is related to a method for genetically modifying a *Trichoderma reesei* strain for increased production of an endogenous protein in the absence of an inducing substrate, the method comprising (i) screening and identifying a *T. reesei* strain comprising a genomic copy of an ace3 gene encoding an Ace3-S protein of SEQ ID NO: 3, an Ace3-SC protein of SEQ ID NO: 8 or an Ace3-LC protein of SEQ ID NO: 10, wherein the *T. reesei* strain identified does not comprise a genomic copy of an ace3 gene encoding an Ace3-L protein of SEQ ID NO: 6, an Ace3-LN protein of SEQ ID NO: 14 or an Ace3-EL protein of SEQ ID NO: 12, (ii) introducing into the *T. reesei* strain identified in step (i) a polynucleotide construct comprising in the 5' to 3' direction: (a) a first nucleic acid sequence comprising a promoter and (b) a second nucleic acid sequence operably linked to the first nucleic acid sequence, wherein the second nucleic acid sequence encodes an Ace3 protein comprising about 90% sequence identity to SEQ ID NO: 6 and comprises "Lys-Ala-Ser-Asp" as the last four C-terminal amino acids or the second nucleic acid sequence encodes an Ace-3 protein comprising about 90% sequence identity to SEQ ID NO: 12, and (iii) fermenting the cells of step (ii) under conditions suitable for fungal cell growth and protein production, wherein such suitable growth conditions do not include an inducing substrate.

In certain other embodiments, the disclosure is directed to a variant filamentous fungal cell derived from a parental filamentous fungal cell, the variant cell comprising a native ace3 gene promoter replaced by an alternative promoter, wherein the variant cell produces an increased amount of a protein of interest (POI) in the absence of an inducing substrate relative to the parental cell, wherein the variant and parental cells are cultivated under similar conditions. In particular embodiments, the alternative promoter is a *Trichoderma reesei* promoter. In another embodiment, the alternative promoter is a promoter selected from the group consisting of a rev3 promoter (SEQ ID NO: 15), a bxl promoter (SEQ ID NO: 16), a tkl1 promoter (SEQ ID NO: 17, a PID104295 promoter (SEQ ID NO: 18), a dld1 promoter (SEQ ID NO: 19), a xyn4 promoter (SEQ ID NO: 20), a PID72526 promoter (SEQ ID NO: 21), an axe1 promoter (SEQ ID NO: 22), a hxk1 promoter (SEQ ID NO: 23), a dic1 promoter (SEQ ID NO: 24), an opt promoter (SEQ ID NO: 25), a gut1 promoter (SEQ ID NO: 26) and a pki1 promoter (SEQ ID NO: 27).

BRIEF DESCRIPTION OF THE DRAWINGS

FIG. 1 presents a schematic representation of the Ace3 protein coding regions. More particularly, -FIG. 1D is an amino acid alignment of the Ace3-L protein (SEQ ID NO: 6) from *T. reesei* strain RUT-C30, the Ace3-S protein from *T. reesei* strain QM6a (SEQ ID NO: 3), the Ace3-SC protein (SEQ ID NO: 8), the Ace3-LN protein (SEQ ID NO: 14), the Ace3-LC protein (SEQ ID NO: 10) and the Ace3-EL protein (SEQ ID NO: 12).

FIG. 13 shows the nucleic acid sequence of the ace3-SC gene form (SEQ ID NO: 7; comprising a 1,713 bp Exon 3, a 148 bp Intron 3 and a 144 bp Exon 4) and the encoded Ace3-SC protein sequence (SEQ ID NO: 8). As presented in FIG. 13 for the ace3-SC gene form, nucleotides shown in bold black text represent intron sequences.

FIG. 14 shows the nucleic acid sequence of the ace3-S gene form (SEQ ID NO: 1; comprising a 1,713 bp Exon 3, a 148 bp Intron 3 and a 177 bp Exon 4) and the encoded Ace3-S protein sequence (SEQ ID NO: 3). As presented in FIG. 14 for the ace3-S gene form, nucleotides shown in bold black text represent intron sequences.

FIG. 15 shows the nucleic acid sequence of the ace3-L gene form (SEQ ID NO: 4, comprising a 258 bp Exon 2, a 423 bp Intron 2, a 1,635 bp Exon 3, a 148 bp Intron 3 and a 144 bp Exon 4) and the encoded Ace3-L protein sequence (SEQ ID NO: 6). As presented in FIG. 15 for the ace3-L gene form, nucleotides shown in bold black text represent intron sequences.

FIG. 16 shows the nucleic acid sequence of the ace3-LC gene form (SEQ ID NO: 9, comprising a 258 bp Exon 2, a 423 bp Intron 2, a 1,635 bp Exon 3, a 148 bp Intron 3 and a 177 bp Exon 4) and the encoded Ace3-LC protein sequence (SEQ ID NO: 10). As presented in FIG. 16 for the ace3-LC gene form, nucleotides shown in bold black text represent intron sequences.

FIG. 17 shows the nucleic acid sequence of the ace3-EL gene form (SEQ ID NO: 11, comprising a 61 bp Exon 1, a 142 bp Intron 1, a 332 bp Exon 2, a 423 bp Intron 2, a 1,635 bp Exon 3, a 148 bp Intron 3 and a 144 bp Exon 4) and the encoded Ace3-EL protein sequence (SEQ ID NO: 12). As presented in FIG. 17 for the ace3-EL gene form, nucleotides shown in bold black text represent intron sequences.

FIG. 18 shows the nucleic acid sequence of the ace3-LN gene form (SEQ ID NO: 13, comprising a 258 bp Exon 2, a 1,635 bp Exon 3, a 148 bp Intron 3 and a 144 bp Exon 4) and the encoded Ace3-LN protein sequence (SEQ ID NO: 14). As presented in FIG. 18 for the ace3-LN gene form, nucleotides shown in bold black text represent intron sequences.

BRIEF DESCRIPTION OF THE BIOLOGICAL SEQUENCES

Figure 1A:
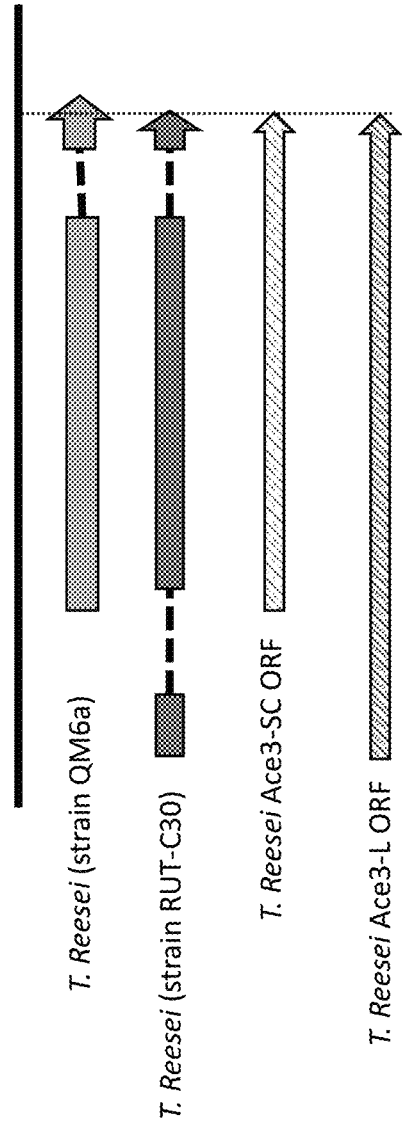
FIG. 1A presents a schematic representation of the Ace3 protein coding regions based on the annotation of *T. reesei* strains QM6a and RUT-C30, which are aligned (FIG. 1A) to the same DNA sequence in the genome. The predicted exons and introns are shown as arrows and dash lines, respectively. The dashed-vertical line indicates a non-sense mutation in RUT-C30 genome. The cloned ace3-S (short) open reading frame of SEQ ID NO: 2 and the cloned ace3-L (long) open reading frame of SEQ ID NO: 5 were screened and tested as set forth in the instant application. Set forth in FIG. 1B
Figure 2A:
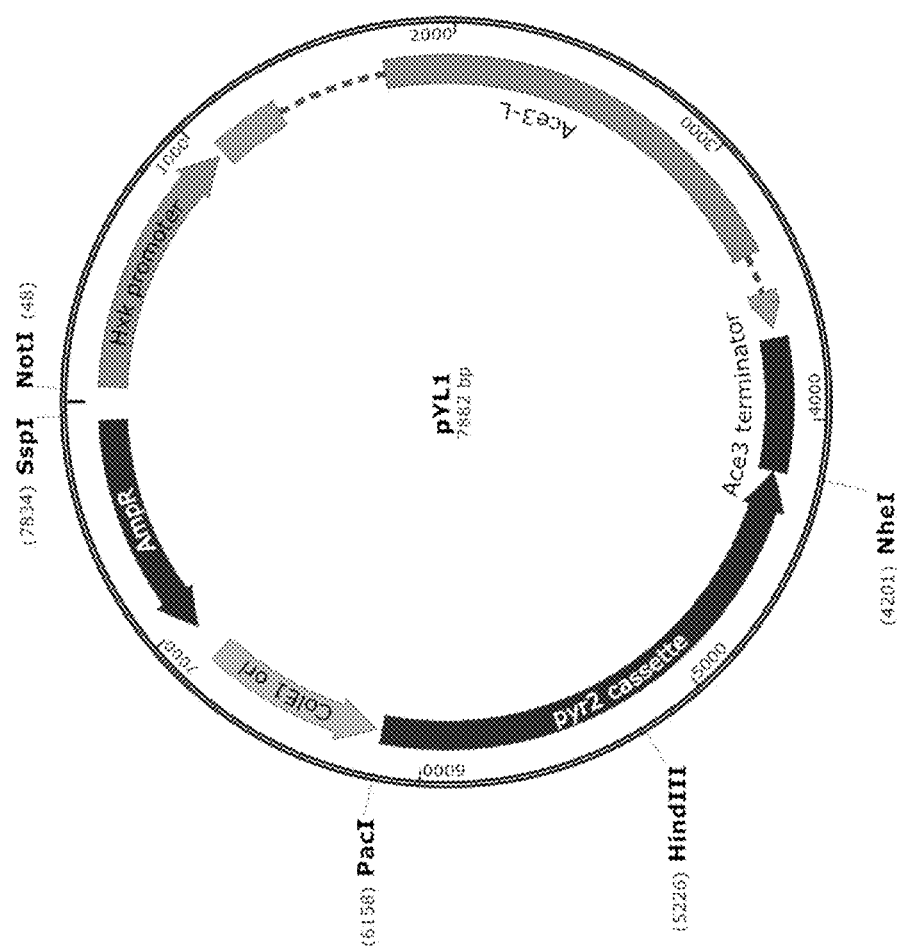
FIG. 2 shows a schematic representation of the Ace3-expression vectors pYL1 (FIG. 2A), pYL2 (FIG. 2B), pYL3 (FIG. 2C) and pYL4 (FIG. 2D).
Figure 2B:
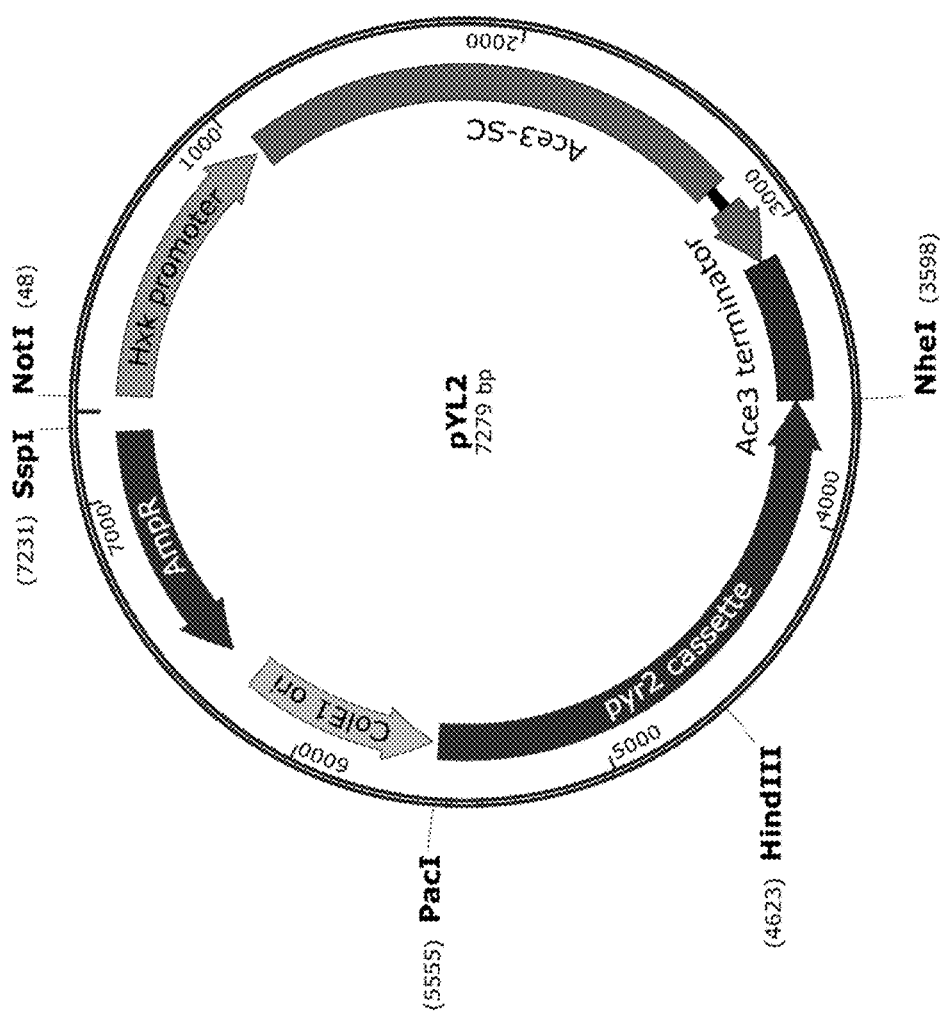
Figure 2C:
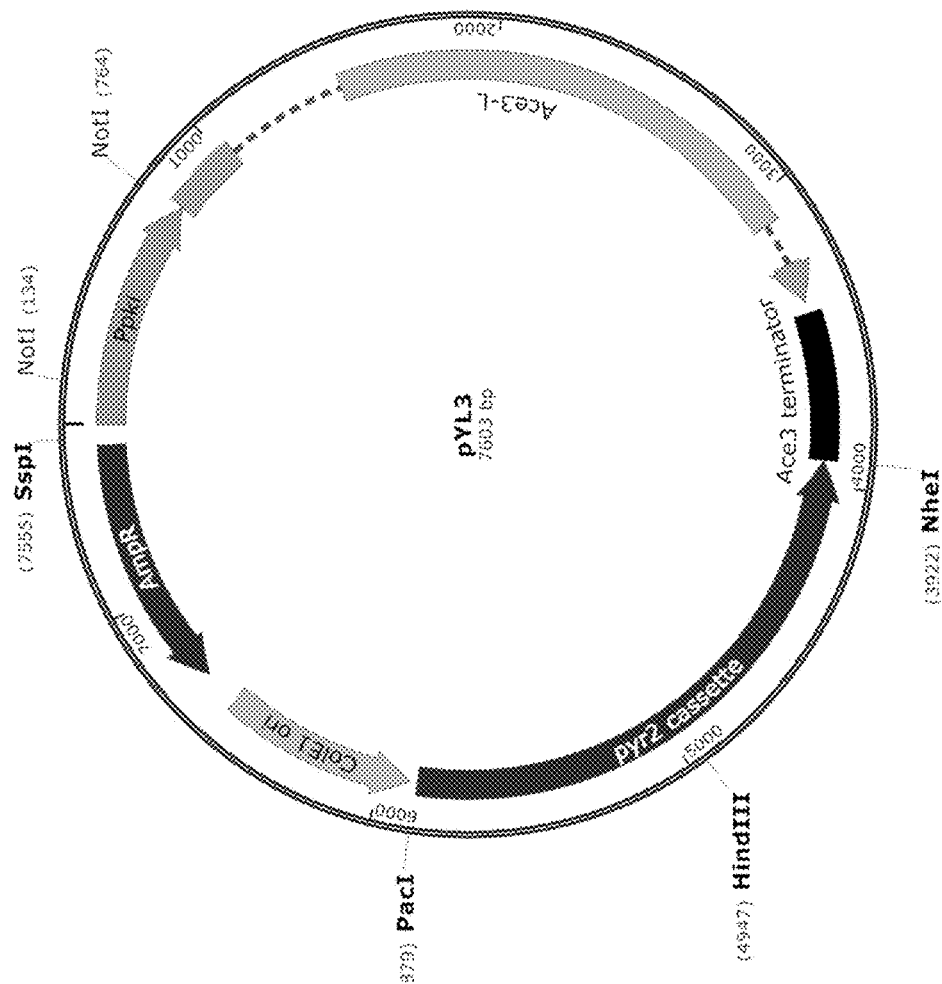
Figure 2D:
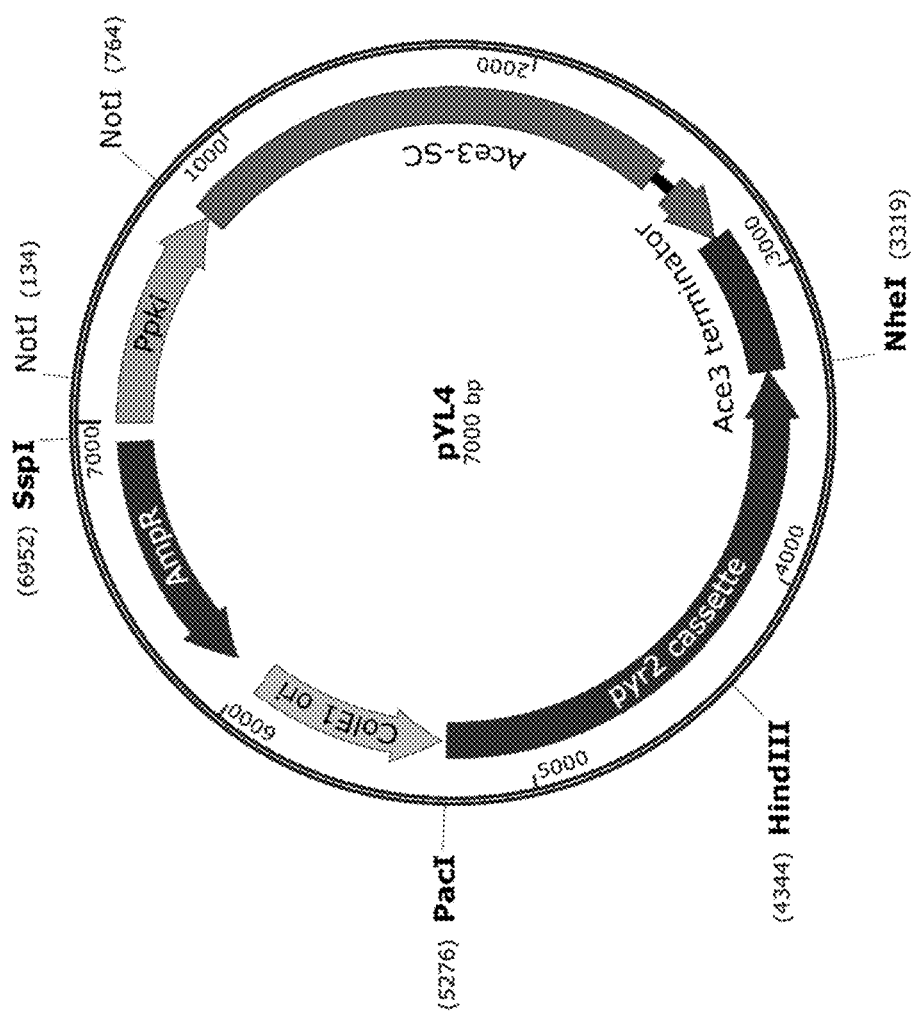

The following sequences comply with 37 C.F.R. §§ 1.821-1.825 ("Requirements for Patent Applications Containing Nucleotide Sequence and/or Amino Acid Sequence Disclosures—the Sequence Rules") and are consistent with WIP Standard ST.25 (2009) and the sequence listing requirements of the European Patent Convention (EPC) and the Patent Cooperation Treaty (PCT) rules 5.2 and 49.5(a-bis), and section 208 and Annex C of the administrative instructions. The symbols and format used for nucleotide and amino acid sequence data comply with the rules set forth in 37 C.F.R. § 1.822.

SEQ ID NO: 1 is a *Trichoderma reesei* wild-type strain QM6a nucleic acid sequence comprising a gene encoding an Ace3-S protein of SEQ ID NO: 3.

SEQ ID NO: 2 is a nucleic acid sequence open reading frame (ORF) encoding an Ace3-S protein of SEQ ID NO: 3.

SEQ ID NO: 3 is the amino acid sequence of a *Trichoderma reesei* (strain QM6a) Ace3 protein, designated hereinafter, "Ace3-S".

SEQ ID NO: 4 is a *Trichoderma reesei* strain Rut-C30 nucleic acid sequence comprising a gene encoding an Ace3-L protein of SEQ ID NO: 6.

SEQ ID NO: 5 is a nucleic acid sequence ORF encoding an Ace3-L protein of SEQ ID NO: 6.

SEQ ID NO: 6 is the amino acid sequence of a *Trichoderma reesei* (strain Rut-C30) Ace3 protein, designated hereinafter, "Ace3-L".

SEQ ID NO: 7 is a *Trichoderma reesei* nucleic acid sequence comprising a gene encoding an Ace3-SC protein of SEQ ID NO: 8.

SEQ ID NO: 8 is the amino acid sequence of a *Trichoderma reesei* Ace3 protein, designated hereinafter, "Ace3-SC".

SEQ ID NO: 9 is a *Trichoderma reesei* nucleic acid sequence comprising a gene encoding an Ace3-LC protein of SEQ ID NO: 10.

SEQ ID NO: 10 is the amino acid sequence of a *Trichoderma reesei* Ace3 protein, designated hereinafter, "Ace3-LC".

SEQ ID NO: 11 is a *Trichoderma reesei* nucleic acid sequence comprising a gene encoding an Ace3-EL protein of SEQ ID NO: 12.

SEQ ID NO: 12 is the amino acid sequence of a *Trichoderma reesei* Ace3 protein, designated hereinafter, "Ace3-EL".

SEQ ID NO: 13 is a *Trichoderma reesei* nucleic acid sequence comprising a gene encoding an Ace3-LN protein of SEQ ID NO: 14.

SEQ ID NO: 14 is the amino acid sequence of a *Trichoderma reesei* Ace3 protein, designated hereinafter, "Ace3-LN".

SEQ ID NO: 15 is a nucleic acid sequence comprising a rev3 promoter sequence.

SEQ ID NO: 16 is a nucleic acid sequence comprising a β-xyl promoter sequence.

SEQ ID NO: 17 is a nucleic acid sequence comprising a tki1 promoter sequence.

SEQ ID NO: 18 is a nucleic acid sequence comprising a PID104295 promoter sequence.

SEQ ID NO: 19 is a nucleic acid sequence comprising a dld1 promoter sequence.

SEQ ID NO: 20 is a nucleic acid sequence comprising a xyn4 promoter sequence.

SEQ ID NO: 21 is a nucleic acid sequence comprising a PID72526 promoter sequence.

SEQ ID NO: 22 is a nucleic acid sequence comprising an axe3 promoter sequence.

SEQ ID NO: 23 is a nucleic acid sequence comprising a hxk1 promoter sequence.

SEQ ID NO: 24 is a nucleic acid sequence comprising an dic1 promoter sequence.

SEQ ID NO: 25 is a nucleic acid sequence comprising an opt promoter sequence.

SEQ ID NO: 26 is a nucleic acid sequence comprising a gut1 promoter sequence.

SEQ ID NO: 27 is a nucleic acid sequence comprising a pki1 promoter sequence.

SEQ ID NO: 28 is a nucleic acid sequence of primer TP13.

SEQ ID NO: 29 is a nucleic acid sequence of primer TP14.

SEQ ID NO: 30 is a nucleic acid sequence of primer TP15.

SEQ ID NO: 31 is a nucleic acid sequence of primer TP16.

SEQ ID NO: 32 is a nucleic acid sequence of primer TP17.

SEQ ID NO: 33 is a nucleic acid sequence of primer TP18.

SEQ ID NO: 34 is a nucleic acid sequence of primer TP19.

SEQ ID NO: 35 is a nucleic acid sequence of primer TP20.

SEQ ID NO: 36 is a nucleic acid sequence of primer TP21.

SEQ ID NO: 37 is a nucleic acid sequence of primer TP22.

SEQ ID NO: 38 is a nucleic acid sequence of primer TP23.

SEQ ID NO: 39 is a nucleic acid sequence of primer TP24.

SEQ ID NO: 40 is a nucleic acid sequence of primer TP25.

SEQ ID NO: 41 is a nucleic acid sequence of primer TP26.

SEQ ID NO: 42 is a nucleic acid sequence of plasmid pYL1.

SEQ ID NO: 43 is a nucleic acid sequence of plasmid pYL2.

SEQ ID NO: 44 is a nucleic acid sequence of plasmid pYL3.

SEQ ID NO: 45 is a nucleic acid sequence of plasmid pYL4.

SEQ ID NO: 46 is an amino acid sequence of a *T. reesei* xyr1 (A824V) variant protein.

SEQ ID NO: 47 is an amino acid sequence of a *T. reesei* Ace2 protein.

SEQ ID NO: 48 is an amino acid sequence of a *T. reesei* wild-type xyr1 protein.

SEQ ID NO: 49 is primer nucleic acid sequence.
SEQ ID NO: 50 is primer nucleic acid sequence.
SEQ ID NO: 51 is primer nucleic acid sequence.
SEQ ID NO: 52 is primer nucleic acid sequence.
SEQ ID NO: 53 is primer nucleic acid sequence.
SEQ ID NO: 54 is primer nucleic acid sequence.
SEQ ID NO: 55 is primer nucleic acid sequence.
SEQ ID NO: 56 is primer nucleic acid sequence.
SEQ ID NO: 57 is primer nucleic acid sequence.
SEQ ID NO: 58 is primer nucleic acid sequence.
SEQ ID NO: 59 is primer nucleic acid sequence.
SEQ ID NO: 60 is primer nucleic acid sequence.
SEQ ID NO: 61 is primer nucleic acid sequence.
SEQ ID NO: 62 is primer nucleic acid sequence.
SEQ ID NO: 63 is primer nucleic acid sequence.
SEQ ID NO: 64 is primer nucleic acid sequence.
SEQ ID NO: 65 is primer nucleic acid sequence.
SEQ ID NO: 66 is primer nucleic acid sequence.
SEQ ID NO: 67 is primer nucleic acid sequence.
SEQ ID NO: 68 is primer nucleic acid sequence.
SEQ ID NO: 69 is primer nucleic acid sequence.
SEQ ID NO: 70 is primer nucleic acid sequence.
SEQ ID NO: 71 is primer nucleic acid sequence.
SEQ ID NO: 72 is primer nucleic acid sequence.
SEQ ID NO: 73 is primer nucleic acid sequence.
SEQ ID NO: 74 is primer nucleic acid sequence.
SEQ ID NO: 75 is primer nucleic acid sequence.
SEQ ID NO: 76 is primer nucleic acid sequence.
SEQ ID NO: 77 is primer nucleic acid sequence.
SEQ ID NO: 78 is primer nucleic acid sequence.
SEQ ID NO: 79 is primer nucleic acid sequence.
SEQ ID NO: 80 is primer nucleic acid sequence.
SEQ ID NO: 81 is primer nucleic acid sequence.
SEQ ID NO: 82 is an artificial nucleic acid sequence.
SEQ ID NO: 83 is an artificial nucleic acid sequence.
SEQ ID NO: 84 is an artificial nucleic acid sequence.
SEQ ID NO: 85 is an artificial nucleic acid sequence.
SEQ ID NO: 86 is an artificial nucleic acid sequence.
SEQ ID NO: 87 is an artificial nucleic acid sequence.
SEQ ID NO: 88 is an artificial nucleic acid sequence.
SEQ ID NO: 89 is an artificial nucleic acid sequence.
SEQ ID NO: 90 is an artificial nucleic acid sequence.
SEQ ID NO: 91 is an artificial nucleic acid sequence.
SEQ ID NO: 92 is primer nucleic acid sequence.
SEQ ID NO: 93 is primer nucleic acid sequence.
SEQ ID NO: 94 is primer nucleic acid sequence.
SEQ ID NO: 95 is primer nucleic acid sequence.
SEQ ID NO: 96 is primer nucleic acid sequence.
SEQ ID NO: 97 is primer nucleic acid sequence.

SEQ ID NO: 98 is an amino acid sequence comprising a forty-five (45) amino acid fragment of N-terminal sequence of the Ace3-EL protein of SEQ ID NO: 12.

SEQ ID NO: 99 is a nucleic acid sequence ORF encoding an Ace3-SC protein.

SEQ ID NO: 100 is a nucleic acid sequence ORF encoding an Ace3-LC protein.

SEQ ID NO: 101 is a nucleic acid sequence ORF encoding an Ace3-EL protein.

SEQ ID NO: 102 is a nucleic acid sequence ORF encoding an Ace3-LN protein.

DETAILED DESCRIPTION

I. Overview

Certain embodiments of the disclosure are directed to variant filamentous fungal cells, compositions thereof and methods thereof for increased production of one or more proteins of interest. More particularly, certain embodiments of the disclosure are directed to variant filamentous fungal cells capable of producing one or more proteins of interest in the absence of an inducing feed (i.e., an inducing substrate such as lactose, sophorose, gentiobiose, cellulose and the like). Thus, certain embodiments of the disclosure are directed to variant filamentous fungal (host) cells derived from parental filamentous fungal cells, wherein the variant host cells comprise a genetic modification which enables the expression of a gene of interest (encoding a protein of interest) in the absence of inducing substrate. The gene of interest (encoding a protein of interest) can be an endogenous filamentous fungal cell gene (e.g., cbh1, chb2, xyn1, xyn2, xyn3, egl1, egl2, egl3, bgl1, bgl2, and the like) or a gene heterologous to the filamentous fungal cell.

Thus, in certain other embodiments, a variant fungal host cell of the disclosure comprises a genetic modification which increases the expression of an "activator of cellulase expression 3" (ace3) gene encoding an Ace3 protein selected from the group consisting of an Ace3-L protein (SEQ ID NO: 6), an Ace3-EL protein (SEQ ID NO: 12) and an Ace3-LN protein (SEQ ID NO: 14). In other embodiments, a variant fungal host cell of the disclosure comprises a genetic modification which increases the expression of a polynucleotide open reading frame (ORF) encoding an Ace3 protein selected from the group consisting of an Ace3-L protein (SEQ ID NO: 6), an Ace3-EL protein (SEQ ID NO: 12) and an Ace3-LN protein (SEQ ID NO: 14). Thus, in certain embodiments, a variant fungal host cell of the disclosure comprises a genetic modification which increases the expression/production of an Ace3 gene or ORF thereof encoding a Ace3 protein comprising about 90% to about 99% sequence identity to an Ace3 protein selected from the group consisting of an Ace3-L protein (SEQ ID NO: 6), an Ace3-EL protein (SEQ ID NO: 12) and an Ace3-LN protein (SEQ ID NO: 14).

In certain embodiments, the genetic modification which increases the expression of an Ace3 protein (i.e., an Ace3-L, Ace3-EL or Ace3-LN protein) is an ace3 expression cassette which has been integrated into the genome (chromosome) of the filamentous fungal host cell. In other embodiments, the genetic modification which increases expression of an Ace3 protein in a filamentous fungal cell is an episomally maintained plasmid construct comprising an ace3 expression cassette (i.e., encoding an Ace3-L, Ace3-EL or Ace3-LN protein). In other embodiments, the genetic modification which increases the expression of an ace3 gene encoding an Ace3-L, Ace3-EL or Ace3-LN protein in a filamentous fungal cell is a telomeric vector/plasmid integrated in a telomere site. In certain embodiments, such expression cassettes or plasmids are present in more than one copy. In certain other embodiments, the ace3 gene, or ace3 ORF, is operably linked to a heterologous promoter. In other embodiments, the genetic modification which increases the expression an ace3 gene (or ORF thereof) encoding an Ace3-L, Ace3-EL or Ace3-LN protein in a filamentous fungal cell is a modification of the native ace3 promoter (i.e., the ace3 promoter region natively associated with the ace3 gene) which modification alters the expression of an ace3 gene encoding an Ace3-L, Ace3-EL or Ace3-LN protein.

II. Definitions

Prior to describing the present compositions and methods in further detail, the following terms and phrases are defined.

Terms not defined should be accorded their ordinary meaning as used and known to one skilled in the art.

All publications and patents cited in this specification are herein incorporated by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of $^{-}10\%$ to $^{+}10\%$ of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

In accordance with this Detailed Description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely", "only", "excluding", "not including" and the like in connection with the recitation of claim elements, or use of a "negative" limitation.

It is further noted that the term "comprising", as used herein, means "including, but not limited to", the component(s) after the term "comprising". The component(s) after the term "comprising" are required or mandatory, but the composition comprising the component(s) may further include other non-mandatory or optional component(s).

It is also noted that the term "consisting of," as used herein, means "including and limited to", the component(s) after the term "consisting of". The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "Ascomycete fungal cell" refers to any organism in the Division Ascomycota in the Kingdom Fungi. Examples of Ascomycetes fungal cells include, but are not limited to, filamentous fungi in the subphylum Pezizomycotina, such as *Trichoderma* spp., *Aspergillus* spp., *Myceliophthora* spp. and *Penicillium* spp.

As used herein, the term "filamentous fungus" refers to all filamentous forms of the subdivision Eumycota and Oomycota. For example, filamentous fungi include, without limitation, *Acremonium, Aspergillus, Emericella, Fusarium, Humicola, Mucor, Myceliophthora, Neurospora, Penicillium, Scytalidium, Thielavia, Tolypocladium*, or *Trichoderma* species. In some embodiments, the filamentous fungus may be an *Aspergillus aculeatus, Aspergillus awamori, Aspergillus foetidus, Aspergillus japonicus, Aspergillus nidulans, Aspergillus niger*, or *Aspergillus oryzae*.

In some embodiments, the filamentous fungus is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*. In some embodiments, the filamentous fungus is a *Humicola insolens, Humicola lanuginosa, Mucor miehei, Myceliophthora thermophila, Neurospora crassa, Scytalidium thermophilum*, or *Thielavia terrestris*.

In some embodiments, a filamentous fungus is a *Trichoderma harzianum, Trichoderma koningii, Trichoderma longibrachiatum, Trichoderma reesei* or *Trichoderma viride*. In some embodiments, the filamentous fungus is a *Trichoderma reesei* cell derived from *T. reesei* strain "Rut-C30", which is available from the American Type Culture Collection as *Trichoderma reesei* ATCC Deposit No. 56765. In some embodiments, the filamentous fungus is a *Trichoderma reesei* cell derived from *T. reesei* strain "RL-P37", which is available from the culture collection of the Northern Regional Research Laboratory, US Department of Agriculture as NRRL No. 15709.

As used herein, the phrases "variant filamentous fungal cell(s)", "variant fungal cell(s)", "variant cell(s)" and the like refer to filamentous fungal cells that are derived (i.e., obtained) from a parental (control) filamentous fungal cell belonging to the Pezizomycotina subphylum. Thus, a "variant" filamentous fungal cell as defined herein is derived from a "parental" filamentous fungal cell, wherein the "variant" cell comprises at least one genetic modification which is not found in the "parental" cell. For example, when comparing a "variant filamentous fungal cell" vis-à-vis a "parental filamentous fungal cell" of the instant disclosure, the "parental" cell serves as the genetically unmodified (parental) "control" cell relative to "variant" cell which comprises the at least one genetic modification.

As used herein, the term "genetic modification" refers to the alteration/change of a nucleic acid sequence. The modification can include, but is not limited to, a substitution, a deletion, an insertion or a chemical modification of at least one nucleotide in the nucleic acid sequence.

As defined herein, the phrases "variant cell(s) comprising a genetic modification" and "variant cell(s) comprising a genetic modification which increases the expression of a gene encoding an Ace3-L protein, an Ace3-EL protein and/or an Ace3-LN protein", includes, but is not limited to, the introduction of at least one copy of a gene or ORF encoding an Ace3-L protein, an Ace3-EL protein and/or an Ace3-LN protein into the filamentous fungal cell. Thus, a filamentous fungal cell comprising the exogenously introduced at least one copy of a gene or ORF encoding the Ace3-L protein, the Ace3-EL protein and/or the Ace3-LN protein is a variant fungal cell comprising a genetic modification, relative to the parental fungal cell (which is unmodified).

In other embodiments, parental fungal cells of the disclosure are screened for the presence of an endogenous ace3 gene encoding any of the Ace3 protein disclosed herein (i.e., an ace3 gene encoding an Ace3-S protein, an Ace3-SC protein, an Ace3-L protein, an Ace3-LC protein, an Ace3-EL protein and an Ace3-LN protein). For example, if a parental fungal cell is determined to comprise an endogenous copy of an ace3 gene encoding an Ace3-L protein, an Ace3-EL protein or an Ace3-LN protein, a variant fungal cell thereof may be generated by genetic modification, such as, e.g., by replacing the endogenous promoter of ace3 gene with a heterologous promoter. Likewise, if a parental fungal cell is determined to comprise an endogenous copy of an ace3 gene encoding an Ace3-S protein, an Ace3-SC protein or an Ace3-LC protein, a variant fungal cell thereof may be generated by genetic modification, e.g., by introducing into the fungal cell a polynucleotide construct encoding an Ace3-L protein, an Ace3-EL protein and/or an Ace3-LN protein of the disclosure, which may further include genetic modification of the endogenous ace3 gene encoding the Ace3-S, Ace3-SC or Ace3-LC protein thereof.

In other embodiments, variant filamentous fungal cells of the disclosure will comprise further genetic modifications. For example, in certain embodiments, such variant filamentous fungal cells (i.e., comprising an exogenously introduced copy of a gene or ORF encoding an Ace3-L protein, Ace3-EL and/or Ace3-LN protein of the disclosure) further comprise a genetic modification which reduces the expression and/or activity of a gene encoding the carbon catabolite repressor protein "Cre1" or the Ace1 repressor protein.

In other embodiments, such variant filamentous fungal cells (i.e., comprising an exogenously introduced copy of a gene or ORF encoding an Ace3-L protein, Ace3-EL and/or Ace3-LN protein of the disclosure) further comprise a genetic modification which introduces at least one copy of a xylanase regulator 1 (Xyr1) set forth in SEQ ID NO: 25 or SEQ ID NO: 27.

As used herein, an "Ace3-L" protein form (SEQ ID NO: 6) and an "Ace3-LN" protein form (SEQ ID NO: 14; see, FIG. 1B) comprise identical amino acid sequences. However, the headings "Ace3-L" and "Ace3-LN" are used in certain embodiments of the disclosure for comparison with certain genes thereof encoding such protein forms, as is in no way meant to limit the present disclosure.

As used herein, the term "host cell" refers to a filamentous fungal cell that has the capacity to act as a host and expression vehicle for an incoming sequence (i.e., a polynucleotide sequence introduced into the cell), as described herein.

A "heterologous" nucleic acid construct or sequence has a portion of the sequence which is not native or existing in a native form to the cell in which it is expressed. Heterologous, with respect to a control sequence refers to a control sequence (i.e., promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell. Similarly, a heterologous protein will often refer to two or more subsequences that are not found in the same relationship to each other in nature (e.g., a fusion protein).

As used herein, the term "DNA construct" or "expression construct" refers to a nucleic acid sequence, which comprises at least two DNA polynucleotide fragments. A DNA or expression construct can be used to introduce nucleic acid sequences into a fungal host cell. The DNA may be generated in vitro (e.g., by PCR) or any other suitable techniques. In some preferred embodiments, the DNA construct comprises a sequence of interest (e.g., encoding a Ace3-L protein). In certain embodiments, a polynucleotide sequence of interest is operably linked to a promoter. In some embodiments, the DNA construct further comprises at least one selectable marker. In further embodiments, the DNA construct comprises sequences homologous to the host cell chromosome. In other embodiments, the DNA construct comprises non-homologous sequences to the host cell chromosome.

As used herein, the terms "cellulase", "cellulolytic enzymes" or "cellulase enzymes" means bacterial or fungal enzymes such as exoglucanases, exocellobiohydrolases, endoglucanases and/or β-glucosidases. These different types of cellulase enzymes act synergistically to convert cellulose and its derivatives to glucose. For example, many microbes make enzymes that hydrolyze cellulose, including the wood rotting fungus *Trichoderma*, the compost bacteria Thermomonospora (now Thermobifida), *Bacillus*, and Cellulomonas; *Streptomyces*; and the fungi *Humicola, Aspergillus* and *Fusarium*. The enzymes made by these microbes are mixtures of proteins with three types of actions useful in the conversion of cellulose to glucose: endoglucanases (EG), cellobiohydrolases (CBH), and β-glucosidase (BG). As defined herein, the terms "endoglucanases" (EG), "cellobiohydrolases" (CBH) and "β-glucosidase" (BG) are used interchangeably with their abbreviations "EG", "CBH" and "BG", respectively.

As used herein, the term "carbon limitation" is a state wherein a microorganism has just enough carbon to produce a desired protein product, but not enough carbon to completely satisfy the organism's requirement, e.g., sustain growth. Therefore, the maximal amount of carbon goes toward protein production.

As used herein, the term "promoter" refers to a nucleic acid sequence that functions to direct transcription of a downstream gene or an open reading frame (ORF) thereof. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. In certain embodiments, the promoter is an inducible promoter. In other embodiments, the promoter is a constitutive promoter.

As used herein, a "promotor sequence" is a DNA sequence which is recognized by the particular filamentous fungus for expression purposes. A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. Thus, a nucleic acid is "operably linked" when it is placed into a functional relationship with another nucleic acid sequence. For example, DNA encoding a secretory leader (i.e., a signal peptide) is operably linked to DNA encoding a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. In other embodiments, linking is accomplished by seamless cloning methods where DNA were joined in a sequence-independent and scar-less manner. The seamless cloning is typically performed with, but not limited to, commercially available systems, such as Gibson Assembly (NEB), NEBuilder HiFi DNA Assembly (NEB), Golden Gate Assembly (NEB), and GeneArt Seamless cloning and Assembly system (ThermoFisher Scientific).

As used herein, the term "coding sequence" refers to a nucleotide sequence, which directly specifies the amino acid sequence of its (encoded) protein product. The boundaries of the coding sequence are generally determined by an open reading frame, which usually begins with an ATG start codon. The coding sequence typically includes DNA, cDNA, and recombinant nucleotide sequences.

As defined herein, an "open reading frame" (hereinafter, an "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

As used herein, the term "gene" means the segment of DNA involved in producing a polypeptide chain, that may or may not include regions preceding and following the coding region (e.g., 5' untranslated (5' UTR) or "leader" sequences and 3' UTR or "trailer" sequences, as well as intervening sequences (introns) between individual coding segments (exons). The gene may encode commercially important industrial proteins or peptides, such as enzymes (e.g., proteases, mannanases, xylanases, amylases, glucoamylases, cellulases, oxidases, lipases and the like). The gene of interest may be a naturally occurring gene, a mutated gene or a synthetic gene.

As used herein, the term "recombinant" when used with reference to a cell, a nucleic acid, a protein, or a vector, indicates that the cell, nucleic acid, protein or vector, has been modified by the introduction of a heterologous nucleic acid or protein, or the alteration of a native nucleic acid or protein, or that the cell is derived from a cell so modified. Thus, for example, recombinant cells express genes that are not found within the native (non-recombinant) form of the cell, or express native genes that are otherwise abnormally expressed, under expressed or not expressed at all.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, a coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, the term "secretory signal sequence" denotes a DNA sequence that encodes a polypeptide (i.e., a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

As used herein, the term "induction" refers to the increased transcription of a gene resulting in the synthesis of a protein of interest (hereinafter, a "POI") in a filamentous fungal cell at a markedly increased rate in response to the presence of an "inducer" (i.e., inducing substrate). To measure the "induction" of a "gene of interest" (hereinafter, a "GO") or an "ORF of interest" encoding a POI, variant filamentous fungal (host) cells are treated with a candidate inducing substrate (inducer) and are compared vis-à-vis to parental filamentous fungal (control, unmodified) cells which are not treated with the inducing substrate (inducer). Thus, the (untreated) parental (control) cells are assigned a relative protein activity value of 100%, wherein induction of the GOI encoding the POI in the variant host cells is achieved when the activity value (i.e., relative to the control cells) is greater than 100%, greater than 110%, more preferably 150%, more preferably 200-500% (i.e., two to five fold higher relative to the control), or more preferably 1000-3000% higher.

As used herein, the terms "inducer", "inducers", "inducing substrate" or "inducing substrates" are used interchangeably and refer to any compounds that cause filamentous fungal cells to produce "increased amounts" of polypeptides (e.g., enzymes, receptors, antibodies and the like) or other compounds/substances than they would produce if the inducing substrate was absent. Examples of inducing substrates include, but are not limited to, sophorose, lactose, gentibiose and cellulose.

As used herein, the term "inducing feed" refers to a composition comprising at least an "inducing substrate" which is fed to filamentous fungal cells, wherein such inducing feed induces the production of a POI.

As used herein, the term "isolated" or "purified" refers to a nucleic acid or amino acid that is removed from at least one component with which it is naturally associated.

As defined herein, the terms "protein of interest" or "PO" refer to a polypeptide that is desired to be expressed in a filamentous fungal cell. Such a protein can be an enzyme, a substrate-binding protein, a surface-active protein, a structural protein, and the like, and can be expressed at high levels, and can be for the purpose of commercialization. The protein of interest can be encoded by an endogenous gene or a heterologous gene (i.e., relative to the variant and/or the parental cells). The protein of interest can be expressed intracellularly or as a secreted (extracellular) protein.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention (e.g., disulfide bond formation, glycosylation, lipidation, acetylation, phosphorylation, or any other manipulation or modification, such as conjugation with a labeling component). Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the phrase "substantially free of an activity," or similar phrases, means that a specified activity is either undetectable in an admixture or present in an amount that would not interfere with the intended purpose of the admixture.

As used herein, the term "derivative polypeptide" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme (s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.); and Devereux et al., 1984).

As used herein, the phrases "substantially similar" and "substantially identical", in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters.

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, fungal cells or strains as found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a functional gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, CRISPR/Cas9 or any other method that abolishes, reduces or mitigates gene expression.

As used herein, the phrase a "variant [host] cell comprising a 'genetic modification' which increases the expression of a gene encoding an Ace3-L protein, Ace3-EL and/or Ace3-LN protein of the disclosure" comprises introducing (e.g., via transformation) into the host cell a plasmid or a chromosomal integration cassette comprising an ace3 gene form (or an ORF thereof) encoding such Ace3-L protein, Ace3-EL and/or Ace3-LN proteins. In certain other embodiments, such as when a parental fungal cell natively comprises an endogenous gene form encoding an Ace3-L protein, Ace3-EL and/or Ace3-LN protein, the phrase a "variant [host] cell comprising a 'genetic modification' which increases the expression of a gene encoding an Ace3-L protein, Ace3-EL and/or Ace3-LN protein" includes replacing the native/wild-type ace3 gene promoter with a heterologous promoter.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

As used herein, a "variant fungal host cell" produces "substantially more protein per unit amount of biomass" than a "parental fungal cell" if the amount of protein produced by the variant cell is at least 5% increased, at least 10% increased, at least 15% increased, or more, compared to the parental cells, wherein the amount of protein is normalized to the total amount of biomass of cells from which protein production is measured, wherein biomass can be expressed in terms of either wet (e.g., of cell pellet) or dry weight.

III. Activator of Cellulase Expression 3 (ace3)

Recently, transcription profiling data from *Trichoderma reesei* cultures (Hakkinen et al., 2014) in which cellulase/hemicellulase production was "induced" (i.e., via the addition different inducing compositions; e.g., sophorose, lactose) was examined to identify putative "regulators" of cellulase and hemicellulase gene expression and a candidate gene encoding a regulatory protein was identified. Hakkinen et al. (2014) identified this candidate gene (see, Hakkinen et al. FIG. 2 and Table 2) as Gene ID No. 77513 (wherein Gene ID Numbers are as in the *T. reesei* database 2.0) and named the candidate gene "Activator of Cellulase Expression 3" (hereinafter, "ace3") and the encoded protein (i.e., a candidate transcription factor) "Ace3". More particularly, the Hakkinen et al. (2014) study used the predicted ace3 ORF (SEQ ID NO: 2), based on the publicly available genome sequence of *T. reesei* strain QM6a (see, genome.jgi.doe.gov/Trire2/Trire2.home.html), wherein the QM6a predicted annotation (Gene ID 77513) consists of two exons and one intron (e.g., see, FIG. 1).

As described herein and further set forth below in the Examples section, Applicants of the instant disclosure discovered surprising and unexpected results when comparing and evaluating the cloned ace3 ORF described in Hakkinen et al., 2014 (i.e., based on the *T. reesei* "QM6a strain" annotation of Ace3) relative to an ace3 ORF based on the *T. reesei* "RUT-C30 strain" annotation. For example, as set forth in Example 1 below, the *T. reesei* "QM6a strain" ace3 gene of SEQ ID NO: 1 (and the ORF of SEQ ID NO: 2) encodes a shorter Ace3 protein of SEQ ID NO: 3 (referred to herein as "Ace3-S") relative to the *T. reesei* "RUT-C30 strain" ace3 gene of SEQ ID NO: 4 (or ORF of SEQ ID NO: 5), which encodes a longer Ace3 protein of SEQ ID NO: 6 (referred to herein as "Ace3-L").

In contrast, the ace3 ORF predicted from the publicly available genome sequence of *T. reesei* strain Rut-C30 (see, genome.jgi.doe.gov/TrireRUTC30_1/TrireRUTC30_1.home.html) (Gene ID 98455) comprises a longer protein sequence (i.e., relative to the Ace3-S from *T. reesei* QM6a) comprising three exons and two introns (FIG. 1A). More particularly, the start codon predicted by the "RUT-C30" model is located upstream of that in the "QM6a" model, and there is a non-sense mutation at the C-terminus (Poggi-Parodi et al., 2014), resulting in a longer N-terminal sequence and shorter C-terminal sequence (e.g., see FIG. 1).

Figure 11:
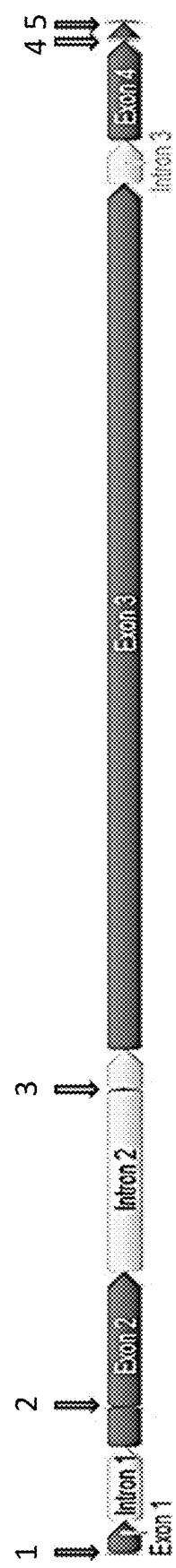
FIG. 11 presents a schematic image of the ace3 locus. The arrows at the 5'-end (N-terminus) of the ace3 locus indicate the different transcription start sites in the form suggested by cDNA sequence (arrow 1), the RutC-30 annotated form (arrow 2) and QM6a annotated form (arrow 3). The arrows at the 3'-end (C-terminus) of the ace3 locus indicate the different Stop codons in the RutC-30 annotated form (arrow 4) and QM6a annotated form (arrow 5).

Likewise, as described in Example 6 below, the position of the 5' end of the ace3 gene coding region is not obvious, and as such, Applicant further evaluated the 5' end of the ace3 gene as described herein. As briefly stated above, annotation of the DNA sequence at the Joint Genome Institute (JGI) differed between mutant strain Rut-C30 and the wild-type strain QM6a, even though the DNA sequence is the same. In the QM6a case, the 5' end of the coding region was suggested to be upstream of exon 3 and within intron 2 (as shown in FIG. 11). In the Rut-C30 case, the 5' end of the coding region is within exon 2 (FIG. 11).

Figure 12:
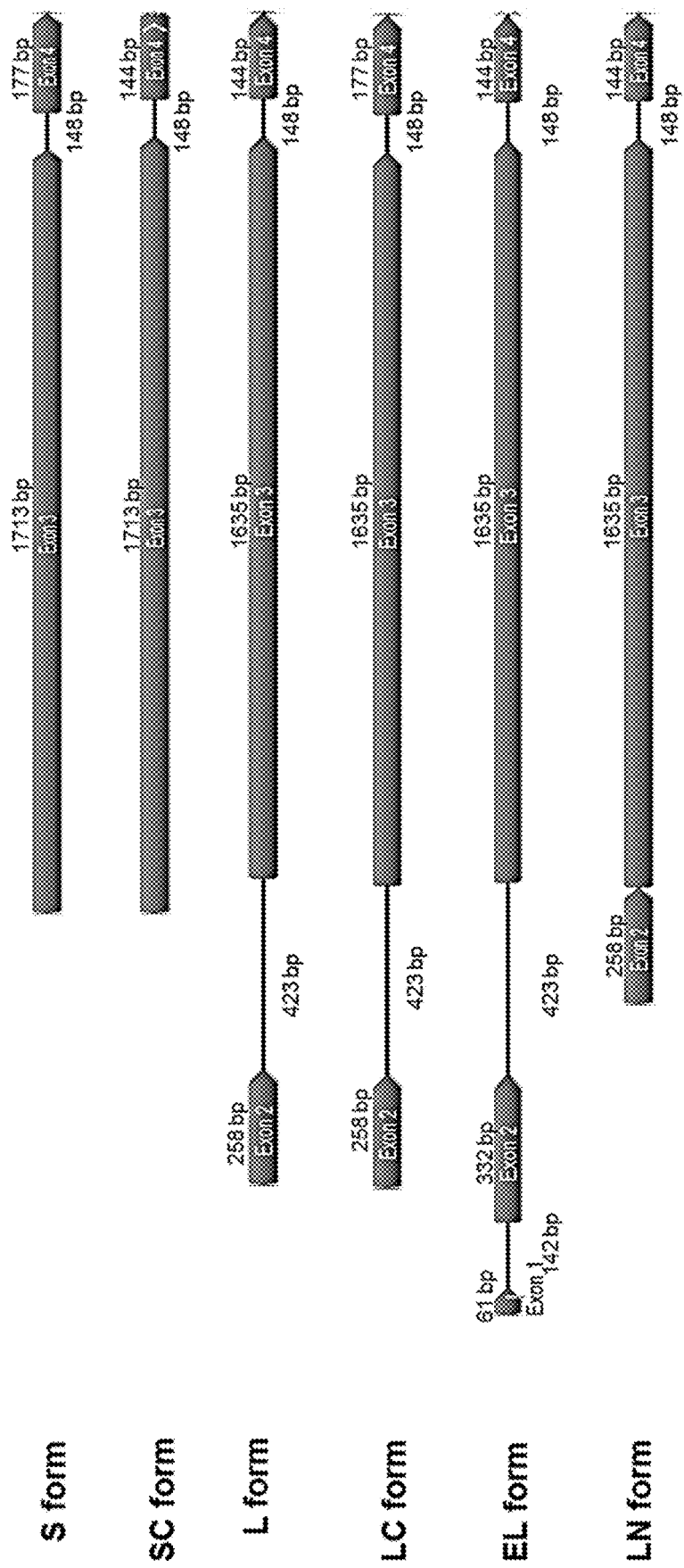
FIG. 12 shows a schematic image of the different ace3 forms cloned. Thus, as presented in FIG. 12 and described in Example 6, the following ace3 forms were cloned and tested: "ace3-S" of SEQ ID NO: 1, comprising a 1,713 bp Exon 3, a 148 bp Intron 3 and a 177 bp Exon 4, "ace3-SC" of SEQ ID NO: 7, comprising a 1,713 bp Exon 3, a 148 bp Intron 3 and a 144 bp Exon 4, "ace3-L" of SEQ ID NO: 4, comprising a 258 bp Exon 2, a 423 bp Intron 2, a 1,635 bp Exon 3, a 148 bp Intron 3 and a 144 bp Exon 4, "ace3-LC" of SEQ ID NO: 9, comprising a 258 bp Exon 2, a 423 bp Intron 2, a 1,635 bp Exon 3, a 148 bp Intron 3 and a 177 bp Exon 4, "ace3-EL" of SEQ ID NO: 11, comprising a 61 bp Exon 1, a 142 bp Intron 1, a 332 bp Exon 2, a 423 bp Intron 2, a 1,635 bp Exon 3, a 148 bp Intron 3 and a 144 bp Exon 4, and "ace3-LN" of SEQ ID NO: 13, comprising a 258 bp Exon 2, a 1,635 bp Exon 3, a 148 bp Intron 3 and a 144 bp Exon 4.

Further analysis of the genomic DNA sequence and additional cDNA sequence suggested the possible existence of "exon 1" and "intron 1" (as shown in FIG. 11). In addition, the 3' end of the ace3 coding region in Rut-C30 comprised a mutation creating a premature stop codon, relative to the sequence of the wild-type isolate QM6a (FIG. 11). Thus, as described in Example 6, Applicant examined the effects of over-expression of these different possible forms of the ace3 gene as shown in FIG. 12.

Furthermore, as set forth in the Examples below, Applicant constructed (Example 1) and tested (Examples 2-4) the genes encoding the Ace3-S protein (SEQ ID NO: 3) and Ace3-L protein (SEQ ID NO: 6) by transforming *T. reesei* cells with one of four different ace3 expression vectors named "pYL1", "pYL2", "pYL3" and "pYL4" (see, FIG. 2A-2D plasmid maps). More specifically (Example 1), these expression vectors contain a vector backbone with the bacterial ColE1 on and AmpR gene for replication and selection in *E. coli*. In addition, the expression vectors (see, FIG. 2A-2D) comprise a *T. reesei* pyr2 selection marker and a heterologous *T. reesei* promoter sequence (i.e., promoters of hxk1 or pki1) operably linked to the ace3 ORF coding sequence (ace3-L or ace3-S) with its native terminator.

Subsequently, the stable *T. reesei* transformants generated (i.e., variant host cells A4-7, B2-1, C2-28 and D3-1) were tested/screened in slow release microtiter plates (srMTPs) (Example 2), shake flasks (Example 3) and small scale fermentation (Example 4) under both "inducing" and "non-inducing" conditions, and the culture supernatants harvested and analyzed via polyacrylamide gel electrophoresis (see, FIG. 3-FIG. 5). As presented in these Examples, all of the host cells tested (i.e., parental, variant A4-7, variant B2-1, variant C2-28 and variant D3-1) secreted a high quantity of proteins in the presence of an inducing substrate (i.e., sophorose or lactose). In contrast, it was surprisingly observed that in the absence of an inducing substrate (i.e., sophorose or lactose), wherein "glucose" was the sole carbon source, only the variant host cells expressing the ace3-L ORF (i.e., variants A4-7 and C2-28) were capable of producing secreted proteins, while the parental (control) cells and variant host cells expressing the ace3-S ORF (i.e., variants B2-1 and D3-1) did not produce any detectable secreted proteins.

Figure 8:
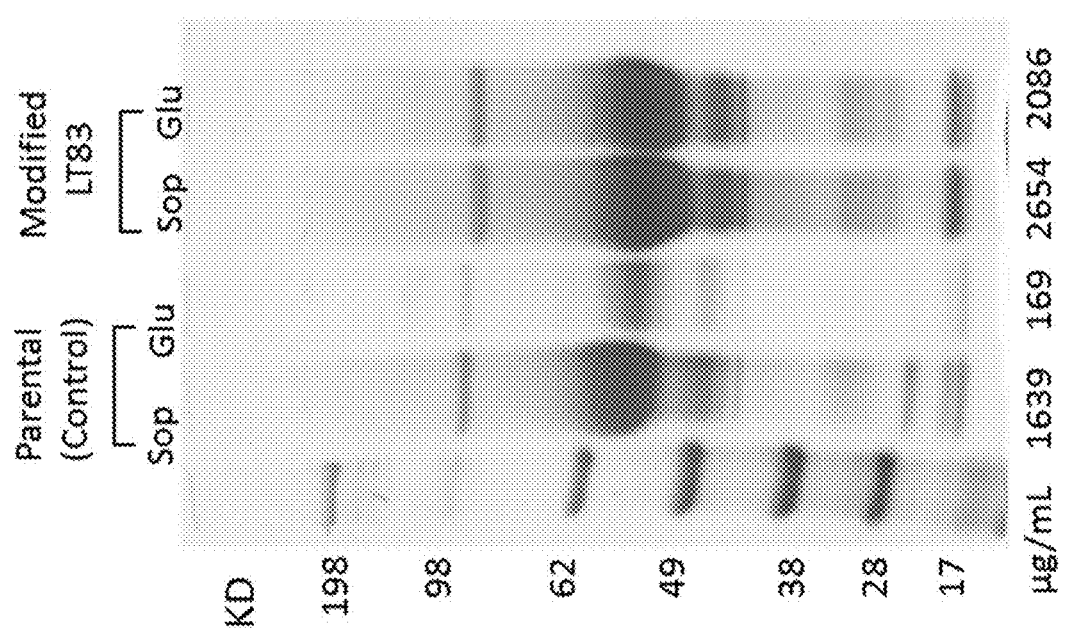
FIG. 8 shows a SDS-PAGE of *T. reesei* parental and its modified (daughter) cell supernatants, wherein the parental and modified strains were grown in defined medium supplemented with either 2.5% glucose/sophorose ("Sop", inducing condition) or 2.5% glucose ("Glu", non-inducing condition) in shake flasks. Equal volumes of culture supernatant were loaded in each lane. M is molecular weight marker and KD is kilodalton.
Figure 9:
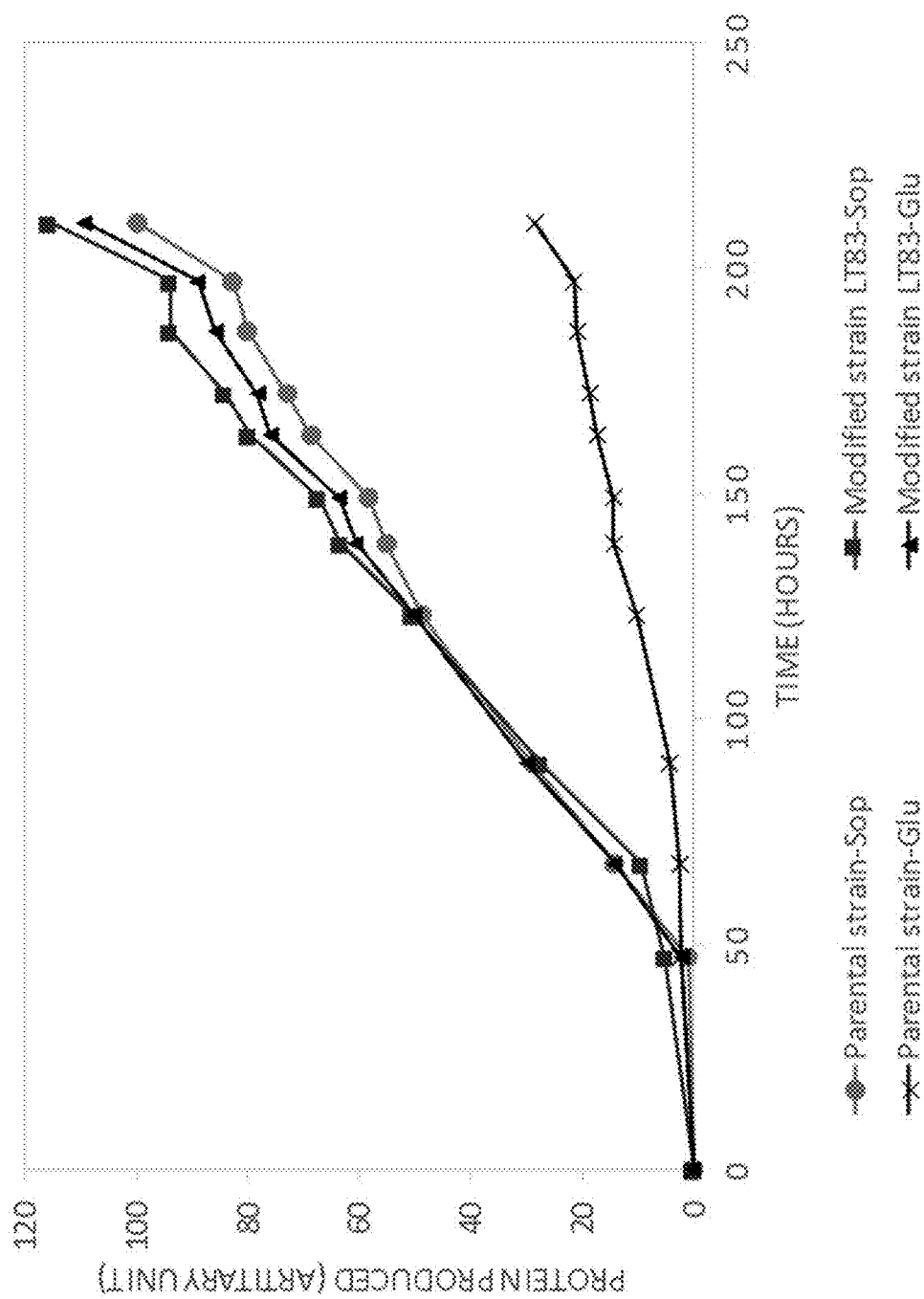
FIG. 9 shows protein production in small scale (2 L) fermentation. The *T. reesei* parental strain and daughter strain "LT83" were grown in defined medium with either glucose/sophorose (Sop, inducing condition) or glucose (Glu, non-inducing condition) as carbon sources. The total protein produced by the parental strain on glucose/sophorose at the end of fermentation was arbitrarily set at 100, and the relative amounts of protein produced by each strain at each time points were plotted.

In other embodiments, the disclosure further demonstrates enhanced protein production under "non-inducing" conditions using thirteen (13) different promoters to drive the expression of ace3-L (Example 5) expression constructs. For example, the thirteen promoters tested included (i) a formamidase gene (rev3; Protein ID 103041) promoter (SEQ ID NO: 15), (ii) a β-xylosidase gene (bxl; Protein ID 121127) promoter (SEQ ID NO: 16), (iii) a transketolase gene (tkl1; Protein ID 2211) promoter (SEQ ID NO: 17), (iv) a gene of unknown function (Protein ID 104295) promoter (SEQ ID NO: 18), (v) an oxidoreductase gene (dld1; Protein ID 5345) promoter (SEQ ID NO: 19), (vi) a xylanase IV gene (xyn4; Protein ID 111849) promoter (SEQ ID NO: 20), (vii) an α-glucuronidase gene (Protein ID 72526) promoter (SEQ ID NO: 21), (viii) an acetyl xylan esterase gene 1 (axe1; Protein ID 73632) promoter (SEQ ID NO: 22), (ix) a hexose kinase gene (hxk1; Protein ID 73665) promoter (SEQ ID NO: 23), (x) a mitochondrial carrier protein gene (dic1; Protein ID 47930) promoter (SEQ ID NO: 24), (xi) an oligopeptide transporter gene (opt; Protein ID 44278) promoter (SEQ ID NO: 25), (xii) a glycerol kinase gene (gut1; Protein ID 58356) promoter (SEQ ID NO: 26) and (xiii) a pyruvate kinase gene (pki1; Protein ID 78439) promoter (SEQ ID NO: 27). As shown in Table 3, the parental *T. reesei* cells only produced secreted proteins in the presence of the sophorose inducer. In contrast, the variant (daughter) *T. reesei* cells, comprising and expressing Ace3-L driven from any one of thirteen different promoters, produced similar amounts of secreted protein, under both inducing and non-inducing conditions. Also describe in Example 5, the *T. reesei* parental strain and transformants thereof were further tested in shake flasks experiments and small scale fermentation. As show in FIG. 8, the parental (control) *T. reesei* cells only produced secreted proteins in the presence of the sophorose ("Sop") inducer, whereas daughter strain LT83 produced similar amounts of secreted protein, under both inducing ("Sop") and non-inducing ("Glu") conditions. Likewise, as shown in FIG. 9, the parental (control) *T. reesei* strain only produced secreted proteins in the presence of the sophorose inducer ("Sop"), whereas daughter strain LT83 produced similar amounts of protein, under both inducing ("Sop") and non-inducing ("Glu") conditions.

Example 6 of the disclosure describes an experimental study of the effects of over-expressing the different possible forms of the ace3 gene (e.g., see, mutant strain Rut-C30/wild-type strain QM6a genome sequence annotations discussion above, FIG. 11 and FIG. 12). Thus, the different forms of ace3 depicted in FIG. 12 were over-expressed in *T. reesei*, wherein the over-expression vectors for the *T. reesei* ace3 genes were designed to enable targeted integration of ace3 at the glucoamylase locus (gla1) in *T. reesei*. Thus, the constructs presented in Table 5 differ by having different forms of the ace3 gene. Likewise, the strains in Table 7 were grown in 24-well microtiter plates in liquid medium with either 2% lactose or 2% glucose as carbon source, wherein the amount of total secreted proteins was measured from the culture supernatants In both media (i.e., 2% lactose or 2% glucose) the over-expression of the ace3-L, ace3-EL and ace3-LN forms (i.e., with the RutC-30 C-terminal mutation), improved the production of total proteins (Table 8). In the medium with lactose as the carbon source, over-expression of all the forms of ace3 gene improved the production of total proteins to some extent, but the level of improvement was highest in the strains over-expressing the ace3-L, ace3-EL and ace3-LN forms of the ace3 gene (Table 8). Thus, it is clear that high levels of secreted protein are observed under the "non-inducing condition" (i.e., when glucose was used as a carbon source) when over-expressing the ace3-L, ace3-EL and ace3-LN forms of the ace3 gene.

Figure 6:
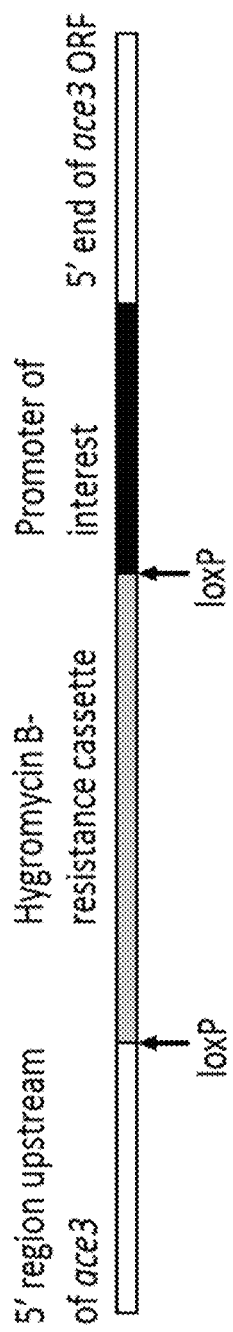
FIG. 6 presents a schematic diagram of a promoter replacement construct made by fusing a DNA fragment comprising a 5' region upstream of the native promoter at the ace3 locus, a loxP-flanked hygromycin B-resistance (selectable marker) cassette and a DNA fragment comprising a promoter of interest operably fused (linked) to the 5' end of the ace3 ORF.

Example 7 of the disclosure describes a promoter replacement construct (see, FIG. 6) made by fusing a DNA fragment comprising a 5' region upstream of the native promoter at the ace3 locus, a loxP-flanked hygromycin B-resistance selectable marker cassette, and a fragment comprising a promoter of interest operably fused to the 5' end of the ace3 open reading frame. For example, in certain embodiments, a promoter replacement construct is used to replace the endogenous ace3 gene promoter in a *Trichoderma reesei* cell with an alternate promoter.

Example 8 of the disclosure describes replacing an endogenous non-lignocellulosic gene of interest promoter, with a lignocellulosic gene of interest promoter. For example, a *T. reesei* glucoamylase expression construct was assembled from DNA polynucleotide fragments, wherein an ORF sequence encoding a *T. reesei* glucoamylase was operably linked to a 5' (upstream) *T. reesei* cbh1 promoter and operably linked to a 3' (downstream) *T. reesei* cbh1 terminator, which construct further comprised a *T. reesei* pyr2 gene as selectable marker. The variant (daughter) *T. reesei* cell (i.e., comprising a genetic modification which increases expression of a gene encoding an Ace3-L protein) was transformed with the glucoamylase expression construct, and transformants were selected and cultured in liquid medium with glucose as carbon source (i.e., without an inducing substrate such as sophorose or lactose) in order to identify those transformants that were able to secrete the *T. reesei* glucoamylase enzyme during culture. As presented in FIG. 10, the parental *T. reesei* cells produced 1,029 μg/mL of glucoamylase in defined medium with glucose/sophorose (inducing condition), and only 38 μg/mL of glucoamylase in defined medium with glucose (non-inducing condition), whereas the modified (daughter) strain "LT88", comprising ace3-L driven from the dic1 promoter, produced 3-fold higher glucoamylase under "inducing" ("Sop") conditions (i.e., relative to the parental (control) strain), and produced 2.5-fold higher glucoamylase under "non-inducing" ("Glu") conditions (i.e., relative to the parental (control) strain). Thus, these results demonstrate that the modified (daughter) cells comprising the Ace3-L ORF not only produce extracellular proteins in the absence of an inducer, but these variant cells also produce more total protein than the parental (control) *T. reesei* cells under such inducing conditions.

Example 9 describes replacing a natively associated heterologous gene of interest promoter with a lignocellulosic gene of interest promoter. For example, an ORF encoding *Buttiauxella* sp. phytase (i.e., a heterologous GOI) is operably linked at the 5' end to a *T. reesei* cbh1 promoter and at the 3' end to a *T. reesei* cbh1 terminator, wherein the DNA construct further comprises a selectable marker. Variant *T. reesei* cells (i.e., comprising a genetic modification which increases expression of a gene encoding an Ace3-L protein) is transformed with the phytase expression construct, transformants are selected and cultured in liquid medium with glucose as carbon source (i.e., without an inducing substrate such as sophorose or lactose) in order to identify those transformants that are able to secrete *Buttiauxella* phytase enzyme during culture.

Figure 23:
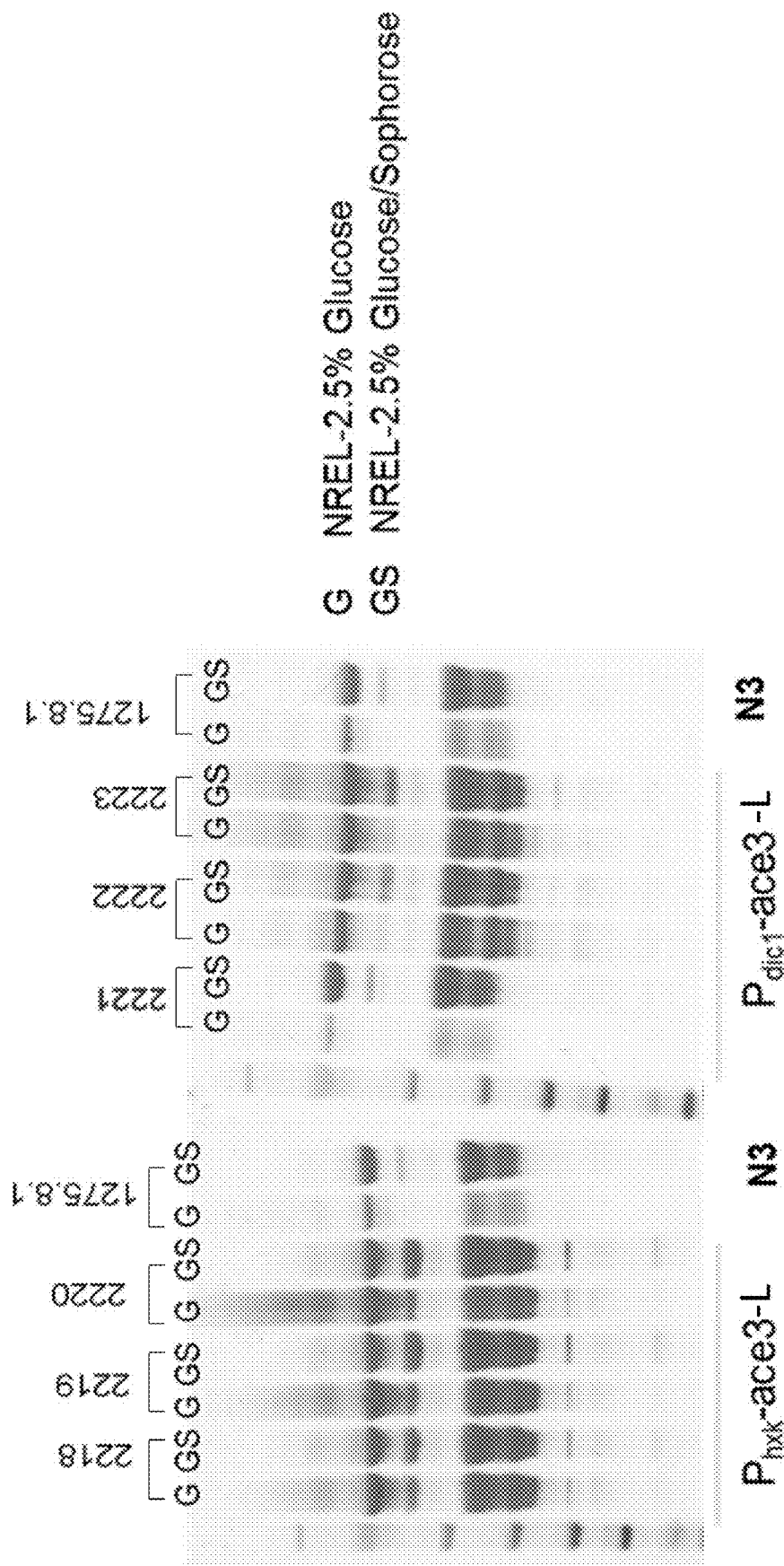
FIG. 23 shows a SDS-PAGE of secreted proteins produced by submerged cultures (i.e., shake flasks) of *T. reesei* parental cells (FIG. 23, cell ID 1275.8.1) and variant *T. reesei* (daughter) cells (FIG. 23, cell ID Nos. 2218, 2219, 2220, 2222 and 2223) under inducing ("Glu/Sop") and non-inducing ("Glu") culture conditions.

Example 10 of the disclosure describes the construction of native ace3 promoter replacement vectors, which vectors contained a *Streptococcus pyogenes* cas9 gene, expressed under the *T. reessei* pki1 promoter and guide RNA expressed under a U6 promoter. For example, the cas9 mediated ace3 promoter replacement vectors (pCHL760 and pCHL761) were transformed into *T. reesei* parental cells, and to test the functionality of ace3 promoter replaced strains, cells were grown in the presence and absence of an inducer substrate (sophorose) in 50 ml submerged culture in shake flasks. As seen on SDS-PAGE, parental cells (FIG. 23, ID 1275.8.1) produced much less secreted protein in defined medium with glucose (non-inducing) compared to glucose/sophorose (induction). In contrast, transformants 2218, 2219, 2220, 2222 and 2223 produced similar amounts of secreted protein under inducing and non-inducing conditions, demonstrating that the variant cells harboring the hxk1 or dic1 promoter (i.e., replacing the native ace3 promoter at ace3 locus) produced extracellular proteins in the absence of an inducer.

Thus, as contemplated and described herein, certain aspects of the present disclosure are directed to the production of one or more endogenous filamentous fungal lignocellulosic degrading enzymes (i.e., cellulolytic enzymes, e.g., a cellobiohydrolase, a xylanase, an endoglucanase and the like). More specifically, certain embodiments of the disclosure are directed to producing such endogenous enzymes in a variant host cell of the disclosure (i.e., a variant host cell comprising a genetic modification which increases expression of an Ace3-L protein, Ace3-EL and/or Ace3-LN protein), in the complete absence of an inducing substrate. The variant host cells, compositions and methods of the instant disclosure are of particular utility for significantly reducing the cost/expense of producing the aforementioned cellulolytic enzymes, particularly due to the fact such variant host cells of the disclosure do not require an inducing substrate to produce such cellulolytic enzymes (i.e., in contrast to the parental cells which only produce such cellulolytic enzymes in presence of inducing substrates).

For example, in certain embodiments, the disclosure is directed to variant fungal host cells capable of expressing/ producing one or more endogenous proteins of interest in the absence of an inducing substrate and/or one or more heterologous proteins of interest in the absence of an inducing substrate. Therefore, in certain embodiments, a variant fungal host cell of the disclosure (i.e., comprising a genetic modification which increases the expression of Ace3-L protein, Ace3-EL and/or Ace3-LN) is further modified to express an endogenous, non-lignocellulosic protein of interest and/or a heterologous protein of interest. For example, in certain embodiments, a gene encoding an endogenous, non-lignocellulosic protein of interest is modified in the variant fungal host cell. Thus, in certain embodiments, the promoter natively associated with a gene (or ORF) encoding an endogenous, non-lignocellulosic protein of interest is replaced with a promoter from a filamentous fungi gene encoding a lignocellulosic protein (e.g., a 5'-lignocellulosic gene promoter operably linked to an endogenous gene encoding a non-lignocellulosic protein of interest). Likewise, in certain other embodiments, a variant fungal host cell of the disclosure (i.e., comprising a genetic modification which increases the expression of Ace3-L protein, Ace3-EL and/or Ace3-LN) is modified to express a heterologous protein of interest. Thus, in certain other embodiments, the promoter natively associated with a gene encoding a heterologous protein of interest is replaced with a promoter from a filamentous fungi gene encoding a lignocellulosic protein (e.g., a 5'-lignocellulosic gene promoter operably linked to a heterologous gene encoding a heterologous protein of interest).

Thus, in certain embodiments, the instant disclosure is directed to a variant filamentous fungal cell derived from a parental filamentous fungal cell, wherein the variant cell comprises a genetic modification which increases the expression of a gene encoding an Ace-L protein relative to the parental cell, wherein the encoded Ace3-L protein comprises about 90% sequence identity to the Ace3-L protein of SEQ ID NO: 6. For example, in certain embodiments, an encoded Ace3 protein comprising about 90% sequence identity to SEQ ID NO: 6, comprises "Lys-Ala-Ser-Asp" as the last four C-terminal amino acids. In other embodiments, an encoded Ace3 protein comprising about 90% sequence identity to SEQ ID NO: 6, further comprises an N-terminal amino acid fragment of SEQ ID NO: 98 operably linked and preceding SEQ ID NO: 6. In another embodiment, an Ace-3 protein comprises about 90% sequence identity to SEQ ID NO: 12.

In certain other embodiments, a polynucleotide of the disclosure comprises a nucleotide sequence comprising about 90% sequence identity to SEQ ID NO: 4, SEQ ID NO: 11 or SEQ ID NO: 13. In other embodiments, a polynucleotide of the disclosure comprises a nucleotide sequence comprising about 90% sequence identity to SEQ ID NO: 5, SEQ ID NO: 101 or SEQ ID NO: 102.

IV. Filamentous Fungal Host Cells

In certain embodiments of the disclosure, variant filamentous fungal cells (i.e., derived from parental filamentous fungal cells) are provided which comprise a genetic modification which increases the expression of a gene or ORF encoding an Ace3-L polypeptide. More particularly, in certain embodiments, variant filamentous fungal cells (i.e., relative to the parental (control) cells) comprise a genetic modification that increases the expression of a gene (or ORF) encoding an Ace3-L protein of SEQ ID NO: 6. In preferred embodiments, such variant fungal cells comprising a genetic modification which increases the expression of a gene (or ORF) encoding an Ace3-L protein of SEQ ID NO: 6 are capable of producing at least one endogenous protein of interest in the absence of an inducing substrate. In other embodiments, such variant fungal cells comprising a genetic modification which increases the expression of a gene (or ORF) encoding an Ace3-L protein of SEQ ID NO: 6 are capable of producing at least one heterologous protein of interest in the absence of an inducing substrate.

Thus, in certain embodiments, a filamentous fungal cell for manipulation and use in the present disclosure includes filamentous fungi from the phylum Ascomycota, subphylum Pezizomycotina, particularly fungi that have a vegetative hyphae state. Such organisms include filamentous fungal cells used for the production of commercially important industrial and pharmaceutical proteins, including, but not limited to Trichoderma spp., Aspergillus spp., Fusarium spp., Scedosporium spp., Penicillium spp., Chrysosporium spp., Cephalosporium spp., Talaromyces spp., Geosmithia spp., Myceliophthora spp. and Neurospora spp.

Particular filamentous fungi include, but are not limited to, Trichoderma reesei (previously classified as Trichoderma longibrachiatum and Hypocrea jecorina), Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum, Myceliophthora thermophila and Chrysosporium lucknowense.

V. Recombinant Nucleic Acids and Molecular Biology

In certain embodiments, the instant disclosure is directed to variant filamentous fungal host cells comprising a genetic modification which increases the expression of a gene or ORF encoding an Ace3-L, Ace3-EL or Ace3-LN protein. As set forth above, such variant host cells are capable of producing one or more proteins of interest in the absence of an inducing substrate (i.e., in contrast to the unmodified parental (control) cells).

Thus, in certain embodiments, the disclosure is directed to recombinant nucleic acids comprising a gene or ORF encoding an Ace3-L, Ace3-EL or Ace3-LN protein. In certain embodiments, a recombinant nucleic acid comprises a polynucleotide expression cassette for production of an Ace3-L, Ace3-EL or Ace3-LN protein in a filamentous fungal host cell. In other embodiments, the polynucleotide expression cassette is comprised within an expression vector. In certain embodiments, the expression vector is a plasmid. In other embodiments, the recombinant nucleic acid, polynucleotide expression cassette or expression vector thereof comprises a nucleotide sequence comprising at least 85% sequence identity to SEQ ID NO: 4, SEQ ID NO: 5, SEQ ID NO: 11, SEQ ID NO: 101, SEQ ID NO: 13 or SEQ ID NO: 102. In another embodiment, the recombinant nucleic acid, polynucleotide expression cassette or expression vector thereof comprises a nucleotide sequence encoding an Ace3-L protein comprising about 90% sequence identity to SEQ ID NO: 6.

In certain other embodiments, the recombinant nucleic acid (or polynucleotide expression cassette thereof or expression vector thereof) further comprises one or more selectable markers. Selectable markers for use in filamentous fungi include, but are not limited to als1, amdS, hygR, pyr2, pyr4, pyrG, sucA, a bleomycin resistance marker, a blasticidin resistance marker, a pyrithiamine resistance marker, a chlorimuron ethyl resistance marker, a neomycin resistance marker, an adenine pathway gene, a tryptophan pathway gene, a thymidine kinase marker and the like. In a particular embodiment, the selectable marker is pyr2, which compositions and methods of use are generally set forth in PCT Publication No. WO2011/153449. Thus, in certain embodiments, a polynucleotide construct encoding an Ace3 protein of the disclosure comprises a nucleic acid sequence encoding a selectable marker operably linked thereto.

In another embodiment, the recombinant nucleic acid, polynucleotide construct, polynucleotide expression cassette or expression vector thereof comprises a heterologous promoter driving the expression of the gene (or ORF) encoding an Ace3-L, Ace3-EL or Ace3-LN protein. More particularly, in certain embodiments, the heterologous promoter is a constitutive or an inducible promoter. In particular embodiments, a heterologous promoter is selected from the group consisting of a rev3 promoter, a bxl promoter, a tkl1 promoter, a PID104295 promoter, a dld1 promoter, a xyn4 promoter, a PID72526 promoter, an axe promoter, a hxk1 promoter, a dic1 promoter, an opt promoter, a gut1 promoter and a pki1 promoter. Without wishing to be bound by a particular theory or mechanism of action, it is contemplated herein that promoters such as rev3, bxl, tkl, PID104295, dld1, xyn4, PID72526, axe1, hxk1, dic1, opt, gut1 and a pki1, which yield higher expression levels under glucose limiting conditions (i.e., vis-à-vis excess glucose concentrations), have particular utility in the instant disclosure. Thus, in certain embodiments, a recombinant nucleic acid (or polynucleotide construct, polynucleotide expression cassette or expression vector thereof) comprises a promoter which is 5' and operably linked to the nucleic acid sequence encoding the Ace3 protein.

In another embodiment, a recombinant nucleic acid (or polynucleotide construct, polynucleotide expression cassette or expression vector thereof) further comprises a nucleic acid sequence encoding a native ace3 terminator sequence. Thus, in certain embodiments, a recombinant nucleic acid (or polynucleotide construct, polynucleotide expression cassette, or expression vector thereof) comprises a promoter which is 5' and operably linked to a nucleic acid sequence encoding an Ace3 protein and a native ace3 terminator sequence which is 3' and operably linked to a nucleic acid sequence encoding an Ace3 protein (e.g., 5'-Pro-ORF-Term-3', where "Pro" is a constitutive promoter, "ORF" encodes Ace3 and "Term" is a native ace3 terminator sequence).

Thus, in certain embodiments, standard techniques for transformation of filamentous fungi and culturing the fungi (which are well known to one skilled in the art) are used to transform a fungal host cell of the disclosure. Thus, the introduction of a DNA construct or vector into a fungal host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated microprojectiles, gene gun or biolistic transformation, protoplast fusion and the like. General transformation techniques are known in the art (see, e.g., Ausubel et al., 1987, Sambrook et al., 2001 and 2012, and Campbell et al., 1989). The expression of heterologous proteins in Trichoderma is described, for example, in U.S. Pat. Nos. 6,022,725; 6,268,328; Harkki et al., 1991 and Harkki et al., 1989. Reference is also made to Cao et al. (2000), for transformation of Aspergillus strains.

Generally, transformation of Trichoderma sp. uses protoplasts or cells that have been subjected to a permeability treatment, typically at a density of $10^5$ to $10^7$/mL, particularly 2×10⁶/mL. A volume of 100 µL of these protoplasts or cells in an appropriate solution (e.g., 1.2 M sorbitol and 50 mM CaCl$_2$)) is mixed with the desired DNA. Generally, a high concentration of polyethylene glycol (PEG) is added to the uptake solution. Additives, such as dimethyl sulfoxide, heparin, spermidine, potassium chloride and the like, may also be added to the uptake solution to facilitate transformation. Similar procedures are available for other fungal host cells. See, e.g., U.S. Pat. Nos. 6,022,725 and 6,268,328, both of which are incorporated by reference.

In certain embodiments, the instant disclosure is directed to the expression and production of one or more proteins of interest which are endogenous to the filamentous fungal host cell (i.e., the endogenous proteins are produced by a variant fungal host cell of the disclosure comprising a genetic modification which increasers expression of Ace3-L). In other embodiments, the disclosure is directed to expressing and producing one or more proteins of interest which are heterologous to the to the filamentous fungal host cell. Therefore, the instant disclosure generally relies on routine techniques in the field of recombinant genetics. Basic texts disclosing the general methods of use in present disclosure include Sambrook et al., (2$^{nd}$ Edition, 1989); Kriegler (1990) and Ausubel et al., (1994).

Thus, in certain embodiments, a heterologous gene or ORF encoding a protein of interest is introduced into a filamentous fungal (host) cell. In certain embodiments, the heterologous gene or ORF is typically cloned into an intermediate vector, before being transformed into a filamentous fungal (host) cells for replication and/or expression. These intermediate vectors can be prokaryotic vectors, such as, e.g., plasmids, or shuttle vectors. In certain embodiments, the expression of the heterologous gene or ORF is under the control of its native promoter. In other embodiments, the expression of the heterologous gene or ORF is placed under the control of a heterologous promoter, which can be a heterologous constitutive promoter or a heterologous inducible promoter.

Those skilled in the art are aware that a natural (native) promoter can be modified by replacement, substitution, addition or elimination of one or more nucleotides, without changing its function. The practice of the invention encompasses but is not constrained by such alterations to the promoter.

The expression vector/construct typically contains a transcription unit or expression cassette that contains all the additional elements required for the expression of the heterologous sequence. For example, a typical expression cassette contains a 5' promoter operably linked to the heterologous nucleic acid sequence encoding a protein of interest and may further comprise sequence signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes. Although any fungal terminator is likely to be functional in the present invention, preferred terminators include: the terminator from *Trichoderma* cbh1 gene, the terminator from *Aspergillus nidulans* trpC gene (Yelton et al., 1984; Mullaney et al., 1985), the *Aspergillus awamori* or *Aspergillus niger* glucoamylase genes (Nunberg et al., 1984; Boel et al., 1984) and/or the *Mucor miehei* carboxyl protease gene (EPO Publication No. 0215594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that can be included in expression vectors may also be a replicon, a gene encoding antibiotic resistance to permit selection of bacteria that harbor recombinant plasmids, or unique restriction sites in nonessential regions of the plasmid to allow insertion of heterologous sequences. The particular antibiotic resistance gene chosen is not dispositive either, as any of the many resistance genes known in the art may be suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Any of the known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other known methods for introducing cloned genomic DNA, cDNA, synthetic DNA or other foreign genetic material into a host cell (see, e.g., Sambrook et al., supra). Also of use is the *Agrobacterium*-mediated transfection method such as the one described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of cellulase gene promoter sequences. Large batches of transformed cells can be cultured as described herein. Finally, product is recovered from the culture using standard techniques.

Thus, the invention herein provides for the expression and enhanced secretion of desired polypeptides whose expression is under control of cellulase gene promoter sequences including naturally occurring cellulase genes, fusion DNA sequences, and various heterologous constructs. The invention also provides processes for expressing and secreting high levels of such desired VI. Proteins of Interest As stated above, certain embodiments of the disclosure are directed to variant filamentous fungal cells (derived from a parental filamentous fungal cells), wherein the variant cells comprise a genetic modification which increases the expression of a gene encoding an Ace3-L, Ace3-EL or Ace3-LN protein (relative to the parental cell), wherein the encoded Ace3-L, Ace3-EL or Ace3-LN protein comprises about 90% sequence identity to the Ace3-L protein of SEQ ID NO: 6 and wherein the variant cells express at least one protein of interest (POI) in the absence of an inducing substrate.

Certain embodiments of the present disclosure are particularly useful for enhancing the intracellular and/or extracellular production of proteins (i.e., proteins of interest) in the absence of an inducing substrate. The protein of interest may be an endogenous protein (i.e., endogenous in the host cell) or a heterologous protein (i.e., not native in the host cell). Proteins that can be produced according to the instant disclosure include, but are not limited to, hormones, enzymes, growth factors, cytokines, antibodies and the like.

For example, a protein of interest can include, but is not limited to, a hemicellulase, a peroxidases, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a β-glucanase, a hyaluronidase, a chondroitinase, a laccase, a amylase, a glucoamylase, an acetyl esterase, an aminopeptidase, amylases, an arabinases, an arabinosidase, an arabinofuranosidase, a carboxypeptidase, a catalase, a deoxyribonuclease, an epimerase, an α-galactosidase, a β-galactosidase, an α-glucanases, a glucan lysase, an endo-β-glucanase, a glucose oxidase, a glucuronidase, an invertase, an isomerase, and the like.

In certain embodiments, a protein of interest includes, but is not limited to, enzymes disclosed in PCT Application Publication Nos. WO03/027306, WO200352118, WO200352054, WO200352057, WO200352055, WO200352056, WO200416760, WO9210581, WO200448592, WO200443980, WO200528636, WO200501065, WO2005/001036, WO2005/093050, WO200593073, WO200674005, WO2009/149202, WO2011/038019, WO2010/141779, WO2011/063308, WO2012/125951, WO2012/125925, WO2012125937, WO/2011/153276, WO2014/093275, WO2014/070837, WO2014/070841, WO2014/070844, WO2014/093281, WO2014/093282, WO2014/093287, WO2014/093294, WO2015/084596 and WO2016/069541.

Optimal conditions for the production of the proteins will vary with the choice of the host cell, and with the choice of the protein(s) to be expressed. Such conditions may be readily ascertained by one skilled in the art through routine experimentation and/or optimization.

The protein of interest can be purified or isolated after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. The degree of purification necessary will vary depending on the intended use of the protein of interest. In certain instances, no purification of the protein will be necessary.

In certain other embodiments, to confirm that a genetically modified fungal cell of the disclosure (i.e., a variant fungal host cell comprising a genetic modification which increases the expression of ace3-L) has the capability of producing an increased level of a protein of interest, various methods of screening may be performed. The expression vector may encode a polypeptide fusion to the target protein which serves as a detectable label or the target protein itself may serve as the selectable or screenable marker. The labeled protein may be detected via western blotting, dot blotting (methods available at the Cold Spring Harbor Protocols website), ELISA, or, if the label is GFP, whole cell fluorescence or FACS. For example, a 6-histidine tag would be included as a fusion to the target protein, and this tag would be detected by western blotting. If the target protein expresses at sufficiently high levels, SDS-PAGE combined with Coomassie/silver staining, may be performed to detect increases in variant host cell expression over parental (control) cell, in which case no label is necessary. In addition, other methods may be used to confirm the improved level of a protein of interest, such as, the detection of the increase of protein activity or amount per cell, protein activity or amount per milliliter of medium, allowing cultures or fermentations to continue efficiently for longer periods of time, or through a combination of these methods.

The detection of specific productivity is another method to evaluate the protein production. Specific productivity (Qp) can be determined by the following equation:

$$Qp = gP/gDCW \cdot hr$$

wherein "gP" is grams of protein produced in the tank, "gDCW" is grams of dry cell weight (DCW) in the tank, "hr" is fermentation time in hours from the time of inoculation, which include the time of production as well as growth time.

In other embodiments, the variant fungal host cell is capable of producing at least about 0.5%, for example, at least about 0.5%, at least about 0.7%, at least about 1%, at least about 1.5%, at least about 2.0%, at least about 2.5%, or even at least about 3%, or more of a protein of interest, as compared vis-à-vis to the (unmodified) parental cell.

VII. Fermentation

In certain embodiments, the present disclosure provides methods of producing a protein of interest comprising fermenting a variant fungal cell, wherein the variant fungal cell secrets the protein of interest. In general, fermentation methods well known in the art are used to ferment the variant fungal cells. In some embodiments, the fungal cells are grown under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Certain embodiments of the instant disclosure are related to fermentation procedures for culturing fungi. Fermentation procedures for production of cellulase enzymes are known in the art. For example, cellulase enzymes can be produced either by solid or submerged culture, including batch, fed-batch and continuous-flow processes. Culturing is generally accomplished in a growth medium comprising an aqueous mineral salts medium, organic growth factors, a carbon and energy source material, molecular oxygen, and, of course, a starting inoculum of the filamentous fungal host to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion.

The fermentation temperature can vary somewhat, but for filamentous fungi such as *Trichoderma reesei*, the temperature generally will be within the range of about 20° C. to 40° C., generally preferably in the range of about 25° C. to 34° C.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. Preferences for pH range of microorganisms are dependent on the media employed to some extent, as well as the particular microorganism, and thus change somewhat with change in media as can be readily determined by those skilled in the art.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this level is not critical and may vary with the particular microorganism and fermentation process being conducted. However, it is well known in the art how to determine the carbon source concentration in the fermentation medium and whether or not the desired level of carbon source has been achieved.

The fermentation can be conducted as a batch or continuous operation, fed batch operation is much to be preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermenter.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermenter, cell density measurable by dry cell weights, light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermenter employed is not critical.

The collection and purification of (e.g., cellulase) enzymes from the fermentation broth can also be done by procedures known to one of skill in the art. The fermentation broth will generally contain cellular debris, including cells, various suspended solids and other biomass contaminants, as well as the desired cellulase enzyme product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate, followed by purification by a variety of chromatographic procedures, e.g., ion exchange chromatography, affinity chromatography or similar art recognized procedures.

EXAMPLES

It should be understood that the following Examples, while indicating embodiments of the disclosure, are given by way of illustration only. From the above discussion and these Examples, one of skill in the art can make various changes and modifications of the disclosure to adapt it to various usages and conditions. Such modifications are also intended to fall within the scope of the claimed invention.

Example 1

Generation of ace3 Over Expression in Filamentous Fungal Cells

1A. Overview

In the present example, variant *Trichoderma reesei* cells (i.e., an exemplary filamentous fungi) expressing an ace3 gene were generated by transforming parental *T. reesei* cells with a nucleic acid containing the pyr2 gene, a heterologous promoter and an ace3 gene, using protoplast transformation. As generally presented in FIG. 1 and FIG. 2, four (4) different ace3-expression vectors were constructed (FIG. 2A-2D) with two (2) different promoters and two different versions of ace3 ORF (FIG. 1; ace3-SC and ace3-L) in four different combinations. Promoters of hxk1 (gene encoding hexokinase) and pki1 (gene encoding pyruvate kinase) were selected to drive constitutive expression of ace3, however, other promoters can also be used and selected by the skilled artisan.

1B. *Trichoderma reesei* Host Cells

The *T. reesei* parental host cells set forth in the following examples were derived from *T. reesei* strain RL-P37 (NRRL Deposit No. 15709), wherein the *T. reesei* pyr2 gene has been deleted, as generally described by Sheir-Neiss and Montenecourt, 1984.

1C. Construction of Ace3 Expression Vectors

As set forth in the Detailed Description of the disclosure above, Ace3 is a *T. reesei* transcriptional factor recently shown to be required for cellulase and hemi-cellulase production under inducing conditions (i.e., in the presence of lactose) (Hakkinen et al., 2014). More particularly, Hakkinen et al. (2014) used the predicted ace3 ORF, based on the publicly available genome sequence of *T. reesei* strain QM6a (see, genome.jgi.doe.gov/Trire2/Trire2.home.html), wherein the QM6a predicted annotation (Protein ID 77513) consists of two exons and one intron (e.g., see, FIG. 1).

In addition, the ace3 ORF predicted from the publicly available genome sequence of *T. reesei* strain Rut-C30 (see, (genome.jgi.doe.gov/TrireRUTC30_1/ TrireRUTC30_1.home.html) (Protein ID 98455) comprises a longer protein sequence (i.e., relative to the (short) ace3 from *T. reesei* QM6a) comprising three exons and two introns (FIG. 1). More particularly, the start codon predicted by the "RUT-C30" model is located upstream of that in the "QM6a" model, and there is a non-sense mutation at the C-terminus (Poggi-Parodi et al., 2014), resulting a longer N-terminal sequence and shorter C-terminal protein sequence (FIG. 1).

In the present Example, both the short ace3 ORF (based on the QM6a annotation, but including the RUT-C30 non-sense mutation that truncates the C-terminus of the protein (Ace3-S)) and the long ace3 ORF (based on the RUT-C30 annotation (Ace3-L)) were cloned. As set forth in FIG. 1, both the short ace3 (Ace3-S) and long ace3 (Ace3-L) ORFs comprise the C-terminal non-sense mutation, as found in RUT-C30 (FIG. 1). To drive the expression of the ace3 ORFs, a heterologous hexose kinase (hxk1) promoter and a heterologous pyruvate kinase (pki1) promoter were tested.

Thus, four (4) Ace3-expression vectors pYL1, pYL2, pYL3 and pYL4 (FIG. 2A-2D) were constructed using standard molecular biological procedures. These expression vectors contain a vector backbone with the bacterial ColE1 on and AmpR gene for replication and selection in *E. coli*. In addition to the *T. reesei* pyr2 selection marker, a *T. reesei* promoter sequence (i.e., promoters of hxk1 or pki1), and the ace3 ORF (ace3-L or ace3-SC) with its native terminator are also present. The *T. reesei* promoters and the ace3 ORFs were PCR amplified from *T. reesei* genomic DNA using Q5 High-fidelity DNA polymerase (New England Biolabs) and the primers set forth below in Table 1.

The specific primers used to PCR amplify fragments for each vector are listed as follows. To construct vector pYL1, the hxk1 promoter was amplified using primer pair TP13 (SEQ ID NO: 7) and TP14 (SEQ ID NO: 8), the Ace3-L ORF was amplified using primers TP15 (SEQ ID NO: 9) and TP16 (SEQ ID NO: 10), and the vector backbone was amplified using primer pair TP17 (SEQ ID NO: 11) and TP18 (SEQ ID NO: 12). The complete sequence of plasmid pYL1 is provided as SEQ ID NO: 21.

To construct vector pYL2, the hxk1 promoter was PCR amplified using primer pair of TP13 (SEQ ID NO: 7) and TP19 (SEQ ID NO: 13), the Ace3-SC ORF was amplified using primers TP20 (SEQ ID NO: 14) and TP16 (SEQ ID NO: 10), and the vector backbone was amplified using primer pair TP17 (SEQ ID NO: 11) and TP18 (SEQ ID NO: 12). The complete sequence of plasmid pYL2 is provided as SEQ ID NO: 22.

To construct vector pYL3, the pki1 promoter was PCR amplified using primer pair of TP21 (SEQ ID NO: 15) and TP22 (SEQ ID NO: 16), the Ace3-L ORF was amplified using primers TP23 (SEQ ID NO: 17) and TP16 (SEQ ID NO: 10), and the vector backbone was amplified using primer pair TP17 (SEQ ID NO: 11) and TP24 (SEQ ID NO: 18). The complete sequence of plasmid pYL3 is provided as SEQ ID NO: 23.

To construct vector pYL4, the pki1 promoter was PCR amplified using primer pair of TP21 (SEQ ID NO: 15) and TP25 (SEQ ID NO: 19), the Ace3-SC ORF was amplified using primers TP26 (SEQ ID NO: 20) and TP16 (SEQ ID NO: 10), and the vector backbone was amplified using primer pair TP17 (SEQ ID NO: 11) and TP24 (SEQ ID NO: 18). The complete sequence of plasmid pYL4 is provided as SEQ ID NO: 24.

For each vector, the three PCR fragments described above were assembled and transformed into NEB DH5α competent cells using Gibson assembly cloning kit (New England Biolabs; Catalogue No.: E5510S) according to manufacturer's protocols. The resulting vectors were sequenced using Sanger sequencing, and their maps are shown in FIG. 2A-2D.

mants were grown on Vogel's minimal medium agar plates to select for uridine prototrophy acquired by the pyr2 marker. Stable transformants were obtained by transfer on Vogel's agar plate for two successive rounds, after which single colonies were obtained by plating dilution of spore suspension. The variant (i.e., modified) host cells harboring pYL1, pYL2, pYL3 and pYL4 were named variant A4-7, variant B2-1, variant C2-28, and variant D3-1, respectively.

Example 2

Protein Production in Slow Release Microtiter Plate (srMTP)

The present example describes the screening method used to identify transformants (see, Example 1) that secrete enzymes under non-inducing conditions. For example, stable transformants obtained from Example 1 were tested in slow release microtiter plates (srMTP). The srMTP used were 24-well PDMS elastomer plates containing either 20% glucose (wt/wt) or 20% lactose (wt/wt), which were prepared as described in PCT International Publication No. WO2014/047520.

The parental and variant T. reesei host cells described in Example 1 were tested under both "non-inducing" and "inducing" conditions. In the "non-inducing condition", cells were grown in 1.25 ml liquid broth of defined medium, supplemented with 2.5% glucose (wt/vol) in a srMTP containing 20% glucose (wt/wt). In the "inducing condition", cells were grown in 1.25 ml liquid broth of defined medium supplemented with 2.5% glucose/sophorose (wt/vol) in a

TABLE 1

Construct Assembly Primers

| Primer | Sequence | SEQ NO: |
|---|---|---|
| TP13 | TCAGGGTTATTGTCTCATGGCCATTTAGGCCTGGCAGGCACTGGCTCGGACGACATGT | 7 |
| TP14 | AGAGCCCTGGGCCGGAGCTGCTGAGCCCATTGTTGAATTCTGGCGGGGTAGCTGTTGA | 8 |
| TP15 | TCAACAGCTACCCCGCCAGAATTCAACAATGGGCTCAGCAGCTCCGGCCCAGGGCTCT | 9 |
| TP16 | TCGTAAATAAACAAGCGTAACTAGCTAGCGTAGGTTATGCGAGCAACATTGCACGAAAC | 10 |
| TP17 | GTTTCGTGCAATGTTGCTCGCATAACCTACGCTAGCTAGTTACGCTTGTTTATTTACGA | 11 |
| TP18 | ACATGTCGTCCGAGCCAGTGCCTGCCAGGCCTAAATGGCCATGAGACAATAACCCTGA | 12 |
| TP19 | AGGTGTAAGACGGGGGAGTAGCGCAGCATTGTTGAATTCTGGCGGGGTAGCTGTTGA | 13 |
| TP20 | TCAACAGCTACCCCGCCAGAATTCAACAATGCTGCGCTACTCCCCCGTCTTACACCT | 14 |
| TP21 | TCAGGGTTATTGTCTCATGGCCATTTAGGCCTAGACTAGCGGCCGGTCCCCTTATCCCA | 15 |
| TP22 | AGAGCCCTGGGCCGGAGCTGCTGAGCCCATGGTGAAGGGGCGGCCGCGGAGCCT | 16 |
| TP23 | AGGCTCCGCGGCCGCCCCCTTCACCATGGGCTCAGCAGCTCCGGCCCAGGGCTCT | 17 |
| TP24 | TGGGATAAGGGGACCGGCCGCTAGTCTAGGCCTAAATGGCCATGAGACAATAACCCTGA | 18 |
| TP25 | TGTAAGACGGGGGAGTAGCGCAGCATGGTGAAGGGGCGGCCGCGGAGCCT | 19 |
| TP26 | AGGCTCCGCGGCCGCCCCCTTCACCATGCTGCGCTACTCCCCCGTCTTACA | 20 |

1D. Transformation of T. reesei

The expression vectors of pYL1, pYL2, pYL3 and pYL4 were linearized using PacI enzyme (New England Biolabs), and transformed into T. reesei parental host cells by polyethylene glycol (PEG)-mediated protoplast transformation (Ouedraogo et al., 2015; Penttila et al., 1987). The transforsrMTP containing 20% lactose (wt/wt), where sophorose and lactose serve as potent inducers for cellulase enzyme expression.

Preparation of glucose/sophorose was performed as described in U.S. Pat. No. 7,713,725. The defined medium was prepared as generally described in PCT International Publication No. WO2013/096056, comprising 9 g/L casamino acids, 5 g/L $(NH_4)_2SO_4$, 4.5 g/L $KH_2PO_4$, 1 g/L $MgSO_4.7H_2O$, 1 g/L $CaCl_2.2H_2O$, 33 g/L PIPPS buffer (at pH 5.5), 0.25 ml/L *T. reesei* trace elements. The *T. reesei* trace elements contains 191.41 g/l citric acid.$H_2O$, 200 g/L $FeSO_4.7H_2O$, 16 g/L $ZnSO_4.7H_2O$, 0.56 g/L $CuSO_4.5H_2O$, 1.2 g/L $MnSO_4.H_2O$ and 0.8 g/L $H_3BO_3$. All srMTP's were incubated at 28° C. for approximately 120 hours with continuous shaking at 280 rpm.

Following incubation, the supernatant from all cultures were harvested and analyzed using Polyacrylamide Gel Electrophoresis (PAGE). Equal volumes of culture supernatants were subjected to a reducing environment for fifteen (15) minutes at 90° C., before addition of loading dye and resolution on a 4-12% NuPage™ (Invitrogen, Carlsbad Calif.) polyacrylamide gel with MOPS-SDS buffer. The gel was stained with SimplyBlue™ (Invitrogen) and imaged (see, FIG. 3).

Figure 3:
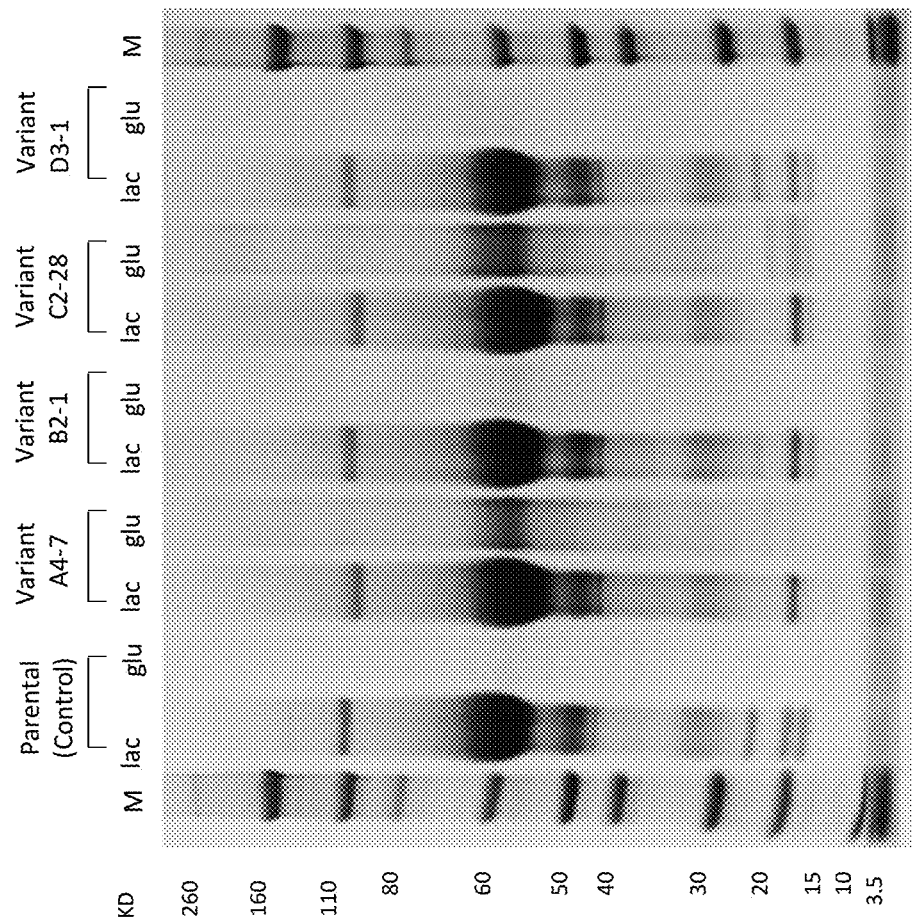
FIG. 3 presents a Polyacrylamide Gel Electrophoresis (SDS-PAGE) of *T. reesei* parental and variant cell supernatants, wherein the parental and variant cells were grown in defined medium in srMTP containing 20% lactose (lac) or 20% glucose (glu). Equal volumes of culture supernatants were loaded in each lane. M is molecular weight marker and the parental *T. reesei* strain served as a control strain.

As shown in FIG. 3, all of the host cells tested secreted a large quantity of proteins in the presence of an inducer (i.e., sophorose in the media and lactose in the srMTP). However, in the absence of an inducer (i.e., sophorose or lactose), where glucose was the only carbon source, only the variant host cells expressing the Ace3-L ORF (i.e., variant A4-7 and variant C2-28) produced secreted proteins, while the parental host cells or variant cells expressing Ace3-SC ORF (i.e., variant B1-1 and variant D3-1) did not produce extracellular proteins above the detection limit of PAGE. This result clearly demonstrates that Ace3-L (i.e., in contrast to Ace3-S) enables inducer-free protein production in *T. reesei*.

The relative concentration of secreted proteins was determined by Zorbax C3 reversed phase (RP) analysis using purified enzymes as a reference. For example, the secreted protein profiles of the host cells described above were analyzed using this method, wherein it was observed that all of the host cells (i.e., parental and variant cells) produced similar cellulase protein profiles under the inducing condition, wherein the cellulases consisted of approximately 40% CBH1, 20% CBH2, 10% EG1 and 7% of EG2. Under the non-inducing conditions, cellulase enzymes were below detection in the parental cells and the variant Ace3-S expressing host cells. In contrast, it was surprisingly found that the variant Ace3-L expressing host cells (i.e., variants A4-7 and C2-28) produced a similar ratio of cellulase enzymes as under the inducing conditions.

Briefly, this method of analysis was performed as follows: supernatant samples were diluted in 50 mM sodium acetate buffer, pH 5.0, and de-glycosylated by addition of 20 ppm EndoH, incubated at 37° C. for 3 hrs. Ten (10) µl 90% acetonitrile was added to 100 L EndoH-treated sample and passed over a 0.22 m filter prior to injection. An Agilent 1290 with DAD detection (Agilent Technologies) HPLC equipped with an Agilent Zorbax300 SB C3 RRHD 1.8 um (2.1×100 mm) column was used. The column was operating at 60° C. at a flow rate of 1.0 mL/min with 0.1% Trifluoroacetic acid (TFA) in MiliQ water as running buffer A and 0.07% TFA in Acetonitrile as running buffer B. The DAD detector was operating at 220 nm and 280 nm with a 4 nm window. The injection volume was 10 µL.

Additionally, it was noted that the variant Ace3-L expressing host cells produced approximately 20-30% total extracellular proteins in the srMTP with glucose (i.e., as compared to the total extracellular proteins produced in the srMTP with lactose). This relatively low expression may be due to the high glucose feed rate in srMTP with glucose. For example, it is well established that the highest cellulase and hemi-cellulase production rate is often observed with low growth rates (Arvas et al., 2011). Nevertheless, the srMTP growth assay was a relatively high-throughput assay to screen stable colonies for protein production.

Taken together, the variant *T. reesei* host cells expressing the Ace3-L ORF were able to produce cellulase and hemicellulase in the absence of an inducer, albeit at a lower protein production rate. More particularly, this low production rate was linked to the srMTP growth method, rather than the production ability of the host cells, as is shown in Example 3 and Example 4 below.

Example 3

Protein Production in Shake Flasks

To further explore and validate the srMTP results presented above, the parental host cell and variant Ace3-L expressing host cells were grown in the presence and absence of an inducer substrate in 50-mL submerged culture in shake flasks. More particularly, the parental *T. reesei* host cells, the variant A4-7 cells and the variant C2-28 cells were grown under both inducing conditions (i.e., glucose/sophorose as carbon source) and non-inducing conditions (i.e., glucose as carbon source) in submerged (liquid) culture and their respective extracellular (secreted) protein production levels were compared. Briefly, mycelia of each host cell (i.e., the *T. reesei* parental host cell, the variant A4-7 host cell and the variant C2-28 host cell) were added separately to 50-mL of YEG broth in a 250-mL Erlenmeyer flask with bottom baffles. The YEG broth contains 5 g/L yeast extract and 22 g/L glucose. The cell cultures were grown for 48 hours, followed by sub-culturing into fresh YEG for another 24 hours. These seed cultures were then inoculated into either 50 mL of defined medium supplemented with 1.5% glucose (non-inducing condition), or 50 mL of defined medium with 1.5% glucose/sophorose (inducing condition) in 250 mL shake flasks with bottom baffles.

All shake flasks were incubated at 28° C. with continuous shaking at 200 rpm. After 3 days of incubation, supernatant from all cell cultures were harvested and analyzed using PAGE as described in Example 2 above. The total protein in the supernatants were measured by the Bradford dye-binding assay at 595 nm using the Bio-Rad reagent (Thermo Scientific©; Catalogue No.: 23236) and five dilutions of bovine serum albumin (BSA) as a standard. The glucose concentrations were measured by High Performance Liquid Chromatography (HPLC) analysis, and no glucose was detected in cultures after 3 days of incubation.

Figure 4:
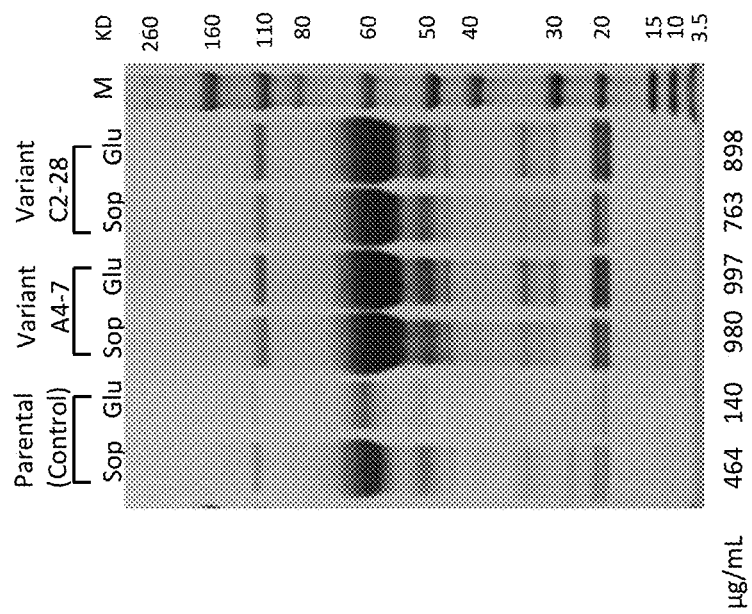
FIG. 4 presents a SDS-PAGE of *T. reesei* parental and variant cell supernatants, wherein the parental and variant cells were grown in defined medium supplemented with either 1.5% glucose/sophorose (sop) or 1.5% glucose (glu) in shake flasks. Equal volumes of culture supernatant were loaded in each lane. The total protein concentrations of the culture supernatants are listed at the bottom of each corresponding lane. M is molecular weight marker and KD is kilodalton.
Figure 5:
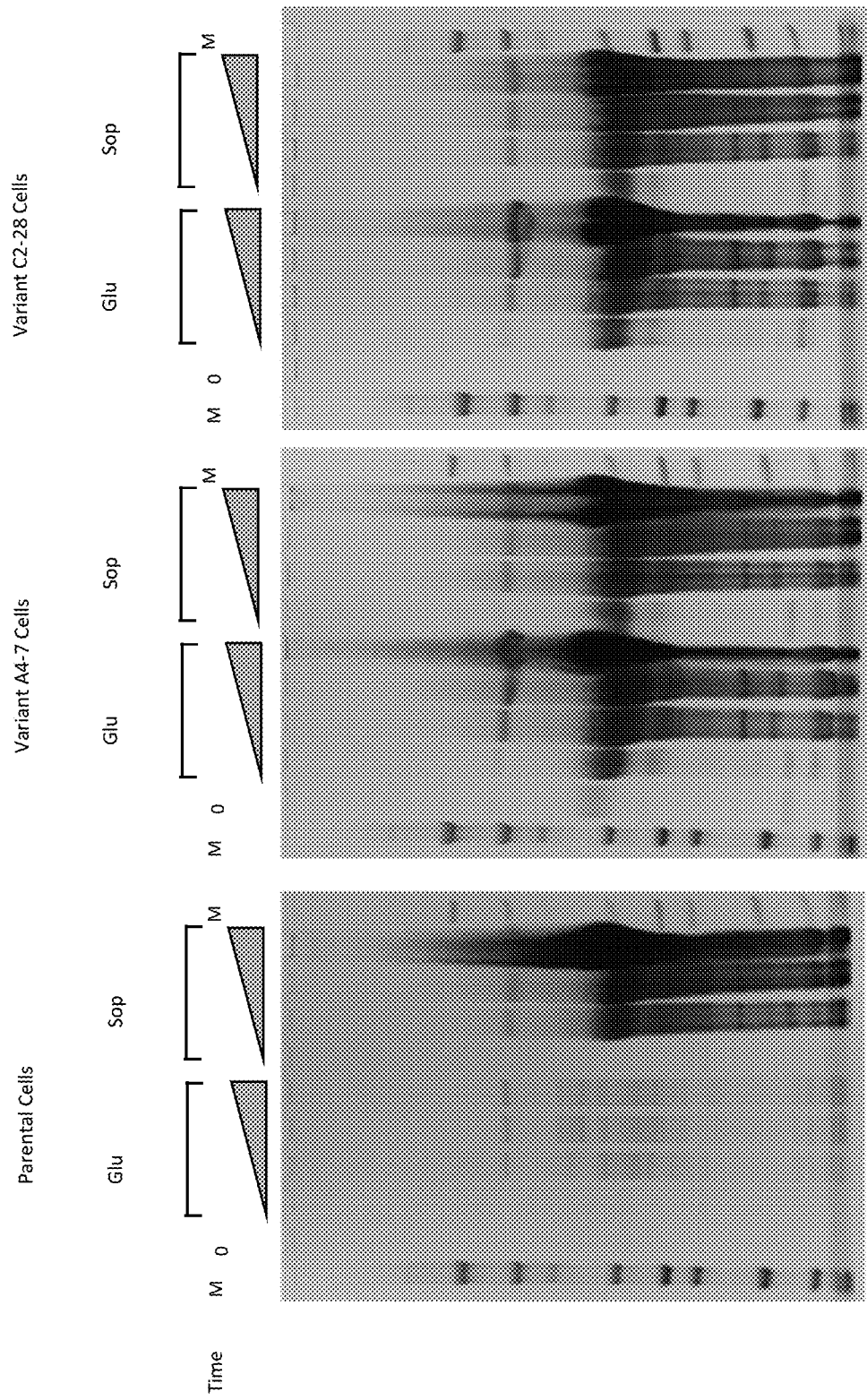
FIG. 5 presents a SDS-PAGE of *T. reesei* parental and variant cells grown in defined medium with either glucose/sophorose (sop) or glucose (glu) as carbon sources in 2 L fermenters. M is molecular weight marker and zero (0) is seed culture supernatant.

As shown in FIG. 4, the parental (control) *T. reesei* cells produced 464 µg/mL total secreted protein in defined medium with glucose/sophorose (inducing), and only 140 µg/L of total secreted protein in defined medium with glucose (non-inducing). In contrast, variant A4-7 cells and C2-28 cells produced similar amounts of secreted protein under inducing and non-inducing conditions, both of which are higher than the secreted protein produced in the parental (control) cells with sophorose (induction). Thus, these results demonstrate that the variant cells harboring the Ace3-L ORF (i.e., the variant A4-7 and C2-28 cells) not only produce extracellular proteins in the absence of an inducer, but these variant cells also produce more total protein than the parental (control) *T. reesei* cells under such inducing conditions.

Example 4

Protein Production in Small Scale Fed-Batch Fermentation

The instant example shows that the variant Ace3-L expressing cells (i.e., variant A4-7 and C2-28 cells) produced similar amounts of cellulase and hemi-cellulase enzymes in the presence and absence of an inducer substrate in a small scale fermentation. More particularly, *T. reesei* fermentation was carried out generally as described in U.S. Pat. No. 7,713,725, using seed cultures in citrate minimal medium in a 2 L bioreactor. More specifically, during fermentation, the supernatant from all cultures was harvested at different time points, and equal volumes of the culture supernatants were subjected to PAGE analysis. As is shown in FIG. 5, the parental (control) *T. reesei* cells only produced secreted proteins in the presence of the sophorose inducer. In contrast, the variant A4-7 and C2-28 cells (FIG. 5) produced similar amounts of protein, both under inducing and non-inducing conditions.

Example 5

Heterologous Promoters for Ace3 Expression

The present example demonstrates enhanced protein production under "non-inducing" conditions using thirteen (13) different promoters driving the expression of ace3-L. More particularly, *T. reesei* cells expressing the ace3-L gene were generated by transforming parental *T. reesei* cells with a telomere vector containing the pyr2 gene, a heterologous promoter and the ace3-L gene, using protoplast transformation.

Thus, thirteen *T. reesei* promoters were selected to drive the expression of ace3-L ORF, wherein the thirteen promoters tested include, but are not limited to: (i) a formamidase gene (rev3; Protein ID 103041) promoter (SEQ ID NO: 15), (ii) a β-xylosidase gene (bxl; Protein ID 121127) promoter (SEQ ID NO: 16), (iii) a transketolase gene (tkl1; Protein ID 2211) promoter (SEQ ID NO: 17), (iv) a gene of unknown function (Protein ID 104295) promoter (SEQ ID NO: 18), (v) an oxidoreductase gene (dld1; Protein ID 5345) promoter (SEQ ID NO: 19), (vi) a xylanase IV gene (xyn4; Protein ID 111849) promoter (SEQ ID NO: 20), (vii) an α-glucuronidase gene (Protein ID 72526) promoter (SEQ ID NO: 21), (viii) an acetyl xylan esterase gene 1 (axe1; Protein ID 73632) promoter (SEQ ID NO: 22), (ix) a hexose kinase gene (hxk1; Protein ID 73665) promoter (SEQ ID NO: 23), (x) a mitochondrial carrier protein gene (dic1; Protein ID 47930) promoter (SEQ ID NO: 24), (xi) an oligopeptide transporter gene (opt; Protein ID 44278) promoter (SEQ ID NO: 25), (xii) a glycerol kinase gene (gut; Protein ID 58356) promoter (SEQ ID NO: 26) and (xiii) a pyruvate kinase gene (pki1; Protein ID 78439) promoter (SEQ ID NO: 27). Protein ID (PID) numbers are from genome.jgi.doe.gov/Trire2/Trire2.home.html. Thus, the thirteen promoters described above were selected to drive expression because the genes thereof are generally expressed at a low level during growth when glucose concentration is high, and are expressed at a higher level when glucose concentration is low, or under sophorose-inducing conditions.

Figure 7:
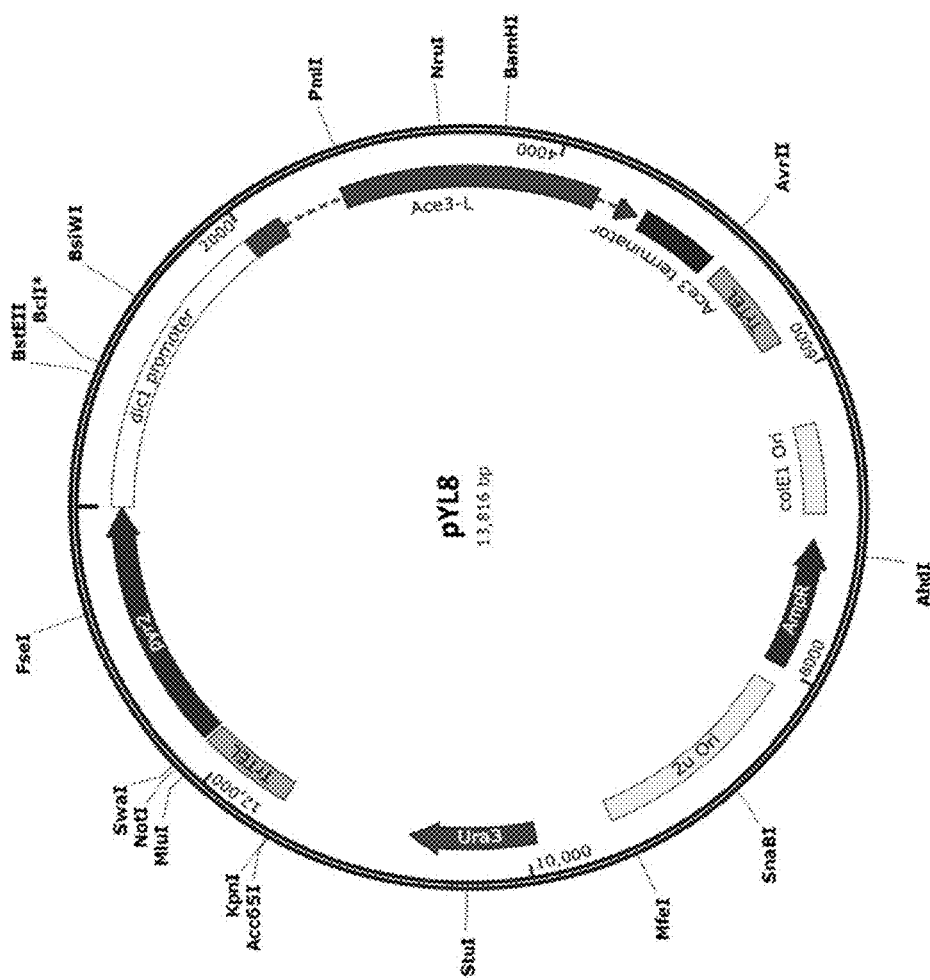
FIG. 7 shows a schematic representation of Ace3-expression vector pYL8 comprising the dic1 promoter.

Table 2 below summarizes the thirteen promoters and expression vectors thereof, which were constructed using standard molecular biological procedures. More particularly, the expression vectors tested in the instant example (Table 2) comprise a vector backbone with the bacterial ColE1 on and AmpR gene for replication and selection in *E. coli*, and the 2μ on and Ura3 gene for replication and selection in *Saccharomyces cerevisiae*. In addition, *T. reesei* telomere sequences ("TrTEL"), *T. reesei* pyr2 selection marker, a *T. reesei* promoter sequence, and the ace3-L ORF, with its native terminator sequence are present. A representative vector map is shown in FIG. 7, depicting vector pYL8 containing the dic1 promoter. Thus, the other vectors (e.g., pYL9, pYL12, etc.) have the same sequences presented in FIG. 7, except for the different promoter sequences.

TABLE 2

ACE3-L EXPRESSION CONSTRUCTS UTILIZING DIFFERENT FUNGAL PROMOTERS TO DRIVE ACE3-L EXPRESSION

| Vector # | Promoter | ace3 ORF |
| --- | --- | --- |
| pYL7 | opt (SEQ ID NO: 25) | ace3-L |
| pYL8 | dic1 (SEQ ID NO: 24) | ace3-L |
| pYL9 | gut1 (SEQ ID NO: 26) | ace3-L |
| pYL12 | hxk1 (SEQ ID NO: 23) | ace3-L |
| pYL13 | pki1 (SEQ ID NO: 27) | ace3-L |
| pYL22 | rev3 (SEQ ID NO: 15) | ace3-L |
| pYL23 | PID 104295 (SEQ ID NO: 18) | ace3-L |
| pYL24 | tkl1 (SEQ ID NO: 17) | ace3-L |
| pYL25 | bxl (SEQ ID NO: 16) | ace3-L |
| pYL27 | dld1 (SEQ ID NO: 19) | ace3-L |
| pYL28 | xyn4 (SEQ ID NO: 20) | ace3-L |
| pYL29 | PID 72526 (SEQ ID NO: 21) | ace3-L |
| pYL30 | axe1 (SEQ ID NO: 22) | ace3-L |

The expression vectors were inserted (transformed) into a *T. reesei* parental host strain (comprising a non-functional pyr2 gene) by polyethylene glycol (PEG)-mediated protoplast transformation (Ouedraogo et al., 2015; Penttila et al., 1987). The transformants were grown on Vogel's minimal medium agar plates to select for uridine prototrophy acquired by the pyr2 marker. Stable transformants were obtained by transferring on Vogel's agar plate for two successive rounds, followed by two successive rounds of growth on non-selective PDA plates, and one round on Vogel's agar plate, after which single colonies were obtained by plating dilutions of a spore suspension.

The parental and transformed (daughter) *T. reesei* host cells described above were tested under both "non-inducing" and "inducing" conditions. For example, in the "non-inducing condition", cells were grown in 1.25 ml liquid broth of defined medium, supplemented with 2.5% glucose (wt/vol) in a regular 24 well microtiter plate (MTP). In the "inducing condition", cells were grown in 1.25 ml liquid broth of defined medium supplemented with 2.5% glucose/sophorose (wt/vol) in a MTP, wherein sophorose serves as a potent inducer for cellulase enzyme expression. Following incubation, the supernatants from all cultures were harvested and the total secreted protein was measured by the Bradford dye-binding assay at 595 nm using the Bio-Rad reagent (Thermo Scientific®; Catalogue No.: 23236), and five dilutions of bovine serum albumin (BSA) as a standard.

As shown in Table 3, the parental *T. reesei* cells only produced high levels of secreted proteins in the presence of the sophorose inducer. In contrast, the variant (daughter) *T. reesei* cells, comprising and expressing Ace3-L driven from thirteen different promoters, produced similar amounts of secreted protein, under both inducing and non-inducing conditions. As shown in Table 3, the protein levels for each modified (daughter) strain are presented as a ratio which is relative to the protein (concentration) produced by the parental strain (LT4) under glucose/sophorose (Glu/Sop) inducing conditions.

TABLE 3

TOTAL SECRETED PROTEIN OF *T. REESEI* PARENTAL STRAIN (LT4) RELATIVE TO MODIFIED *T. REESEI* (DAUGHTER) STRAINS UNDER INDUCING ("GLU/SOP") AND NON-INDUCING ("GLU") CONDITIONS

| Strain ID | Promoter | Glu/Sop[1] | Glu[2] |
|---|---|---|---|
| LT4 (parental) | N/A | 1.00 | 0.20 |
| LT82 | opt | 1.16 | 1.07 |
| LT83 | dic1 | 1.35 | 1.12 |
| LT85 | gut1 | 0.95 | 1.08 |
| LT86 | hxk1 | 0.96 | 0.73 |
| LT87 | pki1 | 1.16 | 0.98 |
| LT149 | rev3 | 0.96 | 0.76 |
| LT150 | PID 104295 | 0.94 | 0.41 |
| LT151 | tkl1 | 1.02 | 1.01 |
| LT152 | bxl | 1.00 | 1.04 |
| LT154 | dld1 | 1.00 | 0.58 |
| LT155 | xyn4 | 0.95 | 0.95 |
| LT156 | PID 72526 | 0.95 | 0.89 |
| LT157 | axe1 | 1.01 | 0.85 |

Glu/Sop[1] is an abbreviation of "Glucose/Sophorose"; Inducing Condition.
Glu[2] is an abbreviation of "Glucose"; Non-Inducing Condition.

Additionally, the *T. reesei* parental strain and transformants thereof described above were further tested in shake flasks experiments as generally described in Example 3. For example, a representative result of *T. reesei* daughter strain "LT83" is shown in FIG. 8, wherein daughter strain LT83 comprises a ace3-L ORF driven from a dic1 promoter (SEQ ID NO: 28). As shown in FIG. 8, the parental (control) *T. reesei* cells only produced secreted proteins in the presence of the sophorose ("Sop") inducer, whereas daughter strain LT83 produced similar amounts of secreted protein, under both inducing ("Sop") and non-inducing ("Glu") conditions.

Likewise, small scale fermentations were performed as generally described in Example 4. More particularly, as shown in FIG. 9, the parental (control) *T. reesei* strain only produced secreted proteins in the presence of the sophorose inducer ("Sop"), whereas daughter strain LT83 produced similar amounts of protein, under both inducing ("Sop") and non-inducing ("Glu") conditions.

Example 6

Cloning of *T. reesei* ACE3 Over Expression Constructs

Although the genome sequence of *T. reesei* is publicly available at the Joint Genome Institute (https://genome.jgi.doe.gov/), the position of the 5' end of the ace3 coding region is not obvious. For example, annotation of the DNA sequence at the Joint Genome Institute differed between mutant strain Rut-C30 (genome.jgi.doe.gov/Trir-eRUTC30_1/TrireRUTC30_1.home.html) and the wild-type strain QM6a (genome.jgi.doe.gov/Trire2/Trire2.home.html), even though the DNA sequence is the same. In the QM6a case, the 5' end of the ace3 coding region was suggested to be upstream (5') of exon 3 and within intron 2, as shown in FIG. 11, arrow 3. In the Rut-C30 case, the 5' end of the ace3 coding region is within exon 2 (FIG. 11, arrow 2). Further analysis of the genomic DNA sequence and additional cDNA sequence suggested the possible existence of exon 1 and intron 1, as shown in FIG. 11. In addition, the 3' end of the ace3 coding region in Rut-C30 comprises a mutation, creating a premature stop codon (FIG. 11, arrow 4), relative to the sequence of the wild-type isolate QM6a (FIG. 11, arrow 5). Thus, in the present example, the effects of over-expressing these different possible forms of the ace3 gene were experimentally studied as described herein (e.g., see, FIG. 11, FIG. 12 and FIG. 13-18).

Thus, the different forms of ace3 depicted in FIG. 12 were over-expressed in *T. reesei*, wherein the over-expression vectors for the *T. reesei* ace3 genes were designed to enable targeted integration of ace3 at the glucoamylase locus (gla1) in *T. reesei*. More particularly, in all of the plasmid (vector) constructs, the *T. reesei* ace3 gene was expressed under control of the *T. reesei* dic1 promoter and with the native ace3 terminator. The vectors further comprise a pyr4 marker with its native promoter and terminator for selection of *T. reesei* transformants. A repeat of the pyr4 promoter was included to enable excision of the pyr4 gene after integration at the gla1 locus. The vector backbone enabling replication and amplification in *E. coli* was EcoRI-XhoI digested pRS426 (Colot et al., 2006). The 5' and 3' flanks of the *T. reesei* gla1 locus needed for targeted integration, the dic1 promoter, the different forms of the ace3 coding region and terminator were produced by PCR using primers given in Table 4. Template for the flanking fragments was genomic DNA from wild type *T. reesei* QM6a (ATCC Deposit No. 13631).

TABLE 4

PRIMERS USED TO GENERATE DNA FRAGMENTS

| PRIMER | SEQUENCE |
|---|---|
| Gla.5F (SID: 49) | GTAACGCCAGGGTTTTCCCAGTCACGACGGTTTAAACTCCATACGCAGCAAACATGGGCTTGGGC |
| Gla.5R (SID: 50) | GTACGAGTACTAGGTGTGAAGATTCCGTCAAGCTTGGGCGGAATGAAGGAGGATGTGTGAGAGG |
| DICprom.F (SID: 51) | CACACATCCTCCTTCATTCCGCCCAAGCTTGACGGAATCTTCACACCTAGTACTCGTAC |
| Ace3RutC.R (SID: 52) | TGACATTTTTGTTGTTCCAACACAGCATGCTTAGTCCGACGCCTTCGAGTCCAGCC |
| Ace3term.F (SID: 53) | CTGGACTCGAAGGCGTCGGACTAAGCATGCTGTGTTGGAACAACAAAAAATGTC |
| Ace3term.R (SID: 54) | GCAGAGCAGCAGTAGTCGATGCTATTAATTAAGTAGGTTATGCGAGCAACATTG |

TABLE 4-continued

PRIMERS USED TO GENERATE DNA FRAGMENTS

| PRIMER | SEQUENCE |
| --- | --- |
| Gla.3F (SID: 55) | CTCAGCCTCTCTCAGCCTCATCAGCCGCGGCCGCTGAATCGGCAAGGGGTAGTACTAG |
| Gla.3R (SID: 56) | GCGGATAACAATTTCACACAGGAAACAGCGTTTAAACCACATGCCAGAGTTCGATGCGCAAG |
| Ace3_nointron.F (SID: 57) | GTACCTCAGCGCTGTCGATAGCTGCACGCACTGCCGCGATGCCCACGTGCAGTGCAC |
| Ace3_nointron.R (SID: 58) | GTGCACTGCACGTGGGCATCGCGGCAGTGCGTGCAGCTATCGACAGCGCTGAGGTACTC |
| Ace3QM.F (SID: 59) | GCGGCGCTTCCGCTGTCGTAACTATGCTGCGCTACTCCCCCGTCTTAC |
| DICpromQM.R (SID: 60) | GTAAGACGGGGGAGTAGCGCAGCATAGTTACGACAGCGGAAGCGCCGCCTTATAAGTG |
| Ace3RutC.F (SID: 61) | GGCGGCGCTTCCGCTGTCGTAACTATGGGCTCAGCAGCTCCGGCCCAGGGCTC |
| DICpromrutc.R (SID: 62) | GCCCTGGGCCGGAGCTGCTGAGCCCATAGTTACGACAGCGGAAGCGCCGCCTTATAAG |
| Ace3cDNA.F (SID: 63) | GGCGGCGCTTCCGCTGTCGTAACTATGGCCACAGCGGCCGCGGCAGCAGCTGG |
| DICprom_cDNA.R (SID: 64) | CAGCTGCTGCCGCGGCCGCTGTGGCCATAGTTACGACAGCGGAAGCGCCGCCTTATAAG |

"SID" in the above table is an abbreviation of "Sequence Identification Number", e.g., "SEQ ID NO"

For the dic1 promoter, ace3 gene and terminator, template was an earlier plasmid pYL8 (See, Example 5) carrying these fragments. Selection marker (pyr4) was obtained from an earlier plasmid with NotI digestion. PCR primers used to generate the desired DNA fragments are shown in Table 4. PCR products and digested fragments were separated using agarose gel electrophoresis. Correct fragments were isolated from the gel with a gel extraction kit (Qiagen) according to manufacturer's protocol. The plasmids were constructed with the fragments described above using yeast homologous recombination method as described in PCT/EP2013/050126 (published as WO2013/102674). Plasmids were rescued from yeast and transformed to E. coli. A few clones were selected, plasmid DNA isolated and sequenced. An overview of the plasmids is presented in Table 5.

TABLE 5

OVER-EXPRESSION PLASMIDS

| Plasmid | Code | Cloned gene | Selection | locus | NOTE | Gene SEQ ID | Protein SEQ ID |
| --- | --- | --- | --- | --- | --- | --- | --- |
| B7683 | SC | ace3 SC form | PYR4 | GLA | QM6a N-term; RutC-30 C-term | 7 | 8 |
| B7684 | S | ace3 S form | PYR4 | GLA | QM6a N-term; QM6a C-term | 1 | 3 |
| B7709 | L | ace3 L form | PYR4 | GLA | RutC-30 N-term; RutC-30 C-term | 4 | 6 |
| B7752 | LC | ace3 LC form | PYR4 | GLA | RutC-30 N-term; QM6a C-term | 9 | 10 |
| B7778 | EL | ace3 EL form | PYR4 | GLA | RutC-30 N-term; RutC-30 C-term | 11 | 12 |
| B7779 | LN | ace3 LN form | PYR4 | GLA | RutC-30 N-term; RutC-30 C-term | 13 | 14 |

Thus, the constructs presented in Table 5 differ by having different forms of the ace3 gene. The SC form is a short form of the gene comprising exons 3 and 4, as well as intron 3 (see, FIG. 12 and FIG. 13, SEQ ID NO: 7). More particularly, SC form of SEQ ID NO: 7 comprises a 1,713 bp Exon 3, a 148 bp Intron 3 and a 144 bp Exon 4. The (3'-end) C-terminus of the SC form (i.e., Exon 4) has the same mutation as the T. reesei RutC-30 strain.

The S form is a short form of the gene comprising exons 3 and 4, as well as intron 3, but without the mutation in the (3'-end) C-terminus of Exon 4 (see, FIG. 12 and FIG. 14, SEQ ID NO: 1). More particularly, the S form comprises a 1,713 bp Exon 3, a 148 bp Intron 3 and a 177 bp Exon 4. In both of these forms (i.e., "SC" and "S"), the translation start codon is in the long intron 2 (see, FIG. 12), as annotated for T. reesei QM6a strain, and both "SC" and "S" forms are missing part of the coding region for the putative DNA binding domain.

The L form is a long form of the gene comprising exons 2, 3 and 4, as well as intron 2 (long intron) and intron 3 (e.g., see, FIG. 12 and FIG. 15, SEQ ID NO: 4). More particularly, the L form comprises a 258 bp Exon 2, a 423 bp Intron 2, a 1,635 bp Exon 3, a 148 bp Intron 3 and a 144 bp Exon 4. The (3'-end) C-terminus of the "L" form has the same mutation as the *T. reesei* RutC-30 strain.

The LC form is a long form of the gene comprising exons 2, 3 and 4, as well as intron 2 (long intron) and intron 3 (e.g., see, FIG. 12 and FIG. 16, SEQ ID NO: 9). More particularly, the LC form comprises a 258 bp Exon 2, a 423 bp Intron 2, a 1,635 bp Exon 3, a 148 bp Intron 3 and a 177 bp Exon 4. The LC form is without the mutation in the C-terminus. In both the "L" and "LC" forms, the translation start codon is within exon 2 as annotated at JGI for the Rut-C30 strain.

The EL form is an extra-long version of the ace3 gene comprising exons 1, 2, 3 and 4, as well as intron 1, intron 2 (long intron) and intron 3 (e.g., see, FIG. 12 and FIG. 17, SEQ ID NO: 11). More particularly, the EL form comprises a 61 bp Exon 1, a 142 bp Intron 1, a 332 bp Exon 2, a 423 bp Intron 2, a 1,635 bp Exon 3, a 148 bp Intron 3 and a 144 bp Exon 4. The (3'-end) C-terminus of the EL form has the same mutation as the *T. reesei* RutC-30 strain.

The LN form is a long form of the gene containing exons 2, 3 and 4, as well as intron 3, but lacking intron 2 (e.g., see, FIG. 12 and FIG. 18, SEQ ID NO: 13). The (3'-end) C-terminus of the LN form has the same mutation as the *T. reesei* RutC-30 strain. Thus, as described above, the L, LC, LN and EL forms of ace3 encode a full putative DNA binding domain.

Transformation into the *T. reesei* RL-P37 Strain

Figure 19:
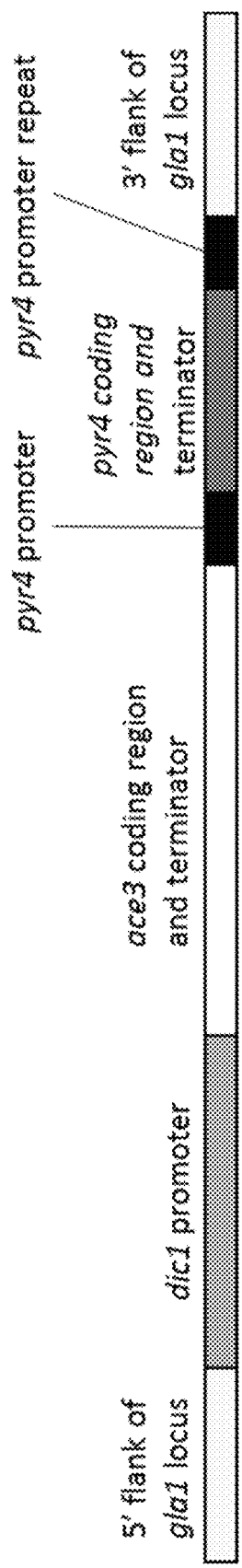
FIG. 19 presents a schematic diagram of the arrangement of DNA fragments designed for integration of ace3 forms at the gla1 locus.

All of the plasmids presented in Table 5 were digested with MssI to release the fragments for targeted integration and separated with agarose gel electrophoresis. For example, FIG. 19 provides a diagram showing the arrangement of DNA sequences within a representative fragment used for transformation of *T. reesei*. Correct fragments were isolated from the gel using a gel extraction kit (Qiagen) according to the manufacturer's protocol. Approximately 10 μg purified fragment was used to transform protoplasts of a pyr4⁻ mutant of *T. reesei* RL-P37 strain. Preparation of protoplasts and transformation were carried out as described in PCT Publication No. WO2013/102674, using pyr4 selection.

Transformants were streaked onto selective medium plates. Growing clones were screened for correct integration by PCR using primers listed in Table 6. Clones giving expected signals were purified to single cell clones and rescreened for correct integration and clone purity by PCR using primers listed in Table 6, as well as by Southern blotting (data not shown).

TABLE 6

PCR PRIMERS

| Primer | Sequence | SEQ ID NO: |
|---|---|---|
| Gla1_5creen.F | GCTGGAAGCTGCTGAGCAGATC | 65 |
| DICprom.R | GTGCCAGCATTCCCCAGACTCG | 66 |
| T061_pyr4_orf_screen | TTAGGCGACCTCTTTTTCCA | 67 |

TABLE 6-continued

PCR PRIMERS

| Primer | Sequence | SEQ ID NO: |
|---|---|---|
| Gla1_3creen.R | GCCGCTCAGGCATACGAGCGAC | 68 |
| DICprom.F2 | CTCTGGTCGGCCTGCCGTTG | 69 |
| ace3.R | TGAGTATAGCGGCTGACTTGTCG | 70 |

Cultivation of the Different ace3 Transformants

The strains in Table 7 were grown in 24-well microtiter plates in liquid medium with either 2% lactose or 2% glucose as carbon source. The other components of the medium were 0.45% KH2PO4, 0.5% (NH4)2SO4, 0.1% MgSO4, 0.1% CaCl$_2$), 0.9% Casamino acids, 0.048% Citric Acid×H2O, 0.05% FeSO4×7H2O, 0.0003% MnSO4×H2O, 0.004% ZnSO4×7H2O, 0.0002% H3BO3 and 0.00014% CuSO4×5H2O. 100 mM PIPPS (Calbiochem) was included to maintain the pH at 5.5.

TABLE 7

*TRICHODERMA REESEI* STRAINS

| Code | Name of the strain | Selection |
|---|---|---|
| M1904 | RL-P37, parental strain | |
| M2015 | ace3 SC clone 2-1 | Pyr4 |
| M2016 | ace3 SC clone 28-3 | Pyr4 |
| M2017 | ace3 S clone 9-1 | Pyr4 |
| M2018 | ace3 S clone 20-1 | Pyr4 |
| M2019 | ace3 L clone 16-1 | Pyr4 |
| M2020 | ace3 L clone 18-1 | Pyr4 |
| M2021 | ace3 LC clone 52-1 | Pyr4 |
| M2022 | ace3 LC clone 14-4 | Pyr4 |
| M2023 | ace3 EL clone 3-3 | Pyr4 |
| M2024 | ace3 EL clone 4-5 | Pyr4 |
| M2025 | ace3 LN clone 3-3 | Pyr4 |
| M2026 | ace3 LN clone 4-1 | Pyr4 |

The cultures were carried out at 28° C. and 800 RPM in Infors HT microton shaker with 80% humidity. Sampling of the cultures was performed at days 3-7. The amount of total secreted proteins was measured from the culture supernatants using Bio Rad Protein Assay according to manufacturer's protocol. In both media, the over-expression of the ace3 L, EL and LN forms with the RutC-30 C-terminal mutation, improved the production of total proteins. In the medium with lactose as the carbon source, over-expression of all the forms of ace3 gene improved the production of total proteins to some extent, but the level of improvement was highest in the strains over-expressing the L, EL and LN forms of the ace3 gene. It is clear that high levels of secreted protein (Table 8) were observed when glucose (i.e., non-inducing condition) was used as a carbon source with transformants in which the L, EL or LN forms of the ace3 gene were over-expressed.

TABLE 8

TOTAL PROTEINS PRODUCED BY THE DIFFERENT STRAINS IN 24-WELL PLATE CULTIVATION

| | Strain | 5 d, mg/ml | 7 d, mg/ml |
|---|---|---|---|
| LACTOSE | M2015 | 0.77 | 1.21 |
| | M2016 | 0.54 | 0.91 |
| | M2017 | 0.47 | 0.81 |

TABLE 8-continued

TOTAL PROTEINS PRODUCED BY THE DIFFERENT STRAINS
IN 24-WELL PLATE CULTIVATION

|  | Strain | 5 d, mg/ml | 7 d, mg/ml |
|---|---|---|---|
|  | M2018 | 1.23 | 1.12 |
|  | M2019 | 2.50 | 6.37 |
|  | M2020 | 1.97 | 6.53 |
|  | M2021 | 0.67 | 1.17 |
|  | M2022 | 1.19 | 1.09 |
|  | M2023 | 1.84 | 4.10 |
|  | M2024 | 2.05 | 4.09 |
|  | M2025 | 1.76 | 3.60 |
|  | M2026 | 1.93 | 4.04 |
|  | M1904 | 0.40 | 0.65 |
| GLUCOSE | M2015 | 0.59 | 0.89 |
|  | M2016 | 0.12 | 0.56 |
|  | M2017 | 0.00 | 0.19 |
|  | M2018 | 0.02 | 0.26 |
|  | M2019 | 1.57 | 2.74 |
|  | M2020 | 1.79 | 2.91 |
|  | M2021 | 0.03 | 0.40 |
|  | M2022 | 0.06 | 0.21 |
|  | M2023 | 1.40 | 2.44 |
|  | M2024 | 1.37 | 2.52 |
|  | M2025 | 1.24 | 2.26 |
|  | M2026 | 1.49 | 2.64 |
|  | M1904 | 0.02 | 0.37 |

Example 7

Endogenous Ace3 Heterologous Promoter Knock-In

A promoter replacement construct (see, FIG. 6) is made by fusing a DNA fragment comprising a 5' region upstream of the native promoter at the ace3 locus, a loxP-flanked hygromycin B-resistance selectable marker cassette, and a fragment comprising a promoter of interest operably fused to the 5' end of the ace3 open reading frame (e.g., see International PCT Application Serial No. PCT/US2016/017113, which further describes gene/promoter replacement cassettes for use in filamentous fungi).

Thus, a *Trichoderma reesei* cell is transformed with the promoter replacement construct described above, wherein transformants are isolated and genomic DNA is extracted for diagnostic PCR to confirm homologous recombination of the promoter replacement construct at the native ace3 locus. Using this method, a transformant may be identified in which the native ace3 promoter is replaced by the hygromycin-B resistance cassette and any promoter of interest. Subsequently, the hygromycin B-resistance cassette is removed by the action of cre recombinase (Nagy, 2000).

The efficiency of homologous integration at the ace3 locus may be enhanced by the action of cas9 directed to the native ace3 promoter by a suitably designed guide RNA as exemplified in International PCT Publication Nos: WO2016/100272, WO2016/100571 and WO2016/100568.

A conditional promoter replacement (CPR) strategy is described for *Aspergillus fumigatus* in the publication by Hu et al. (2007), which generally describes a strategy that uses the *A. fumigatus* NiiA nitrogen regulatable promoter (pNiiA) to delete and replace the endogenous promoter of selected genes. Thus, in certain embodiments, an analogous method can be used to replace the endogenous promoter of the ace3 gene in *Trichoderma reesei* with alternate promoters.

Example 8

Replacing an Endogenous Non-Lignocellulosic Gene of Interest Promoter with a Lignocellulosic Gene of Interest Promoter A *Trichoderma reesei* glucoamylase expression construct was assembled from DNA polynucleotide fragments (e.g., see U.S. Pat. No. 7,413,879), wherein an ORF sequence encoding a *T. reesei* glucoamylase was operably linked to a 5' (upstream) *T. reesei* cbh promoter and operably linked to a 3' (downstream) *T. reesei* cbh1 terminator. The DNA construct further comprised a *T. reesei* pyr2 gene as selectable marker.

Thus, a variant (daughter) *T. reesei* cell of the disclosure (i.e., comprising a genetic modification which increases expression of a gene encoding an Ace3-L protein) was transformed with the glucoamylase expression construct. Transformants were selected and cultured in liquid medium with glucose as carbon source (i.e., without an inducing substrate such as sophorose or lactose) in order to identify those transformants that were able to secrete the *T. reesei* glucoamylase enzyme during culture.

Thus, a *T. reesei* glucoamylase expressing (parental) strain (control) and a modified *T. reesei* (daughter) glucoamylase expressing strain (i.e., comprising and expressing an Ace3-L ORF) were grown in shake flask, and supernatant from all cell cultures were harvested and analyzed using PAGE as generally described in Example 2 and Example 3 above.

Figure 10:
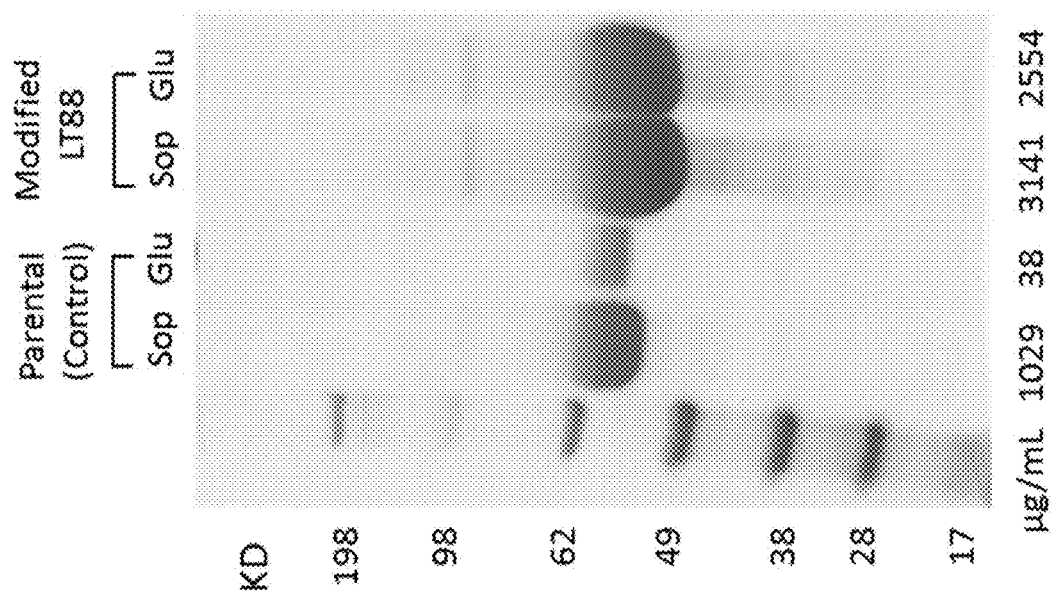
FIG. 10 shows a SDS-PAGE of *T. reesei* parental and its modified (daughter) cell supernatants, wherein the parental and modified strains were grown in defined medium supplemented with either 2.5% glucose/sophorose ("Sop", inducing condition) or 2.5% glucose ("Glu", non-inducing condition) in shake flasks. Equal volumes of culture supernatant were loaded in each lane. M is molecular weight marker and KD is kilodalton.

More particularly, as shown in FIG. 10, the parental *T. reesei* cells produced 1,029 µg/mL of glucoamylase in defined medium with glucose/sophorose (inducing condition), and only 38 µg/mL of glucoamylase in defined medium with glucose (non-inducing condition). In contrast, the modified (daughter) strain "LT88", comprising ace3-L driven from the dic1 promoter, produced 3-fold higher glucoamylase under "inducing" ("Sop") conditions (i.e., relative to the parental (control) strain under inducing conditions), and produced 2.5-fold higher glucoamylase under "non-inducing" ("Glu") conditions (i.e., relative to the parental (control) strain under inducing conditions) or 67-fold higher glucoamylase under "non-inducing" ("Glu") conditions relative to the parental (control) strain under non-inducing conditions. Thus, these results demonstrate that the modified (daughter) cells comprising the Ace3-L ORF not only produce extracellular proteins in the absence of an inducer, but these variant cells also produce more total protein than the parental (control) *T. reesei* cells under such inducing conditions.

Example 9

Replacing a Natively Associated Heterologous Gene of Interest Promoter with a Lignocellulosic Gene of Interest Promoter A phytase expression construct is assembled from DNA polynucleotide fragments as follows (e.g., see U.S. Pat. No. 8,143,046). The ORF encoding *Buttiauxella* sp. phytase is operably linked at the 5' end to the *T. reesei* cbh1 promoter and at the 3' end to the *T. reesei* cbh1 terminator. The DNA construct further comprises a selectable marker, the *Aspergillus nidulans* amdS gene. A variant *T. reesei* cell (i.e., comprising a genetic modification which increases expression of a gene encoding an Ace3-L protein) is transformed with the phytase expression construct. Transformants are selected and cultured in liquid medium with glucose as carbon source (i.e., without an inducing substrate such as sophorose or lactose) in order to identify those transformants that are able to secrete *Buttiauxella* phytase enzyme during culture.

Example 10

Construction of Native ace3 Promoter Replacement Vectors

Figure 20:
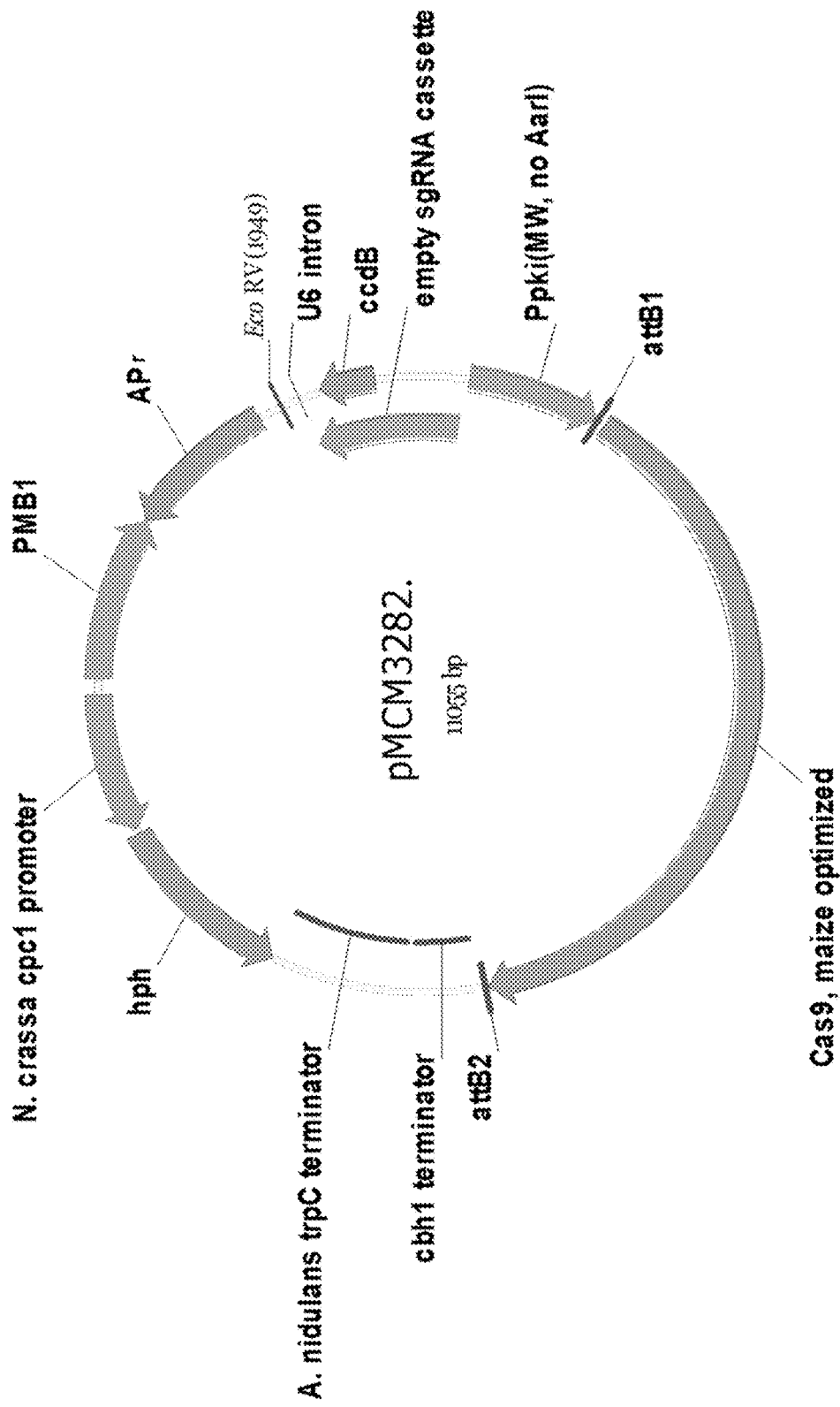
FIG. 20 shows a schematic representation of vector pMCM3282.

In the present example, two ace3 promoter replacement vectors pCHL760 and pCHL761 were constructed using standard molecular biological procedures. Vector backbone pMCM3282 (FIG. 20) contained pMB1 on and AmpR gene for replication and selection in *E. coli*. In addition, the hph hygromycin selection marker for *Trichoderma reesei*, expressed under *N. crassa* cpc1 promoter and *A. nidulans* trpC terminator, was included. For promoter replacement, the vectors contained a *Streptococcus pyogenes* cas9 codon optimized for maize, expressed under *T. reessei* pki1 promoter and guide RNA expressed under U6 promoter (e.g., see, PCT Publication No: WO2016/100568 and WO2016/100272).

Figure 21:
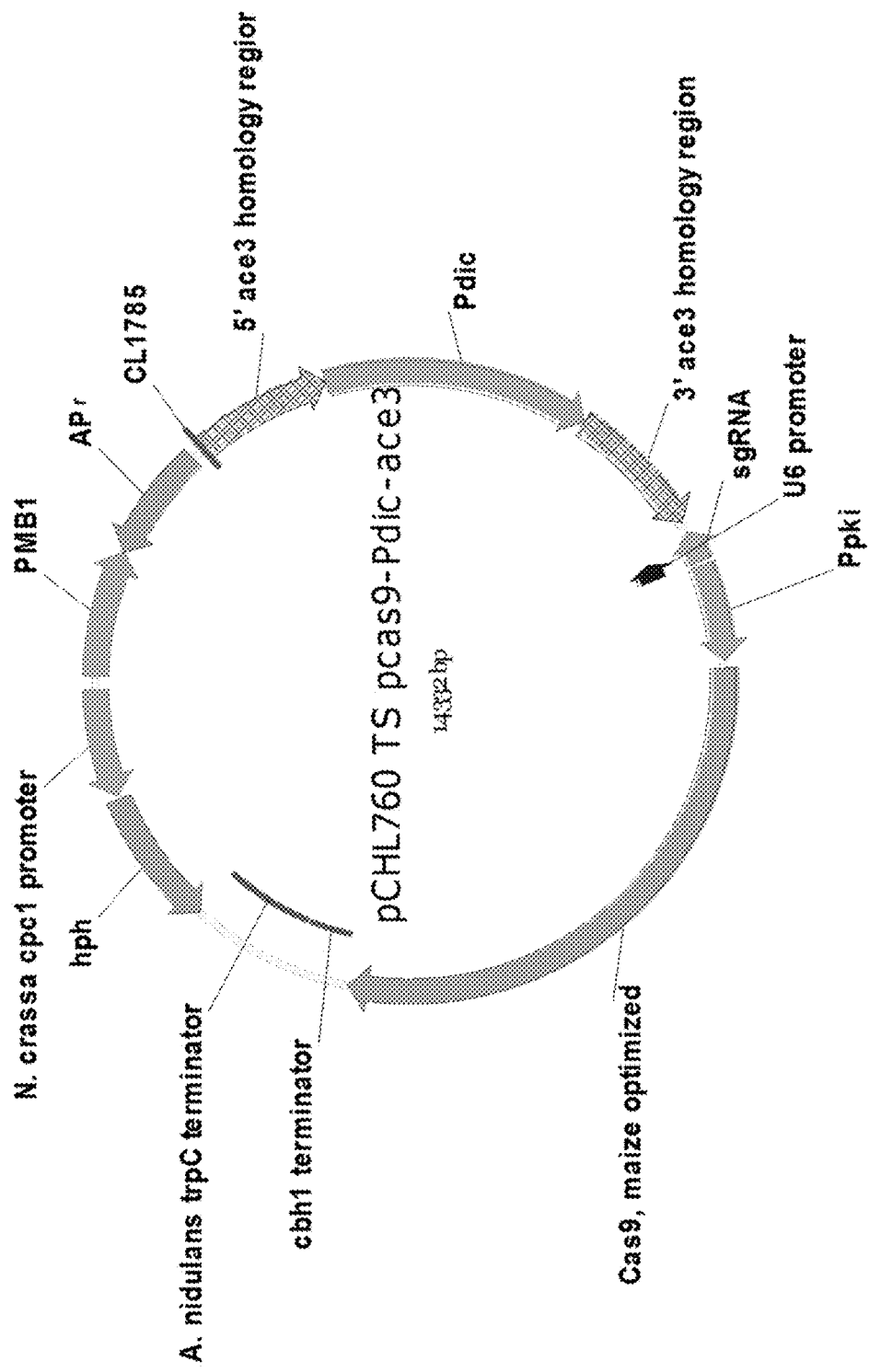
FIG. 21 shows a schematic representation of vector pCHL760.
Figure 22:
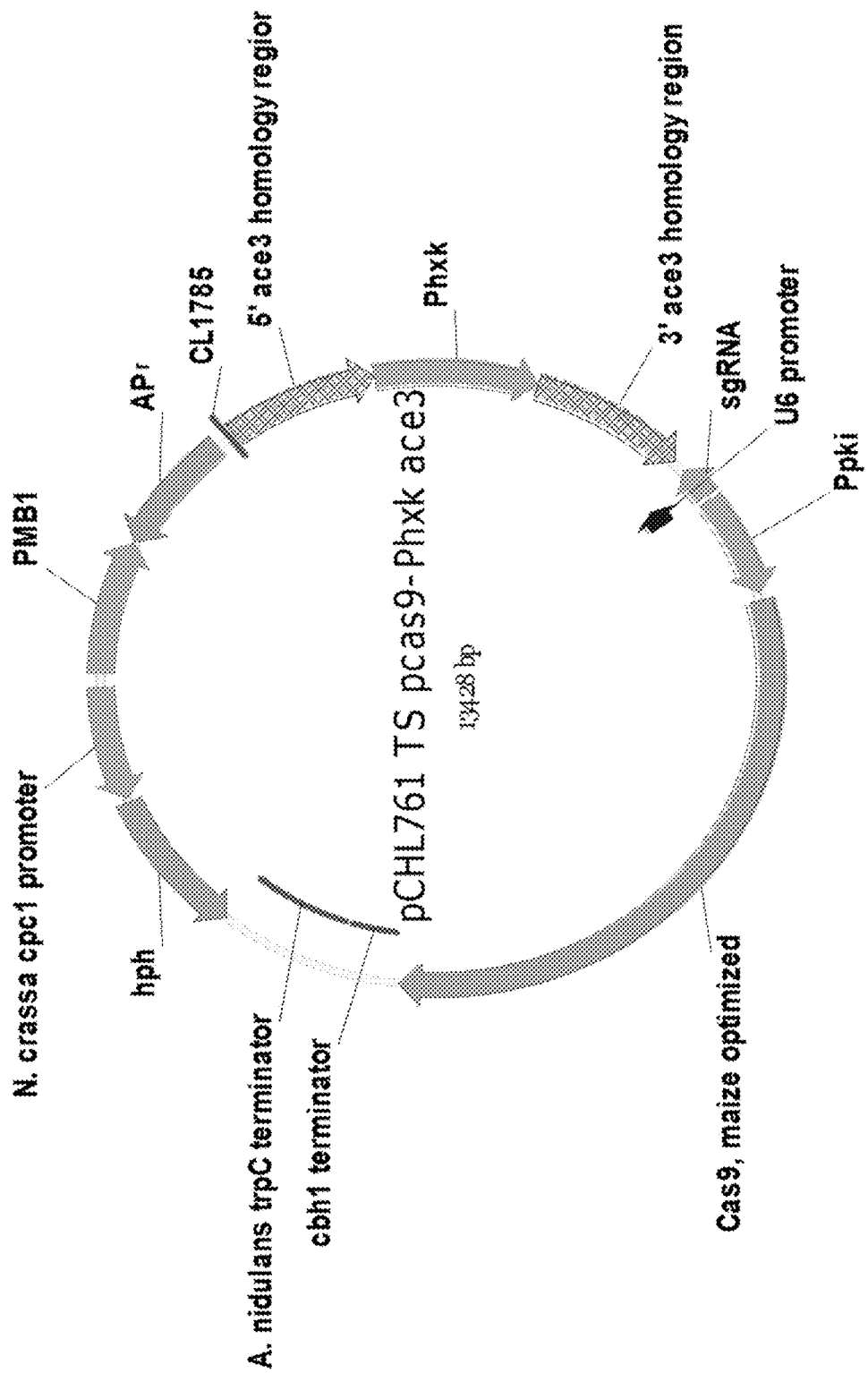
FIG. 22 shows a schematic representation of vector pCHL761.

Thus, pMCM3282 was digested with EcoRV and 3 fragments having 5' and 3' homology sequences of ~1 kb from the *T. reesei* ace3 locus flanking either the *T. reesei* hxk1 or dic1 promoter regions replacing the ace3 native promoter, were cloned into pMCM3282/EcoRV by Gibson assembly, resulted in pCHL760 (FIG. 21) and pCHL761 (FIG. 22).

The 5' and 3' ace3 homology sequences, along with either the hxk1 or dic1 promoter were PCR amplified from *T. reesei* genomic DNA using Q5 High-fidelity DNA polymerase (New England Biolabs) and the primers set forth below in Table 9.

TABLE 9

| | PCR PRIMERS |
|---|---|
| CL1791 (SID: 71) | TCTAGTATGTACGAGTACTAGGTGTGAAGATTCCGTCATTTCCTCGACATGCGAATGCG |
| CL1792 (SID: 72) | TGCCATGCAAACCCCGCATTCGCATGTCGAGGAAATGACGGAATCTTCACACCTAGTAC |
| CL1793 (SID: 73) | TGCAGCTACAGAGCCCTGGGCCGGAGCTGCTGAGCCCATAGTTACGACAGCGGAAGCGC |
| CL1794 (SID: 74) | ATAGCACTTATAAGGCGGCGCTTCCGCTGTCGTAACTATGGGCTCAGCAGCTCCGGC |
| CL1840 (SID: 75) | TAAACAAATAGGGGTTCCGCGCACATTTCCCCGAAAAGTGCCACCTGGATAGACTAGCATCTGAGCCATTGCAGC |
| CL1786 (SID: 76) | AGTGGCACCGAGTCGGTGGTGCTTTTTTTTCTATCGAGAGCATTGGTCAGTGGTGGCAAG |
| CL1800 (SID: 77) | ACCAATATACAAAACATGTCGTCCGAGCCAGTGCCTGCCATTTCCTCGACATGCGAATGC |
| CL1801 (SID: 78) | GTTGCCATGCAAACCCCGCATTCGCATGTCGAGGAAATGGCAGGCACTGGCTCGGACGAC |
| CL1802 (SID: 79) | AGCTACAGAGCCCTGGGCCGGAGCTGCTGAGCCCATTGTTGAATTCTGGCGGGGTAGCTG |
| CL1803 (SID: 80) | CTTTTACACTTTTCAACAGCTACCCCGCCAGAATTCAACAATGGGCTCAGCAGCTCCGGC |
| CL1831 (SID: 81) | TAGTCCGTTATCAACTTGAAAAAGTGGCACCGAGTCGGTGGTGCTTTTTTTTCTATCGAGATGTTCTGGATGGTGGAGAGG |

"SID" in the above table is an abbreviation of "Sequence Identification Number", e.g., "SEQ ID NO"

More particularly, the specific primers used to PCR amplify fragments for each vector are listed as follows. To construct pCHL760, 5' upstream homology region was amplified using primer pair CL1840 and CL1791, 3' downstream homology region was amplified using primers CL1794 and CL1831, dic1 promoter was amplified using primer pair CL1792 and CL1793.

To construct pCHL761, 5' upstream homology region was amplified using primer pair CL1840 and CL1800, 3' downstream homology region was amplified using primers CL1803 and CL1831, hxk1 promoter was amplified using primer pair CL1801 and CL1802.

Vector pMCM3282 (FIG. 20) includes, from 5' to 3' direction, the *T. reesei* U6 promoter, an *E. coli* ccdB cassette, and the structural region of a single-guide RNA (sgRNA) involved in Cas9 binding, including an intron from the U6 gene. The ccdB cassette was replaced with sequences specific for five different target sites within the *Trichoderma* ace3 gene. Insertion of guide RNA sequences into pCHL760 (FIG. 21) and pCHL761 (FIG. 22) to construct final ace3 promoter replacement vectors.

Thus, the following oligonucleotides presented in Table 10 with Aar1 restriction site were designed for production of different sgRNA sequences.

TABLE 10

Oligonucleotide sgRNA Sequences

| Oligo ID | Oligonucleotide Description | Oligonucleotide Sequence | SEQ ID NO: |
|---|---|---|---|
| CL1821 | top oligo for TS1 | AGTCTATCGCAGCCTTGCCTTAGCTAATGTTT | 82 |
| CL1822 | bottom oligo for TS1 | TCTAAAACATTAGCTAAGGCAAGGCTGCGATA | 83 |
| CL1823 | top oligo for TS4 | AGTCTATCGGCAGAGTCGCGTCTTCCGGGTTT | 84 |
| CL1824 | bottom oligo for TS4 | TCTAAAACCCGGAAGACGCGACTCTGCCGATA | 85 |
| CL1825 | top oligo for TS5 | AGTCTATCGAATGAGTGTAGGTACGAGTAGTTT | 86 |
| CL1826 | bottom oligo for TS5 | TCTAAAACTACTCGTACCTACACTCATTCGATA | 87 |
| CL1827 | top oligo for TS8 | AGTCTATCGGCCGCAATAGCTTCCTAATGTTT | 88 |
| CL1828 | bottom oligo for TS8 | TCTAAAACATTAGGAAGCTATTGCGGCCGATA | 89 |
| CL1829 | top oligo for TS10 | AGTCTATCGCAGCGCAATCAGTGCAGTGGTTT | 90 |
| CL1830 | bottom oligo for TS10 | TCTAAAACCACTGCACTGATTGCGCTGCGATA | 91 |

More particularly, CL1821 and CL1822, CL1823 and CL1824, CL1825 and CL1826, CL1827 and CL1828, CL1829 and CL1830 were annealed to create double stranded DNAs, which were cloned individually into pCHL760 and pCHL761 at Aar1 site using typeIIS seamless cloning method. The final plasmids with correctly inserted guide RNA sequences lost the toxic ccdB gene.

Transformation of *T. reesei*

The cas9 mediated ace3 promoter replacement vectors of pCHL760 and pCHL761 were transformed into *T. reesei* parental cells by polyethylene glycol (PEG)-mediated protoplast transformation. The transformants were grown on Vogel's minimal medium agar with hygromycin to select for hygromycin resistant transformants. Some of these transformants were unstable, having taken up the plasmid, but without stable integration into the genomic DNA. Transformants were transferred onto Vogel's non-selective agar medium to allow loss of the plasmid and hygromycin-resistance marker.

To screen for dic1 promoter replaced transformants, genomic DNA was extracted and PCR using primer pairs CL1858 and CL1848 (expected size product for desired integration was 2,412 bp), and CL1853 and CL1818 (expected size product for desired integration was 2,431 bp), e.g. see Table 11. PCR products were subsequently analyzed by DNA sequencing to confirm the desired promoter integration.

To screen for hxk1 promoter replaced transformants, PCR using primer pairs CL1858 and CL1898 (expected size product for desired integration was 1,784 bp), and CL1853 and CL1850 (expected size product for desired integration was 2,178 bp) was performed and correct integration subsequently confirmed by DNA sequencing the PCR products, e.g. see Table 11.

TABLE 11

PCR Primers

| Primer ID | Primer Sequence | SEQ ID NO: |
|---|---|---|
| CL1858 | TGGAGAGACTCGGAGAGGATAGG | 92 |
| CL1853 | AGCGTGGAGGCAGTTGGAGTGG | 93 |
| CL1848 | TGGACAAAGCCTGGGTCCTGCTCC | 94 |
| CL1818 | ATCCTGACTCGTCCTGTGTCGG | 95 |
| CL1898 | AGTGCTTCGTTTAGTGGACTTG | 96 |
| CL1850 | CTCGGTAGCTGCTTGAATATAG | 97 |

Protein Production in Shake Flasks

To test the functionality of ace3 promoter replaced strains, cells were grown in the presence and absence of an inducer substrate (sophorose) in 50 ml submerged culture in shake flasks. The parental *T. reesei* host cells (ID No. 1275.8.1) and the variant cells ID Nos. 2218, 2219, 2220, 2221, 2222 and 2223, were grown under both inducing conditions (glucose/sophorose as carbon source) and non-inducing conditions (glucose as carbon source) in liquid culture, and their respective extracellular secreted protein production levels were compared. Briefly, mycelia of each host cell (i.e., the *T. reesei* parental host cell and the variant cells thereof) were added separately to 50 mL of YEG broth in a 250 mL Erlenmeyer flask with bottom baffles. The YEG broth contained 5 g/L yeast extract and 22 g/L glucose. The cell cultures were grown for 48 hours, followed by sub-culturing into fresh YEG for another 24 hours. These seed cultures were then inoculated into either 50 mL of defined medium supplemented with 2.5% glucose (non-inducing condition), or 50 mL of defined medium with 2.5% glucose/sophorose (inducing condition) in 250 mL shake flasks with bottom baffles. All shake flasks were incubated at 28° C. with continuous shaking at 200 rpm. After 4 days of incubation, supernatant from all cell cultures were harvested and analyzed using SDS-PAGE, as presented in FIG. 23.

As seen on above SDS-PAGE, parental cells (FIG. 23, ID 1275.8.1) produced much less secreted protein in defined medium with glucose (non-inducing) compared to glucose/sophorose (induction). In contrast, transformants 2218, 2219, 2220, 2222 and 2223 produced similar amounts of secreted protein under inducing and non-inducing conditions. Thus, these results demonstrate that the variant cells harboring the hxk1 or dic1 promoter replacing the native ace3 promoter at ace3 locus produced extracellular proteins in the absence of an inducer.

REFERENCES

European Patent Application No. EP 215,594
European Patent Application No. EP 244,234
European Publication No. EP 0215594
PCT International Application Serial No. PCT/EP2013/050126
PCT International Application Serial No. PCT/US2016/017113
PCT International Publication No. WO03/027306
PCT International Publication No. WO1992/06183
PCT International Publication No. WO1992/06209
PCT International Publication No. WO1992/06221
PCT International Publication No. WO1992/10581
PCT International Publication No. WO1998/15619
PCT International Publication No. WO2002/12465
PCT International Publication No. WO2003/52054
PCT International Publication No. WO2003/52055
PCT International Publication No. WO2003/52056
PCT International Publication No. WO2003/52057
PCT International Publication No. WO2003/52118
PCT International Publication No. WO2004/16760
PCT International Publication No. WO2004/43980
PCT International Publication No. WO2004/48592
PCT International Publication No. WO2005/001036
PCT International Publication No. WO2005/01065
PCT International Publication No. WO2005/028636
PCT International Publication No. WO2005/093050
PCT International Publication No. WO2005/28636
PCT International Publication No. WO2005/93073
PCT International Publication No. WO2006/074005
PCT International Publication No. WO2006/74005
PCT International Publication No. WO2009/149202
PCT International Publication No. WO2010/141779
PCT International Publication No. WO2011/038019
PCT International Publication No. WO2011/063308
PCT International Publication No. WO2011/153276
PCT International Publication No. WO2012/125925
PCT International Publication No. WO2012/125951
PCT International Publication No. WO2012125937
PCT International Publication No. WO2013/102674
PCT International Publication No. WO2014/047520
PCT International Publication No. WO2014/070837
PCT International Publication No. WO2014/070841
PCT International Publication No. WO2014/070844
PCT International Publication No. WO2014/093275
PCT International Publication No. WO2014/093281
PCT International Publication No. WO2014/093282
PCT International Publication No. WO2014/093287
PCT International Publication No. WO2014/093294
PCT International Publication No. WO2015/084596
PCT International Publication No. WO2016/069541
PCT International Publication No. WO2016/100272
PCT International Publication No. WO2016/100568
PCT International Publication No. WO2016/100571
U.S. Pat. No. 6,022,725
U.S. Pat. No. 6,268,328
U.S. Pat. No. 7,413,879
U.S. Pat. No. 7,713,725
U.S. Pat. No. 8,143,046

Alexopoulos, C. J., *Introductory Mycology*, New York: Wiley, 1962.
Allen and Mortensen, *Biotechnol. Bioeng.*, 2641-45, 1981.
Arvas, M., Pakula, T., Smit, B., Rautio, J., Koivistoinen, H., Jouhten, P., Lindfors, E., Wiebe, M., Penttila, M., and Saloheimo, M., "Correlation of gene expression and protein production rate—a system wide study", *BMC Genomics* 12, 616, 2011.
Ausbel et al., "Current Protocols in Molecular Biology", Green Publishing Associates/Wiley Interscience, New York, 1987.
Ausubel et al., Current Protocols in Molecular Biology, Green Publishing Associates/Wiley Interscience, New York, 1994.
Boel et al., *EMBO J.* 3:1581-1585, 1984.
Campbell et al., *Curr. Genet.*, 16: 53-56, 1989.
Cao et al., *Science*, 9: 991-1001, 2000.
Colot et al., *PNAS* 103(27):10352-10357, 2006.
Devereux et al., *Nucleic Acids Res.* 12:387-395, 1984.
el-Gogary et al., "Mechanism by which cellulose triggers cellobiohydrolase I gene expression in Trichoderma reesei", *PNAS*, 86(16)-6138-6141, 1989.
Hakkinen, M., Valkonen, M. J., Westerholm-Parvinen, A., Aro, N., Arvas, M., Vitikainen, M., Penttila, M., Saloheimo, M., and Pakula, T. M., "Screening of candidate regulators for cellulase and hemicellulase production in Trichoderma reesei and identification of a factor essential for cellulase production", *Biotechnol Biofuels* 7, 14, 2014.
Harkki et al., *BioTechnol.*, 7: 596-603, 1989.
Harkki et al., *Enzyme Microb. Technol.*, 13: 227-233, 1991.
Hu et al., "Essential gene identification and drug target prioritization in *Aspergillus fumigatus*" *PLoS Pathog.*, 3(3), 2007.
Ilmen et al., "Regulation of cellulase gene expression in the filamentous fungus *Trichoderma reesei*", *Applied and Environmental Microbiology*, 63(4)-1298-1306,1997.
Ju and Afolabi, *Biotechnol. Prog.*, 91-97, 1999.
Kriegler, Gene Transfer and Expression: A Laboratory Manual, 1990.
Martinez et al., "Genome sequencing and analysis of the bio-mass-degrading fungi Trichoderma reesei (syn. Hypocrea jecorina)", *Nature Biotechnology*, 26:533-560, 2008.
Mullaney et al., *MGG* 199:37-45, 1985.
Nagy, "Cre recombinase: the universal reagent for genome tailoring", Genesis 26(2), 99-109, 2000.
Needleman and Wunsch, *J. Mol. Biol.*, 48:443, 1970.
Nunberg et al., *Mol. Cell Biol.* 4:2306, 1984.
Ouedraogo, J. P., Arentshorst, M., Nikolaev, I., Barends, S., and Ram, A. F., "I-SceI-mediated double-strand DNA breaks stimulate efficient gene targeting in the industrial fungus Trichoderma reesei" Applied microbiology and biotechnology 99, 10083-10095, 2015.
Pearson and Lipman, *Proc. Natl. Acad. Sci. USA* 85:2444, 1988.
Penttila, M., Nevalainen, H., Ratto, M., Salminen, E., and Knowles, J., "A versatile transformation system for the cellulolytic filamentous fungus Trichoderma reesei", Gene 61, 155-164, 1987.
Poggi-Parodi, D., Bidard, F., Pirayre, A., Portnoy, T., Blugeon, C., Seiboth, B., Kubicek, C. P., Le Crom, S., and Margeot, A., "Kinetic transcriptome analysis reveals an essentially intact induction system in a cellulase hyperproducer Trichoderma reesei strain", *Biotechnol Biofuels* 7, 173, 2014.

Sambrook et al., Molecular Cloning, A Laboratory Manual, 2nd Edition, Cold Spring Harbor Laboratory Press, Cold Spring, N.Y., 1989.

Sambrook et al., Molecular Cloning, A Laboratory Manual, 4th Edition, Cold Spring Harbor Laboratory Press, Cold Spring, New York, 2012.

Seiboth, et. al., *Mol. Genet. Genomics*, 124-32, 2002.

Sheir-Neiss and Montenecourt, "Characterization of the secreted cellulases of *Trichoderma reesei* wild type and mutants during controlled fermentations", Applied Microbiology and Biotechnology, 20(1):46-53, 1984.

Smith and Waterman, *Adv. Appl. Math.* 2:482, 1981.

Vaheri et al., "Transglycosylation products of the cellulase system of *Trichoderma reesei*", *Biotechnol. Lett.*, 1:41-46, 1979.

Yelton et al., *PNAS USA* 81:1470-1474, 1984.

The invention claimed is:

1. A variant filamentous fungal cell obtained from a parental *Trichoderma* filamentous fungal cell, the variant cell comprising an introduced polynucleotide construct encoding a functional activator of cellulase 3 (Ace3} transcription factor (TF) protein comprising at least 95% sequence identity to the Ace3 protein of SEQ ID NO: 6, wherein the variant cell produces lignocellulosic degrading enzyme in the absence of an inducing substrate relative to the parental cell, wherein the variant and parental cells are cultivated under similar conditions.

2. The variant cell of claim 1, wherein the variant cell further produces an increased amount of a lignocellulosic degrading enzyme in the presence of an inducing substrate relative to the parental cell, wherein the variant and parental cells are cultivated under similar conditions.

3. The variant cell of claim 1, wherein the variant cell comprises an introduced polynucleotide construct encoding a heterologous lignocellulosic degrading enzyme.

4. The variant cell of claim 1, wherein the lignocellulose degrading enzyme is selected from the group consisting of cellulase enzymes, hemi-cellulase enzymes, or a combination thereof.

5. The variant cell of claim 3, wherein the heterologous POI is selected from the group consisting of an α-amylase, an alkaline α-amylase, a β-amylase, a cellulase, a dextranase, an α-glucosidase, an α-galactosidase, a glucoamylase, a hemicellulase, a pentosanase, a xylanase, an invertase, a lactase, a naringanase, a pectinase, a pullulanase, an acid protease, an alkali protease, a bromelain, a neutral protease, a papain, a pepsin, a peptidase, a rennet, a rennin, a chymosin, a subtilisin, a thermolysin, an aspartic proteinase, a trypsin, a lipase, an esterase, a phospholipase, a phosphatase, a phytase, an amidase, an iminoacylase, a glutaminase, a lysozyme, a penicillin acylase; an isomerase, an oxidoreductases, a catalase, a chloroperoxidase, a glucose oxidase, a hydroxysteroid dehydrogenase, a peroxidase, a lyase, an aspartic β-decarboxylase, a fumarase, a histadase, a transferase, a ligase, an aminopeptidase, a carboxypeptidase, a chitinase, a cutinase, a deoxyribonuclease, an α-galactosidase, a β-galactosidase, a β-glucosidase, a laccase, a mannosidase, a mutanase, a polyphenol oxidase, a ribonuclease and a transglutaminase.

6. The variant cell of claim 1, wherein the polynucleotide construct is integrated into the fungal cell genome.

7. The variant cell of claim 6, wherein the polynucleotide construct is integrated into a telomere site of the fungal cell genome.

8. The variant cell of claim 6, wherein the polynucleotide construct is integrated into a glucoamylase (gla1) gene locus of the fungal cell genome.

9. The variant cell of claim 1, wherein the polynucleotide construct comprises a nucleotide sequence comprising at least 95% sequence identity to SEQ ID NO: 4, SEQ ID NO: 11 or SEQ ID NO: 13.

10. A polynucleotide ORF encoding a functional Ace3 TF protein comprising at least 95% sequence identity to SEQ ID NO: 6, SEQ ID NO: 12 or SEQ ID NO: 14.

* * * * *

SEQUENCE LISTING

```
<160> NUMBER OF SEQ ID NOS: 102

<210> SEQ ID NO 1
<211> LENGTH: 2038
<212> TYPE: DNA
<213> ORGANISM: Trichoderma reesei

<400> SEQUENCE: 1
atgctgcgct actccccgt cttacacctg gatactctct ccttgccacc actgaccaat      60
gctcttcccc gcccaaagtg cgagtacctc agcgctgtcg atagctgcac gcactgccgc    120
gatgcccacg tgcagtgcac tttcgacctg ccctggcgc gacgcggccc caaagcgagg     180
aagaagagcg accagcccgg ccagccgcct cctgatccga gctcgctctc caccgcggct    240
cgacccggcc agatgccgcc gccgctgacc ttctccggcc ccgcagtagc cgcgctgcag    300
cccttcgcct cgtcgtcgct gtcgcccgac gcggcctggg agcccgtcga gccgctcagc    360
attgacaacg gcctgccccg gcagccgctg ggcgacctgc ccggcctctc caccatccag    420
aacatctcga cgcgccagcg atggatacac ctggccaacg ccatgacgct gcgcaacacg    480
acgctagagc gcgtctcgaa gcgatgtatc gacctcttct tcgactacct ctacccctc     540 acccccctgg tgtacgagcc ggccctccgg gacgtgctcg catacatctt ctcccagccc    600
ttgcctggcg tcaaccaacc atcgccgctg tcacagctca cgccagaccc gaccaccggc    660 accaccccc tcaacgctgc cgagtcgtgg gccggctttg gccagcccag cggctcgcga    720
accgtcggca gcaggctggc tccctgggcc gactcgacct tcaccctggt cacggccgtc    780
tgcgcagagg cagcattcat gctacccaag gacattttcc ccgaaggaga atccgtctct    840
gagatcttgc tcgaagcctc tcgggactgc ctgcaccagc acctcgaggc cgacctggag    900
aatccgacgg ccaactcgat tgccattcgc tacttccact ccaactgcct ccacgctgcg    960
gggaagccca agtactcgtg gcacatattt ggcgaggcca tccgcctggc gcaggtcatg   1020
cagctgcacg aggaggctgc cctcgagggg ctcgtcccca tcgaggcaga gttccgccgt   1080
cgctgctttt ggatcctgta cttgggcgac aagtcagccg ctatactcaa caatcggccc   1140
atcaccatcc acaagtactg cttcgacgcc ggcatcacca cgctataccc gtcgggtatc   1200
gaggacgagt tcctgagcac ggcgtccgag ccgccccgga agagcttcat atccggcttc   1260
aacgcaaatg tgcggctctg gcagtccgcg gctgatttgc tgctggaaat ccgcgtgctg   1320
caagatcaga tgatgcagca cttcgaggg accatgcccc gaaccatgt gctgccctcc    1380 gccgacaggc agcatctcga ttctctctat gtccgcttca tcacctgctt ggacgatctc   1440
ccgccgtacc tccagtcgtg cactctggcg atggcagcga tggcagaagg caacgggtct   1500
gccgagtcca agcagtacgt gatacagtgc atcaacctgc aggtgacgtt tcactgtctg   1560
cgcatggtaa ttacgcagaa attcgaagac ctctcttatt ttgctcctgg cgttgagcag   1620
gctgatctca gaaagtcgga gattgtgcga gacatgctga gggtgatgaa cgaggcgccc   1680
ttttggggcc tgcaggccaa tggcgagcca aacgtgagtc gtttccttgt ctcttctctt   1740
```

```
ttctgcacac ccttttcttc gacgaccccc cctctctctt tatatccctg cggatatgta    1800
tatcatcaag cctcggcact tgttgctaat ctgtcctgat tatgttgtct ggatgctgca    1860
ggttgaaaag attcgcctta tcggagctag tttgctggcc atcatccatc gcaaccagga    1920
ttcacccttg gctacgcgag ccaggagcga cttttccgtg cttttggata ttctcacgcg    1980
gctggactcg aaggcgtcgg accaactgag gaatacgtcc actaccgttg ttggctaa     2038
```

<210> SEQ ID NO 2
<211> LENGTH: 1890
<212> TYPE: DNA
<213> ORGANISM: Trichoderma reesei

<400> SEQUENCE: 2

```
atgctgcgct actcccccgt cttacacctg gatactctct ccttgccacc actgaccaat      60
gctcttcccc gcccaaagtg cgagtacctc agcgctgtcg atagctgcac gcactgccgc     120
gatgcccacg tgcagtgcac tttcgacctg cccctggcgc gacgcggccc caaagcgagg     180
aagaagagcg accagcccgg ccagccgcct cctgatccga gctcgctctc caccgcggct     240
cgacccggcc agatgccgcc gccgctgacc ttctccggcc ccgcagtagc cgcgctgcag     300
cccttcgcct cgtcgtcgct gtcgcccgac gcggcctggg agcccgtcga gccgctcagc     360
attgacaacg gcctgcccg  gcagccgctg ggcgacctgc ccggcctctc caccatccag     420
aacatctcga cgcgccagcg atggatacac ctggccaacg ccatgacgct gcgcaacacg     480
acgctagagc gcgtctcgaa gcgatgtatc gacctcttct tcgactacct ctaccccctc     540 accccctgg  tgtacgagcc ggccctccgg gacgtgctcg catacatctt ctcccagccc     600
ttgcctggcg tcaaccaacc atcgccgctg tcacagctca cgccagaccc gaccaccggc     660 accaccccc  tcaacgctgc cgagtcgtgg gccggctttg gccagcccag cggctcgcga     720
accgtcggca gcaggctggc tccctgggcc gactcgacct tcaccctggt cacggccgtc     780
tgcgcagagg cagcattcat gctacccaag gacattttcc ccgaaggaga atccgtctct     840
gagatcttgc tcgaagcctc tcgggactgc ctgcaccagc acctcgaggc cgacctggag     900
aatccgacgg ccaactcgat tgccattcgc tacttccact ccaactgcct ccacgctgcg     960
gggaagccca gtactcgtg  gcacatattt ggcgaggcca tccgcctggc gcaggtcatg    1020
cagctgcacg aggaggctgc cctcgagggg ctcgtcccca tcgaggcaga gttccgccgt    1080
cgctgctttt ggatcctgta cttgggcgac aagtcagccg ctatactcaa caatcggccc    1140
atcaccatcc acaagtactg cttcgacgcc ggcatcacca cgctataccc gtcgggtatc    1200
gaggacgagt tcctgagcac ggcgtccgag ccgccccgga agagcttcat atccggcttc    1260
aacgcaaatg tgcggctctg gcagtccgcg gctgatttgc tgctggaaat ccgcgtgctg    1320
caagatcaga tgatgcagca ctttcgaggg accatgcccc gaaccatgt  gctgccctcc    1380 gccgacaggc agcatctcga ttctctctat gtccgcttca tcacctgctt ggacgatctc    1440
ccgccgtacc tccagtcgtg cactctggcg atggcagcga tggcagaagg caacgggtct    1500
gccgagtcca agcagtacgt gatacagtgc atcaacctgc aggtgacgtt tcactgtctg    1560
cgcatggtaa ttacgcagaa attcgaagac ctctcttatt ttgctcctgg cgttgagcag    1620
gctgatctca gaaagtcgga gattgtgcga gacatgctga gggtgatgaa cgaggcgccc    1680
ttttggggcc tgcaggccaa tggcgagcca acgttgaaaa agattcgcct tatcggagct    1740
agtttgctgg ccatcatcca tcgcaaccag gattcaccct tggctacgcg agccaggagc    1800
```

```
gactttccg tgcttttgga tattctcacg cggctggact cgaaggcgtc ggaccaactg   1860
aggaatacgt ccactaccgt tgttggctaa                                    1890
```

<210> SEQ ID NO 3
<211> LENGTH: 629
<212> TYPE: PRT
<213> ORGANISM: Trichoderma reesei

<400> SEQUENCE: 3

```
Met Leu Arg Tyr Ser Pro Val Leu His Leu Asp Thr Leu Ser Leu Pro
1               5                   10                  15

Pro Leu Thr Asn Ala Leu Pro Arg Pro Lys Cys Glu Tyr Leu Ser Ala
            20                  25                  30

Val Asp Ser Cys Thr His Cys Arg Asp Ala His Val Gln Cys Thr Phe
        35                  40                  45

Asp Leu Pro Leu Ala Arg Arg Gly Pro Lys Ala Arg Lys Lys Ser Asp
    50                  55                  60

Gln Pro Gly Gln Pro Pro Asp Pro Ser Ser Leu Ser Thr Ala Ala
65                  70                  75                  80

Arg Pro Gly Gln Met Pro Pro Leu Thr Phe Ser Gly Pro Ala Val
                85                  90                  95

Ala Ala Leu Gln Pro Phe Ala Ser Ser Leu Ser Pro Asp Ala Ala
            100                 105                 110

Trp Glu Pro Val Glu Pro Leu Ser Ile Asp Asn Gly Leu Pro Arg Gln
            115                 120                 125

Pro Leu Gly Asp Leu Pro Gly Leu Ser Thr Ile Gln Asn Ile Ser Thr
    130                 135                 140

Arg Gln Arg Trp Ile His Leu Ala Asn Ala Met Thr Leu Arg Asn Thr
145                 150                 155                 160

Thr Leu Glu Arg Val Ser Lys Arg Cys Ile Asp Leu Phe Phe Asp Tyr
                165                 170                 175

Leu Tyr Pro Leu Thr Pro Leu Val Tyr Glu Pro Ala Leu Arg Asp Val
            180                 185                 190

Leu Ala Tyr Ile Phe Ser Gln Pro Leu Pro Gly Val Asn Gln Pro Ser
        195                 200                 205

Pro Leu Ser Gln Leu Thr Pro Asp Pro Thr Thr Gly Thr Thr Pro Leu
    210                 215                 220

Asn Ala Ala Glu Ser Trp Ala Gly Phe Gly Gln Pro Ser Gly Ser Arg
225                 230                 235                 240

Thr Val Gly Ser Arg Leu Ala Pro Trp Ala Asp Ser Thr Phe Thr Leu
                245                 250                 255

Val Thr Ala Val Cys Ala Glu Ala Ala Phe Met Leu Pro Lys Asp Ile
            260                 265                 270

Phe Pro Glu Gly Glu Ser Val Ser Glu Ile Leu Leu Glu Ala Ser Arg
        275                 280                 285

Asp Cys Leu His Gln His Leu Glu Ala Asp Leu Glu Asn Pro Thr Ala
    290                 295                 300

Asn Ser Ile Ala Ile Arg Tyr Phe His Ser Asn Cys Leu His Ala Ala
305                 310                 315                 320

Gly Lys Pro Lys Tyr Ser Trp His Ile Phe Gly Glu Ala Ile Arg Leu
                325                 330                 335

Ala Gln Val Met Gln Leu His Glu Glu Ala Ala Leu Glu Gly Leu Val
            340                 345                 350

Pro Ile Glu Ala Glu Phe Arg Arg Cys Phe Trp Ile Leu Tyr Leu
```

```
                    355                 360                 365
Gly Asp Lys Ser Ala Ala Ile Leu Asn Asn Arg Pro Ile Thr Ile His
    370                 375                 380
Lys Tyr Cys Phe Asp Ala Gly Ile Thr Thr Leu Tyr Pro Ser Gly Ile
385                 390                 395                 400
Glu Asp Glu Phe Leu Ser Thr Ala Ser Glu Pro Pro Arg Lys Ser Phe
                405                 410                 415
Ile Ser Gly Phe Asn Ala Asn Val Arg Leu Trp Gln Ser Ala Ala Asp
            420                 425                 430
Leu Leu Leu Glu Ile Arg Val Leu Gln Asp Gln Met Met Gln His Phe
        435                 440                 445
Arg Gly Thr Met Pro Pro Asn His Val Leu Pro Ser Ala Asp Arg Gln
    450                 455                 460
His Leu Asp Ser Leu Tyr Val Arg Phe Ile Thr Cys Leu Asp Asp Leu
465                 470                 475                 480
Pro Pro Tyr Leu Gln Ser Cys Thr Leu Ala Met Ala Ala Met Ala Glu
                485                 490                 495
Gly Asn Gly Ser Ala Glu Ser Lys Gln Tyr Val Ile Gln Cys Ile Asn
            500                 505                 510
Leu Gln Val Thr Phe His Cys Leu Arg Met Val Ile Thr Gln Lys Phe
        515                 520                 525
Glu Asp Leu Ser Tyr Phe Ala Pro Gly Val Gln Ala Asp Leu Arg
    530                 535                 540
Lys Ser Glu Ile Val Arg Asp Met Leu Arg Val Met Asn Glu Ala Pro
545                 550                 555                 560
Phe Trp Gly Leu Gln Ala Asn Gly Glu Pro Asn Val Glu Lys Ile Arg
                565                 570                 575
Leu Ile Gly Ala Ser Leu Leu Ala Ile Ile His Arg Asn Gln Asp Ser
            580                 585                 590
Pro Leu Ala Thr Arg Ala Arg Ser Asp Phe Ser Val Leu Leu Asp Ile
        595                 600                 605
Leu Thr Arg Leu Asp Ser Lys Ala Ser Asp Gln Leu Arg Asn Thr Ser
    610                 615                 620
Thr Thr Val Val Gly
625

<210> SEQ ID NO 4
<211> LENGTH: 2608
<212> TYPE: DNA
<213> ORGANISM: Trichoderma reesei

<400> SEQUENCE: 4
atgggctcag cagctccggc ccagggctct gtagctgcag ctgcaggcgg ccctccagct      60
gctggcgctg gcgctggcgc tgtccacgcc ctcaccacct cgcccgagtc tgcctcggcc     120
tcgcagcccg ctcgccaac cgcctcaacc acgccgccgc agaactcact cgtgtcggct     180
gcaacctcgt tccaccacca tcccagaggc cgtctggtga cagagcctg cgaccgctgc     240 cgccggcgca aggccaaggt cagtctagcc ccttttgctgt tgcttgcatc tctgttgtca     300
ttgctcctcc tcctgctgct gctgatgctg ctgctcctcc tcctcctcct cctccccgtc     360
tcctggtccc tggtccctgc tcttcatatg tccttactgc ccgtgtctcc tctccccgtt     420
cccgttcccc ctcctcccgt cctcttctcc tgcgtgtctg tcatgcgtac aaagcataca     480
tacaatacat cagcatacat ggcaagcgtt gtgttgtgtt gagagttgtg tgtattgtat     540
```

```
tgcactgcct tcacaactcg ttcatactgc tgcagcctca ccccaacacc gacctcgtct    600
tccatgctgc gctactcccc cgtcttacac ctggatactc tctccttgcc accactgacc    660
aatgctcttc cccgcccaaa gtgcgagtac ctcagcgctg tcgatagctg cacgcactgc    720
cgcgatgccc acgtgcagtg cactttcgac ctgcccctgg cgcgacgcgg ccccaaagcg    780
aggaagaaga gcgaccagcc cggccagccg cctcctgatc cgagctcgct ctccaccgcg    840
gctcgacccg ccagatgcc gccgccgctg accttctccg gccccgcagt agccgcgctg    900
cagcccttcg cctcgtcgtc gctgtcgccc gacgcggcct gggagcccgt cgagccgctc    960
agcattgaca acggcctgcc ccggcagccg ctgggcgacc tgcccggcct ctccaccatc   1020
cagaacatct cgacgcgcca gcgatggata cacctggcca acgccatgac gctgcgcaac   1080
acgacgctag agcgcgtctc gaagcgatgt atcgacctct tcttcgacta cctctacccc   1140
ctcacccccc tggtgtacga gccggcctc cgggacgtgc tcgcatacat cttctcccag    1200
cccttgcctg gcgtcaacca accatcgccg ctgtcacagc tcacgccaga cccgaccacc   1260
ggcaccaccc cctcaacgc tgccgagtcg tgggccggct tggccagcc cagcggctcg     1320
cgaaccgtcg gcagcaggct ggctccctgg gccgactcga ccttcaccct ggtcacggcc   1380
gtctgcgcag aggcagcatt catgctaccc aaggacattt cccccgaagg agaatccgtc   1440
tctgagatct tgctcgaagc ctctcgggac tgcctgcacc agcacctcga ggccgacctg   1500
gagaatccga cggccaactc gattgccatt cgctacttcc actccaactg cctccacgct   1560
gcggggaagc ccaagtactc gtggcacata tttggcgagg ccatccgcct ggcgcaggtc   1620
atgcagctgc acgaggaggc tgccctcgag gggctcgtcc ccatcgaggc agagttccgc   1680
cgtcgctgct tttggatcct gtacttgggc gacaagtcag ccgctatact caacaatcgg   1740
cccatcacca tccacaagta ctgcttcgac gccggcatca ccacgctata cccgtcgggt   1800
atcgaggacg agttcctgag cacggcgtcc gagccgcccc ggaagagctt catatccggc   1860
ttcaacgcaa atgtgcggct ctggcagtcc gcggctgatt tgctgctgga atccgcgtg    1920
ctgcaagatc agatgatgca gcactttcga gggaccatgc cccgaacca tgtgctgccc    1980
tccgccgaca ggcagcatct cgattctctc tatgtccgct tcatcacctg cttggacgat   2040
ctcccgccgt acctccagtc gtgcactctg gcgatggcag cgatggcaga aggcaacggg   2100
tctgccgagt ccaagcagta cgtgatacag tgcatcaacc tgcaggtgac gtttcactgt   2160
ctgcgcatgg taattacgca gaaattcgaa gacctctctt attttgctcc tggcgttgag   2220
caggctgatc tcagaaagtc ggagattgtg cgagacatgc tgagggtgat gaacgaggcg   2280
ccctttggg gcctgcaggc caatggcgag ccaaacgtga gtcgtttcct tgtctcttct    2340
cttttctgca cccctttttc ttcgacgacc ccctctctc ttttatatcc ctgcggatat    2400
gtatatcatc aagcctcggc acttgttgct aatctgtcct gattatgttg tctggatgct   2460
gcaggttgaa aagattcgcc ttatcggagc tagtttgctg ccatcatcc atcgcaacca    2520
ggattcaccc ttggctacgc gagccaggag cgacttttcc gtgcttttgg atattctcac   2580
gcggctggac tcgaaggcgt cggactaa                                     2608
```

<210> SEQ ID NO 5
<211> LENGTH: 2037
<212> TYPE: DNA
<213> ORGANISM: Trichoderma reesei

<400> SEQUENCE: 5

```
atgggctcag cagctccggc ccagggctct gtagctgcag ctgcaggcgg ccctccagct     60
```

```
gctggcgctg gcgctggcgc tgtccacgcc ctcaccacct cgcccgagtc tgcctcggcc      120
tcgcagcccg gctcgccaac cgcctcaacc acgccgccgc agaactcact cgtgtcggct      180
gcaacctcgt tccaccacca tcccagaggc cgtctggtga gcagagcctg cgaccgctgc      240
cgccggcgca aggccaagtg cgagtacctc agcgctgtcg atagctgcac gcactgccgc      300
gatgcccacg tgcagtgcac tttcgacctg ccctggcgc gacgcggccc aaagcgagg       360 aagaagagcg accagcccgg ccagccgcct cctgatccga gctcgctctc caccgcggct      420
cgacccggcc agatgccgcc gccgctgacc ttctccggcc ccgcagtagc gcgctgcag      480 ccttcgcct cgtcgtcgct gtcgcccgac gcggcctggg agcccgtcga gccgctcagc      540
attgacaacg gcctgccccg gcagccgctg ggcgacctgc ccggcctctc caccatccag      600
aacatctcga cgcgccagcg atggatacac ctggccaacg ccatgacgct gcgcaacacg      660
acgctagagc gcgtctcgaa gcgatgtatc gacctcttct tcgactacct ctaccccctc      720 accccctgg tgtacgagcc ggccctccgg gacgtgctcg catacatctt ctcccagccc       780
ttgcctggcg tcaaccaacc atcgccgctg tcacagctca cgccagaccc gaccaccggc      840
accacccccc tcaacgctgc cgagtcgtgg gccggctttg ccagcccag cggctcgcga       900 accgtcggca gcaggctggc tccctgggcc gactcgacct tcaccctggt cacggccgtc      960
tgcgcagagg cagcattcat gctacccaag gacattttcc ccgaaggaga atccgtctct      1020
gagatcttgc tcgaagcctc tcgggactgc ctgcaccagc acctcgaggc cgacctggag      1080
aatccgacgg ccaactcgat tgccattcgc tacttccact ccaactgcct ccacgctgcg      1140
gggaagccca gtactcgtg gcacatattt ggcgaggcca tccgcctggc gcaggtcatg       1200
cagctgcacg aggaggctgc cctcgagggg ctcgtcccca tcgaggcaga gttccgccgt      1260
cgctgctttt ggatcctgta cttgggcgac aagtcagccg ctatactcaa caatcggccc      1320
atcaccatcc acaagtactg cttcgacgcc ggcatcacca cgctataccc gtcgggtatc      1380
gaggacgagt tcctgagcac ggcgtccgag ccgccccgga gagcttcat atccggcttc       1440 aacgcaaatg tgcggctctg gcagtccgcg gctgatttgc tgctggaaat ccgcgtgctg      1500
caagatcaga tgatgcagca ctttcgaggg accatgcccc cgaaccatgt gctgccctcc      1560
gccgacaggc agcatctcga ttctctctat gtccgcttca tcacctgctt ggacgatctc      1620
ccgccgtacc tccagtcgtg cactctggcg atggcagcga tggcagaagg caacgggtct      1680
gccgagtcca gcagtacgt gatacagtgc atcaacctgc aggtgacgtt tcactgtctg       1740
cgcatggtaa ttacgcagaa attcgaagac ctctcttatt ttgctcctgg cgttgagcag      1800
gctgatctca gaaagtcgga gattgtgcga gacatgctga gggtgatgaa cgaggcgccc      1860
ttttggggcc tgcaggccaa tggcgagcca aacgttgaaa agattcgcct tatcggagct      1920
agtttgctgg ccatcatcca tcgcaaccag gattcaccct ggctacgcg agccaggagc       1980 gacttttccg tgcttttgga tattctcacg cggctggact cgaaggcgtc ggactaa        2037
```

<210> SEQ ID NO 6
<211> LENGTH: 678
<212> TYPE: PRT
<213> ORGANISM: Trichoderma reesei

<400> SEQUENCE: 6

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr

```
            20                  25                  30
Thr Ser Pro Glu Ser Ala Ser Gln Pro Gly Ser Pro Thr Ala
            35                  40                  45

Ser Thr Thr Pro Pro Gln Asn Ser Leu Val Ser Ala Ala Thr Ser Phe
            50                  55                  60

His His His Pro Arg Gly Arg Leu Val Ser Arg Ala Cys Asp Arg Cys
 65              70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
                100                 105                 110

Ala Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
            130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
            210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
                260                 265                 270

Leu Thr Pro Asp Pro Thr Thr Gly Thr Thr Pro Leu Asn Ala Ala Glu
            275                 280                 285

Ser Trp Ala Gly Phe Gly Gln Pro Ser Gly Ser Arg Thr Val Gly Ser
            290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
            340                 345                 350

Gln His Leu Glu Ala Asp Leu Glu Asn Pro Thr Ala Asn Ser Ile Ala
            355                 360                 365

Ile Arg Tyr Phe His Ser Asn Cys Leu His Ala Gly Lys Pro Lys
            370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
                420                 425                 430

Ala Ala Ile Leu Asn Asn Arg Pro Ile Thr Ile His Lys Tyr Cys Phe
            435                 440                 445
```

Asp Ala Gly Ile Thr Thr Leu Tyr Pro Ser Gly Ile Glu Asp Glu Phe
        450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
                500                 505                 510

Pro Pro Asn His Val Leu Pro Ser Ala Asp Arg Gln His Leu Asp Ser
            515                 520                 525

Leu Tyr Val Arg Phe Ile Thr Cys Leu Asp Asp Leu Pro Pro Tyr Leu
        530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
            595                 600                 605

Val Arg Asp Met Leu Arg Val Met Asn Glu Ala Pro Phe Trp Gly Leu
        610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
                660                 665                 670

Asp Ser Lys Ala Ser Asp
            675

<210> SEQ ID NO 7
<211> LENGTH: 2005
<212> TYPE: DNA
<213> ORGANISM: Trichoderma reesei

<400> SEQUENCE: 7
atgctgcgct actcccccgt cttacacctg gatactctct ccttgccacc actgaccaat      60
gctcttcccc gcccaaagtg cgagtacctc agcgctgtcg atagctgcac gcactgccgc     120
gatgcccacg tgcagtgcac tttcgacctg cccctggcgc gacgcggccc caaagcgagg     180
aagaagagcg accagcccgg ccagccgcct cctgatccga gctcgctctc caccgcggct     240
cgacccggcc agatgccgcc gccgctgacc ttctccggcc ccgcagtagc cgcgctgcag     300
cccttcgcct cgtcgtcgct gtcgcccgac gcggcctggg agcccgtcga ccgctcagc     360 attgacaacg gctgccccg gcagccgctg gcgacctgc ccggcctctc caccatccag     420
aacatctcga cgcgccagcg atggatacac ctggccaacg ccatgacgct gcgcaacacg     480
acgctagagc gcgtctcgaa gcgatgtatc gacctcttct tcgactacct ctaccccctc     540
acccccctgg tgtacgagcc ggccctccgg gacgtgctcg catacatctt ctcccagccc     600
ttgcctggcg tcaaccaacc atcgccgctg tcacagctca cgccagaccc gaccaccggc     660
accacccccc tcaacgctgc cgagtcgtgg gccggctttg ccagcccag cggctcgcga     720 accgtcggca gcaggctggc tccctgggcc gactcgacct tcaccctggt cacggccgtc     780

-continued

```
tgcgcagagg cagcattcat gctacccaag gacattttcc ccgaaggaga atccgtctct    840
gagatcttgc tcgaagcctc tcgggactgc ctgcaccagc acctcgaggc cgacctggag    900
aatccgacgg ccaactcgat tgccattcgc tacttccact ccaactgcct ccacgctgcg    960
gggaagccca agtactcgtg gcacatattt ggcgaggcca tccgcctggc gcaggtcatg   1020
cagctgcacg aggaggctgc cctcgagggg ctcgtcccca tcgaggcaga gttccgccgt   1080
cgctgctttt ggatcctgta cttgggcgac aagtcagccg ctatactcaa caatcggccc   1140
atcaccatcc acaagtactg cttcgacgcc ggcatcacca cgctataccc gtcgggtatc   1200
gaggacgagt tcctgagcac ggcgtccgag ccgccccgga agagcttcat atccggcttc   1260
aacgcaaatg tgcggctctg gcagtccgcg gctgatttgc tgctggaaat ccgcgtgctg   1320
caagatcaga tgatgcagca ctttcgaggg accatgcccc cgaaccatgt gctgccctcc   1380
gccgacaggc agcatctcga ttctctctat gtccgcttca tcacctgctt ggacgatctc   1440
ccgccgtacc tccagtcgtg cactctggcg atggcagcga tggcagaagg caacgggtct   1500
gccgagtcca agcagtacgt gatacagtgc atcaacctgc aggtgacgtt tcactgtctg   1560
cgcatggtaa ttacgcagaa attcgaagac ctctcttatt ttgctcctgg cgttgagcag   1620
gctgatctca gaaagtcgga gattgtgcga gacatgctga gggtgatgaa cgaggcgccc   1680
ttttggggcc tgcaggccaa tggcgagcca acgtgagtc gtttccttgt ctcttctctt   1740
ttctgcacac cctttcttc gacgaccccc cctctctctt tatatccctg cggatatgta   1800
tatcatcaag cctcggcact tgttgctaat ctgtcctgat tatgttgtct ggatgctgca   1860
ggttgaaaag attcgcctta tcggagctag tttgctggcc atcatccatc gcaaccagga   1920
ttcacccttg gctacgcgag ccaggagcga cttttccgtg cttttggata ttctcacgcg   1980
gctggactcg aaggcgtcgg actaa                                         2005
```

<210> SEQ ID NO 8
<211> LENGTH: 618
<212> TYPE: PRT
<213> ORGANISM: Trichoderma reesei

<400> SEQUENCE: 8

Met Leu Arg Tyr Ser Pro Val Leu His Leu Asp Thr Leu Ser Leu Pro
1               5                   10                  15

Pro Leu Thr Asn Ala Leu Pro Arg Pro Lys Cys Glu Tyr Leu Ser Ala
                20                  25                  30

Val Asp Ser Cys Thr His Cys Arg Asp Ala His Val Gln Cys Thr Phe
            35                  40                  45

Asp Leu Pro Leu Ala Arg Arg Gly Pro Lys Ala Arg Lys Lys Ser Asp
        50                  55                  60

Gln Pro Gly Gln Pro Pro Asp Pro Ser Ser Leu Ser Thr Ala Ala
65                  70                  75                  80

Arg Pro Gly Gln Met Pro Pro Leu Thr Phe Ser Gly Pro Ala Val
                85                  90                  95

Ala Ala Leu Gln Pro Phe Ala Ser Ser Leu Ser Pro Asp Ala Ala
            100                 105                 110

Trp Glu Pro Val Glu Pro Leu Ser Ile Asp Asn Gly Leu Pro Arg Gln
        115                 120                 125

Pro Leu Gly Asp Leu Pro Gly Leu Ser Thr Ile Gln Asn Ile Ser Thr
    130                 135                 140

Arg Gln Arg Trp Ile His Leu Ala Asn Ala Met Thr Leu Arg Asn Thr

```
              145                 150                 155                 160
        Thr Leu Glu Arg Val Ser Lys Arg Cys Ile Asp Leu Phe Phe Asp Tyr
                        165                 170                 175
        Leu Tyr Pro Leu Thr Pro Leu Val Tyr Glu Pro Ala Leu Arg Asp Val
                        180                 185                 190
        Leu Ala Tyr Ile Phe Ser Gln Pro Leu Pro Gly Val Asn Gln Pro Ser
                        195                 200                 205
        Pro Leu Ser Gln Leu Thr Pro Asp Pro Thr Thr Gly Thr Thr Pro Leu
        210                 215                 220
        Asn Ala Ala Glu Ser Trp Ala Gly Phe Gly Gln Pro Ser Gly Ser Arg
        225                 230                 235                 240
        Thr Val Gly Ser Arg Leu Ala Pro Trp Ala Asp Ser Thr Phe Thr Leu
                        245                 250                 255
        Val Thr Ala Val Cys Ala Glu Ala Ala Phe Met Leu Pro Lys Asp Ile
                        260                 265                 270
        Phe Pro Glu Gly Glu Ser Val Ser Glu Ile Leu Leu Glu Ala Ser Arg
                        275                 280                 285
        Asp Cys Leu His Gln His Leu Glu Ala Asp Leu Glu Asn Pro Thr Ala
        290                 295                 300
        Asn Ser Ile Ala Ile Arg Tyr Phe His Ser Asn Cys Leu His Ala Ala
        305                 310                 315                 320
        Gly Lys Pro Lys Tyr Ser Trp His Ile Phe Gly Glu Ala Ile Arg Leu
                        325                 330                 335
        Ala Gln Val Met Gln Leu His Glu Glu Ala Ala Leu Glu Gly Leu Val
                        340                 345                 350
        Pro Ile Glu Ala Glu Phe Arg Arg Cys Phe Trp Ile Leu Tyr Leu
                        355                 360                 365
        Gly Asp Lys Ser Ala Ala Ile Leu Asn Asn Arg Pro Ile Thr Ile His
                        370                 375                 380
        Lys Tyr Cys Phe Asp Ala Gly Ile Thr Thr Leu Tyr Pro Ser Gly Ile
        385                 390                 395                 400
        Glu Asp Glu Phe Leu Ser Thr Ala Ser Glu Pro Pro Arg Lys Ser Phe
                        405                 410                 415
        Ile Ser Gly Phe Asn Ala Asn Val Arg Leu Trp Gln Ser Ala Ala Asp
                        420                 425                 430
        Leu Leu Leu Glu Ile Arg Val Leu Gln Asp Gln Met Met Gln His Phe
                        435                 440                 445
        Arg Gly Thr Met Pro Pro Asn His Val Leu Pro Ser Ala Asp Arg Gln
        450                 455                 460
        His Leu Asp Ser Leu Tyr Val Arg Phe Ile Thr Cys Leu Asp Asp Leu
        465                 470                 475                 480
        Pro Pro Tyr Leu Gln Ser Cys Thr Leu Ala Met Ala Ala Met Ala Glu
                        485                 490                 495
        Gly Asn Gly Ser Ala Glu Ser Lys Gln Tyr Val Ile Gln Cys Ile Asn
                        500                 505                 510
        Leu Gln Val Thr Phe His Cys Leu Arg Met Val Ile Thr Gln Lys Phe
                        515                 520                 525
        Glu Asp Leu Ser Tyr Phe Ala Pro Gly Val Glu Gln Ala Asp Leu Arg
                        530                 535                 540
        Lys Ser Glu Ile Val Arg Asp Met Leu Arg Val Met Asn Glu Ala Pro
        545                 550                 555                 560
        Phe Trp Gly Leu Gln Ala Asn Gly Glu Pro Asn Val Glu Lys Ile Arg
                        565                 570                 575
```

Leu Ile Gly Ala Ser Leu Leu Ala Ile Ile His Arg Asn Gln Asp Ser
            580                 585                 590

Pro Leu Ala Thr Arg Ala Arg Ser Asp Phe Ser Val Leu Leu Asp Ile
        595                 600                 605

Leu Thr Arg Leu Asp Ser Lys Ala Ser Asp
        610                 615

<210> SEQ ID NO 9
<211> LENGTH: 2641
<212> TYPE: DNA
<213> ORGANISM: Trichoderma reesei

<400> SEQUENCE: 9

```
atgggctcag cagctccggc ccagggctct gtagctgcag ctgcaggcgg ccctccagct    60
gctggcgctg gcgctggcgc tgtccacgcc ctcaccacct cgcccgagtc tgcctcggcc   120
tcgcagcccg gctcgccaac cgcctcaacc acgccgccgc agaactcact cgtgtcggct   180
gcaacctcgt tccaccacca tcccagaggc cgtctggtga gcagagcctg cgaccgctgc   240
cgccggcgca aggccaaggt cagtctagcc cctttgctgt tgcttgcatc tctgttgtca   300
ttgctcctcc tcctgctgct gctgatgctg ctgctcctcc tcctcctcct cctccccgtc   360
tcctggtccc tggtccctgc tcttcatatg tccttactgc ccgtgtctcc tctcccgtt    420
cccgttcccc ctcctcccgt cctcttctcc tgcgtgtctg tcatgcgtac aaagcataca   480
tacaatacat cagcatacat ggcaagcgtt gtgttgtgtt gagagttgtg tgtattgtat   540
tgcactgcct tcacaactcg ttcatactgc tgcagcctca ccccaacacc gacctcgtct   600
tccatgctgc gctactcccc cgtcttacac ctggatactc tctccttgcc accactgacc   660
aatgctcttc cccgcccaaa gtgcgagtac ctcagcgctg tcgatagctg cacgcactgc   720
cgcgatgccc acgtgcagtg cactttcgac ctgcccctgg cgcgacgcgg cccaaaagcg   780
aggaagaaga cgaccagcc cggccagccg cctcctgatc cgagctcgct ctccaccgcg   840
gctcgacccg ccagatgcc gccgccgctg accttctccg gccccgcagt agccgcgctg   900
cagcccttcg cctcgtcgtc gctgtcgccc gacgcgcct gggagcccgt cgagccgctc   960
agcattgaca acggcctgcc ccggcagccg ctgggcgacc tgcccggcct cccaccatc   1020
cagaacatct cgacgcgcca gcgatggata cacctggcca acgccatgac gctgcgcaac   1080
acgacgctag agcgcgtctc gaagcgatgt atcgacctct tcttcgacta cctctacccc   1140
ctcacccccc tggtgtacga gccggccctc cgggacgtgc tcgcatacat cttctcccag   1200
cccttgcctg gcgtcaacca accatcgccg ctgtcacagc tcacgccaga cccgaccacc   1260
ggcaccaccc cctcaacgc tgccgagtcg tgggccggct ttggccagcc cagcggctcg   1320
cgaaccgtcg gcagcaggct ggctccctgg gccgactcga ccttcaccct ggtcacggcc   1380
gtctgcgcag aggcagcatt catgctaccc aaggacattt ccccgaagg agaatccgtc   1440
tctgagatct tgctcgaagc ctctcgggac tgcctgcacc agcacctcga ggccgacctg   1500
gagaatccga cggccaactc gattgccatt cgctacttcc actccaactg cctccacgct   1560
gcggggaagc ccaagtactc gtggcacata tttggcgagg ccatccgcct ggcgcaggtc   1620
atgcagctgc acgaggaggc tgccctcgag gggctcgtcc ccatcgaggc agagttccgc   1680
cgtcgctgct tttggatcct gtacttgggc gacaagtcag ccgctatact caacaatcgg   1740
cccatcacca tccacaagta ctgcttcgac gccggcatca ccacgctata cccgtcgggt   1800
atcgaggacg agttcctgag cacggcgtcc gagccgcccc ggaagagctt catatccggc   1860
```

```
ttcaacgcaa atgtgcggct ctggcagtcc gcggctgatt tgctgctgga aatccgcgtg   1920
ctgcaagatc agatgatgca gcactttcga gggaccatgc ccccgaacca tgtgctgccc   1980
tccgccgaca ggcagcatct cgattctctc tatgtccgct tcatcacctg cttggacgat   2040
ctcccgccgt acctccagtc gtgcactctg gcgatggcag cgatggcaga aggcaacggg   2100
tctgccgagt ccaagcagta cgtgatacag tgcatcaacc tgcaggtgac gtttcactgt   2160
ctgcgcatgg taattacgca gaaattcgaa gacctctctt attttgctcc tggcgttgag   2220
caggctgatc tcagaaagtc ggagattgtg cgagacatgc tgagggtgat gaacgaggcg   2280
ccctttggg gcctgcaggc caatggcgag ccaaacgtga gtcgtttcct tgtctcttct   2340
cttttctgca cccctttttc ttcgacgacc ccccctctct ctttatatcc ctgcggatat   2400
gtatatcatc aagcctcggc acttgttgct aatctgtcct gattatgttg tctggatgct   2460
gcaggttgaa aagattcgcc ttatcggagc tagtttgctg gccatcatcc atcgcaacca   2520
ggattcaccc ttggctacgc gagccaggag cgacttttcc gtgcttttgg atattctcac   2580
gcggctggac tcgaaggcgt cggaccaact gaggaatacg tccactaccg ttgttggcta   2640
a                                                                   2641

<210> SEQ ID NO 10
<211> LENGTH: 689
<212> TYPE: PRT
<213> ORGANISM: Trichoderma reesei

<400> SEQUENCE: 10

Met Gly Ser Ala Ala Pro Ala Gln Gly Ser Val Ala Ala Ala Gly
1               5                   10                  15

Gly Pro Pro Ala Ala Gly Ala Gly Ala Val His Ala Leu Thr
            20                  25                  30

Thr Ser Pro Glu Ser Ala Ser Ala Ser Gln Pro Gly Ser Pro Thr Ala
        35                  40                  45

Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
        115                 120                 125

Pro Pro Pro Asp Pro Ser Ser Leu Ser Thr Ala Ala Arg Pro Gly Gln
    130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
        195                 200                 205

Ile His Leu Ala Asn Ala Met Thr Leu Arg Asn Thr Thr Leu Glu Arg
    210                 215                 220
```

```
Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
            245                 250                 255

Phe Ser Gln Pro Leu Pro Gly Val Asn Gln Pro Ser Pro Leu Ser Gln
        260                 265                 270

Leu Thr Pro Asp Pro Thr Thr Gly Thr Thr Pro Leu Asn Ala Ala Glu
    275                 280                 285

Ser Trp Ala Gly Phe Gly Gln Pro Ser Gly Ser Arg Thr Val Gly Ser
290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
            325                 330                 335

Glu Ser Val Ser Glu Ile Leu Leu Glu Ala Ser Arg Asp Cys Leu His
        340                 345                 350

Gln His Leu Glu Ala Asp Leu Glu Asn Pro Thr Ala Asn Ser Ile Ala
    355                 360                 365

Ile Arg Tyr Phe His Ser Asn Cys Leu His Ala Ala Gly Lys Pro Lys
370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
            405                 410                 415

Glu Phe Arg Arg Arg Cys Phe Trp Ile Leu Tyr Leu Gly Asp Lys Ser
        420                 425                 430

Ala Ala Ile Leu Asn Asn Arg Pro Ile Thr Ile His Lys Tyr Cys Phe
    435                 440                 445

Asp Ala Gly Ile Thr Thr Leu Tyr Pro Ser Gly Ile Glu Asp Glu Phe
450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
            485                 490                 495

Ile Arg Val Leu Gln Asp Gln Met Met Gln His Phe Arg Gly Thr Met
        500                 505                 510

Pro Pro Asn His Val Leu Pro Ser Ala Asp Arg Gln His Leu Asp Ser
    515                 520                 525

Leu Tyr Val Arg Phe Ile Thr Cys Leu Asp Asp Leu Pro Pro Tyr Leu
530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
            565                 570                 575

Phe His Cys Leu Arg Met Val Ile Thr Gln Lys Phe Glu Asp Leu Ser
        580                 585                 590

Tyr Phe Ala Pro Gly Val Glu Gln Ala Asp Leu Arg Lys Ser Glu Ile
    595                 600                 605

Val Arg Asp Met Leu Arg Val Met Asn Glu Ala Pro Phe Trp Gly Leu
610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
```

```
                    645                 650                 655
Arg Ala Arg Ser Asp Phe Ser Val Leu Leu Asp Ile Leu Thr Arg Leu
            660                 665                 670

Asp Ser Lys Ala Ser Asp Gln Leu Arg Asn Thr Ser Thr Thr Val Val
        675                 680                 685

Gly

<210> SEQ ID NO 11
<211> LENGTH: 2885
<212> TYPE: DNA
<213> ORGANISM: Trichoderma reesei

<400> SEQUENCE: 11
```

| | | | | | |
|---|---|---|---|---|---|
| atggccacag | cggccgcggc | agcagctggc | ggcgcggcgg | ttgctgcggg | tgcagacaca | 60 |
| ggtgcgttga | gtcccgtccc | gtccgctcgc | gttccctccc | agctgccagc | ccgcgtgggt | 120 |
| ggcactggaa | cgcagtgcag | cgcaatcagt | gcagtgcggc | cccccaact | aacgctgccc | 180 |
| cccgtggctc | ctcggccaca | caggcgctgc | aggctccagc | tctacaggcc | tccaggcct | 240 |
| tccagggctt | ccaggcaccc | ggacaggctc | cgtggcgatg | ggctcagcag | ctccggccca | 300 |
| gggctctgta | gctgcagctg | caggcggcc | tccagctgct | ggcgctggcg | ctggcgctgt | 360 |
| ccacgccctc | accacctcgc | ccgagtctgc | ctcggcctcg | cagcccggct | cgccaaccgc | 420 |
| ctcaaccacg | ccgccgcaga | actcactcgt | gtcggctgca | acctcgttcc | accaccatcc | 480 |
| cagaggccgt | ctggtgagca | gagcctgcga | ccgctgccgc | cggcgcaagg | ccaaggtcag | 540 |
| tctagcccct | tgctgttgc | ttgcatctct | gttgtcattg | ctcctcctcc | tgctgctgct | 600 |
| gatgctgctg | ctcctcctcc | tcctcctcct | ccccgtctcc | tggtccctgg | tcctgctct | 660 |
| tcatatgtcc | ttactgcccg | tgtctcctct | ccccgttccc | gttcccctc | ctccgtcct | 720 |
| cttctcctgc | gtgtctgtca | tgcgtacaaa | gcatacatac | aatacatcag | catacatggc | 780 |
| aagcgttgtg | ttgtgttgag | agttgtgtgt | attgtattgc | actgccttca | caactcgttc | 840 |
| atactgctgc | agcctcaccc | caacaccgac | ctcgtcttcc | atgctgcgct | actccccgt | 900 |
| cttacacctg | gatactctct | ccttgccacc | actgaccaat | gctcttcccc | gcccaaagtg | 960 |
| cgagtacctc | agcgctgtcg | atagctgcac | gcactgccgc | gatgcccacg | tgcagtgcac | 1020 |
| tttcgacctg | ccctggcgc | gacgcggccc | caaagcgagg | aagaagagcg | accagcccgg | 1080 |
| ccagccgcct | cctgatccga | gctcgctctc | caccgcggct | cgacccggcc | agatgccgcc | 1140 |
| gccgctgacc | ttctccggcc | ccgcagtagc | cgcgctgcag | cccttcgcct | cgtcgtcgct | 1200 |
| gtcgcccgac | gcggcctggg | agcccgtcga | gccgctcagc | attgacaacg | gcctgccccg | 1260 |
| gcagccgctg | ggcgacctgc | ccggcctctc | caccatccag | aacatctcga | gcgccagcg | 1320 |
| atggatacac | ctggccaacg | ccatgacgct | gcgcaacacg | acgctagagc | gcgtctcgaa | 1380 |
| gcgatgtatc | gacctcttct | tcgactacct | ctaccccctc | acccccctgg | tgtacgagcc | 1440 |
| ggccctccgg | gacgtgctcg | catacatctt | ctcccagccc | ttgcctggcg | tcaaccaacc | 1500 |
| atcgccgctg | tcacagctca | cgccagaccc | gaccaccggc | accaccccc | tcaacgctgc | 1560 |
| cgagtcgtgg | gccggctttg | gccagcccag | cggctcgcga | acgtcggca | gcaggctggc | 1620 |
| tccctgggcc | gactcgacct | tcaccctggt | cacggccgtc | tgcgcagagg | cagcattcat | 1680 |
| gctacccaag | gacatttttcc | ccgaaggaga | atccgtctct | gagatcttgc | tcgaagcctc | 1740 |
| tcgggactgc | ctgcaccagc | acctcgaggc | cgacctggaa | atccgacgg | ccaactcgat | 1800 |
| tgccattcgc | tacttccact | ccaactgcct | ccacgctgcg | gggaagccca | agtactcgtg | 1860 |

-continued

```
gcacatattt ggcgaggcca tccgcctggc gcaggtcatg cagctgcacg aggaggctgc      1920
cctcgagggg ctcgtcccca tcgaggcaga gttccgccgt cgctgctttt ggatcctgta      1980
cttgggcgac aagtcagccg ctatactcaa caatcggccc atcaccatcc acaagtactg      2040
cttcgacgcc ggcatcacca cgctataccc gtcgggtatc gaggacgagt tcctgagcac      2100
ggcgtccgag ccgccccgga agagcttcat atccggcttc aacgcaaatg tgcggctctg      2160
gcagtccgcg gctgatttgc tgctggaaat ccgcgtgctg caagatcaga tgatgcagca      2220
ctttcgaggg accatgcccc cgaaccatgt gctgccctcc gccgacaggc agcatctcga      2280
ttctctctat gtccgcttca tcacctgctt ggacgatctc ccgccgtacc tccagtcgtg      2340
cactctggcg atggcagcga tggcagaagg caacgggtct gccgagtcca agcagtacgt      2400
gatacagtgc atcaacctgc aggtgacgtt tcactgtctg cgcatggtaa ttacgcagaa      2460
attcgaagac ctctcttatt ttgctcctgg cgttgagcag gctgatctca gaaagtcgga      2520
gattgtgcga gacatgctga gggtgatgaa cgaggcgccc ttttggggcc tgcaggccaa      2580
tggcgagcca aacgtgagtc gtttccttgt ctcttctctt ttctgcacac ccttttcttc      2640
gacgaccccc cctctctctt tatatccctg cggatatgta tatcatcaag cctcggcact      2700
tgttgctaat ctgtcctgat tatgttgtct ggatgctgca ggttgaaaag attcgcctta      2760
tcggagctag tttgctggcc atcatccatc gcaaccagga ttcacccttg gctacgcgag      2820
ccaggagcga cttttccgtg cttttggata ttctcacgcg gctggactcg aaggcgtcgg      2880
actaa                                                                  2885
```

<210> SEQ ID NO 12
<211> LENGTH: 723
<212> TYPE: PRT
<213> ORGANISM: Trichoderma reesei

<400> SEQUENCE: 12

```
Met Ala Thr Ala Ala Ala Ala Ala Gly Gly Ala Ala Val Ala Ala
1               5                   10                  15

Gly Ala Asp Thr Gly Ala Ala Gly Ser Ser Ser Thr Gly Pro Pro Gly
            20                  25                  30

Leu Pro Gly Leu Pro Gly Thr Arg Thr Gly Ser Val Ala Met Gly Ser
        35                  40                  45

Ala Ala Pro Ala Gln Gly Ser Val Ala Ala Ala Gly Gly Pro Pro
    50                  55                  60

Ala Ala Gly Ala Gly Ala Gly Val His Ala Leu Thr Thr Ser Pro
65                  70                  75                  80

Glu Ser Ala Ser Ala Ser Gln Pro Gly Ser Pro Thr Ala Ser Thr Thr
                85                  90                  95

Pro Pro Gln Asn Ser Leu Val Ser Ala Ala Thr Ser Phe His His His
            100                 105                 110

Pro Arg Gly Arg Leu Val Ser Arg Ala Cys Asp Arg Cys Arg Arg
        115                 120                 125

Lys Ala Lys Cys Glu Tyr Leu Ser Ala Val Asp Ser Cys Thr His Cys
    130                 135                 140

Arg Asp Ala His Val Gln Cys Thr Phe Asp Leu Pro Leu Ala Arg Arg
145                 150                 155                 160

Gly Pro Lys Ala Arg Lys Lys Ser Asp Gln Pro Gly Gln Pro Pro
                165                 170                 175

Asp Pro Ser Ser Leu Ser Thr Ala Ala Arg Pro Gly Gln Met Pro Pro
```

```
            180                 185                 190
Pro Leu Thr Phe Ser Gly Pro Ala Val Ala Ala Leu Gln Pro Phe Ala
                195                 200                 205
Ser Ser Ser Leu Ser Pro Asp Ala Ala Trp Glu Pro Val Glu Pro Leu
210                 215                 220
Ser Ile Asp Asn Gly Leu Pro Arg Gln Pro Leu Gly Asp Leu Pro Gly
225                 230                 235                 240
Leu Ser Thr Ile Gln Asn Ile Ser Thr Arg Gln Arg Trp Ile His Leu
                245                 250                 255
Ala Asn Ala Met Thr Leu Arg Asn Thr Thr Leu Glu Arg Val Ser Lys
                260                 265                 270
Arg Cys Ile Asp Leu Phe Phe Asp Tyr Leu Tyr Pro Leu Thr Pro Leu
                275                 280                 285
Val Tyr Glu Pro Ala Leu Arg Asp Val Leu Ala Tyr Ile Phe Ser Gln
                290                 295                 300
Pro Leu Pro Gly Val Asn Gln Pro Ser Pro Leu Ser Gln Leu Thr Pro
305                 310                 315                 320
Asp Pro Thr Thr Gly Thr Thr Pro Leu Asn Ala Ala Glu Ser Trp Ala
                325                 330                 335
Gly Phe Gly Gln Pro Ser Gly Ser Arg Thr Val Gly Ser Arg Leu Ala
                340                 345                 350
Pro Trp Ala Asp Ser Thr Phe Thr Leu Val Thr Ala Val Cys Ala Glu
                355                 360                 365
Ala Ala Phe Met Leu Pro Lys Asp Ile Phe Pro Glu Gly Glu Ser Val
                370                 375                 380
Ser Glu Ile Leu Leu Glu Ala Ser Arg Asp Cys Leu His Gln His Leu
385                 390                 395                 400
Glu Ala Asp Leu Glu Asn Pro Thr Ala Asn Ser Ile Ala Ile Arg Tyr
                405                 410                 415
Phe His Ser Asn Cys Leu His Ala Ala Gly Lys Pro Lys Tyr Ser Trp
                420                 425                 430
His Ile Phe Gly Glu Ala Ile Arg Leu Ala Gln Val Met Gln Leu His
                435                 440                 445
Glu Glu Ala Ala Leu Glu Gly Leu Val Pro Ile Glu Ala Glu Phe Arg
                450                 455                 460
Arg Arg Cys Phe Trp Ile Leu Tyr Leu Gly Asp Lys Ser Ala Ala Ile
465                 470                 475                 480
Leu Asn Asn Arg Pro Ile Thr Ile His Lys Tyr Cys Phe Asp Ala Gly
                485                 490                 495
Ile Thr Thr Leu Tyr Pro Ser Gly Ile Glu Asp Glu Phe Leu Ser Thr
                500                 505                 510
Ala Ser Glu Pro Pro Arg Lys Ser Phe Ile Ser Gly Phe Asn Ala Asn
                515                 520                 525
Val Arg Leu Trp Gln Ser Ala Ala Asp Leu Leu Leu Glu Ile Arg Val
                530                 535                 540
Leu Gln Asp Gln Met Met Gln His Phe Arg Gly Thr Met Pro Pro Asn
545                 550                 555                 560
His Val Leu Pro Ser Ala Asp Arg Gln His Leu Asp Ser Leu Tyr Val
                565                 570                 575
Arg Phe Ile Thr Cys Leu Asp Asp Leu Pro Pro Tyr Leu Gln Ser Cys
                580                 585                 590
Thr Leu Ala Met Ala Ala Met Ala Glu Gly Asn Gly Ser Ala Glu Ser
                595                 600                 605
```

Lys Gln Tyr Val Ile Gln Cys Ile Asn Leu Gln Val Thr Phe His Cys
610                 615                 620

Leu Arg Met Val Ile Thr Gln Lys Phe Glu Asp Leu Ser Tyr Phe Ala
625                 630                 635                 640

Pro Gly Val Glu Gln Ala Asp Leu Arg Lys Ser Glu Ile Val Arg Asp
            645                 650                 655

Met Leu Arg Val Met Asn Glu Ala Pro Phe Trp Gly Leu Gln Ala Asn
            660                 665                 670

Gly Glu Pro Asn Val Glu Lys Ile Arg Leu Ile Gly Ala Ser Leu Leu
            675                 680                 685

Ala Ile Ile His Arg Asn Gln Asp Ser Pro Leu Ala Thr Arg Ala Arg
            690                 695                 700

Ser Asp Phe Ser Val Leu Leu Asp Ile Leu Thr Arg Leu Asp Ser Lys
705                 710                 715                 720

Ala Ser Asp

<210> SEQ ID NO 13
<211> LENGTH: 2185
<212> TYPE: DNA
<213> ORGANISM: Trichoderma reesei

<400> SEQUENCE: 13

```
atgggctcag cagctccggc ccagggctct gtagctgcag ctgcaggcgg ccctccagct    60
gctggcgctg gcgctggcgc tgtccacgcc ctcaccacct cgcccgagtc tgcctcggcc   120
tcgcagcccg gctcgccaac cgcctcaacc acgccgccgc agaactcact cgtgtcggct   180
gcaacctcgt tccaccacca tcccagaggc cgtctggtga gcagagcctg cgaccgctgc   240
cgccggcgca aggccaagtg cgagtacctc agcgctgtcg atagctgcac gcactgccgc   300
gatgcccacg tgcagtgcac tttcgacctg ccctggcgc gacgcggccc caaagcgagg   360
aagaagagcg accagcccgg ccagccgcct cctgatccga gctcgctctc caccgcggct   420
cgacccggcc agatgccgcc gccgctgacc ttctccggcc ccgcagtagc cgcgctgcag   480
cccttcgcct cgtcgtcgct gtcgcccgac gcggcctggg agcccgtcga ccgctcagc   540
attgacaacg gcctgccccg gcagccgctg ggcgacctgc ccggcctctc caccatccag   600
aacatctcga cgcgccagcg atggatacac ctggccaacg ccatgacgct gcgcaacacg   660
acgctagagc gcgtctcgaa gcgatgtatc gacctcttct tcgactacct ctaccccctc   720
accccctgg tgtacgagcc ggccctccgg gacgtgctcg catacatctt ctcccagccc   780
ttgcctggcg tcaaccaacc atcgccgctg tcacagctca cgccagaccc gaccaccggc   840
accaccccc tcaacgctgc cgagtcgtgg gccggctttg ccagcccag cggctcgcga   900
accgtcggca gcaggctggc tccctgggcc gactcgacct tcaccctggt cacggccgtc   960
tgcgcagagg cagcattcat gctacccaag gacattttcc ccgaaggaga atccgtctct  1020
gagatcttgc tcgaagcctc tcgggactgc ctgcaccagc acctcgaggc cgacctggag  1080
aatccgacgg ccaactcgat tgccattcgc tacttccact ccaactgcct ccacgctgcg  1140
gggaagccca gtactcgtg gcacatattt ggcgaggcca tccgcctggc gcaggtcatg  1200
cagctgcacg aggaggctgc cctcgagggg ctcgtcccca tcgaggcaga gttccgccgt  1260
cgctgctttt ggatcctgta cttgggcgac aagtcagccg ctatactcaa caatcggccc  1320
atcaccatcc acaagtactg cttcgacgcc ggcatcacca cgctataccc gtcgggtatc  1380
gaggacgagt tcctgagcac ggcgtccgag ccgccccgga agagcttcat atccggcttc  1440
```

```
aacgcaaatg tgcggctctg gcagtccgcg gctgatttgc tgctggaaat ccgcgtgctg    1500
caagatcaga tgatgcagca ctttcgaggg accatgcccc cgaaccatgt gctgccctcc    1560
gccgacaggc agcatctcga ttctctctat gtccgcttca tcacctgctt ggacgatctc    1620
ccgccgtacc tccagtcgtg cactctggcg atggcagcga tggcagaagg caacgggtct    1680
gccgagtcca agcagtacgt gatacagtgc atcaacctgc aggtgacgtt tcactgtctg    1740
cgcatggtaa ttacgcagaa attcgaagac ctctcttatt ttgctcctgg cgttgagcag    1800
gctgatctca gaaagtcgga gattgtgcga gacatgctga gggtgatgaa cgaggcgccc    1860 tttggggcc tgcaggccaa tggcgagcca acgtgagtc gtttccttgt ctcttctctt    1920
ttctgcacac cctttcttc gacgaccccc cctctctctt tatatccctg cggatatgta    1980
tatcatcaag cctcggcact tgttgctaat ctgtcctgat tatgttgtct ggatgctgca    2040
ggttgaaaag attcgcctta tcggagctag tttgctggcc atcatccatc gcaaccagga    2100
ttcacccttg gctacgcgag ccaggagcga cttttccgtg cttttggata ttctcacgcg    2160
gctggactcg aaggcgtcgg actaa                                          2185
```

```
<210> SEQ ID NO 14
<211> LENGTH: 678
<212> TYPE: PRT
<213> ORGANISM: Trichoderma reesei

<400> SEQUENCE: 14

Met Gly Ser Ala Ala Pro Ala Gln Gly Ser Val Ala Ala Ala Gly
1               5                   10                  15

Gly Pro Pro Ala Ala Gly Ala Gly Ala Val His Ala Leu Thr
            20                  25                  30

Thr Ser Pro Glu Ser Ala Ser Ala Ser Gln Pro Gly Pro Thr Ala
            35                  40                  45

Ser Thr Thr Pro Pro Gln Asn Ser Leu Val Ser Ala Ala Thr Ser Phe
50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
        115                 120                 125

Pro Pro Pro Asp Pro Ser Ser Leu Ser Thr Ala Ala Arg Pro Gly Gln
130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
        195                 200                 205

Ile His Leu Ala Asn Ala Met Thr Leu Arg Asn Thr Thr Leu Glu Arg
    210                 215                 220

Val Ser Lys Arg Cys Ile Asp Leu Phe Phe Asp Tyr Leu Tyr Pro Leu
225                 230                 235                 240
```

```
Thr Pro Leu Val Tyr Glu Pro Ala Leu Arg Asp Val Leu Ala Tyr Ile
            245                 250                 255

Phe Ser Gln Pro Leu Pro Gly Val Asn Gln Pro Ser Pro Leu Ser Gln
        260                 265                 270

Leu Thr Pro Asp Pro Thr Thr Gly Thr Thr Pro Leu Asn Ala Ala Glu
    275                 280                 285

Ser Trp Ala Gly Phe Gly Gln Pro Ser Gly Ser Arg Thr Val Gly Ser
290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
            340                 345                 350

Gln His Leu Glu Ala Asp Leu Glu Asn Pro Thr Ala Asn Ser Ile Ala
        355                 360                 365

Ile Arg Tyr Phe His Ser Asn Cys Leu His Ala Ala Gly Lys Pro Lys
    370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
            420                 425                 430

Ala Ala Ile Leu Asn Asn Arg Pro Ile Thr Ile His Lys Tyr Cys Phe
        435                 440                 445

Asp Ala Gly Ile Thr Thr Leu Tyr Pro Ser Gly Ile Glu Asp Glu Phe
    450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
            500                 505                 510

Pro Pro Asn His Val Leu Pro Ser Ala Asp Arg Gln His Leu Asp Ser
        515                 520                 525

Leu Tyr Val Arg Phe Ile Thr Cys Leu Asp Asp Leu Pro Pro Tyr Leu
    530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
            580                 585                 590

Tyr Phe Ala Pro Gly Val Glu Gln Ala Asp Leu Arg Lys Ser Glu Ile
        595                 600                 605

Val Arg Asp Met Leu Arg Val Met Asn Glu Ala Pro Phe Trp Gly Leu
    610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655
```

Arg Ala Arg Ser Asp Phe Ser Val Leu Leu Asp Ile Leu Thr Arg Leu
            660                 665                 670

Asp Ser Lys Ala Ser Asp
        675

<210> SEQ ID NO 15
<211> LENGTH: 930
<212> TYPE: DNA
<213> ORGANISM: Artificial Sequence
<220> FEATURE:
<223> OTHER INFORMATION: promoter sequence

<400> SEQUENCE: 15
agcagtggct tatagcaata tcgtgcttgt ctctgccctc gctgaagcta tccctccctc    60
gtgtccccct tcgtggagaa tgactgcagt aaaggagacg atacgctctt gggaaggtcc   120 tgaaggggt ggctgttggg attgcaacct ctggcatttg tcgaatggcg ctttatgcgt    180
cgcgctcgcg agtgatgttg agaggaaagt caacgttgtg acggcttcac aatttgccct   240
ttcattaagg cttattgccc gctaaattac tataaggaag tcggcagct gggattacgc    300 atgtgttgct agacacaatc tcgaacgaga cgctatcaga ggacaagttt tctgacaatc   360
tgtcgtggta ttgaacgctt tcgtgtttg taaaccagca ttcatgaggt tcgagggccc    420
acgcattcat tgggatctca tcaatgaagc ggaatagtac aagaagaccg agcatccatt   480
acagacctca tgcagctaag gaaacggatc acccttaaag acgtggatgt agtttccgtt   540
gctcgcgcac attagaaggc tggtactata ggtgagggaa gcgcatgctt gttgtttatc   600
cgccatgata agaggagtgt aagccggctg catggacttt ttccataccc tgtcttgcct    660
gtccatcttg aaattggcaa gctccacctt ccggttaaaa tcgcaggctt aaggtcttct   720
aataaccact cagcatttgc tcaaccatgt ctttgctcct ctcacctgac ctgcatctcc   780
ttttagcctc caggagttgg cgaattgatg ccgattttga cgtcaaatcg cattgagata   840
actcacgata ttcgttttac aggctaaaga attgcctcca gcgttccagt tcccgtcgta   900
ggccgagacg acactgcctc actaccagcc                                    930

<210> SEQ ID NO 16
<211> LENGTH: 930
<212> TYPE: DNA
<213> ORGANISM: Artificial Sequence
<220> FEATURE:
<223> OTHER INFORMATION: promoter sequence

<400> SEQUENCE: 16
accccaatct gaggttcagg tttggcttcc ttcgagttct ccaagttctc tgaatcgtat    60
gtccgcattc attggtatcg aagtttgtga ttaatctcga gaatgtgcat acttcagtca   120
cctcaacata cacggaatcc agcctcttca tgaggaatcc ttactccttc ataccccaag   180
tgcccgggca gataattgta cccattcaca aatgaactta gactgtactc cgcacttctt   240
tcaggctcct ctctcctcac gatgccccaa tgcttgccac tccacaaggt acatgtagta   300
atctgcagtt actccccgc ttttgcctac ttagccggca agaatgagat gcaagtttgt    360
tcctgtcggg agtattggct aaatggaaac acaagtagaa gaagagaaac agaaaaggtc   420
caataccggc tattcacaac ggatctgcgt ctgtgtctga tagaactagt aaaagtcggc   480
agtatccgct gtcatcaaga tcatatacta aaacgtaagc taaacgcaat ggcttggaaa   540
aggggattga gacagaagat acaccaacga ccaccctgt tagtgacaga gatggcagtc    600
attcgactag cggctggcaa ttggtgtccg ccttgtattc aggctaaata tctcgaggtg   660

```
ccgggaaatc atgGtgagga ggagttggca tgtgtggagc cgtgatgcag gtcggaccac    720
accaagaagc tggggtagca tttccgtccc gtatggggtt aacatgggGt aacatgctgg    780
aattgcaaat gatgcatggg ggaagaatgc aacatcgtca tcgtcatacc gctcaattta    840
aatattgggc ttttccgggg atcagatgga agaaggcaac agagagagag acaaggaaga    900
ccgtgagcca ttgaaggaca gccggacgca                                     930
```

<210> SEQ ID NO 17
<211> LENGTH: 930
<212> TYPE: DNA
<213> ORGANISM: Artificial Sequence
<220> FEATURE:
<223> OTHER INFORMATION: promoter sequence

<400> SEQUENCE: 17

```
tctatggcca ctctgtcgcc tgttcatctg tatcagcacc aaagccatga ccgtgatgta     60
ttgatgtgcc atcttggcgt tctttcggca acacaccggg cttgaggttt gtcactccct    120
ctccgcactt gagcacaacg ccggctgcct cgtgtcccag aatacagtct ccttcgaaga    180
cgagggagcc gattctccca gacttccaga aatggacatc cgatcttgca ctctgtcagc    240
ctgcagttga atgcgagttt gttgaagacc ttcagcactc acccgcatat gccagtagct    300
ttgatttgca gcaagacttg tccgcgctct ggtttataca ctggtgcttc gaccagcttc    360
aggttgtggt cggcagttgc ttgtagtgat ggattgggtc gtggagcttg aatgatccta    420
tgctcaagat cccgagctac agaaacgttg ccgctgggca tggttgctga ggccatggtt    480
taggtcgagg caatcgacag aagctcgaaa gtagtgaagt ttggtgtaag tagaatgctg    540
acggtgactt tgcgaatgcc caaatgtcaa gtgtaaagta ccaaactact gtcggtcagg    600
tgcaagaaac gcaatattgc tgggaattat aaatcagaa gggtagacaa taagacgtga     660
tggcctctga ggagctcaaa tgatcgcgct ccaagaggtg gctaaaactt cccgattcgg    720
caatcctcac ggcttcctcg atgcggatgc aataacctct attagcctat atctgcggaa    780
gctatagacc gagcatttgc gtttgtcata tcttcgacat catttctctg atccttttct    840
ttttattata tagaagctga agttgtacgg cacaactgtc aacacaccgt tgccgcggaa    900
ttctccccta tacttgacca atccatcaag                                     930
```

<210> SEQ ID NO 18
<211> LENGTH: 930
<212> TYPE: DNA
<213> ORGANISM: Artificial Sequence
<220> FEATURE:
<223> OTHER INFORMATION: promoter sequence

<400> SEQUENCE: 18

```
tcaacatatg gttggactag gctcgtctca cgtccagttt cttcaagtca tatgttccag     60
gaccgggaag atgtctgcaa attggatagt ttttctttcg tagctgccct cgatcaacct    120
gggacgcgat acgcctcagt tcaagtactt gatctgaagt accgtatgtt taggctgata    180
tccgatggga tgccccaaa tacaaggctc gtcaacctga ttatgagaca attctttcac    240
ctacgtcaat ctcgggtcat tctttgcaag aaacacgatc agtccatctc tcaggagcct    300
gtcgtgtttt tctgctgaga ccattgggct tcccctcgac agtatgttgc cccttggcta    360
actctcctcc acgcctacct ggcctacctg acctaccagg gaggcggtct tcttacctac    420
ctatcaaagg gcctccacgt ggctgcgatg ctctaatcaa caaattcctt cctcgcaagc    480
```

| ttcttctttc | tgactgtctt | ccaggttctg | ctggccttgt | tcctcggcaa | ccagagcgat | 540 |
| cggtgcagga | agcagcgaga | agcgagctct | caggagaata | agcgagtcga | tactccatcg | 600 |
| gaagtctctc | gcgcgtgcag | ctgccgattc | cgaggccact | cgctctttgc | cgaatgagcg | 660 |
| tcacgacggc | cctacagata | taccgatagc | gttgccctgc | cacctgatca | agttgtcgcc | 720 |
| tactatatgt | ctcgaggcat | gaccgtatcc | aaagctgcag | cttggattct | cacctcctca | 780 |
| gagccgacct | tggaatagca | ggggacacat | ttggcctcct | cagcaccgct | ctttggcgcg | 840 |
| tctcctctgc | gtttgatttg | ttcttccact | tctctcttcc | ctgatatctc | ttcttgaact | 900 |
| gccggctgcg | ttgtcgaact | cgtgctcacg | | | | 930 |

<210> SEQ ID NO 19
<211> LENGTH: 930
<212> TYPE: DNA
<213> ORGANISM: Artificial Sequence
<220> FEATURE:
<223> OTHER INFORMATION: promoter sequence

<400> SEQUENCE: 19

| gcgattagca | cgcatcgctg | ctgggaccgt | gagctcgacg | ggctcaacag | catggtggcg | 60 |
| tactgaggga | tatcgttcac | atcgttgaac | gaggcggaca | tgagaaacga | cttgatatct | 120 |
| gtattattta | cttgtacatg | tacggcagtc | actaatacct | gtctcaatca | atgaagattg | 180 |
| atgtaaataa | gcttaatcaa | actgtctaaa | atatgtttac | attttaagtc | tttgctcctg | 240 |
| gtttgtgcta | ataaatgcgt | gaggtgacat | cgtccgggaa | tagtgagacg | aagtggtatc | 300 |
| accaagtgga | gggactcatt | attgttcatg | cacgtcccat | gtacaaggcc | taaatccgcc | 360 |
| agctattccc | cgtatgacct | gtcaatactc | gatacgatac | agtagctgta | tggacaagca | 420 |
| agtactactg | gtatgggtgt | aaccccagct | gctacaaacc | ctgggaagca | gactctcaca | 480 |
| acctattact | aggtactctc | gttcgttttc | tcaaagttta | gggcatctcg | catgagagca | 540 |
| agacgttgcc | ggcatcgcct | cagctactta | tgatgccatc | tcatcaagcc | catgagacca | 600 |
| cctatgcact | gtcacaagag | aacaaacttc | gccttttgga | acccgcaaaa | acaggggaga | 660 |
| tgcccgttgg | tctttgcttg | tctttaatcc | gcttgatctg | tgtccacagg | aacggggaa | 720 |
| aaaacaactc | gggttcgtat | ttgcggtgtg | gcagcttcca | acaggggtat | ggaaaatcga | 780 |
| ccttcccaca | cgacgggtta | atatccacaa | gccggcgaaa | tggtaaattt | ataaatcgag | 840 |
| catcattccc | atctgggtgg | atttcaaaca | aaagaaaagg | aagcgcatcg | tggaaagggt | 900 |
| gcaaggctcg | gataaagtcc | tcttctcgcc | | | | 930 |

<210> SEQ ID NO 20
<211> LENGTH: 930
<212> TYPE: DNA
<213> ORGANISM: Artificial Sequence
<220> FEATURE:
<223> OTHER INFORMATION: promoter sequence

<400> SEQUENCE: 20

| tgcgaactgg | caatgagttt | tcaaccatca | aagtcacggc | gcagttgtcg | tacatggtgg | 60 |
| tccgagaata | aaaaggctac | atggtaaatt | cgttaaaggg | caaggtcaat | aggagcacag | 120 |
| tgatgcttcc | ttggacagtg | ttgcttacat | ccgatcatcc | caccttgaca | tacactcgct | 180 |
| ttgagtattc | gatcgtgcca | acccgattga | tacattacaa | gcagaactga | gccgctgtta | 240 |
| tcgacacact | tgcggtcttc | tcagtgagac | gcttctacct | cgcttgcgtt | gatatcacga | 300 |
| gggcattgat | acgtcaacca | cttcatatca | agtctgattg | ctgaatgcct | tcaatcattc | 360 |

| | |
|---|---|
| aggcccacaa atatccctac agcatgctca ctttgaaatg agtttttctc tctctttcgg | 420 |
| ccagcaggcc cgtttggcgc gtatgagcgc cgaagctgac actccagcga cgtgctgatc | 480 |
| tagattctgg acacgaatag attcctattg aagggagtga cgtccccacg atgaactccc | 540 |
| gtcgagacag ttttgcatgc atacagccgt ttaacagcca gcggtgtact ttatacaaag | 600 |
| aacaacgtcg ctgtgttagt tgcgccaact tggcgtgatt ggacggacgc cgactcaacc | 660 |
| cctgcatcac aatccgccaa gaagcgtcac cgcggataaa aaggctaaat ggatggtctt | 720 |
| caactcttcg cgacatggaa cgcgagcagg tattacagaa tgatgaccgg ttaaatctgg | 780 |
| cagtctccat ggtactgaag tcaaagcaag agggacaatt cacaatggcc ttgatataaa | 840 |
| agcgataaca tgtctccggt caaggcctgg atgagcagag tttagagcaa actgcctgct | 900 |
| tgggaatctt ctctctactt tctcctcgac | 930 |

<210> SEQ ID NO 21
<211> LENGTH: 930
<212> TYPE: DNA
<213> ORGANISM: Artificial Sequence
<220> FEATURE:
<223> OTHER INFORMATION: promoter sequence

<400> SEQUENCE: 21

| | |
|---|---|
| ctggggtaac agagctgttt gcggggatga agatcttgat gaatatggtg aatgaggaat | 60 |
| ttttcctatt ggaggaagca ttgtcgaatc caagggtatg cgggctcggg aagggcatc | 120 |
| tctccttagc tgtcaaggct ctagatactg tgatactcga tgatatataa gccaaaccca | 180 |
| agcaaagatc cgctggttgt ctgaacaagc cgaatgccag gcccttttg ccggagcccc | 240 |
| tcatcgaaat ccgctgtgca agcggttcat gggttcaaca ttcggaatag cttctccgca | 300 |
| agtctgtggg gtagcagcag cactccggca gatgccactg tgcctgtgaa tgtggggaga | 360 |
| ggccagagta tggggaacca tgtgggaggc agcacggaga cactcgaagg tcatgccttg | 420 |
| gagttgtgcg tactttgttt ttgcatgcct tggttccatc atcgaaagga gagcagcggt | 480 |
| agatagagcc ttaagcatgg gtaaaactcc ttccgacaac tctataacag acgttaggaa | 540 |
| aacaacaagt tcccagttat tacccagagc tttctttacc catcggcaca acgtgcaacg | 600 |
| gccaagaatc gctgccgatc tcctcatctc cagcccctca agtctccaa gctgcatcca | 660 |
| gcatctccag gcggaccttg cttgcccaca ctttaggcta aaggcttctg ccctggtcg | 720 |
| gcagtggcag aagcaacctg ctacttgacg acatgaaccc gtttgtaccg gctcggccat | 780 |
| gagatgatgc agtgttccaa tggcatagtt gagtcgaagc ggtgttttca ccccttaatg | 840 |
| atgtaacatg tatataacgg atgaccatgc cctccttgac ttcacttcaa cggctctatt | 900 |
| atcctgcctc gagccacaag cagcgcagtc | 930 |

<210> SEQ ID NO 22
<211> LENGTH: 930
<212> TYPE: DNA
<213> ORGANISM: Artificial Sequence
<220> FEATURE:
<223> OTHER INFORMATION: promoter sequence

<400> SEQUENCE: 22

| | |
|---|---|
| catccacatc atcttgacga ggaaccatcg ggtggtcgga cggactctgc agatctgggg | 60 |
| tgcgtctgac cgacgaggtg tcaattagcc tacgtgtgag tacccatgct gagaattgat | 120 |
| acctatggat gcaagtgcct ctgaactatt actttatcca taggagcatc cgctaccaat | 180 |

```
gtgcggttaa aattgccttt cagccaccct gtcctcggtt aattgagtga gacgtgcata    240
acatggccgg cagcatggca tggtagatga tattgggtga acgtgtcaga agaaaaggct    300
agaatattcg agacagcttg ctgatatgtg caaaacttct caagatattt gatatgtgta    360
gagttactct tggcattata ctgtaatgtg aatgtagagt gtacgctaca gtacctcaat    420
ccaagaactt ataacatacc tacatacccta ctgagctaca ttttaggcag tgcctccgct    480
gagaagcttt gaattctact tttgtcgttt taactcgtga cgcattgact ggcgggtcat    540
cctgatacag aatcaggacc attgcatatg aaaaacagtc tgagaccaaa catccaatcg    600
ggagacaatg ctgccatgaa agctgattta gcctatttcg acttctcaca actcaaagag    660
atgctttatg ttcgggggaa gggaatatga ctgtgactag aatgcatcgg ggtcctgcca    720
aagaatgagt tgactatgag gaggcaaata tctgagtcat gtgagtagac cagtaaatga    780
cagctggggg taatcactta tgtgttcacc ggatatactt catattgata taaaatgcta    840
tgatctccaa gtcccaacga tactgagatg aacagcatct cttaacagtt gctttccaca    900
taaataattc ctcctgttac aagagccaaa                                     930
```

```
<210> SEQ ID NO 23
<211> LENGTH: 1059
<212> TYPE: DNA
<213> ORGANISM: Artificial Sequence
<220> FEATURE:
<223> OTHER INFORMATION: promoter sequence

<400> SEQUENCE: 23
```

```
ggcaggcact ggctcggacg acatgttttg tatattggtt gggactgcgg ccgcagcggg     60
ggcgggagct ggtggcggcg atatgaattt ccggcgttg ctacaacagg taccactttg    120
accacccatg gctgccgtcg ccctgcttgg agctttcagg tcgcttccgg gcgttggcga    180
ggcaagttgg acggtgggga aatgacgaaa aatggtgcat cgcctttgta ggtgtgtgtg    240
agtagtagtt ctactatgag gtacgtatgt agcagaagga tcgagctaga atctgccggc    300
attgcaaagg ttatctggaa agaggaaaag ggcctgaacc ggcatatgga tgcattcttc    360
gtacgaacta ctatctgata acagttaggt actgttatcc atacaaagag tcttatagaa    420
acactgcatc gtaataaaat actcggtagc tgcttgaata tagtaataag atcaacatcc    480
tttcacctct agtctccgtg gattccagta aaagcgctca attctgactt ccgactctgt    540
tgatgccccg tgtctgccca tcggggtggt ctagacgctg cctcaacgcc catgtaccgg    600
cctgatgggg cccttggggg caccacaagt ccactaaacg aagcactggg gacgggactc    660
gatagccctg agcagcagcc ggtctcagca gccaaccagc ccagctggaa gcatcggcta    720 ggggagggg gcccaactac tacgtgtact actaggtaca taatgaattg gatgggaccc     780
agccagccca acctaacttt ccagccttta tagctgcagc ctgcttcccc gtgcctcacg    840
ctttttgctc ctctgctggc cggactcgga cctcttgcga cctctgctcg accaacaatc    900
cctcttgttg caccctctcg cttttgctac ctcgacgctc aattcctcgc tgccgcctca    960
cctaaccgcg tgtgcttgac tgccctcacg ctcggctcgc ctcctgctcc gcgagcctcc   1020
ttttacactt ttcaacagct accccgccag aattcaaca                         1059
```

```
<210> SEQ ID NO 24
<211> LENGTH: 1963
<212> TYPE: DNA
<213> ORGANISM: Artificial Sequence
<220> FEATURE:
<223> OTHER INFORMATION: promoter sequence
```

<400> SEQUENCE: 24

```
gacggaatct tcacacctag tactcgtaca tactagatca gatgctgggc gagtctgggg      60
aatgctggca ctggatggta taaacacccg actgcttgac gccggatcag cggcgatgca     120
ccgagctgga cgtgtcaata ctacatgtat catgacgcag agctgtttct cctctggcac     180
atgaacccaa agacacaagc gtcacctcgt tcctgagcag atcaggtaca gacttccata     240
tctcactggt cccatctctc gagcctaaac cggcctccca ctttgcacaa gatgccccaa     300
gccgttgcgc agagacgacg tggactcgac ctcgtcagcc atcgatgccg tctcagctgc     360
cgcttcggcc aaccaacttg ctgcgaggca aaagtatttg ctgcattgat gccagccaac     420
ctcctcctcc ttgcctcctc cattcagccg gcagcaatcc aaccacccac ccaccggcgc     480
agcgccacgc aaggcacagt caggactaac actcttaggc tgcctggata catgtagaac     540
ggtcttttgg tggttggggt tgctgcacat aaggtatata ctgtacatgc atatagtatg     600
catacagtag acgctgcttg gcggcccgtg tatgtagggga tacatcatcg tccatctgct     660
gctcccccgc aatccgctat ccggcatacc gagagctcag gagccggtcg ttgcccgtcc     720
ttgtacgagt tacacctcca agtctccccc ggcctcccat cacagctgcc tccgcacggt     780
gaccatcccc caagcaagtc gctccttgcc acttggtgga gggtcgccag tggacgagag     840
ctgctgccaa tgcccatgat cagcaccggc ctgcgctggc tgactggata cttgcaagta     900
ttaaaacggt cgacctcgcc ggttgttctc gtcgtcaact cttgccctct gactctgact     960
ctgactcttt ccgtatcccc gtcgcatcgt gttggaagct gctcctcttg tcttttttctc    1020
tgccaaaccc tctcgctact aggtatctca acctttgtat acgagatcag tatcgcgggc    1080
acgcagggtc tcatcctgac tcgtcctgtg tcggaatcgt ctcacgtctc actgccaaca    1140
agcagtttgc gatacgcaaa tcaatcgctt gcatcaggtg cattccagat ccggcctccg    1200
gacgtcgtta tataatcgcc agcgcccttc tccccaagag cccagccttt tggagcagga    1260
cccaggcttt gtccatattt tgggtcgtac gcctgccttt tgccatcgcc atctgcttcc    1320
tcccacccaa cccacgcccc tcatcaatct ccatctcccc cgccaaaggc gactcgatcc    1380
ccgcgtgcac acacaaacca ccccggggaa aacgagacca acgctatatc ctgtggcagc    1440
gcccgctcaa tccccttccc agcgtgcgcc ttgaccgcgg agtttgttat ccggtgagtg    1500
cagctcccgt cttccgacca tccctccctc tctgcttgtt agtggcttgt cccacccgcc    1560
aatctgcgcc ggccagcgga gcccagcctg agcccgccct cgagctcggg gccgttctgc    1620
gaccctatac tttccgaggg cccaaaggcc gacgtcaaaa ctgctcgggt atcctgccgg    1680
ctctggtcgg cctgccgttg ggcttggctt tgaaagaggt tgccgatgac gggatcgcag    1740
tccccaagtt caaccctctc tctgccccac caatcatgac ccccatgccc gtcgttatgc    1800
cactcatgtc atcgcagtgt gaacattgac ggagcttgac taatgtgaca gagtcattca    1860
ggttgttgga gagccaagca gggtcctcag ctagcgaggc ccgacccgag gcgcagagtc    1920
ccgaccatag cacttataag gcggcgcttc cgctgtcgta act                       1963
```

<210> SEQ ID NO 25
<211> LENGTH: 1067
<212> TYPE: DNA
<213> ORGANISM: Artificial Sequence
<220> FEATURE:
<223> OTHER INFORMATION: promoter sequence

<400> SEQUENCE: 25

```
gtgctgcagt tgctacgcgt agtctcaact ggcatgcgat cgacaatact aaaatcagca      60
aagcctgagg tccgttgggt gaaaacttca ttcgtactcg tactcagacc gcaaattctg     120
gtatggtttg atgggttggt tcatagtgat catccatatc atgggaagcg ccgcctgctc     180
cgagaagcaa caagtagcca acagcatcgg cactatcgtg catcatgccc caactctctc     240
ctagccgtag cggacctccc tcaaccagac agtgcccaag atcctttgac gcactatcag     300
cgagtctatg tacactgacc aacatgcagc cccggcgact tcccagatgg gccaacttca     360
gtcgagacgg cgttgttttg cagttaattg ccgccgcttg atatgcgctt aatggaaggc     420
gttccgctgg aacttccctg cgccacgtt gttggatctc atgattgtgg tattttccg      480 tgcctcatca gttctcgagg aacttctgta caccgaatgc catgtgaggc ccccgctcag     540
ccccagctgc agcactccgt accccatata ccaggcaaat tatcgacccc gattgcttgc     600
aatcaaaatc gcttggcggc gtcttgatat gcccgctagc aaggaaaagg caggatgctc     660
gttattggtt gctcaatatc gtcgtcgacg ggggaatgtc ccgctttcgt ccaatatcct     720
gtggcgacaa gggctatcaa aaagttcctc atccgcgatg tgccaacaac cgtggcagta     780
gacaaaggtg ccttccaaaa gaggcgataa ctggatcgcc ccccatgcat gcttgagtct     840
atcaaacggc cagctggagc ttctgttctg ttctggagtt cgtgatggtg ggtgcttggg     900
tgtaccttgc ccgttgcgtg gccggtgctc tcttgtgtga cattgcattt aaatatcatc     960
gtgcctgtcg ccagtcttta ccgacttgga gattcttgtc agctattcct ctgcaagcgt    1020
tcaactgccg ccggtgagga acactcggtc agtgccaaca caacacc                  1067
```

<210> SEQ ID NO 26
<211> LENGTH: 1124
<212> TYPE: DNA
<213> ORGANISM: Artificial Sequence
<220> FEATURE:
<223> OTHER INFORMATION: promoter sequence

<400> SEQUENCE: 26

```
cgaggcagat accgagatgt tgtagcacgg aagtcatctc gtctagctgc ccgtggggaa      60
aaaaaaaaaa gtaagccgga accgcaggtc caggcctgcg gctgtacaaa ggagcaaaca     120
cgatacaaac acaataccac cctatggtag catcaataat ccgtaatcgt aatagcatgg     180
gcgaatattt gccctctcgg tacgcgctc cgtaataaaa ataacacccc cccaaatctc      240
ggtgccccca attcgggtct ttttctccac cagttcggaa ccctccctcc tatgtactct     300
ctctctctct ctcgttggtt gggggagagc gagcgagcga gagagagagg cagtgaaagg     360
ctcaggctcg gtctttgctg cgccaaccct cgcccatgtc atctccccct gattagcgcc     420
ctcacctcag tttctcgccc cctcgtgacc gtttccgcct ccacaatctg gggagcctgg     480
aattagcaac tgtggaactg aggggtagat cccacgcgtc ccgttagtaa gtgcttaagc     540
gccgtgcgaa agggtgcgag caccggagtc gatgtcgaaa tactgatgtc ctccctggaa     600
cccaattact ccggggggcg actaaagcag cccagccagc caaactagca gcaaggcaca     660
cgctcacact agtaatgccc ggccggcgga tgatgttgct tgtctgcttg tttcttgtgt     720
cagggccagg aagccaaatc ttgtctgggg gggcgacata aagggccgct cgtcggccta     780
ccttgagcca cgcaaccaca cacctgtccg gtttcctcaa ttccttatac caccaaacga     840
accataacaa caacgctctc ctcctccttc atcctccttc atcattgtat catcgtcata     900
gcattgcgtt gccagctctg ttgtgtctgt cagttcatat aacaaagcct tccgtgtctc     960
tttcttcctc tcacactata tttttttttt ttcacctctc atcacaaaga cccacacctt    1020
```

```
ttccgccaca actgctccta ccaaaggcac actcgcacct ttgaatgatc tcctccttgt    1080
ccaaaagact caagtccaga agaagttcac ggagttccaa agcc                     1124
```

<210> SEQ ID NO 27
<211> LENGTH: 780
<212> TYPE: DNA
<213> ORGANISM: Artificial Sequence
<220> FEATURE:
<223> OTHER INFORMATION: promoter sequence

<400> SEQUENCE: 27

```
agactagcgg ccggtcccct tatcccagct gttccacgtt ggcctgcccc tcagttagcg      60
ctcaactcaa tgcccctcac tggcgaggcg agggcaagga tggagggca gcatcgcctg     120 agttggagca aagcggccgc catgggagca gcgaaccaac ggagggatgc cgtgctttgt    180
cgtggctgct gtggccaatc cgggcccttg gttggctcac agagcgttgc tgtgagacca    240
tgagctatta ttgctaggta cagtatagag agaggagaga gagagagaga gagagagggg    300
aaaaaaggtg aggttgaagt gagaaaaaaa aaaaaaaaa aaatccaacc actgacggct     360
gccggctctg ccaccccccct cccctccaccc cagacaacct gcacactcag cgcgcagcat    420
cacctaatct tggctcgcct tcccgcagct caggttgttt tttttttctc tctccctcgt    480
cgaagccgcc cttgttccct tatttatttc cctctccatc cttgtctgcc tttggtccat    540
ctgccccttt gtctgcatct cttttgcacg catcgcctta tcgtcgtctc tttttttcact   600 cacgggagct tgacgaagac ctgactcgtg agcctaacct gctgatttct ctccccccct    660
cccgaccggc ttgactttg tttctcctcc agtaccttat cgcgaagccg gaagaaccct     720 cttaacccc atcaaacaag tttgtacaaa aaagcaggct ccgcggccgc ccccttcacc     780
```

<210> SEQ ID NO 28
<211> LENGTH: 58
<212> TYPE: DNA
<213> ORGANISM: Artificial Sequence
<220> FEATURE:
<223> OTHER INFORMATION: primer

<400> SEQUENCE: 28

```
tcagggttat tgtctcatgg ccatttaggc ctggcaggca ctggctcgga cgacatgt       58
```

<210> SEQ ID NO 29
<211> LENGTH: 58
<212> TYPE: DNA
<213> ORGANISM: Artificial Sequence
<220> FEATURE:
<223> OTHER INFORMATION: primer

<400> SEQUENCE: 29

```
agagccctgg gccggagctg ctgagcccat tgttgaattc tggcggggta gctgttga       58
```

<210> SEQ ID NO 30
<211> LENGTH: 58
<212> TYPE: DNA
<213> ORGANISM: Artificial Sequence
<220> FEATURE:
<223> OTHER INFORMATION: primer

<400> SEQUENCE: 30

```
tcaacagcta ccccgccaga attcaacaat gggctcagca gctccggccc agggctct       58
```

<210> SEQ ID NO 31

```
<211> LENGTH: 59
<212> TYPE: DNA
<213> ORGANISM: Artificial Sequence
<220> FEATURE:
<223> OTHER INFORMATION: primer

<400> SEQUENCE: 31
tcgtaaataa acaagcgtaa ctagctagcg taggttatgc gagcaacatt gcacgaaac      59

<210> SEQ ID NO 32
<211> LENGTH: 59
<212> TYPE: DNA
<213> ORGANISM: Artificial Sequence
<220> FEATURE:
<223> OTHER INFORMATION: primer

<400> SEQUENCE: 32
gtttcgtgca atgttgctcg cataacctac gctagctagt tacgcttgtt tatttacga      59

<210> SEQ ID NO 33
<211> LENGTH: 58
<212> TYPE: DNA
<213> ORGANISM: Artificial Sequence
<220> FEATURE:
<223> OTHER INFORMATION: primer

<400> SEQUENCE: 33
acatgtcgtc cgagccagtg cctgccaggc ctaaatggcc atgagacaat aaccctga       58

<210> SEQ ID NO 34
<211> LENGTH: 57
<212> TYPE: DNA
<213> ORGANISM: Artificial Sequence
<220> FEATURE:
<223> OTHER INFORMATION: primer

<400> SEQUENCE: 34
aggtgtaaga cgggggagta gcgcagcatt gttgaattct ggcggggtag ctgttga        57

<210> SEQ ID NO 35
<211> LENGTH: 57
<212> TYPE: DNA
<213> ORGANISM: Artificial Sequence
<220> FEATURE:
<223> OTHER INFORMATION: primer

<400> SEQUENCE: 35
tcaacagcta ccccgccaga attcaacaat gctgcgctac tcccccgtct tacacct        57

<210> SEQ ID NO 36
<211> LENGTH: 59
<212> TYPE: DNA
<213> ORGANISM: Artificial Sequence
<220> FEATURE:
<223> OTHER INFORMATION: primer

<400> SEQUENCE: 36
tcagggttat tgtctcatgg ccatttaggc ctagactagc ggccggtccc cttatccca      59

<210> SEQ ID NO 37
<211> LENGTH: 55
<212> TYPE: DNA
<213> ORGANISM: Artificial Sequence
<220> FEATURE:
<223> OTHER INFORMATION: primer

<400> SEQUENCE: 37
```

```
agagccctgg gccggagctg ctgagcccat ggtgaagggg gcggccgcgg agcct         55
```

<210> SEQ ID NO 38
<211> LENGTH: 55
<212> TYPE: DNA
<213> ORGANISM: Artificial Sequence
<220> FEATURE:
<223> OTHER INFORMATION: primer

<400> SEQUENCE: 38

```
aggctccgcg gccgcccct tcaccatggg ctcagcagct ccggcccagg gctct          55
```

<210> SEQ ID NO 39
<211> LENGTH: 59
<212> TYPE: DNA
<213> ORGANISM: Artificial Sequence
<220> FEATURE:
<223> OTHER INFORMATION: primer

<400> SEQUENCE: 39

```
tgggataagg ggaccggccg ctagtctagg cctaaatggc catgagacaa taaccctga     59
```

<210> SEQ ID NO 40
<211> LENGTH: 51
<212> TYPE: DNA
<213> ORGANISM: Artificial Sequence
<220> FEATURE:
<223> OTHER INFORMATION: primer

<400> SEQUENCE: 40

```
tgtaagacgg gggagtagcg cagcatggtg aaggggcgg ccgcggagcc t              51
```

<210> SEQ ID NO 41
<211> LENGTH: 51
<212> TYPE: DNA
<213> ORGANISM: Artificial Sequence
<220> FEATURE:
<223> OTHER INFORMATION: primer

<400> SEQUENCE: 41

```
aggctccgcg gccgccccct tcaccatgct gcgctactcc cccgtcttac a             51
```

<210> SEQ ID NO 42
<211> LENGTH: 7882
<212> TYPE: DNA
<213> ORGANISM: Artificial Sequence
<220> FEATURE:
<223> OTHER INFORMATION: plasmid pYL1

<400> SEQUENCE: 42

```
ggcaggcact ggctcggacg acatgttttg tatattggtt gggactgcgg ccgcagcggg    60
ggcgggagct ggtggcggcg atatgaattt ccgggcgttg ctacaacagg taccactttg   120
accacccatg gctgccgtcg ccctgcttgg agctttcagg tcgcttccgg gcgttggcga   180
ggcaagttgg acggtgggga aatgacgaaa aatggtgcat cgcctttgta ggtgtgtgtg   240
agtagtagtt ctactatgag gtacgtatgt agcagaagga tcgagctaga atctgccggc   300
attgcaaagg ttatctggaa agaggaaaag ggcctgaacc ggcatatgga tgcattcttc   360
gtacgaacta ctatctgata acagttaggt actgttatcc atacaaagag tcttatagaa   420
acactgcatc gtaataaaat actcggtagc tgcttgaata tagtaataag atcaacatcc   480
tttcacctct agtctccgtg gattccagta aaagcgctca attctgactt ccgactctgt   540
```

-continued

```
tgatgccccg tgtctgccca tcggggtggt ctagacgctg cctcaacgcc catgtaccgg      600
cctgatgggg cccttgggg caccacaagt ccactaaacg aagcactggg gacgggactc      660
gatagccctg agcagcagcc ggtctcagca gccaaccagc ccagctggaa gcatcggcta      720
ggggaggggg gcccaactac tacgtgtact actaggtaca taatgaattg gatgggaccc      780
agccagccca acctaacttt ccagccttta tagctgcagc ctgcttcccc gtgcctcacg      840 cttttttgctc ctctgctggc cggactcgga cctcttgcga cctctgctcg accaacaatc      900
cctcttgttg caccctctcg cttttgctac ctcgacgctc aattcctcgc tgccgcctca      960
cctaaccgcg tgtgcttgac tgccctcacg ctcggctcgc ctcctgctcc gcgagcctcc     1020
ttttacactt ttcaacagct accccgccag aattcaacaa tgggctcagc agctccggcc     1080
cagggctctg tagctgcagc tgcaggcggc cctccagctg ctggcgctgg cgctggcgct     1140
gtccacgccc tcaccacctc gcccgagtct gcctcggcct cgcagccgg ctcgccaacc      1200 gcctcaacca cgccgccgca gaactcactc gtgtcggctg caacctcgtt ccaccaccat     1260
cccagaggcc gtctggtgag cagagcctgc gaccgctgcc gccggcgcaa ggccaaggtc     1320
agtctagccc ctttgctgtt gcttgcatct ctgttgtcat tgctcctcct cctgctgctg     1380
ctgatgctgc tgctcctcct cctcctcctc ctccccgtct cctggtccct ggtccctgct     1440
cttcatatgt ccttactgcc cgtgtctcct ctccccgttc ccgttccccc tcctcccgtc     1500
ctcttctcct gcgtgtctgt catgcgtaca aagcatacat acaatacatc agcatacatg     1560
gcaagcgttg tgttgtgttg agagttgtgt gtattgtatt gcactgccctt cacaactcgt     1620 tcatactgct gcagcctcac cccaacaccg acctcgtctt ccatgctgcg ctactccccc     1680
gtcttacacc tggatactct ctccttgcca ccactgacca atgctcttcc ccgcccaaag     1740
tgcgagtacc tcagcgctgt cgatagctgc acgcactgcc gcgatgccca cgtgcagtgc     1800
actttcgacc tgcccctggc gcgacgcggc cccaaagcga ggaagaagag cgaccagccc     1860
ggccagccgc tcctgatcc gagctcgctc tccaccgcgg ctcgacccgg ccagatgccg     1920
ccgccgctga ccttctccgg ccccgcagta gccgcgctgc agcccttcgc ctcgtcgtcg     1980
ctgtcgcccg acgcggcctg ggagcccgtc gagccgctca gcattgacaa cggcctgccc     2040
cggcagccgc tgggcgacct gccccggcctc tccaccatcc agaacatctc gacgcgccag     2100
cgatggatac acctggccaa cgccatgacg ctgcgcaaca cgacgctaga gcgcgtctcg     2160
aagcgatgta tcgacctctt cttcgactac ctctaccccc tcaccccccct ggtgtacgag     2220 ccggccctcc gggacgtgct cgcatacatc ttctcccagc ccttgcctgg cgtcaaccaa     2280
ccatcgccgc tgtcacagct cacgccagac ccgaccaccg gcaccacccc cctcaacgct     2340
gccgagtcgt gggccggctt tggccagccc agcggctcgc gaaccgtcgg cagcaggctg     2400
gctccctggg ccgactcgac cttcaccctg gtcacggccg tctgcgcaga ggcagcattc     2460
atgctaccca aggacatttt ccccgaagga gaatccgtct ctgagatctt gctcgaagcc     2520
tctcgggact gcctgcacca gcacctcgag gccgacctgg agaatccgac ggccaactcg     2580
attgccattc gctacttcca ctccaactgc ctccacgctg cggggaagcc caagtactcg     2640
tggcacatat ttggcgaggc catccgcctg gcgcaggtca tgcagctgca cgaggaggct     2700
gccctcgagg ggctcgtccc catcgaggca gagttccgcc gtcgctgctt ttggatcctg     2760
tacttgggcg acaagtcagc cgctatactc aacaatcggc ccatcaccat ccacaagtac     2820
tgcttcgacg ccggcatcac cacgctatac ccgtcgggta tcgaggacga gttcctgagc     2880
acggcgtccg agccgccccg gaagagcttc atatccggct tcaacgcaaa tgtgcggctc     2940
```

```
tggcagtccg cggctgattt gctgctggaa atccgcgtgc tgcaagatca gatgatgcag    3000
cactttcgag ggaccatgcc cccgaaccat gtgctgccct ccgccgacag gcagcatctc    3060
gattctctct atgtccgctt catcacctgc ttggacgatc tcccgccgta cctccagtcg    3120
tgcactctgg cgatggcagc gatggcagaa ggcaacgggt ctgccgagtc caagcagtac    3180
gtgatacagt gcatcaacct gcaggtgacg tttcactgtc tgcgcatggt aattacgcag    3240
aaattcgaag acctctctta ttttgctcct ggcgttgagc aggctgatct cagaaagtcg    3300
gagattgtgc gagacatgct gagggtgatg aacgaggcgc ccttttgggg cctgcaggcc    3360
aatggcgagc caaacgtgag tcgtttcctt gtctcttctc ttttctgcac acccttttct    3420
tcgacgaccc cccctctctc tttatatccc tgcggatatg tatatcatca agcctcggca    3480
cttgttgcta atctgtcctg attatgttgt ctggatgctg caggttgaaa agattcgcct    3540
tatcggagct agtttgctgg ccatcatcca tcgcaaccag gattcaccct ggctacgcg    3600 agccaggagc gacttttccg tgcttttgga tattctcacg cggctggact cgaaggcgtc    3660
ggaccaactg aggaatacgt ccactaccgt tgttggctaa atgtgtgttg gaacaacaaa    3720
aaatgtcaaa gtcggtgtaa atatggccag gatctttgtg ttattccccc ttcagcgttg    3780
ctgggtattt ccccttttgtt tactctttc tgttttttcc agcacttgtt tttccagcag    3840 tgggggggaac aaaaggcgtt tctttcccct atgccagggg ttgtccgatt tagcatttga    3900
gtgtacatct tccctacatt actaggtact taatgagctt atggagatct cccgtcattc    3960
cggatattca tcacgttggt gtatatatcc gtggttggct ttgaaacctg gagttgggtt    4020
gcaatgcagt gacgcctttt gcgaaggacc aaaataagcg aaggatgaag tctgaatagg    4080
atacgaactg gctacctatg ggtgagcatg aaatgaagcg gtcggggaaa tggcggagaa    4140
acgctcgacg taacgctgtt ggttttctcc gtttcgtgca atgttgctcg cataacctac    4200
gctagctagt tacgcttgtt tatttacgac aagatctaga agattcgaga tagaataata    4260
ataataacaa caatttgcct cttctttcca ccttttcagt cttactctcc cttctgacat    4320
tgaacgcctc aatcagtcag tcgccttgta cttggcacgg taatcctccg tgttcttgat    4380
atcctcaggg gtagcaaagc ccttcatgcc atcgataatg tcatccagag tgaggatggc    4440
aaagatgggg atgccgtact ccttcctcag ctcgccaatg gcactcggtc caggcttgga    4500
gtcgtcgcca tccgcagcgg ggagcttctc catgcgtgtcc agggccacga cgatgccggc    4560
gacgatgccg ccctccttgg tgatcttctc aatggcgtcc ctcttggcgg tgccggcggt    4620
gatgacgtcg tcgacaatca ggaccctctt gcccttgagc gaagcgccga cgatgttgcc    4680
gccctcgccg tggtccttgg cctccttgcg gtcaaacgag taggagacgc ggtccaggtt    4740
ctggggcgcc agtcgccga gcttgatggt gatggcggag cacagcggga tgcccttgta    4800
ggccgggccg aagacgatgt cgaactctag gccggccttc tcctgggcct cgatgatggt    4860
ctttgcaaag gcggaggcga tggcgccggc gaggcgcgcc gtgtgaatt cgcccgcgtt    4920 gaagaagtag ggggatatcc gcttggactt gagctcgaag ctgccaaact tgaggacgcc    4980
gccgtcgatg gcggatttga ggaagtcctg cttgtaggca ggcagctggg aggtggtagc    5040
cattctgttg gatttggata gtgtccttat tctctgattt gaacagtaga tcaggacgag    5100
tgagagggat gcagaggttg gattggagtg gttgagctat aaaatttaga ggcgcgccgt    5160
atcgagtttt cacatggaag tcaaagcgta cagtgcgagc ttgtacgttg gtcttagtat    5220
cccacaagct tctgtctagg tatgatgatg gctataagtc acccaaggca gaactcatct    5280
```

```
tgaagattgt ctagagtgat tttaccgctg atgaaatgac tggactccct cctcctgctc    5340
ttatacgaaa aattgcctga ctctgcaaag gttgtttgtc ttggaagatg atgtgccccc    5400
ccatcgctct tatctcatac cccgccatct ttctagattc tcatcttcaa caagagggc    5460 aatccatgat ctgcgatcca gatgtgcttc tggcctcata ctctgccttc aggttgatgt    5520
tcacttaatt ggtgacgaat tcagctgatt tgctgcagta tgctttgtgt tggttctttc    5580
caggcttgtg ccagccatga gcgctttgag agcatgttgt cacctataaa ctcgagtaac    5640
ggccacatat tgttcactac ttgaatcaca tacctaattt tgatagaatt gacatgttta    5700
aagagctgag gtagctttaa tgcctctgaa gtattgtgac acagcttctc acagagtgag    5760
aatgaaaagt tggactcccc ctaatgaagt aaaagtttcg tctctgaacg gtgaagagca    5820
tagatccggc atcaactacc tggctagact acgacgtcaa ttctgcggcc ttttgacctt    5880
tatatatgtc cattaatgca atagattctt tttttttttt tttttttttt tttttttttt    5940 ttttttttg cccaatttcg cagatcaaag tggacgttat agcatcataa ctaagctcag    6000
ttgctgaggg aagccgtcta ctaccttagc ccatccatcc agctccatac cttgatactt    6060
tagacgtgaa gcaattcaca ctgtacgtct cgcagctctc cttcccgctc ttgcttcccc    6120 actgggtcc atggtgcgtg tatcgtcccc tccttaatta aggccattta ggccgttgct    6180 ggcgttttc cataggctcc gccccctga cgagcatcac aaaaatcgac gctcaagtca    6240
gaggtggcga aacccgacag gactataaag ataccaggcg tttccccctg gaagctccct    6300
cgtgcgctct cctgttccga ccctgccgct taccggatac ctgtccgcct ttctcccttc    6360
gggaagcgtg gcgctttctc atagctcacg ctgtaggtat ctcagttcgg tgtaggtcgt    6420
tcgctccaag ctgggctgtg tgcacgaacc cccgttcag cccgaccgct gcgccttatc    6480
cggtaactat cgtcttgagt ccaacccggt aagacacgac ttatcgccac tggcagcagc    6540
cactggtaac aggattagca gagcgaggta tgtaggcggt gctacagagt tcttgaagtg    6600
gtggcctaac tacggctaca ctagaaggac agtatttggt atctgcgctc tgctgaagcc    6660
agttaccttc ggaaaaagag ttggtagctc ttgatccggc aaacaaacca ccgctggtag    6720
cggtggtttt tttgtttgca agcagcagat tacgcgcaga aaaaaaggat ctcaagaaga    6780
tcctttgatc ttttctacgg ggtctgacgc tcagtggaac gaaaactcac gttaaggcct    6840
gcagggccga ttttggtcat gagattatca aaaaggatct tcaccctagat cctttttaaat    6900 taaaaatgaa gttttaaatc aatctaaagt atatatgagt aaacttggtc tgacagttac    6960
caatgcttaa tcagtgaggc acctatctca gcgatctgtc tatttcgttc atccatagtt    7020
gcctgactcc ccgtcgtgta gataactacg atacgggagg gcttaccatc tggccccagt    7080
gctgcaatga taccgcgaga cccacgctca ccggctccag atttatcagc aataaaccag    7140
ccagccggaa gggccgagcg cagaagtggt cctgcaactt tatccgcctc catccagtct    7200
attaattgtt gccgggaagc tagagtaagt agttcgccag ttaatagttt gcgcaacgtt    7260
gttgccattg ctacaggcat cgtggtgtca cgctcgtcgt ttggtatggc ttcattcagc    7320
tccggttccc aacgatcaag gcgagttaca tgatccccca tgttgtgcaa aaaagcggtt    7380
agctccttcg gtcctccgat cgttgtcaga agtaagttgg ccgcagtgtt atcactcatg    7440
gttatggcag cactgcataa ttctcttact gtcatgccat ccgtaagatg cttttctgtg    7500
actggtgagt actcaaccaa gtcattctga gaatagtgta tgcggcgacc gagttgctct    7560
tgcccggcgt caatacggga taataccgcg ccacatagca gaactttaaa agtgctcatc    7620
attggaaaac gttcttcggg gcgaaaactc tcaaggatct taccgctgtt gagatccagt    7680
```

```
tcgatgtaac ccactcgtgc acccaactga tcttcagcat ctttttacttt caccagcgtt    7740
tctgggtgag caaaaacagg aaggcaaaat gccgcaaaaa agggaataag ggcgacacgg    7800
aaatgttgaa tactcatact cttccttttt caatattatt gaagcattta tcagggttat    7860
tgtctcatgg ccatttaggc ct                                             7882

<210> SEQ ID NO 43
<211> LENGTH: 7279
<212> TYPE: DNA
<213> ORGANISM: Artificial Sequence
<220> FEATURE:
<223> OTHER INFORMATION: plasmid pYL2

<400> SEQUENCE: 43
ggcaggcact ggctcggacg acatgttttg tatattggtt gggactgcgg ccgcagcggg      60
ggcgggagct ggtggcggcg atatgaattt ccgggcgttg ctacaacagg taccactttg     120
accacccatg gctgccgtcg ccctgcttgg agctttcagg tcgcttccgg gcgttggcga     180
ggcaagttgg acggtgggga atgacgaaaa atggtgcat cgccttttgta ggtgtgtgtg     240
agtagtagtt ctactatgag gtacgtatgt agcagaagga tcgagctaga atctgccggc     300
attgcaaagg ttatctggaa agaggaaaag ggcctgaacc ggcatatgga tgcattcttc     360
gtacgaacta ctatctgata acagttaggt actgttatcc atacaaagag tcttatagaa     420
acactgcatc gtaataaaat actcggtagc tgcttgaata tagtaataag atcaacatcc     480
tttcacctct agtctccgtg gattccagta aaagcgctca attctgactt ccgactctgt     540
tgatgccccg tgtctgccca tcggggtggt ctagacgctg cctcaacgcc catgtaccgg     600
cctgatgggg ccctcggggg caccacaagt ccactaaacg aagcactggg gacgggactc     660
gatagccctg agcagcagcc ggtctcagca gccaaccagc ccagctggaa gcatcggcta     720
ggggaggggg gcccaactac tacgtgtact actaggtaca taatgaattg gatgggaccc     780
agccagccca acctaacttt ccagccttta tagctgcagc ctgcttcccc gtgcctcacg     840
cttttttgctc ctctgctggc cggactcgga cctcttgcga cctctgctcg accaacaatc     900
cctcttgttg caccctctcg ctttgctac ctcgacgctc aattcctcgc tgccgcctca     960
cctaaccgcg tgtgcttgac tgccctcacg ctcggctcgc ctcctgctcc gcgagcctcc    1020
ttttacactt tcaacagct accccgccag aattcaacaa tgctgcgcta ctccccccgtc    1080
ttacacctgg atactctctc cttgccacca ctgaccaatg ctcttccccg cccaaagtgc    1140
gagtacctca gcgctgtcga tagctgcacg cactgccgcg atgcccacgt gcagtgcact    1200
ttcgacctgc ccctggcgcg acgcggcccc aaagcgagga agaagagcga ccagcccggc    1260
cagccgcctc ctgatccgag ctcgctctcc accgcggctc gacccggcca gatgccgccg    1320
ccgctgacct tctccggccc cgcagtagcc gcgctgcagc ccttcgcctc gtcgtcgctg    1380
tcgcccgacg cggcctggga gcccgtcgag ccgctcagca ttgacaacgg cctgccccgg    1440
cagccgctgg gcgacctgcc cggcctctcc accatccaga acatctcgac gcgccagcga    1500
tggatacacc tggccaacgc catgacgctg cgcaacacga cgctagagcg cgtctcgaag    1560
cgatgtatcg acctcttctt cgactacctc tacccccctca ccccccctggt gtacgagccg    1620
gccctccggg acgtgctcgc atacatcttc tcccagccct tgcctggcgt caaccaacca    1680
tcgccgctgt cacagctcac gccagacccg accaccggca ccaccccct caacgctgcc    1740
gagtcgtggg ccggctttgg ccagcccagc ggctcgcgaa ccgtcggcag caggctggct    1800
```

```
ccctgggccg actcgacctt caccctggtc acggccgtct gcgcagaggc agcattcatg    1860
ctacccaagg acattttccc cgaaggagaa tccgtctctg agatcttgct cgaagcctct    1920
cgggactgcc tgcaccagca cctcgaggcc gacctggaga atccgacggc caactcgatt    1980
gccattcgct acttccactc caactgcctc cacgctgcgg ggaagcccaa gtactcgtgg    2040
cacatatttg gcgaggccat ccgcctggcg caggtcatgc agctgcacga ggaggctgcc    2100 ctcgagggc tcgtcccat cgaggcagag ttccgccgtc gctgcttttg gatcctgtac      2160
ttgggcgaca agtcagccgc tatactcaac aatcggccca tcaccatcca caagtactgc    2220
ttcgacgccg gcatcaccac gctatacccg tcgggtatcg aggacgagtt cctgagcacg    2280
gcgtccgagc cgccccggaa gagcttcata tccggcttca acgcaaatgt gcggctctgg    2340
cagtccgcgg ctgatttgct gctggaaatc cgcgtgctgc aagatcagat gatgcagcac    2400
tttcgaggga ccatgccccc gaaccatgtg ctgccctccg ccgacaggca gcatctcgat    2460
tctctctatg tccgcttcat cacctgcttg gacgatctcc cgccgtacct ccagtcgtgc    2520
actctggcga tggcagcgat ggcagaaggc aacgggtctg ccgagtccaa gcagtacgtg    2580
atacagtgca tcaacctgca ggtgacgttt cactgtctgc gcatggtaat tacgcagaaa    2640
ttcgaagacc tctcttattt tgctcctggc gttgagcagg ctgatctcag aaagtcggag    2700
attgtgcgag acatgctgag ggtgatgaac gaggcgccct ttggggcct gcaggccaat     2760 ggcgagccaa acgtgagtcg tttccttgtc tcttctcttt tctgcacacc ttttcttcg     2820 acgacccccc ctctctcttt atatccctgc ggatatgtat atcatcaagc ctcggcactt    2880
gttgctaatc tgtcctgatt atgttgtctg gatgctgcag gttgaaaaga ttcgccttat    2940
cggagctagt ttgctggcca tcatccatcg caaccaggat tcacccttgg ctacgcgagc    3000
caggagcgac ttttccgtgc ttttggatat tctcacgcgg ctggactcga aggcgtcgga    3060
ccaactgagg aatacgtcca ctaccgttgt tggctaaatg tgtgttggaa caacaaaaaa    3120
tgtcaaagtc ggtgtaaata tggccaggat cttttgtgtta ttcccccttc agcgttgctg   3180
ggtatttccc cttttgtttac tcttttctgt tttttccagc acttgttttt ccagcagtgg   3240
ggggaacaaa aggcgtttct ttccccctatg ccaggggttg tccgatttag catttgagtg  3300
tacatcttcc ctacattact aggtacttaa tgagcttatg gagatctccc gtcattccgg    3360
atattcatca cgttggtgta tatatccgtg gttggctttg aaacctggag ttgggttgca    3420
atgcagtgac gccttttgcg aaggaccaaa ataagcgaag gatgaagtct gaataggata    3480
cgaactggct acctatgggt gagcatgaaa tgaagcggtc ggggaaatgg cggagaaacg    3540
ctcgacgtaa cgctgttggt tttctccgtt tcgtgcaatg ttgctcgcat aacctacgct    3600
agctagttac gcttgtttat ttacgacaag atctagaaga ttcgagatag aataataata    3660
ataacaacaa tttgcctctt cttttccacct tttcagtctt actctccctt ctgacattga   3720
acgcctcaat cagtcagtcg ccttgtactt ggcacggtaa tcctccgtgt tcttgatatc    3780 ctcagggta gcaaagccct tcatgccatc gataatgtca tccagagtga ggatggcaaa     3840
gatggggatg ccgtactcct tcctcagctc gccaatggca ctcggtccag gcttggagtc    3900
gtcgccatcc gcagcgggga gcttctccat gcggtccagg ccacgacga tgccggcgac    3960 gatgccgccc tccttggtga tcttctcaat ggcgtccctc ttggcggtgc cggcggtgat    4020
gacgtcgtcg acaatcagga ccctcttgcc cttgagcgaa gcgccgacga tgttgccgcc    4080
ctcgccgtgg tccttggcct ccttgcgtgc aaacgagtag gagacgcggt ccaggttctg    4140
gggcgccagc tcgccgagct tgatggtgat ggcggagcac agcgggatgc ccttgtaggc    4200
```

```
cgggccgaag acgatgtcga actctaggcc ggccttctcc tgggcctcga tgatggtctt    4260
tgcaaaggcg gaggcgatgg cgccggcgag gcgcgccgtg tggaattcgc ccgcgttgaa    4320
gaagtagggg gatatccgct tggacttgag ctcgaagctg ccaaacttga ggacgccgcc    4380
gtcgatggcg gatttgagga agtcctgctt gtaggcaggc agctgggagg tggtagccat    4440
tctgttggat ttggatagtg tccttattct ctgatttgaa cagtagatca ggacgagtga    4500
gagggatgca gaggttggat tggagtggtt gagctataaa atttagaggc gcgccgtatc    4560
gagttttcac atggaagtca aagcgtacag tgcgagcttg tacgttggtc ttagtatccc    4620
acaagcttct gtctaggtat gatgatggct ataagtcacc caaggcagaa ctcatcttga    4680
agattgtcta gagtgatttt accgctgatg aaatgactgg actccctcct cctgctctta    4740
tacgaaaaat tgcctgactc tgcaaaggtt gtttgtcttg aagatgatg tgcccccccca    4800 tcgctcttat ctcatacccc gccatctttc tagattctca tcttcaacaa gagggcaat    4860 ccatgatctg cgatccagat gtgcttctgg cctcatactc tgccttcagg ttgatgttca    4920
cttaattggt gacgaattca gctgatttgc tgcagtatgc tttgtgttgg ttctttccag    4980
gcttgtgcca gccatgagcg ctttgagagc atgttgtcac ctataaactc gagtaacggc    5040
cacatattgt tcactacttg aatcacatac ctaattttga tagaattgac atgtttaaag    5100
agctgaggta gctttaatgc ctctgaagta ttgtgacaca gcttctcaca gagtgagaat    5160
gaaaagttgg actcccccta atgaagtaaa agtttcgtct ctgaacggtg aagagcatag    5220
atccggcatc aactacctgg ctagactacg acgtcaattc tgcggccttt tgacctttat    5280
atatgtccat taatgcaata gattctttt ttttttttt tttttttttt ttttttttt      5340 ttttttgccc aatttcgcag atcaaagtgg acgttatagc atcataacta agctcagttg    5400
ctgagggaag ccgtctacta ccttagccca tccatccagc tccataccttt gatactttag    5460 acgtgaagca attcacactg tacgtctcgc agctctcctt cccgctcttg cttccccact    5520
ggggtccatg gtgcgtgtat cgtcccctcc ttaattaagg ccatttaggc cgttgctggc    5580 gttttccat aggctccgcc ccctgacga gcatcacaaa atcgacgct caagtcagag      5640 gtggcgaaac ccgacaggac tataaagata ccaggcgttt cccctggaa gctccctcgt    5700 gcgctctcct gttccgaccc tgccgcttac cggatacctg tccgccttc tcccttcggg    5760 aagcgtggcg ctttctcata gctcacgctg taggtatctc agttcggtgt aggtcgttcg    5820
ctccaagctg ggctgtgtgc acgaaccccc cgttcagccc gaccgctgcg ccttatccgg    5880
taactatcgt cttgagtcca acccggtaag cacgactta tcgccactgg cagcagccac    5940
tggtaacagg attagcagag cgaggtatgt aggcggtgct acagagttct gaagtggtg    6000 gcctaactac ggctacacta aaggacagt atttggtatc tgcgctctgc tgaagccagt    6060
taccttcgga aaaagagttg gtagctcttg atccggcaaa caaaccaccg ctggtagcgg    6120 tggtttttt gtttgcaagc agcagattac gcgcagaaaa aaaggatctc aagaagatcc    6180
tttgatcttt tctacggggt ctgacgctca gtggaacgaa aactcacgtt aaggcctgca    6240
gggccgattt tggtcatgag attatcaaaa aggatcttca cctagatcct tttaaattaa    6300
aaatgaagtt ttaaatcaat ctaaagtata tatgagtaaa cttggtctga cagttaccaa    6360
tgcttaatca gtgaggcacc tatctcagcg atctgtctat ttcgttcatc catagttgcc    6420
tgactccccg tcgtgtagat aactacgata cgggagggct taccatctgg ccccagtgct    6480
gcaatgatac cgcgagaccc acgctcaccg gctccagatt tatcagcaat aaaccagcca    6540
```

```
gccggaaggg ccgagcgcag aagtggtcct gcaactttat ccgcctccat ccagtctatt    6600
aattgttgcc gggaagctag agtaagtagt tcgccagtta atagtttgcg caacgttgtt    6660
gccattgcta caggcatcgt ggtgtcacgc tcgtcgtttg gtatggcttc attcagctcc    6720
ggttcccaac gatcaaggcg agttacatga tccccccatgt tgtgcaaaaa agcggttagc    6780
tccttcggtc ctccgatcgt tgtcagaagt aagttggccg cagtgttatc actcatggtt    6840
atggcagcac tgcataattc tcttactgtc atgccatccg taagatgctt ttctgtgact    6900
ggtgagtact caaccaagtc attctgagaa tagtgtatgc ggcgaccgag ttgctcttgc    6960
ccggcgtcaa tacgggataa taccgcgcca catagcagaa ctttaaaagt gctcatcatt    7020
ggaaaacgtt cttcggggcg aaaactctca aggatcttac cgctgttgag atccagttcg    7080
atgtaaccca ctcgtgcacc caactgatct tcagcatctt ttactttcac cagcgtttct    7140
gggtgagcaa aaacaggaag gcaaaatgcc gcaaaaaagg gaataagggc gacacggaaa    7200
tgttgaatac tcatactctt cctttttcaa tattattgaa gcatttatca gggttattgt    7260
ctcatggcca tttaggcct                                                 7279

<210> SEQ ID NO 44
<211> LENGTH: 7603
<212> TYPE: DNA
<213> ORGANISM: Artificial Sequence
<220> FEATURE:
<223> OTHER INFORMATION: plasmid pYL3

<400> SEQUENCE: 44
agactagcgg ccggtcccct tatcccagct gttccacgtt ggcctgcccc tcagttagcg      60
ctcaactcaa tgcccctcac tggcgaggcg agggcaagga tggaggggca gcatcgcctg     120
agttggagca aagcggccgc catgggagca gcgaaccaac ggagggatgc cgtgctttgt     180
cgtggctgct gtggccaatc cgggcccttg gttggctcac agagcgttgc tgtgagacca     240
tgagctatta ttgctaggta cagtatagag agaggagaga gagagagaga gagagagggg     300 aaaaaggtg aggttgaagt gagaaaaaaa aaaaaaaaaa aaatccaacc actgacggct     360
gccggctctg ccacccccct ccctccaccc cagacaacct gcacactcag cgcgcagcat     420
cacctaatct tggctcgcct tcccgcagct caggttgttt ttttttttctc tctccctcgt     480 cgaagccgcc cttgttccct tatttatttc cctctccatc cttgtctgcc tttggtccat     540
ctgccccttt gtctgcatct cttttgcacg catcgcctta tcgtcgtctc ttttttcact     600
cacgggagct tgacgaagac ctgactcgtg agcctaacct gctgatttct ctcccccct      660 cccgaccggc ttgactttg tttctcctcc agtaccttat cgcgaagccg gaagaaccct     720
ctttaacccc atcaaacaag tttgtacaaa aaagcaggct ccgcggccgc ccccttcacc     780
atgggctcag cagctccggc ccagggctct gtagctgcag ctgcaggcgg ccctccagct     840
gctggcgctg gcgctggcgc tgtccacgcc ctcaccacct cgcccgagtc tgcctcggcc     900
tcgcagcccg gctcgccaac cgcctcaacc acgccgccgc agaactcact cgtgtcggct     960
gcaacctcgt tccaccacca tcccagaggc cgtctggtga gcagagcctg cgaccgctgc    1020
cgccggcgca aggccaaggt cagtctagcc cctttgctgt tgcttgcatc tctgttgtca    1080
ttgctcctcc tcctgctgct gctgatgctg ctgctcctcc tcctcctcct cctccccgtc    1140
tcctggtccc tggtccctgc tcttcatatg tccttactgc ccgtgtctcc tctcccgtt    1200 cccgttcccc ctcctcccgt cctcttctcc tgcgtgtctg tcatgcgtac aaagcataca    1260
tacaatacat cagcatacat ggcaagcgtt gtgttgtgtt gagagttgtg tgtattgtat    1320
```

```
tgcactgcct tcacaactcg ttcatactgc tgcagcctca ccccaacacc gacctcgtct   1380
tccatgctgc gctactcccc cgtcttacac ctggatactc tctccttgcc accactgacc   1440
aatgctcttc cccgcccaaa gtgcgagtac ctcagcgctg tcgatagctg cacgcactgc   1500
cgcgatgccc acgtgcagtg cactttcgac ctgcccctgg cgcgacgcgg ccccaaagcg   1560
aggaagaaga gcgaccagcc cggccagccg cctcctgatc cgagctcgct ctccaccgcg   1620
gctcgacccg ccagatgcc gccgccgctg accttctccg gccccgcagt agccgcgctg    1680
cagcccttcg cctcgtcgtc gctgtcgccc gacgcggcct gggagcccgt cgagccgctc   1740
agcattgaca acgcctgcc ccggcagccg ctgggcgacc tgcccggcct ctccaccatc    1800
cagaacatct cgacgcgcca gcgatggata cacctggcca acgccatgac gctgcgcaac   1860
acgacgctag agcgcgtctc gaagcgatgt atcgacctct tcttcgacta cctctacccc   1920
ctcacccccc tggtgtacga gccggccctc cgggacgtgc tcgcatacat cttctcccag   1980
cccttgcctg gcgtcaacca accatcgccg ctgtcacagc tcacgccaga cccgaccacc   2040
ggcaccaccc ccctcaacgc tgccgagtcg tgggccggct ttggccagcc cagcggctcg   2100
cgaaccgtcg gcagcaggct ggctccctgg gccgactcga ccttcacccct ggtcacggcc  2160
gtctgcgcag aggcagcatt catgctaccc aaggacattt ccccgaagg agaatccgtc    2220
tctgagatct tgctcgaagc ctctcgggac tgcctgcacc agcacctcga ggccgacctg   2280
gagaatccga cggccaactc gattgccatt cgctacttcc actccaactg cctccacgct   2340
gcggggaagc ccaagtactc gtggcacata tttggcgagg ccatccgcct ggcgcaggtc   2400
atgcagctgc acgaggaggc tgccctcgag gggctcgtcc ccatcgaggc agagttccgc   2460
cgtcgctgct tttggatcct gtacttgggc gacaagtcag ccgctatact caacaatcgg   2520
cccatcacca tccacaagta ctgcttcgac gccggcatca ccacgctata cccgtcgggt   2580
atcgaggacg agttcctgag cacggcgtcc gagccgcccc ggaagagctt catatccggc   2640
ttcaacgcaa atgtgcggct ctggcagtcc gcggctgatt tgctgctgga aatccgcgtg   2700
ctgcaagatc agatgatgca gcactttcga gggaccatgc ccccgaacca tgtgctgccc   2760
tccgccgaca ggcagcatct cgattctctc tatgtccgct tcatcacctg cttggacgat   2820
ctcccgccgt acctccagtc gtgcactctg gcgatggcag cgatggcaga aggcaacggg   2880
tctgccgagt ccaagcagta cgtgatacag tgcatcaacc tgcaggtgac gtttcactgt   2940
ctgcgcatgg taattacgca gaaattcgaa gacctctctt attttgctcc tggcgttgag   3000
caggctgatc tcagaaagtc ggagattgtg cgagacatgc tgagggtgat gaacgaggcg   3060
cccttttggg gcctgcaggc caatggcgag ccaaacgtga gtcgtttcct tgtctcttct   3120
cttttctgca cacccttttc ttcgacgacc ccccctctct ctttatatcc ctgcggatat   3180
gtatatcatc aagcctcggc acttgttgct aatctgtcct gattatgttg tctggatgct   3240
gcaggttgaa aagattcgcc ttatcggagc tagtttgctg ccatcatcc atcgcaacca    3300
ggattcaccc ttggctacgc gagccaggag cgacttttcc gtgcttttgg atattctcac   3360
gcggctggac tcgaaggcgt cggaccaact gaggaatacg tccactaccg ttgttggcta   3420
aatgtgtgtt ggaacaacaa aaaatgtcaa agtcggtgta aatatggcca ggatctttgt   3480
gttattcccc cttcagcgtt gctgggtatt tcccctttgt ttactctttt ctgttttttc   3540
cagcacttgt ttttcagca gtgggggggaa caaaaggcgt ttctttcccc tatgccaggg   3600
gttgtccgat ttagcatttg agtgtacatc ttccctacat tactaggtac ttaatgagct   3660
```

```
tatggagatc tcccgtcatt ccggatattc atcacgttgg tgtatatatc cgtggttggc    3720
tttgaaacct ggagttgggt tgcaatgcag tgacgccttt tgcgaaggac caaaataagc    3780
gaaggatgaa gtctgaatag gatacgaact ggctaccttat gggtgagcat gaaatgaagc   3840
ggtcggggaa atggcggaga aacgctcgac gtaacgctgt tggttttctc cgtttcgtgc    3900
aatgttgctc gcataaccta cgctagctag ttacgcttgt ttatttacga caagatctag    3960
aagattcgag atagaataat aataataaca acaatttgcc tcttctttcc accttttcag    4020
tcttactctc ccttctgaca ttgaacgcct caatcagtca gtcgccttgt acttggcacg    4080
gtaatcctcc gtgttcttga tatcctcagg ggtagcaaag cccttcatgc catcgataat    4140
gtcatccaga gtgaggatgg caaagatggg gatgccgtac tccttcctca gctcgccaat    4200
ggcactcggt ccaggcttgg agtcgtcgcc atccgcagcg gggagcttct ccatgcggtc    4260
cagggccacg acgatgccgg cgacgatgcc gccctccttg gtgatcttct caatggcgtc    4320
cctcttggcg gtgccggcgg tgatgacgtc gtcgacaatc aggaccctct tgcccttgag    4380
cgaagcgccg acgatgttgc cgccctcgcc gtggtccttg gctccttgc ggtcaaacga    4440 gtaggagacg cggtccaggt tctggggcgc cagctcgccg agcttgatgg tgatggcgga    4500
gcacagcggg atgcccttgt aggccgggcc gaagacgatg tcgaactcta ggccggcctt    4560
ctcctgggcc tcgatgatgg tctttgcaaa ggcggaggcg atggcgccgg cgaggcgcgc    4620
cgtgtggaat tcgcccgcgt tgaagaagta ggggatatc cgcttggact tgagctcgaa    4680
gctgccaaac ttgaggacgc cgccgtcgat ggcggatttg aggaagtcct gcttgtaggc    4740
aggcagctgg gaggtggtag ccattctgtt ggatttggat agtgtcctta ttctctgatt    4800
tgaacagtag atcaggacga gtgagaggga tgcagaggtt ggattggagt ggttgagcta    4860
taaaatttag aggcgcgccg tatcgagttt tcacatggaa gtcaaagcgt acagtgcgag    4920
cttgtacgtt ggtcttagta tcccacaagc ttctgtctag gtatgatgat ggctataagt    4980
cacccaaggc agaactcatc ttgaagattg tctagagtga ttttaccgct gatgaaatga    5040
ctggactccc tcctcctgct cttatacgaa aaattgcctg actctgcaaa ggttgtttgt    5100
cttggaagat gatgtgcccc cccatcgctc ttatctcata ccccgccatc tttctagatt    5160
ctcatcttca acaagagggg caatccatga tctgcgatcc agatgtgctt ctggcctcat    5220
actctgcctt caggttgatg ttcacttaat tggtgacgaa ttcagctgat ttgctgcagt    5280
atgctttgtg ttggttcttt ccaggcttgt gccagccatg agcgctttga gagcatgttg    5340
tcacctataa actcgagtaa cggccacata ttgttcacta cttgaatcac ataccctaatt   5400 ttgatagaat tgacatgttt aaagagctga ggtagcttta atgcctctga agtattgtga    5460
cacagcttct cacagagtga gaatgaaaag ttggactccc cctaatgaag taaaagtttc    5520
gtctctgaac ggtgaagagc atagatccgg catcaactac ctggctagac tacgacgtca    5580
attctgcggc ctttttgacct ttatatatgt ccattaatgc aatagattct tttttttttt   5640
tttttttttt tttttttttt tttttttttt gcccaatttc gcagatcaaa gtggacgtta    5700
tagcatcata actaagctca gttgctgagg gaagccgtct actaccttag cccatccatc    5760
cagctccata ccttgatact ttagacgtga agcaattcac actgtacgtc tcgcagctct    5820
ccttcccgct cttgcttccc cactggggtc catggtgcgt gtatcgtccc ctccttaatt    5880
aaggccattt aggccgttgc tggcgttttt ccataggctc cgcccccctg acgagcatca    5940
caaaaatcga cgctcaagtc agaggtggcg aaacccgaca ggactataaa gataccaggc    6000
gtttccccct ggaagctccc tcgtgcgctc tcctgttccg accctgccgc ttaccggata    6060
```

| | |
|---|---:|
| cctgtccgcc tttctcccct tcgggaagcgt ggcgctttct catagctcac gctgtaggta | 6120 |
| tctcagttcg gtgtaggtcg ttcgctccaa gctgggctgt gtgcacgaac cccccgttca | 6180 |
| gcccgaccgc tgcgccttat ccggtaacta tcgtcttgag tccaacccgg taagacacga | 6240 |
| cttatcgcca ctggcagcag ccactggtaa caggattagc agagcgaggt atgtaggcgg | 6300 |
| tgctacagag ttcttgaagt ggtggcctaa ctacggctac actagaagga cagtatttgg | 6360 |
| tatctgcgct ctgctgaagc cagttacctt cggaaaaaga gttggtagct cttgatccgg | 6420 |
| caaacaaacc accgctggta gcggtggttt ttttgtttgc aagcagcaga ttacgcgcag | 6480 |
| aaaaaaagga tctcaagaag atcctttgat cttttctacg gggtctgacg ctcagtggaa | 6540 |
| cgaaaactca cgttaaggcc tgcagggccg attttggtca tgagattatc aaaaaggatc | 6600 |
| ttcacctaga tccttttaaa ttaaaaatga agttttaaat caatctaaag tatatatgag | 6660 |
| taaacttggt ctgacagtta ccaatgctta atcagtgagg cacctatctc agcgatctgt | 6720 |
| ctatttcgtt catccatagt tgcctgactc cccgtcgtgt agataactac gatacgggag | 6780 |
| ggcttaccat ctggccccag tgctgcaatg ataccgcgag acccacgctc accggctcca | 6840 |
| gatttatcag caataaacca gccagccgga agggccgagc gcagaagtgg tcctgcaact | 6900 |
| ttatccgcct ccatccagtc tattaattgt tgccgggaag ctagagtaag tagttcgcca | 6960 |
| gttaatagtt tgcgcaacgt tgttgccatt gctacaggca tcgtggtgtc acgctcgtcg | 7020 |
| tttggtatgg cttcattcag ctccggttcc caacgatcaa ggcgagttac atgatccccc | 7080 |
| atgttgtgca aaaaagcggt tagctccttc ggtcctccga tcgttgtcag aagtaagttg | 7140 |
| gccgcagtgt tatcactcat ggttatggca gcactgcata attctcttac tgtcatgcca | 7200 |
| tccgtaagat gcttttctgt gactggtgag tactcaacca agtcattctg agaatagtgt | 7260 |
| atgcggcgac cgagttgctc ttgcccggcg tcaatacggg ataataccgc gccacatagc | 7320 |
| agaactttaa aagtgctcat cattggaaaa cgttcttcgg ggcgaaaact ctcaaggatc | 7380 |
| ttaccgctgt tgagatccag ttcgatgtaa cccactcgtg cacccaactg atcttcagca | 7440 |
| tcttttactt tcaccagcgt ttctgggtga gcaaaaacag gaaggcaaaa tgccgcaaaa | 7500 |
| aagggaataa gggcgacacg gaaatgttga atactcatac tcttcctttt tcaatattat | 7560 |
| tgaagcattt atcagggtta ttgtctcatg ccatttagg cct | 7603 |

<210> SEQ ID NO 45
<211> LENGTH: 7000
<212> TYPE: DNA
<213> ORGANISM: Artificial Sequence
<220> FEATURE:
<223> OTHER INFORMATION: plasmid pYL4

<400> SEQUENCE: 45

| | |
|---|---:|
| agactagcgg ccggtcccct tatcccagct gttccacgtt ggcctgcccc tcagttagcg | 60 |
| ctcaactcaa tgcccctcac tggcgaggcg agggcaagga tggaggggca gcatcgcctg | 120 |
| agttggagca agcggccgc catgggagca gcgaaccaac ggagggatgc cgtgctttgt | 180 |
| cgtggctgct gtggccaatc cgggcccttg gttggctcac agagcgttgc tgtgagacca | 240 |
| tgagctatta ttgctaggta cagtatagag agaggagaga gagagagaga gagagagggg | 300 |
| aaaaaaggtg aggttgaagt gagaaaaaaa aaaaaaaaaa aaatccaacc actgacggct | 360 |
| gccggctctg ccaccccccct ccctccaccc cagacaacct gcacactcag cgcgcagcat | 420 |
| cacctaatct tggctcgcct tcccgcagct caggttgttt tttttttctc tctccctcgt | 480 |

```
cgaagccgcc cttgttccct tatttatttc cctctccatc cttgtctgcc tttggtccat    540
ctgccccttt gtctgcatct cttttgcacg catcgcctta tcgtcgtctc tttttttcact   600
cacgggagct tgacgaagac ctgactcgtg agcctaacct gctgatttct ctcccccct     660
cccgaccggt tgacttttg tttctcctcc agtaccttat cgcgaagccg gaagaaccct     720
ctttaacccc atcaaacaag tttgtacaaa aaagcaggct ccgcggccgc cccttcacc    780
atgctgcgct actccccgt cttacacctg gatactctct ccttgccacc actgaccaat    840
gctcttcccc gcccaaagtg cgagtacctc agcgctgtcg atagctgcac gcactgccgc   900
gatgcccacg tgcagtgcac tttcgacctg cccctggcgc gacgcggccc caaagcgagg   960
aagaagagcg accagcccgg ccagccgcct cctgatccga gctcgctctc caccgcggct  1020
cgacccggcc agatgccgcc gccgctgacc ttctccggcc ccgcagtagc cgcgctgcag  1080
cccttcgcct cgtcgtcgct gtcgcccgac gcggcctggg agcccgtcga gccgctcagc  1140
attgacaacg gcctgccccg gcagccgctg ggcgacctgc ccggcctctc caccatccag  1200
aacatctcga cgcgccagcg atggatacac ctggccaacg ccatgacgct gcgcaacacg  1260
acgctagagc gcgtctcgaa gcgatgtatc gacctcttct tcgactacct ctacccctc   1320
acccccctgg tgtacgagcc ggccctccgg gacgtgctcg catacatctt ctcccagccc  1380
ttgcctggcg tcaaccaacc atcgccgctg tcacagctca cgccagaccc gaccaccggc  1440
accacccccc tcaacgctgc cgagtcgtgg gccggctttg gccagcccag cggctcgcga  1500
accgtcggca gcaggctggc tccctgggcc gactcgacct tcaccctggt cacggccgtc  1560
tgcgcagagg cagcattcat gctacccaag gacatttttcc ccgaaggaga atccgtctct  1620
gagatcttgc tcgaagcctc tcgggactgc ctgcaccagc acctcgaggc cgacctggag  1680
aatccgacgg ccaactcgat tgccattcgc tacttccact ccaactgcct ccacgctgcg  1740
gggaagccca gtactcgtg gcacatattt ggcgaggcca tccgcctggc gcaggtcatg  1800
cagctgcacg aggaggctgc cctcgagggg ctcgtcccca tcgaggcaga gttccgccgt  1860
cgctgctttt ggatcctgta cttgggcgac aagtcagccg ctatactcaa caatcggccc  1920
atcaccatcc acaagtactg cttcgacgcc ggcatcacca cgctatacccc gtcgggtatc  1980
gaggacgagt tcctgagcac ggcgtccgag ccgccccgga agagcttcat atccggcttc  2040
aacgcaaatg tgcggctctg gcagtccgcg gctgatttgc tgctggaaat ccgcgtgctg  2100
caagatcaga tgatgcagca ctttcgaggg accatgcccc cgaaccatgt gctgccctcc  2160
gccgacaggc agcatctcga ttctctctat gtccgcttca tcacctgctt ggacgatctc  2220
ccgccgtacc tccagtcgtg cactctggcg atggcagcga tggcagaagg caacgggtct  2280
gccgagtcca agcagtacgt gatacagtgc atcaacctgc aggtgacgtt tcactgtctg  2340
cgcatggtaa ttacgcagaa attcgaagac ctctcttatt ttgctcctgg cgttgagcag  2400
gctgatctca gaaagtcgga gattgtgcga gacatgctga gggtgatgaa cgaggcgccc  2460
ttttggggcc tgcaggccaa tggcgagcca acgtgagtc gtttccttgt ctcttctctt  2520
ttctgcacac ccttttcttc gacgaccccc cctctctctt tatatccctg cggatatgta  2580
tatcatcaag cctcggcact tgttgctaat ctgtcctgat tatgttgtct ggatgctgca  2640
ggttgaaaag attcgcctta tcggagctag tttgctggcc atcatccatc gcaaccagga  2700
ttcacccttg gctacgcgag ccaggagcga ctttttccgtg cttttggata ttctcacgcg  2760
gctggactcg aaggcgtcgg accaactgag gaatacgtcc actaccgttg ttggctaaat  2820
gtgtgttgga acaacaaaaa atgtcaaagt cggtgtaaat atggccagga tctttgtgtt  2880
```

-continued

```
attcccccett cagcgttgct gggtatttcc cctttgttta ctcttttctg ttttttccag    2940
cacttgtttt tccagcagtg gggggaacaa aaggcgtttc tttcccctat gccagggggtt    3000 gtccgattta gcatttgagt gtacatcttc cctacattac taggtactta atgagcttat    3060
ggagatctcc cgtcattccg gatattcatc acgttggtgt atatatccgt ggttggcttt    3120
gaaacctgga gttgggttgc aatgcagtga cgccttttgc gaaggaccaa ataagcgaa     3180 ggatgaagtc tgaataggat acgaactggc tacctatggg tgagcatgaa atgaagcggt    3240
cggggaaatg gcggagaaac gctcgacgta acgctgttgg ttttctccgt ttcgtgcaat    3300
gttgctcgca taacctacgc tagctagtta cgcttgttta tttacgacaa gatctagaag    3360
attcgagata gaataataat aataacaaca atttgcctct tctttccacc ttttcagtct    3420
tactctccct tctgacattg aacgcctcaa tcagtcagtc gccttgtact tggcacggta    3480
atcctccgtg ttcttgatat cctcaggggt agcaaagccc ttcatgccat cgataatgtc    3540
atccagagtg aggatggcaa agatggggat gccgtactcc ttcctcagct cgccaatggc    3600
actcggtcca ggcttggagt cgtcgccatc cgcagcgggg agcttctcca tgcggtccag    3660
ggccacgacg atgccggcga cgatgccgcc ctccttggtg atcttctcaa tggcgtccct    3720
cttggcggtg ccggcggtga tgacgtcgtc gacaatcagg accctcttgc ccttgagcga    3780
agcgccgacg atgttgccgc cctgccgtg gtccttggcc tccttgcggt caaacgagta    3840
ggagacgcgg tccaggttct ggggcgccag ctcgccgagc ttgatggtga tggcggagca    3900
cagcgggatg cccttgtagg ccgggccgaa gacgatgtcg aactctaggc cggccttctc    3960
ctgggcctcg atgatggtct ttgcaaaggc ggaggcgatg gcgccggcga ggcgcgccgt    4020
gtggaattcg cccgcgttga agaagtaggg ggatatccgc ttggacttga gctcgaagct    4080
gccaaacttg aggacgccgc cgtcgatggc ggatttgagg aagtcctgct tgtaggcagg    4140
cagctgggag gtggtagcca ttctgttgga tttggatagt gtccttattc tctgatttga    4200
acagtagatc aggacgagtg agagggatgc agaggttgga ttggagtggt tgagctataa    4260
aatttagagg cgcgccgtat cgagttttca catggaagtc aaagcgtaca gtgcgagctt    4320
gtacgttggt cttagtatcc cacaagcttc tgtctaggta tgatgatggc tataagtcac    4380
ccaaggcaga actcatcttg aagattgtct agagtgattt taccgctgat gaaatgactg    4440
gactccctcc tcctgctctt atacgaaaaa ttgcctgact ctgcaaaggt tgtttgtctt    4500
ggaagatgat gtgcccccec atcgctctta tctcataccc cgccatcttt ctagattctc    4560
atcttcaaca agagggggcaa tccatgatct gcgatccaga tgtgcttctg gcctcatact    4620
ctgccttcag gttgatgttc acttaattgg tgacgaattc agctgatttg ctgcagtatg    4680
ctttgtgttg gttcttttcca ggcttgtgcc agccatgagc gctttgagag catgttgtca    4740
cctataaact cgagtaacgg ccacatattg ttcactactt gaatcacata cctaattttg    4800
atagaattga catgtttaaa gagctgaggt agctttaatg cctctgaagt attgtgacac    4860
agcttctcac agagtgagaa tgaaaagttg gactccccct aatgaagtaa aagtttcgtc    4920
tctgaacggt gaagagcata gatccggcat caactacctg gctagactac gacgtcaatt    4980
ctgcggcctt ttgaccttta tatatgtcca ttaatgcaat agattctttt ttttttttttt    5040 tttttttttt ttttttttttt tttttttgcc caatttcgca gatcaaagtg gacgttatag    5100
catcataact aagctcagtt gctgagggaa gccgtctact accttagccc atccatccag    5160
ctccatacct tgatacttta gacgtgaagc aattcacact gtacgtctcg cagctctcct    5220
```

-continued

| | |
|---|---|
| tcccgctctt gcttccccac tggggtccat ggtgcgtgta tcgtcccctc cttaattaag | 5280 |
| gccatttagg ccgttgctgg cgttttttcca taggctccgc cccctgacg agcatcacaa | 5340 |
| aaatcgacgc tcaagtcaga ggtggcgaaa cccgacagga ctataaagat accaggcgtt | 5400 |
| tcccctgga agctccctcg tgcgctctcc tgttccgacc ctgccgctta ccggatacct | 5460 |
| gtccgccttt ctcccttcgg gaagcgtggc gctttctcat agctcacgct gtaggtatct | 5520 |
| cagttcggtg taggtcgttc gctccaagct gggctgtgtg cacgaacccc ccgttcagcc | 5580 |
| cgaccgctgc gccttatccg gtaactatcg tcttgagtcc aacccggtaa gacacgactt | 5640 |
| atcgccactg gcagcagcca ctggtaacag gattagcaga gcgaggtatg taggcggtgc | 5700 |
| tacagagttc ttgaagtggt ggcctaacta cggctacact agaaggacag tatttggtat | 5760 |
| ctgcgctctg ctgaagccag ttaccttcgg aaaagagtt ggtagctctt gatccggcaa | 5820 |
| acaaaccacc gctggtagcg gtggtttttt tgtttgcaag cagcagatta cgcgcagaaa | 5880 |
| aaaaggatct caagaagatc ctttgatctt ttctacgggg tctgacgctc agtggaacga | 5940 |
| aaactcacgt taaggcctgc agggccgatt ttggtcatga gattatcaaa aggatcttc | 6000 |
| acctagatcc ttttaaatta aaaatgaagt tttaaatcaa tctaaagtat atatgagtaa | 6060 |
| acttggtctg acagttacca atgcttaatc agtgaggcac ctatctcagc gatctgtcta | 6120 |
| tttcgttcat ccatagttgc ctgactcccc gtcgtgtaga taactacgat acgggagggc | 6180 |
| ttaccatctg gccccagtgc tgcaatgata ccgcgagacc cacgctcacc ggctccagat | 6240 |
| ttatcagcaa taaaccagcc agccggaagg gccgagcgca gaagtggtcc tgcaacttta | 6300 |
| tccgcctcca tccagtctat taattgttgc cgggaagcta gagtaagtag ttcgccagtt | 6360 |
| aatagtttgc gcaacgttgt tgccattgct acaggcatcg tggtgtcacg ctcgtcgttt | 6420 |
| ggtatggctt cattcagctc cggttcccaa cgatcaaggc gagttacatg atcccccatg | 6480 |
| ttgtgcaaaa aagcggttag ctccttcggt cctccgatcg ttgtcagaag taagttggcc | 6540 |
| gcagtgttat cactcatggt tatggcagca ctgcataatt ctcttactgt catgccatcc | 6600 |
| gtaagatgct tttctgtgac tggtgagtac tcaaccaagt cattctgaga atagtgtatg | 6660 |
| cggcgaccga gttgctcttg cccggcgtca tacgggata ataccgcgcc acatagcaga | 6720 |
| actttaaaag tgctcatcat tggaaaacgt tcttcgggc gaaaactctc aaggatctta | 6780 |
| ccgctgttga gatccagttc gatgtaaccc actcgtgcac ccaactgatc ttcagcatct | 6840 |
| tttactttca ccagcgtttc tgggtgagca aaaacaggaa ggcaaaatgc cgcaaaaaag | 6900 |
| ggaataaggg cgacacggaa atgttgaata ctcatactct tccttttca atattattga | 6960 |
| agcatttatc agggttattg tctcatggcc atttaggcct | 7000 |

<210> SEQ ID NO 46
<211> LENGTH: 940
<212> TYPE: PRT
<213> ORGANISM: Trichoderma reesei

<400> SEQUENCE: 46

Met Leu Ser Asn Pro Leu Arg Arg Tyr Ser Ala Tyr Pro Asp Ile Ser
1               5                   10                  15

Ser Ala Ser Phe Asp Pro Asn Tyr His Gly Ser Gln Ser His Leu His
            20                  25                  30

Ser Ile Asn Val Asn Thr Phe Gly Asn Ser His Pro Tyr Pro Met Gln
        35                  40                  45

His Leu Ala Gln His Ala Glu Leu Ser Ser Ser Arg Met Ile Arg Ala
    50                  55                  60

```
Ser Pro Val Gln Pro Lys Gln Arg Gln Gly Ser Leu Ile Ala Ala Arg
 65                  70                  75                  80

Lys Asn Ser Thr Gly Thr Ala Gly Pro Ile Arg Arg Ile Ser Arg
                 85                  90                  95

Ala Cys Asp Gln Cys Asn Gln Leu Arg Thr Lys Cys Asp Gly Leu His
                100                 105                 110

Pro Cys Ala His Cys Ile Glu Phe Gly Leu Gly Cys Glu Tyr Val Arg
                115                 120                 125

Glu Arg Lys Lys Arg Gly Lys Ala Ser Arg Lys Asp Ile Ala Ala Gln
130                 135                 140

Gln Ala Ala Ala Ala Ala Gln His Ser Gly Gln Val Gln Asp Gly
145                 150                 155                 160

Pro Glu Asp Gln His Arg Lys Leu Ser Arg Gln Gln Ser Glu Ser Ser
                165                 170                 175

Arg Gly Ser Ala Glu Leu Ala Gln Pro Ala His Asp Pro Pro His Gly
                180                 185                 190

His Ile Glu Gly Ser Val Ser Phe Ser Asp Asn Gly Leu Ser Gln
                195                 200                 205

His Ala Ala Met Gly Gly Met Asp Gly Leu Glu Asp His His Gly His
210                 215                 220

Val Gly Val Asp Pro Ala Leu Gly Arg Thr Gln Leu Glu Ala Ser Ser
225                 230                 235                 240

Ala Met Gly Leu Gly Ala Tyr Gly Glu Val His Pro Gly Tyr Glu Ser
                245                 250                 255

Pro Gly Met Asn Gly His Val Met Val Pro Pro Ser Tyr Gly Ala Gln
                260                 265                 270

Thr Thr Met Ala Gly Tyr Ser Gly Ile Ser Tyr Ala Ala Gln Ala Pro
                275                 280                 285

Ser Pro Ala Thr Tyr Ser Ser Asp Gly Asn Phe Arg Leu Thr Gly His
                290                 295                 300

Ile His Asp Tyr Pro Leu Ala Asn Gly Ser Ser Pro Ser Trp Gly Val
305                 310                 315                 320

Ser Leu Ala Ser Pro Ser Asn Gln Phe Gln Leu Gln Leu Ser Gln Pro
                325                 330                 335

Ile Phe Lys Gln Ser Asp Leu Arg Tyr Pro Val Leu Glu Pro Leu Leu
                340                 345                 350

Pro His Leu Gly Asn Ile Leu Pro Val Ser Leu Ala Cys Asp Leu Ile
                355                 360                 365

Asp Leu Tyr Phe Ser Ser Ser Ser Ala Gln Met His Pro Met Ser
                370                 375                 380

Pro Tyr Val Leu Gly Phe Val Phe Arg Lys Arg Ser Phe Leu His Pro
385                 390                 395                 400

Thr Asn Pro Arg Arg Cys Gln Pro Ala Leu Leu Ala Ser Met Leu Trp
                405                 410                 415

Val Ala Ala Gln Thr Ser Glu Ala Ser Phe Leu Thr Ser Leu Pro Ser
                420                 425                 430

Ala Arg Ser Lys Val Cys Gln Lys Leu Leu Glu Leu Thr Val Gly Leu
                435                 440                 445

Leu Gln Pro Leu Ile His Thr Gly Thr Asn Ser Pro Ser Pro Lys Thr
                450                 455                 460

Ser Pro Val Val Gly Ala Ala Leu Gly Val Leu Gly Val Ala Met
465                 470                 475                 480
```

```
Pro Gly Ser Leu Asn Met Asp Ser Leu Ala Gly Glu Thr Gly Ala Phe
            485                 490                 495
Gly Ala Ile Gly Ser Leu Asp Asp Val Ile Thr Tyr Val His Leu Ala
        500                 505                 510
Thr Val Val Ser Ala Ser Glu Tyr Lys Gly Ala Ser Leu Arg Trp Trp
    515                 520                 525
Gly Ala Ala Trp Ser Leu Ala Arg Glu Leu Lys Leu Gly Arg Glu Leu
530                 535                 540
Pro Pro Gly Asn Pro Pro Ala Asn Gln Glu Asp Gly Glu Gly Leu Ser
545                 550                 555                 560
Glu Asp Val Asp Glu His Asp Leu Asn Arg Asn Asn Thr Arg Phe Val
                565                 570                 575
Thr Glu Glu Glu Arg Glu Glu Arg Arg Arg Ala Trp Trp Leu Val Tyr
            580                 585                 590
Ile Val Asp Arg His Leu Ala Leu Cys Tyr Asn Arg Pro Leu Phe Leu
        595                 600                 605
Leu Asp Ser Glu Cys Ser Asp Leu Tyr His Pro Met Asp Asp Ile Lys
    610                 615                 620
Trp Gln Ala Gly Lys Phe Arg Ser His Asp Ala Gly Asn Ser Ser Ile
625                 630                 635                 640
Asn Ile Asp Ser Ser Met Thr Asp Glu Phe Gly Asp Ser Pro Arg Ala
                645                 650                 655
Ala Arg Gly Ala His Tyr Glu Cys Arg Gly Arg Ser Ile Phe Gly Tyr
            660                 665                 670
Phe Leu Ser Leu Met Thr Ile Leu Gly Glu Ile Val Asp Val His His
        675                 680                 685
Ala Lys Ser His Pro Arg Phe Gly Val Gly Phe Arg Ser Ala Arg Asp
    690                 695                 700
Trp Asp Glu Gln Val Ala Glu Ile Thr Arg His Leu Asp Met Tyr Glu
705                 710                 715                 720
Glu Ser Leu Lys Arg Phe Val Ala Lys His Leu Pro Leu Ser Ser Lys
                725                 730                 735
Asp Lys Glu Gln His Glu Met His Asp Ser Gly Ala Val Thr Asp Met
            740                 745                 750
Gln Ser Pro Leu Ser Val Arg Thr Asn Ala Ser Ser Arg Met Thr Glu
        755                 760                 765
Ser Glu Ile Gln Ala Ser Ile Val Ala Tyr Ser Thr His Val Met
    770                 775                 780
His Val Leu His Ile Leu Leu Ala Asp Lys Trp Asp Pro Ile Asn Leu
785                 790                 795                 800
Leu Asp Asp Asp Leu Trp Ile Ser Ser Glu Gly Phe Val Thr Ala
                805                 810                 815
Thr Ser His Ala Val Ser Ala Val Glu Ala Ile Ser Gln Ile Leu Glu
            820                 825                 830
Phe Asp Pro Gly Leu Glu Phe Met Pro Phe Phe Tyr Gly Val Tyr Leu
        835                 840                 845
Leu Gln Gly Ser Phe Leu Leu Leu Ile Ala Asp Lys Leu Gln Ala
    850                 855                 860
Glu Ala Ser Pro Ser Val Ile Lys Ala Cys Thr Ile Val Arg Ala
865                 870                 875                 880
His Glu Ala Cys Val Val Thr Leu Ser Thr Glu Tyr Gln Arg Asn Phe
                885                 890                 895
Ser Lys Val Met Arg Ser Ala Leu Ala Leu Ile Arg Gly Arg Val Pro
```

```
                  900                 905                 910
Glu Asp Leu Ala Glu Gln Gln Gln Arg Arg Glu Leu Leu Ala Leu
            915                 920                 925

Tyr Arg Trp Thr Gly Asn Gly Thr Gly Leu Ala Leu
        930                 935                 940

<210> SEQ ID NO 47
<211> LENGTH: 341
<212> TYPE: PRT
<213> ORGANISM: Trichoderma reesei

<400> SEQUENCE: 47

Met Asp Leu Arg Gln Ala Cys Asp Arg Cys His Asp Lys Lys Leu Arg
1               5                   10                  15

Cys Pro Arg Ile Ser Gly Ser Pro Cys Cys Ser Arg Cys Ala Lys Ala
            20                  25                  30

Asn Val Ala Cys Val Phe Ser Pro Pro Ser Arg Pro Phe Arg Pro His
        35                  40                  45

Glu Pro Leu Asn His Ser His Glu His Ser His Ser His Ser His Asn
    50                  55                  60

His Asn Gly Val Gly Val Ser Phe Asp Trp Leu Asp Leu Met Ser Leu
65                  70                  75                  80

Glu Gln Gln Gln Glu Gln Gln Gly Gln Pro Gln His Pro Pro Pro
                85                  90                  95

Pro Val Gln Thr Leu Ser Glu Arg Leu Ala Ala Leu Leu Cys Ala Leu
            100                 105                 110

Asp Arg Met Leu Gln Ala Val Pro Ser Ser Leu Asp Met His His Val
        115                 120                 125

Ser Arg Gln Gln Leu Arg Glu Tyr Ala Asp Thr Val Gly Thr Gly Phe
    130                 135                 140

Asp Leu Gln Ser Thr Leu Asp Ser Leu Leu His His Ala Gln Asp Leu
145                 150                 155                 160

Ala Ser Leu Tyr Ser Glu Ala Val Pro Ala Ser Phe Asn Lys Arg Thr
                165                 170                 175

Thr Ala Ala Glu Ala Asp Ala Leu Cys Ala Val Pro Asp Cys Val His
            180                 185                 190

Gln Asp Arg Thr Ser Leu His Thr Thr Pro Leu Pro Lys Leu Asp His
        195                 200                 205

Ala Leu Leu Asn Leu Val Met Ala Cys His Ile Arg Leu Leu Asp Val
    210                 215                 220

Met Asp Thr Leu Ala Glu His Gly Arg Met Cys Ala Phe Met Val Ala
225                 230                 235                 240

Thr Leu Pro Pro Asp Tyr Asp Pro Lys Phe Ala Val Pro Glu Ile Arg
                245                 250                 255

Val Gly Thr Phe Val Ala Pro Thr Asp Thr Ala Ala Ser Met Leu Leu
            260                 265                 270

Ser Val Val Glu Leu Gln Thr Val Leu Val Ala Arg Val Lys Asp
        275                 280                 285

Leu Val Ala Met Val Asp Gln Val Lys Asp Ala Arg Ala Ala Arg
    290                 295                 300

Glu Ala Lys Val Val Arg Leu Gln Cys Gly Ile Leu Leu Glu Arg Ala
305                 310                 315                 320

Glu Ser Thr Leu Gly Glu Trp Ser Arg Phe Lys Asp Gly Leu Val Ser
                325                 330                 335
```

Ala Arg Leu Leu Lys
            340

<210> SEQ ID NO 48
<211> LENGTH: 940
<212> TYPE: PRT
<213> ORGANISM: Trichoderma reesei

<400> SEQUENCE: 48

```
Met Leu Ser Asn Pro Leu Arg Arg Tyr Ser Ala Tyr Pro Asp Ile Ser
1               5                   10                  15

Ser Ala Ser Phe Asp Pro Asn Tyr His Gly Ser Gln Ser His Leu His
            20                  25                  30

Ser Ile Asn Val Asn Thr Phe Gly Asn Ser His Pro Tyr Pro Met Gln
        35                  40                  45

His Leu Ala Gln His Ala Glu Leu Ser Ser Arg Met Ile Arg Ala
    50                  55                  60

Ser Pro Val Gln Pro Lys Gln Arg Gln Gly Ser Leu Ile Ala Ala Arg
65                  70                  75                  80

Lys Asn Ser Thr Gly Thr Ala Gly Pro Ile Arg Arg Ile Ser Arg
                85                  90                  95

Ala Cys Asp Gln Cys Asn Gln Leu Arg Thr Lys Cys Asp Gly Leu His
            100                 105                 110

Pro Cys Ala His Cys Ile Glu Phe Gly Leu Gly Cys Glu Tyr Val Arg
        115                 120                 125

Glu Arg Lys Lys Arg Gly Lys Ala Ser Arg Lys Asp Ile Ala Ala Gln
    130                 135                 140

Gln Ala Ala Ala Ala Ala Gln His Ser Gly Gln Val Gln Asp Gly
145                 150                 155                 160

Pro Glu Asp Gln His Arg Lys Leu Ser Arg Gln Ser Glu Ser Ser
                165                 170                 175

Arg Gly Ser Ala Glu Leu Ala Gln Pro Ala His Asp Pro Pro His Gly
            180                 185                 190

His Ile Glu Gly Ser Val Ser Ser Phe Ser Asp Asn Gly Leu Ser Gln
        195                 200                 205

His Ala Ala Met Gly Gly Met Asp Gly Leu Glu Asp His His Gly His
    210                 215                 220

Val Gly Val Asp Pro Ala Leu Gly Arg Thr Gln Leu Glu Ala Ser Ser
225                 230                 235                 240

Ala Met Gly Leu Gly Ala Tyr Gly Glu Val His Pro Gly Tyr Glu Ser
                245                 250                 255

Pro Gly Met Asn Gly His Val Met Val Pro Pro Ser Tyr Gly Ala Gln
            260                 265                 270

Thr Thr Met Ala Gly Tyr Ser Gly Ile Ser Tyr Ala Ala Gln Ala Pro
        275                 280                 285

Ser Pro Ala Thr Tyr Ser Ser Asp Gly Asn Phe Arg Leu Thr Gly His
    290                 295                 300

Ile His Asp Tyr Pro Leu Ala Asn Gly Ser Ser Pro Ser Trp Gly Val
305                 310                 315                 320

Ser Leu Ala Ser Pro Ser Asn Gln Phe Gln Leu Gln Leu Ser Gln Pro
                325                 330                 335

Ile Phe Lys Gln Ser Asp Leu Arg Tyr Pro Val Leu Glu Pro Leu Leu
            340                 345                 350

Pro His Leu Gly Asn Ile Leu Pro Val Ser Leu Ala Cys Asp Leu Ile
        355                 360                 365
```

```
Asp Leu Tyr Phe Ser Ser Ser Ser Ala Gln Met His Pro Met Ser
        370                 375                 380

Pro Tyr Val Leu Gly Phe Val Phe Arg Lys Arg Ser Phe Leu His Pro
385                 390                 395                 400

Thr Asn Pro Arg Arg Cys Gln Pro Ala Leu Leu Ala Ser Met Leu Trp
                405                 410                 415

Val Ala Ala Gln Thr Ser Glu Ala Ser Phe Leu Thr Ser Leu Pro Ser
                420                 425                 430

Ala Arg Ser Lys Val Cys Gln Lys Leu Leu Glu Leu Thr Val Gly Leu
            435                 440                 445

Leu Gln Pro Leu Ile His Thr Gly Thr Asn Ser Pro Ser Pro Lys Thr
        450                 455                 460

Ser Pro Val Val Gly Ala Ala Leu Gly Val Leu Gly Val Ala Met
465                 470                 475                 480

Pro Gly Ser Leu Asn Met Asp Ser Leu Ala Gly Glu Thr Gly Ala Phe
                485                 490                 495

Gly Ala Ile Gly Ser Leu Asp Asp Val Ile Thr Tyr Val His Leu Ala
                500                 505                 510

Thr Val Val Ser Ala Ser Glu Tyr Lys Gly Ala Ser Leu Arg Trp Trp
        515                 520                 525

Gly Ala Ala Trp Ser Leu Ala Arg Glu Leu Lys Leu Gly Arg Glu Leu
530                 535                 540

Pro Pro Gly Asn Pro Pro Ala Asn Gln Glu Asp Gly Glu Gly Leu Ser
545                 550                 555                 560

Glu Asp Val Asp Glu His Asp Leu Asn Arg Asn Thr Arg Phe Val
                565                 570                 575

Thr Glu Glu Arg Glu Glu Arg Arg Ala Trp Trp Leu Val Tyr
        580                 585                 590

Ile Val Asp Arg His Leu Ala Leu Cys Tyr Asn Arg Pro Leu Phe Leu
                595                 600                 605

Leu Asp Ser Glu Cys Ser Asp Leu Tyr His Pro Met Asp Asp Ile Lys
        610                 615                 620

Trp Gln Ala Gly Lys Phe Arg Ser His Asp Ala Gly Asn Ser Ser Ile
625                 630                 635                 640

Asn Ile Asp Ser Ser Met Thr Asp Glu Phe Gly Asp Ser Pro Arg Ala
                645                 650                 655

Ala Arg Gly Ala His Tyr Glu Cys Arg Gly Arg Ser Ile Phe Gly Tyr
                660                 665                 670

Phe Leu Ser Leu Met Thr Ile Leu Gly Glu Ile Val Asp Val His His
        675                 680                 685

Ala Lys Ser His Pro Arg Phe Gly Val Gly Phe Arg Ser Ala Arg Asp
        690                 695                 700

Trp Asp Glu Gln Val Ala Glu Ile Thr Arg His Leu Asp Met Tyr Glu
705                 710                 715                 720

Glu Ser Leu Lys Arg Phe Val Ala Lys His Leu Pro Leu Ser Ser Lys
                725                 730                 735

Asp Lys Glu Gln His Glu Met His Asp Ser Gly Ala Val Thr Asp Met
                740                 745                 750

Gln Ser Pro Leu Ser Val Arg Thr Asn Ala Ser Ser Arg Met Thr Glu
            755                 760                 765

Ser Glu Ile Gln Ala Ser Ile Val Val Ala Tyr Ser Thr His Val Met
        770                 775                 780
```

His Val Leu His Ile Leu Ala Asp Lys Trp Asp Pro Ile Asn Leu
785                 790                 795                 800

Leu Asp Asp Asp Leu Trp Ile Ser Ser Glu Gly Phe Val Thr Ala
            805                 810                 815

Thr Ser His Ala Val Ser Ala Ala Glu Ala Ile Ser Gln Ile Leu Glu
        820                 825                 830

Phe Asp Pro Gly Leu Glu Phe Met Pro Phe Phe Tyr Gly Val Tyr Leu
        835                 840                 845

Leu Gln Gly Ser Phe Leu Leu Leu Ile Ala Asp Lys Leu Gln Ala
    850                 855                 860

Glu Ala Ser Pro Ser Val Ile Lys Ala Cys Glu Thr Ile Val Arg Ala
865                 870                 875                 880

His Glu Ala Cys Val Val Thr Leu Ser Thr Glu Tyr Gln Arg Asn Phe
            885                 890                 895

Ser Lys Val Met Arg Ser Ala Leu Ala Leu Ile Arg Gly Arg Val Pro
            900                 905                 910

Glu Asp Leu Ala Glu Gln Gln Gln Arg Arg Glu Leu Leu Ala Leu
    915                 920                 925

Tyr Arg Trp Thr Gly Asn Gly Thr Gly Leu Ala Leu
930                 935                 940

<210> SEQ ID NO 49
<211> LENGTH: 65
<212> TYPE: DNA
<213> ORGANISM: Artificial Sequence
<220> FEATURE:
<223> OTHER INFORMATION: primer

<400> SEQUENCE: 49
gtaacgccag ggttttccca gtcacgacgg tttaaactcc atacgcagca aacatgggct    60
tgggc                                                                65

<210> SEQ ID NO 50
<211> LENGTH: 64
<212> TYPE: DNA
<213> ORGANISM: Artificial Sequence
<220> FEATURE:
<223> OTHER INFORMATION: primer

<400> SEQUENCE: 50
gtacgagtac taggtgtgaa gattccgtca agcttgggcg aatgaagga ggatgtgtga    60 gagg                                                                 64

<210> SEQ ID NO 51
<211> LENGTH: 59
<212> TYPE: DNA
<213> ORGANISM: Artificial Sequence
<220> FEATURE:
<223> OTHER INFORMATION: primer

<400> SEQUENCE: 51
cacacatcct ccttcattcc gcccaagctt gacggaatct tcacacctag tactcgtac    59

<210> SEQ ID NO 52
<211> LENGTH: 57
<212> TYPE: DNA
<213> ORGANISM: Artificial Sequence
<220> FEATURE:
<223> OTHER INFORMATION: primer

<400> SEQUENCE: 52

```
tgacattttt tgttgttcca acacagcatg cttagtccga cgccttcgag tccagcc      57
```

<210> SEQ ID NO 53
<211> LENGTH: 54
<212> TYPE: DNA
<213> ORGANISM: Artificial Sequence
<220> FEATURE:
<223> OTHER INFORMATION: primer

<400> SEQUENCE: 53

```
ctggactcga aggcgtcgga ctaagcatgc tgtgttggaa caacaaaaaa tgtc          54
```

<210> SEQ ID NO 54
<211> LENGTH: 54
<212> TYPE: DNA
<213> ORGANISM: Artificial Sequence
<220> FEATURE:
<223> OTHER INFORMATION: primer

<400> SEQUENCE: 54

```
gcagagcagc agtagtcgat gctattaatt aagtaggtta tgcgagcaac attg          54
```

<210> SEQ ID NO 55
<211> LENGTH: 58
<212> TYPE: DNA
<213> ORGANISM: Artificial Sequence
<220> FEATURE:
<223> OTHER INFORMATION: primer

<400> SEQUENCE: 55

```
ctcagcctct ctcagcctca tcagccgcgg ccgctgaatc ggcaaggggt agtactag      58
```

<210> SEQ ID NO 56
<211> LENGTH: 62
<212> TYPE: DNA
<213> ORGANISM: Artificial Sequence
<220> FEATURE:
<223> OTHER INFORMATION: primer

<400> SEQUENCE: 56

```
gcggataaca atttcacaca ggaaacagcg tttaaaccac atgccagagt tcgatgcgca    60
ag                                                                   62
```

<210> SEQ ID NO 57
<211> LENGTH: 57
<212> TYPE: DNA
<213> ORGANISM: Artificial Sequence
<220> FEATURE:
<223> OTHER INFORMATION: primer

<400> SEQUENCE: 57

```
gtacctcagc gctgtcgata gctgcacgca ctgccgcgat gcccacgtgc agtgcac       57
```

<210> SEQ ID NO 58
<211> LENGTH: 59
<212> TYPE: DNA
<213> ORGANISM: Artificial Sequence
<220> FEATURE:
<223> OTHER INFORMATION: primer

<400> SEQUENCE: 58

```
gtgcactgca cgtgggcatc gcggcagtgc gtgcagctat cgacagcgct gaggtactc     59
```

<210> SEQ ID NO 59

```
<211> LENGTH: 48
<212> TYPE: DNA
<213> ORGANISM: Artificial Sequence
<220> FEATURE:
<223> OTHER INFORMATION: primer

<400> SEQUENCE: 59
gcggcgcttc cgctgtcgta actatgctgc gctactcccc cgtcttac            48

<210> SEQ ID NO 60
<211> LENGTH: 58
<212> TYPE: DNA
<213> ORGANISM: Artificial Sequence
<220> FEATURE:
<223> OTHER INFORMATION: primer

<400> SEQUENCE: 60
gtaagacggg ggagtagcgc agcatagtta cgacagcgga agcgccgcct tataagtg    58

<210> SEQ ID NO 61
<211> LENGTH: 53
<212> TYPE: DNA
<213> ORGANISM: Artificial Sequence
<220> FEATURE:
<223> OTHER INFORMATION: primer

<400> SEQUENCE: 61
ggcggcgctt ccgctgtcgt aactatgggc tcagcagctc cggcccaggg ctc         53

<210> SEQ ID NO 62
<211> LENGTH: 58
<212> TYPE: DNA
<213> ORGANISM: Artificial Sequence
<220> FEATURE:
<223> OTHER INFORMATION: primer

<400> SEQUENCE: 62
gccctgggcc ggagctgctg agcccatagt tacgacagcg gaagcgccgc cttataag    58

<210> SEQ ID NO 63
<211> LENGTH: 53
<212> TYPE: DNA
<213> ORGANISM: Artificial Sequence
<220> FEATURE:
<223> OTHER INFORMATION: primer

<400> SEQUENCE: 63
ggcggcgctt ccgctgtcgt aactatggcc acagcggccg cggcagcagc tgg         53

<210> SEQ ID NO 64
<211> LENGTH: 59
<212> TYPE: DNA
<213> ORGANISM: Artificial Sequence
<220> FEATURE:
<223> OTHER INFORMATION: primer

<400> SEQUENCE: 64
cagctgctgc cgcggccgct gtggccatag ttacgacagc ggaagcgccg ccttataag   59

<210> SEQ ID NO 65
<211> LENGTH: 22
<212> TYPE: DNA
<213> ORGANISM: Artificial Sequence
<220> FEATURE:
<223> OTHER INFORMATION: primer

<400> SEQUENCE: 65
```

```
gctggaagct gctgagcaga tc                                              22
```

<210> SEQ ID NO 66
<211> LENGTH: 22
<212> TYPE: DNA
<213> ORGANISM: Artificial Sequence
<220> FEATURE:
<223> OTHER INFORMATION: primer

<400> SEQUENCE: 66

```
gtgccagcat tccccagact cg                                              22
```

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67

```
ttaggcgacc tcttttccca                                                 20
```

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68

```
gccgctcagg catacgagcg ac                                              22
```

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69

```
ctctggtcgg cctgccgttg                                                 20
```

<210> SEQ ID NO 70
<211> LENGTH: 23
<212> TYPE: DNA
<213> ORGANISM: Artificial Sequence
<220> FEATURE:
<223> OTHER INFORMATION: primer

<400> SEQUENCE: 70

```
tgagtatagc ggctgacttg tcg                                             23
```

<210> SEQ ID NO 71
<211> LENGTH: 59
<212> TYPE: DNA
<213> ORGANISM: Artificial Sequence
<220> FEATURE:
<223> OTHER INFORMATION: primer

<400> SEQUENCE: 71

```
tctagtatgt acgagtacta ggtgtgaaga ttccgtcatt tcctcgacat gcgaatgcg      59
```

<210> SEQ ID NO 72
<211> LENGTH: 59
<212> TYPE: DNA

```
<213> ORGANISM: Artificial Sequence
<220> FEATURE:
<223> OTHER INFORMATION: primer

<400> SEQUENCE: 72
tgccatgcaa accccgcatt cgcatgtcga ggaaatgacg gaatcttcac acctagtac      59

<210> SEQ ID NO 73
<211> LENGTH: 59
<212> TYPE: DNA
<213> ORGANISM: Artificial Sequence
<220> FEATURE:
<223> OTHER INFORMATION: primer

<400> SEQUENCE: 73
tgcagctaca gagccctggg ccggagctgc tgagcccata gttacgacag cggaagcgc      59

<210> SEQ ID NO 74
<211> LENGTH: 57
<212> TYPE: DNA
<213> ORGANISM: Artificial Sequence
<220> FEATURE:
<223> OTHER INFORMATION: primer

<400> SEQUENCE: 74
atagcactta taaggcggcg cttccgctgt cgtaactatg ggctcagcag ctccggc        57

<210> SEQ ID NO 75
<211> LENGTH: 75
<212> TYPE: DNA
<213> ORGANISM: Artificial Sequence
<220> FEATURE:
<223> OTHER INFORMATION: primer

<400> SEQUENCE: 75
taaacaaata ggggttccgc gcacatttcc ccgaaaagtg ccacctggat agactagcat     60
ctgagccatt gcagc                                                     75

<210> SEQ ID NO 76
<211> LENGTH: 60
<212> TYPE: DNA
<213> ORGANISM: Artificial Sequence
<220> FEATURE:
<223> OTHER INFORMATION: primer

<400> SEQUENCE: 76
agtggcaccg agtcggtggt gcttttttttt ctatcgagag cattggtcag tggtggcaag   60

<210> SEQ ID NO 77
<211> LENGTH: 60
<212> TYPE: DNA
<213> ORGANISM: Artificial Sequence
<220> FEATURE:
<223> OTHER INFORMATION: primer

<400> SEQUENCE: 77
accaatatac aaaacatgtc gtccgagcca gtgcctgcca tttcctcgac atgcgaatgc    60

<210> SEQ ID NO 78
<211> LENGTH: 60
<212> TYPE: DNA
<213> ORGANISM: Artificial Sequence
<220> FEATURE:
<223> OTHER INFORMATION: primer

<400> SEQUENCE: 78
```
gttgccatgc aaaccccgca ttcgcatgtc gaggaaatgg caggcactgg ctcggacgac    60

<210> SEQ ID NO 79
<211> LENGTH: 60
<212> TYPE: DNA
<213> ORGANISM: Artificial Sequence
<220> FEATURE:
<223> OTHER INFORMATION: primer

<400> SEQUENCE: 79
agctacagag ccctgggccg gagctgctga gcccattgtt gaattctggc ggggtagctg    60

<210> SEQ ID NO 80
<211> LENGTH: 60
<212> TYPE: DNA
<213> ORGANISM: Artificial Sequence
<220> FEATURE:
<223> OTHER INFORMATION: primer

<400> SEQUENCE: 80
cttttacact tttcaacagc taccccgcca gaattcaaca atgggctcag cagctccggc    60

<210> SEQ ID NO 81
<211> LENGTH: 81
<212> TYPE: DNA
<213> ORGANISM: Artificial Sequence
<220> FEATURE:
<223> OTHER INFORMATION: primer

<400> SEQUENCE: 81
tagtccgtta tcaacttgaa aaagtggcac cgagtcggtg gtgcttttttt ttctatcgag    60 atgttctgga tggtggagag g                                              81

<210> SEQ ID NO 82
<211> LENGTH: 32
<212> TYPE: DNA
<213> ORGANISM: Artificial Sequence
<220> FEATURE:
<223> OTHER INFORMATION: primer

<400> SEQUENCE: 82
agtctatcgc agccttgcct tagctaatgt tt                                  32

<210> SEQ ID NO 83
<211> LENGTH: 32
<212> TYPE: DNA
<213> ORGANISM: Artificial Sequence
<220> FEATURE:
<223> OTHER INFORMATION: primer

<400> SEQUENCE: 83
tctaaaacat tagctaaggc aaggctgcga ta                                  32

<210> SEQ ID NO 84
<211> LENGTH: 32
<212> TYPE: DNA
<213> ORGANISM: Artificial Sequence
<220> FEATURE:
<223> OTHER INFORMATION: primer

<400> SEQUENCE: 84
agtctatcgg cagagtcgcg tcttccgggt tt                                  32

<210> SEQ ID NO 85

```
<210> SEQ ID NO 85
<211> LENGTH: 32
<212> TYPE: DNA
<213> ORGANISM: Artificial Sequence
<220> FEATURE:
<223> OTHER INFORMATION: primer

<400> SEQUENCE: 85
tctaaaaccc ggaagacgcg actctgccga ta                                32

<210> SEQ ID NO 86
<211> LENGTH: 33
<212> TYPE: DNA
<213> ORGANISM: Artificial Sequence
<220> FEATURE:
<223> OTHER INFORMATION: primer

<400> SEQUENCE: 86
agtctatcga atgagtgtag gtacgagtag ttt                               33

<210> SEQ ID NO 87
<211> LENGTH: 33
<212> TYPE: DNA
<213> ORGANISM: Artificial Sequence
<220> FEATURE:
<223> OTHER INFORMATION: primer

<400> SEQUENCE: 87
tctaaaacta ctcgtaccta cactcattcg ata                               33

<210> SEQ ID NO 88
<211> LENGTH: 32
<212> TYPE: DNA
<213> ORGANISM: Artificial Sequence
<220> FEATURE:
<223> OTHER INFORMATION: primer

<400> SEQUENCE: 88
agtctatcgg ccgcaatagc ttcctaatgt tt                                32

<210> SEQ ID NO 89
<211> LENGTH: 32
<212> TYPE: DNA
<213> ORGANISM: Artificial Sequence
<220> FEATURE:
<223> OTHER INFORMATION: primer

<400> SEQUENCE: 89
tctaaaacat taggaagcta ttgcggccga ta                                32

<210> SEQ ID NO 90
<211> LENGTH: 32
<212> TYPE: DNA
<213> ORGANISM: Artificial Sequence
<220> FEATURE:
<223> OTHER INFORMATION: primer

<400> SEQUENCE: 90
agtctatcgc agcgcaatca gtgcagtggt tt                                32

<210> SEQ ID NO 91
<211> LENGTH: 32
<212> TYPE: DNA
<213> ORGANISM: Artificial Sequence
<220> FEATURE:
<223> OTHER INFORMATION: primer

<400> SEQUENCE: 91
```
tctaaaacca ctgcactgat tgcgctgcga ta                                    32

<210> SEQ ID NO 92
<211> LENGTH: 23
<212> TYPE: DNA
<213> ORGANISM: Artificial Sequence
<220> FEATURE:
<223> OTHER INFORMATION: primer

<400> SEQUENCE: 92
tggagagact cggagaggat agg                                              23

<210> SEQ ID NO 93
<211> LENGTH: 22
<212> TYPE: DNA
<213> ORGANISM: Artificial Sequence
<220> FEATURE:
<223> OTHER INFORMATION: primer

<400> SEQUENCE: 93
agcgtggagg cagttggagt gg                                               22

<210> SEQ ID NO 94
<211> LENGTH: 24
<212> TYPE: DNA
<213> ORGANISM: Artificial Sequence
<220> FEATURE:
<223> OTHER INFORMATION: primer

<400> SEQUENCE: 94
tggacaaagc ctgggtcctg ctcc                                             24

<210> SEQ ID NO 95
<211> LENGTH: 22
<212> TYPE: DNA
<213> ORGANISM: Artificial Sequence
<220> FEATURE:
<223> OTHER INFORMATION: primer

<400> SEQUENCE: 95
atcctgactc gtcctgtgtc gg                                               22

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
agtgcttcgt ttagtggact tg                                               22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
ctcggtagct gcttgaatat ag                                               22

<210> SEQ ID NO 98
<211> LENGTH: 45
<212> TYPE: PRT

<213> ORGANISM: Artificial Sequence
<220> FEATURE:
<223> OTHER INFORMATION: EL form N-terminal extension

<400> SEQUENCE: 98

Met Ala Thr Ala Ala Ala Ala Ala Gly Gly Ala Ala Val Ala Ala
1               5                   10                  15

Gly Ala Asp Thr Gly Ala Ala Gly Ser Ser Thr Gly Pro Pro Gly
                20                  25                  30

Leu Pro Gly Leu Pro Gly Thr Arg Thr Gly Ser Val Ala
            35                  40                  45

<210> SEQ ID NO 99
<211> LENGTH: 1857
<212> TYPE: DNA
<213> ORGANISM: Trichoderma reesei

<400> SEQUENCE: 99

| atgctgcgct | actcccccgt | cttacacctg | gatactctct | ccttgccacc | actgaccaat | 60 |
| gctcttcccc | gcccaaagtg | cgagtacctc | agcgctgtcg | atagctgcac | gcactgccgc | 120 |
| gatgcccacg | tgcagtgcac | tttcgacctg | cccctggcgc | gacgcggccc | caaagcgagg | 180 |
| aagaagagcg | accagcccgg | ccagccgcct | cctgatccga | gctcgctctc | caccgcggct | 240 |
| cgacccggcc | agatgccgcc | gccgctgacc | ttctccggcc | ccgcagtagc | cgcgctgcag | 300 |
| cccttcgcct | cgtcgtcgct | gtcgcccgac | gcggcctggg | agcccgtcga | gccgctcagc | 360 |
| attgacaacg | gcctgccccg | gcagccgctg | ggcgacctgc | ccggcctctc | caccatccag | 420 |
| aacatctcga | cgcgccagcg | atggatacac | ctggccaacg | ccatgacgct | gcgcaacacg | 480 |
| acgctagagc | gcgtctcgaa | gcgatgtatc | gacctcttct | tcgactacct | ctaccccctc | 540 |
| accccctgg | tgtacgagcc | ggccctccgg | gacgtgctcg | catacatctt | ctcccagccc | 600 |
| ttgcctggcg | tcaaccaacc | atcgccgctg | tcacagctca | cgccagaccc | gaccaccggc | 660 |
| accacccccc | tcaacgctgc | cgagtcgtgg | gccggctttg | gccagcccag | cggctcgcga | 720 |
| accgtcggca | gcaggctggc | tccctgggcc | gactcgacct | tcaccctggt | cacggccgtc | 780 |
| tgcgcagagg | cagcattcat | gctacccaag | gacatttttcc | ccgaaggaga | atccgtctct | 840 |
| gagatcttgc | tcgaagcctc | tcgggactgc | ctgcaccagc | acctcgaggc | cgacctggag | 900 |
| aatccgacgg | ccaactcgat | tgccattcgc | tacttccact | ccaactgcct | ccacgctgcg | 960 |
| gggaagccca | gtactcgtg | gcacatattt | ggcgaggcca | tccgcctggc | gcaggtcatg | 1020 |
| cagctgcacg | aggaggctgc | cctcgagggg | ctcgtcccca | tcgaggcaga | gttccgccgt | 1080 |
| cgctgctttt | ggatcctgta | cttgggcgac | aagtcagccg | ctatactcaa | caatcggccc | 1140 |
| atcaccatcc | acaagtactg | cttcgacgcc | ggcatcacca | cgctataccc | gtcgggtatc | 1200 |
| gaggacgagt | tcctgagcac | ggcgtccgag | ccgccccgga | agagcttcat | atccggcttc | 1260 |
| aacgcaaatg | tgcggctctg | gcagtccgcg | gctgatttgc | tgctggaaat | ccgcgtgctg | 1320 |
| caagatcaga | tgatgcagca | ctttcgaggg | accatgcccc | gaaccatgt | gctgccctcc | 1380 |
| gccgacaggc | agcatctcga | ttctctctat | gtccgcttca | tcacctgctt | ggacgatctc | 1440 |
| ccgccgtacc | tccagtcgtg | cactctgcg | atggcagcga | tggcagaagg | caacgggtct | 1500 |
| gccgagtcca | agcagtacgt | gatacagtgc | atcaacctgc | aggtgacgtt | tcactgtctg | 1560 |
| cgcatggtaa | ttacgcagaa | attcgaagac | ctctctttatt | ttgctcctgg | cgttgagcag | 1620 |
| gctgatctca | gaaagtcgga | gattgtgcga | gacatgctga | gggtgatgaa | cgaggcgccc | 1680 |

```
ttttggggcc tgcaggccaa tggcgagcca aacgttgaaa agattcgcct tatcggagct    1740
agtttgctgg ccatcatcca tcgcaaccag gattcaccct tggctacgcg agccaggagc    1800
gacttttccg tgcttttgga tattctcacg cggctggact cgaaggcgtc ggactaa      1857

<210> SEQ ID NO 100
<211> LENGTH: 2070
<212> TYPE: DNA
<213> ORGANISM: Trichoderma reesei

<400> SEQUENCE: 100
atgggctcag cagctccggc ccagggctct gtagctgcag ctgcaggcgg ccctccagct      60
gctggcgctg gcgctggcgc tgtccacgcc ctcaccacct cgcccgagtc tgcctcggcc     120
tcgcagcccg gctcgccaac cgcctcaacc acgccgccgc agaactcact cgtgtcggct     180
gcaacctcgt tccaccacca tcccagaggc cgtctggtga gcagagcctg cgaccgctgc     240
cgccggcgca aggccaagtg cgagtacctc agcgctgtcg atagctgcac gcactgccgc     300
gatgcccacg tgcagtgcac tttcgacctg ccccctgcgc gacgcggccc caaagcgagg     360
aagaagagcg accagcccgg ccagccgcct cctgatccga gctcgctctc caccgcggct     420
cgacccggcc agatgccgcc gccgctgacc ttctccggcc ccgcagtagc cgcgctgcag     480
cccttcgcct cgtcgtcgct gtcgcccgac gcggcctggg agcccgtcga gccgctcagc     540
attgacaacg gcctgcccg gcagccgctg gcgacctgc ccggcctctc caccatccag     600
aacatctcga cgcgccagcg atggatacac ctggccaacg ccatgacgct gcgcaacacg     660
acgctagagc gcgtctcgaa gcgatgtatc gacctcttct tcgactacct ctacccctc     720 accccctgg tgtacgagcc ggccctccgg gacgtgctcg catacatctt ctcccagccc     780
ttgcctggcg tcaaccaacc atcgccgctg tcacagctca cgccagaccc gaccaccggc     840
accacccccc tcaacgctgc cgagtcgtgg gccggctttg gccagcccag cggctcgcga     900
accgtcggca gcaggctggc tccctgggcc gactcgacct tcaccctggt cacggccgtc     960
tgcgcagagg cagcattcat gctacccaag gacatttttcc ccgaaggaga atccgtctct    1020
gagatcttgc tcgaagcctc tcgggactgc ctgcaccagc acctcgaggc cgacctggag    1080
aatccgacgg ccaactcgat tgccattcgc tacttccact ccaactgcct ccacgctgcg    1140
gggaagccca gtactcgtg cacatatttt ggcgaggcca tccgcctggc gcaggtcatg    1200
cagctgcacg aggaggctgc cctcgagggg ctcgtcccca tcgaggcaga gttccgccgt    1260
cgctgctttt ggatcctgta cttgggcgac aagtcagccg ctatactcaa caatcggccc    1320
atcaccatcc acaagtactg cttcgacgcc ggcatcacca cgctataccc gtcgggtatc    1380
gaggacgagt tcctgagcac ggcgtccgag ccgccccgga agagcttcat atccggcttc    1440
aacgcaaatg tgcggctctg gcagtccgcg gctgatttgc tgctggaaat ccgcgtgctg    1500
caagatcaga tgatgcagca ctttcgaggg accatgcccc cgaaccatgt gctgccctcc    1560
gccgacaggc agcatctcga ttctctctat gtccgcttca tcacctgctt ggacgatctc    1620
ccgccgtacc tccagtcgtg cactctggcg atggcagcga tggcagaagg caacgggtct    1680
gccgagtcca agcagtacgt gatacagtgc atcaacctgc aggtgacgtt tcactgtctg    1740
cgcatggtaa ttacgcagaa attcgaagac ctctcttatt ttgctcctgg cgttgagcag    1800
gctgatctca gaaagtcgga gattgtgcga gacatgctga gggtgatgaa cgaggcgccc    1860
ttttggggcc tgcaggccaa tggcgagcca aacgttgaaa agattcgcct tatcggagct    1920
agtttgctgg ccatcatcca tcgcaaccag gattcaccct tggctacgcg agccaggagc    1980
```

```
gacttttccg tgcttttgga tattctcacg cggctggact cgaaggcgtc ggaccaactg    2040
aggaatacgt ccactaccgt tgttggctaa                                     2070

<210> SEQ ID NO 101
<211> LENGTH: 2172
<212> TYPE: DNA
<213> ORGANISM: Trichoderma reesei

<400> SEQUENCE: 101
atggccacag cggccgcggc agcagctggc ggcgcggcgg ttgctgcggg tgcagacaca      60
ggcgctgcag gctccagctc tacaggccct ccaggccttc cagggcttcc aggcacccgg     120
acaggctccg tggcgatggg ctcagcagct ccggcccagg gctctgtagc tgcagctgca     180
ggcggccctc cagctgctgg cgctggcgct ggcgctgtcc acgccctcac cacctcgccc     240
gagtctgcct cggcctcgca gcccggctcg ccaaccgcct caaccacgcc gccgcagaac     300
tcactcgtgt cggctgcaac ctcgttccac caccatccca gaggccgtct ggtgagcaga     360
gcctgcgacc gctgccgccg gcgcaaggcc aagtgcgagt acctcagcgc tgtcgatagc     420
tgcacgcact gccgcgatgc ccacgtgcag tgcactttcg acctgcccct ggcgcgacgc     480
ggccccaaag cgaggaagaa gagcgaccag cccggccagc cgcctcctga tccgagctcg     540
ctctccaccg cggctcgacc cggccagatg ccgccgccgc tgaccttctc cggccccgca     600
gtagccgcgc tgcagcccct tcgcctcgtcg tcgctgtcgc ccgacgcggc ctgggagccc     660
gtcgagccgc tcagcattga caacggcctg ccccggcagc cgctgggcga cctgcccggc     720
ctctccacca tccagaacat ctcgacgcgc cagcgatgga tacacctggc caacgccatg     780
acgctgcgca cacgacgct agagcgcgtc tcgaagcgat gtatcgacct cttcttcgac     840
tacctctacc ccctcacccc cctggtgtac gagccggccc tccgggacgt gctcgcatac     900
atcttctccc agcccttgcc tggcgtcaac caaccatcgc cgctgtcaca gctcacgcca     960
gacccgacca ccggcaccac ccccctcaac gctgccgagt cgtgggccgg ctttggccag    1020
cccagcggct cgcgaaccgt cggcagcagg ctggctccct gggccgactc gaccttcacc    1080
ctggtcacgg ccgtctgcgc agaggcagca ttcatgctac ccaaggacat tttccccgaa    1140
ggagaatccg tctctgagat cttgctcgaa gcctctcggg actgcctgca ccagcacctc    1200
gaggccgacc tggagaatcc gacggccaac tcgattgcca ttcgctactt ccactccaac    1260
tgcctccacg ctgcggggaa gcccaagtac tcgtggcaca tatttggcga ggccatccgc    1320
ctggcgcagg tcatgcagct gcacgaggag gctgccctcg aggggctcgt ccccatcgag    1380
gcagagttcc gccgtcgctg cttttggatc ctgtacttgg gcgacaagtc agccgctata    1440
ctcaacaatc ggcccatcac catccacaag tactgcttcg acgccggcat caccacgcta    1500
tacccgtcgg gtatcgagga cgagttcctg agcacggcgt ccgagccgcc ccggaagagc    1560
ttcatatccg gcttcaacgc aaatgtgcgg ctctggcagt ccgcggctga tttgctgctg    1620
gaaatccgcg tgctgcaaga tcagatgatg cagcactttc gagggaccat gccccgaac     1680 catgtgctgc cctccgccga caggcagcat ctcgattctc tctatgtccg cttcatcacc    1740
tgcttggacg atctcccgcc gtacctccag tcgtgcactc tggcgatggc agcgatggca    1800
gaaggcaacg ggtctgccga gtccaagcag tacgtgatac agtgcatcaa cctgcaggtg    1860
acgtttcact gtctgcgcat ggtaattacg cagaaattcg aagacctctc ttattttgct    1920
cctggcgttg agcaggctga tctcagaaag tcggagattg tgcagacat gctgagggtg      1980
```

```
atgaacgagg cgcccttttg gggcctgcag gccaatggcg agccaaacgt tgaaaagatt   2040
cgccttatcg gagctagttt gctggccatc atccatcgca accaggattc acccttggct   2100
acgcgagcca ggagcgactt ttccgtgctt ttggatattc tcacgcggct ggactcgaag   2160
gcgtcggact aa                                                      2172
```

<210> SEQ ID NO 102
<211> LENGTH: 2037
<212> TYPE: DNA
<213> ORGANISM: Trichoderma reesei

<400> SEQUENCE: 102

```
atgggctcag cagctccggc ccagggctct gtagctgcag ctgcaggcgg ccctccagct     60
gctggcgctg cgctggcgc tgtccacgcc ctcaccacct cgcccgagtc tgcctcggcc    120
tcgcagcccg gctcgccaac cgcctcaacc acgccgccgc agaactcact cgtgtcggct    180
gcaacctcgt tccaccacca tcccagaggc cgtctggtga gcagagcctg cgaccgctgc    240
cgccggcgca aggccaagtg cgagtacctc agcgctgtcg atagctgcac gcactgccgc    300 gatgccacg tgcagtgcac tttcgacctg cccctggcgc gacgcggccc caaagcgagg    360
aagaagagcg accagcccgg ccagccgcct cctgatccga gctcgctctc caccgcggct    420
cgacccggcc agatgccgcc gccgctgacc ttctccggcc ccgcagtagc cgcgctgcag    480 ccctttcgcct cgtcgtcgct gtcgcccgac gcggcctggg agcccgtcga gccgctcagc    540
attgacaacg gcctgccccg gcagccgctg ggcgacctgc ccggcctctc caccatccag    600
aacatctcga cgcgccagcg atggatacac ctggccaacg ccatgacgct gcgcaacacg    660
acgctagagc gcgtctcgaa gcgatgtatc gacctcttct tcgactacct ctaccccctc    720
acccccctgg tgtacgagcc ggccctccgg gacgtgctcg catacatctt ctcccagccc    780
ttgcctggcg tcaaccaacc atcgccgctg tcacagctca cgccagaccc gaccaccggc    840 accaccccccc tcaacgctgc cgagtcgtgg gccggctttg gccagcccag cggctcgcga    900
accgtcggca gcaggctggc tccctgggcc gactcgacct tcaccctggt cacggccgtc    960
tgcgcagagg cagcattcat gctacccaag gacattttcc ccgaaggaga atccgtctct   1020
gagatcttgc tcgaagcctc tcgggactgc ctgcaccagc acctcgaggc cgacctggag   1080
aatccgacgg ccaactcgat tgccattcgc tacttccact ccaactgcct ccacgctgcg   1140
gggaagccca agtactcgtg gcacatattt ggcgaggcca tccgcctggc gcaggtcatg   1200
cagctgcacg aggaggctgc cctcgagggg ctcgtcccca tcgaggcaga gttccgccgt   1260
cgctgctttt ggatcctgta cttgggcgac aagtcagccg ctatactcaa caatcggccc   1320
atcaccatcc acaagtactg cttcgacgcc ggcatcacca cgctataccc gtcgggtatc   1380
gaggacgagt tcctgagcac ggcgtccgag ccgccccgga agagcttcat atccggcttc   1440
aacgcaaatg tgcggctctg gcagtccgcg gctgatttgc tgctggaaat ccgcgtgctg   1500
caagatcaga tgatgcagca ctttcgaggg accatgcccc cgaaccatgt gctgccctcc   1560
gccgacaggc agcatctcga ttctctctat gtccgcttca tcacctgctt ggacgatctc   1620
ccgccgtacc tccagtcgtg cactctggcg atggcagcga tggcagaagg caacgggtct   1680
gccgagtcca agcagtacgt gatacagtgc atcaacctgc aggtgacgtt tcactgtctg   1740
cgcatggtaa ttacgcagaa attcgaagac ctctcttatt ttgctcctgg cgttgagcag   1800
```

-continued

```
gctgatctca gaaagtcgga gattgtgcga gacatgctga gggtgatgaa cgaggcgccc    1860
ttttggggcc tgcaggccaa tggcgagcca aacgttgaaa agattcgcct tatcggagct    1920
agtttgctgg ccatcatcca tcgcaaccag gattcaccct tggctacgcg agccaggagc    1980
gacttttccg tgcttttgga tattctcacg cggctggact cgaaggcgtc ggactaa      2037
```